US 10,590,490 B2

(12) United States Patent
Falak et al.

(10) Patent No.: US 10,590,490 B2
(45) Date of Patent: Mar. 17, 2020

(54) QTLS ASSOCIATED WITH AND METHODS FOR IDENTIFYING WHOLE PLANT FIELD RESISTANCE TO *SCLEROTINIA*

(71) Applicant: PIONEER HI-BRED INTERNATIONAL, INC., Johnston, IA (US)

(72) Inventors: Igor Falak, Guelph (CA); Valerio Primomo, Toronto (CA); Lomas Tulsieram, Mississauga (CA)

(73) Assignee: PIONEER HI-BRED INTERNATIONAL, INC. IA (US)

( * ) Notice: Subject to any disclaimer, the term of this patent is extended or adjusted under 35 U.S.C. 154(b) by 75 days.

(21) Appl. No.: 15/416,050

(22) Filed: Jan. 26, 2017

(65) Prior Publication Data
US 2017/0152575 A1 Jun. 1, 2017

Related U.S. Application Data

(62) Division of application No. 13/992,780, filed as application No. PCT/US2011/066526 on Dec. 21, 2011, now Pat. No. 9,702,013.

(60) Provisional application No. 61/426,170, filed on Dec. 22, 2010, provisional application No. 61/449,776, filed on Mar. 7, 2011, provisional application No. 61/566,064, filed on Dec. 2, 2011.

(51) Int. Cl.
*C12Q 1/68* (2018.01)
*C12Q 1/6895* (2018.01)
*C12N 15/82* (2006.01)
*A01H 1/02* (2006.01)
*A01H 1/04* (2006.01)
*A01H 5/10* (2018.01)

(52) U.S. Cl.
CPC ............ *C12Q 1/6895* (2013.01); *A01H 1/02* (2013.01); *A01H 1/04* (2013.01); *A01H 5/10* (2013.01); *C12N 15/8282* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS 8,558,068 B2   10/2013   Falek et al.

FOREIGN PATENT DOCUMENTS

| AU | 2011265450 A1 | 1/2012 |
| CN | 101921776 B | 6/2012 |
| CN | 102174525 B | 8/2012 |
| WO | 02/099385 A2 | 12/2002 |

OTHER PUBLICATIONS

Dwayne Hegedus et al., Development of Sclerotinia Resistant *Brassica napus* Lines and Molecular Markers for Marker-Assisted Breeding, Agriculture and Agri-Food Canada, Saskatoon, Project Code: CGDP SCDC/DIAP 2010, Final Report Apr. 2013
Jiaqin Mei et al., Identification of genomic regions involved in resistance against *Sclerotinia sclerotiorum* from wild *Brassica oleracea*, Theor Appl Genet, 2013, pp. 549-556, vol. 126.
Jian Wu et al., Identification of QTLs for Resistance to Sclerotinia Stem Rot and BnaC.IGMT5.a as a Candidate Gene of the Major Resistant QTL SRC6 in *Brassica napus*, Plosone, Jul. 2013, e67740, pp. 1-12, vol. 8, Issue 7.
U.S. Appl. No. 11/422,623, filed Jun. 7, 2006, now U.S. Pat. No. 7,939,722.
U.S. Appl. No. 12/173,311, filed Jul. 15, 2008, now U.S. Pat. No. 7,977,537.
U.S. Appl. No. 12/173,521, filed Jul. 15, 2008, now U.S. Pat. No. 7,977,538.
U.S. Appl. No. 12/173,893, filed Jul. 16, 2008, now U.S. Pat. No. 7,982,100.
U.S. Appl. No. 12/174,134, filed Jul. 16, 2008, now U.S. Pat. No. 7,977,539.
U.S. Appl. No. 12/175,620, filed Jul. 18, 2008, now U.S. Pat. No. 7,977,540.
U.S. Appl. No. 12/177,233, filed Jul. 22, 2008, now U.S. Pat. No. 7,985,893.
U.S. Appl. No. 12/177,245, filed Jul. 22, 2008, now U.S. Pat. No. 7,982,101.
U.S. Appl. No. 13/149,069, filed May 31, 2011, now U.S. Pat. No. 8,263,827.
U.S. Appl. No. 13/567,117, filed Aug. 6, 2012, now U.S. Pat. No. 8,558,066.
U.S. Appl. No. 13/567,120, filed Aug. 6, 2012, now U.S. Pat. No. 8,558,067.
U.S. Appl. No. 13/567,121, filed Aug. 6, 2012, now U.S. Pat. No. 8,558,068.
Buchwaldt et al., Sclerotinia research at AAFC, Saskatoon, Canola Industry Meeting, Dec. 8, 2010.
Piquemal, J. et al., Construction of an oilseed rape (*Brassica napus* L.) genetic map with SSR markers, Theor. Appl. Genet, 2005, vol. 111:1514-1523.
Yu, B. et al., Improvement of Sclerotinia resistance of a Polima CMS restorer line of rapeseed via phenotypic selection, marker-assisted background selection and microspore culture, Plant Breeding, 2010, vol. 129:39-44.
Saxena, B. et al., Molecular tagging of gene for resistance to stalk rot (Sclerotinia sclerotiorum deBary) in cauliflower (*Brassica oleracea* var. *botrytis*) using RPD markers, Adv. Hort. Sci., 2009, vol. 23(2):108-112.
Yin, Xiangrui et al., Mapping of QTLs detected in a *Brassica napus* DH population for resistance to Sclerotinia sclerotiorum in multiple environments; Euphytica, 2010, vol. 173:25-35.

(Continued)

*Primary Examiner* — Medina A Ibrahim

(57) ABSTRACT

Markers associated with *Sclerotinia* whole plant field resistance are provided. Methods of identifying *Sclerotinia* resistant and susceptible plants, using the markers are provided. Methods for identifying and isolating QTLs are a feature of the invention, as are QTLs associated with *Sclerotinia* whole plant field resistance.

6 Claims, No Drawings

Specification includes a Sequence Listing.

(56) References Cited

OTHER PUBLICATIONS

Zhao, Jianwei et al., Genetic analysis of loci associated with partial resistance to Sclerotinia sclerotiorum in rapeseed (*Brassica napus* L.), Theor Appl Genet., 2003, vol. 106:759-764.
Zhao, Jianwei et al., Quantitative trait loci for resistance to Sclerotinia sclerotiorum and its association with a homeologous non-reciprocal transposition in *Brassica napus* L., Theor Appl Genet, 2006, vol. 112:509-516.
Database EMBL, *Brassica rapa* subsp. *pekinensis* clone, Database Accession No. AC24115.
International Search Report and Written Opinion—PCT/US2011/066529—dated Oct. 29, 2012.

QTLS ASSOCIATED WITH AND METHODS FOR IDENTIFYING WHOLE PLANT FIELD RESISTANCE TO SCLEROTINIA

CROSS-REFERENCE TO RELATED APPLICATIONS

This application is a Divisional of U.S. application Ser. No. 13/992,780, filed Jun. 10, 2013, which is a 371 of International Application No. PCT/US11/66526, filed Dec. 21, 2011. Benefit is claimed under 35 U.S.C. § 1.19(e) to the filing dates of U.S. Provisional Application No. 61/426,170, filed Dec. 22, 2010, U.S. Provisional Application No. 61/449,776, filed Mar. 7, 2011 and U.S. Provisional Application No. 61/566,064, filed Dec. 2, 2011, the entire contents of each of which are incorporated by reference herein.

FIELD OF THE INVENTION

The present invention relates generally to plant molecular biology. More specifically, it relates to quantitative trait loci (QTLs) associated with whole plant field resistance to *Sclerotinia* in *Brassica*, and use of those QTLs to identify whole plant field resistance to *Sclerotinia* in *Brassica* and other plant species.

BACKGROUND OF THE INVENTION

*Sclerotinia* infects over 400 species of plants throughout Canada, including numerous economically important crops such as *Brassica* species, sunflowers, dry beans, field peas, lentils, and potatoes (Boland and Hall (1994) *Can. J. Plant Pathol*. 16:93-108). *Sclerotinia sclerotiorum* is responsible for over 99% of the disease, while *Sclerotinia minor* produces less than 1% of the disease. *Sclerotinia* produces sclerotia, which are irregularly shaped dark overwintering bodies that can endure in soil for four to five years. The sclerotia can germinate carpogenically or myceliogenically depending on the environmental conditions and crop canopies. The two types of germination cause two distinct types of diseases. Sclerotia that germinate carpogenically produce apothecia and ascospores that infect above-ground tissues, resulting in stem blight, stalk rot, head rot, pod rot, white mold and blossom blight of plants. Sclerotia that germinate myceliogenically produce mycelia that can infect root tissues, causing crown rot, root rot and basal stalk rot.

*Sclerotinia* causes *Sclerotinia* stem rot, also known as white mold, in *Brassica*, including canola. Canola is a type of *Brassica* having a low level of glucosinolates and erucic acid in the seed. The sclerotia germinate carpogenically in the summer, producing apothecia. The apothecia release wind-borne ascospores that travel up to one kilometer. The disease is favored by moist soil conditions (at least 10 days at or near field capacity) and temperatures of 15-25° C., prior to and during canola flowering. The spores cannot infect leaves and stems directly. They must first land on flowers, fallen petals, and pollen on the stems and leaves. Petal age affects the efficiency of infection, with older petals better able to effect infection (Heran et al. (1999) "The Effect of Petal Characteristics, Inoculum Density and Environmental Factors on Infection of Oilseed Rape by *Sclerotinia sclerotiorum*" The Regional Institute Ltd. http://www.regional.org.au/au/gcirc/3/428.htm). The fungal spores use the flower parts as a food source to germinate and infect the plant.

*Brassica* can also develop root rot under certain conditions. For example, winter and spring canola occasionally develop root rot during mild winters in Europe (winter canola) and in Georgia, US (spring canola).

The severity of *Sclerotinia* in *Brassica* is variable, and is dependent on the time of infection and climatic conditions (Heran et al., supra). The disease is favored by cool temperatures and prolonged periods of precipitation. Temperatures between 20 and 25° C. and relative humidities of greater than 80% are required for optimal plant infection (Heran et al., supra). Losses ranging from 5 to 100% have been reported for individual fields (Manitoba Agriculture, Food and Rural Initiatives, 2004). On average, yield losses equal 0.4 to 0.5 times the percentage infection. For example, if a field has 20% infection (20/100 infected plants), then the yield loss would be about 10%. Further, *Sclerotinia* can cause heavy losses in wet swaths.

The symptoms of *Sclerotinia* infection usually develop several weeks after flowering begins. The plants develop pale-grey to white lesions, at or above the soil line and on upper branches and pods. The infections often develop where the leaf and the stem join because the infected petals lodge there. Infected stems appear bleached and tend to shred. Hard black fungal sclerotia develop within the infected stems, branches, or pods. Plants infected at flowering produce little or no seed. Plants with girdled stems wilt and ripen prematurely. Severely infected crops frequently lodge, shatter at swathing, and make swathing more time consuming. Infections can occur in all above ground plant parts especially in dense or lodged stands. Once plants are infected, the mold continues to grow into the stem and invade healthy tissue. New sclerotia are formed to carry the disease over to the next season.

Some varieties of canola with certain morphological traits are better able to withstand *Sclerotinia* infection. For example, Polish varieties (*Brassica rapa*) have lighter canopies and seem to have much lower infection levels. In addition, petal-less varieties (apetalous varieties) do not provide the initial infection source (i.e., the flower petal) and avoid *Sclerotinia* infection to a greater extent (Okuyama et al. (1995) *Bulletin of the Tohoku National Agricultural Experiment Station*. National Agriculture Research Center, Tsukuba, Ibaraki 305, JAP 3-1-1an. 89: 11-20; Fu (1990) *Acta Agriculture Shanghai*. Economic Crop Research Institute, Jiangsu Province Academy of Agricultural Sciences, Nanjing 210024, China 6 (3): 76-77. Other examples of morphological traits that confer a degree of reduced susceptibility to *Sclerotinia* in *Brassica* include increased standability, lower petal retention, higher branching (both extent and position), flowering (early start and/or short duration) and early leaf abscission. Jurke and Fernando ("Plant Morphology of Canola and its Effects on *Sclerotinia sclerotiorum* infection in ICPP" 2003 8th International Congress of Plant Pathology, New Zealand) screened eleven canola genotypes for *Sclerotinia* disease incidence. Significant variation in disease incidence was explained by plant morphology and the difference in petal retention was identified as the most important factor. However, these morphological traits alone do not confer resistance to *Sclerotinia* and most canola lines in Canada are considered susceptible to *Sclerotinia*.

The primary means of controlling *Sclerotinia* in infected canola crops is by spraying with fungicide. Typical fungicides used for controlling *Sclerotinia* on *Brassica* include Rovral™/Proline from Bayer and Ronilan™/Lance™ from BASF. If infection is already evident, there is no use in applying fungicide as it is too late to have an effect. Accordingly, growers must assess their fields for disease risk to decide whether to apply a fungicide. This can be done by using a government provided checklist or by using a petal testing kit. Either way, the method is cumbersome and prone to errors.

Numerous efforts have been made to develop *Sclerotinia* resistant spring *Brassica* plants. Built in resistance would be more convenient, economical, and environmentally friendly compared to controlling *Sclerotinia* by application of fungicides. Since the trait is polygenic it would be stable and not prone to changes in efficacy, as fungicides may be. Winter canola is also susceptible to *Sclerotinia*.

Spring canola (*Brassica napus* subsp. *oleifera* var. *annua*) differs from winter canola (*Brassica napus* subsp. *oleifera* var. *biennis*) primarily in the absence of an obligate vernalization requirement. Asiatic rapeseed and canola versions have a low to intermediate requirement for vernalization. While winter canola cannot finish its reproduction cycle when planted in the spring, Asiatic material cannot finish its reproduction cycle if planted in late spring, but early spring planting and exposure to cold enables Asiatic material to flower and set seed. In controlled conditions winter material requires 12-14 weeks of vernalization while Asiatic material requires 2-8 weeks. Table 1 summarizes the differences between winter, semi-winter (Asiatic) and spring canola varieties.

TABLE 1

Main determinations of growth habit in *Brassica napus* materials

| Type | Spring* | Spring | Semi Winter | Winter |
|---|---|---|---|---|
| Growing areas | Canada, Europe | Australia | China, Japan | Europe |
| Vernalization Requirement | None | None | 2-8 weeks Intermediate | 12-14 weeks strong or full |
| Time of seeding | Spring (Increasing Day Length) | Fall (Decreasing Day Length) | Fall (Decreasing Day Length) | Fall (Decreasing Day Length) |
| Number of days until flowering | 30-90 | 90-150 | 120-180 | 150-270 |

*Canadian, European and Australian spring materials can be planted and grown in any environment or seeding time for spring canola.

Some Chinese cultivars of rapeseed/canola are partially resistant to *Sclerotinia*. For example, ChunYun et al. ((2003) *Acta Agronomica Sinica* 29 (5): 715-718); HanZhong et al. ((2004) *Scientia Agricultura Sinica* 37 (1): 23-28); WeiXin et al. ((2002) *Chinese Journal of Oil Crop Sciences* 24 (3): 47-49); YongJu et al. ((2000) *Chinese Journal of Oil Crop Sciences* 22 (4): 1-5) describe partially resistant varieties of rapeseed. However, some of these varieties are not canola quality and all of them require vernalization. The partial field resistance in Chinese varieties originated from the rapeseed variety Zhong you 821. Despite improvements in partial resistance in Zhong you 821, its reaction to pathogens is less stable under environmental conditions favorable for development of *Sclerotinia* (Li et al. (1999) "Breeding, inheritance, and biochemical studies on *Brassica napus* cv. Zhongyou 821: Tolerance to *Sclerotinia sclerotiorum* (stem rot)". Proceedings of the 10th International Rapeseed Congress, Canberra, Australia).

Some Japanese cultivars of rapeseed have partial stem resistance to *Sclerotinia*. Partial stem resistance was detected by indoor tests in comparison with winter canola (Brun et al. (1987) "A field study of rapeseed (*Brassica napus*) resistance to *Sclerotinia sclerotiorum*." 7th International Rapeseed Congress, Poznan, Poland). However, these varieties are not canola quality and are semi-winter types (see Table 1).

Breeding for *Sclerotinia* resistance in canola has been very difficult due to the quantitative nature of this trait. Further, the incorporation of physiological resistance with morphological traits that avoid or reduce infection multiplies the complexity of breeding for resistance. In addition, it has been very difficult to screen for resistance because of the direct environment by genetic (GXE) interaction (i.e., temperature and humidity requirements, as well as microenvironment requirements) with the plant. As stated above, there are few Canadian spring *Brassica* varieties with resistance to *Sclerotinia*, this despite many years of co-evolution and environmental pressure to select for this trait. A level of field resistance in rapeseed (and recently some canola materials) was attained via breeding efforts in China as described with Zhong you 821 (Li et al., supra). However, the levels of such partial resistance or tolerance are relatively low and fungicide applications are still recommended on all rapeseed and canola materials in China (verbal communication) (Hu et al. (1999) "Effect of cultural control on rapeseed stem rot (*Sclerotinia sclerotiorum*) in *Brassica napus*." Proceedings of the 10th International Rapeseed Congress, Canberra, Australia). Other breeding efforts included quantitative trait loci analysis (Zhao and Meng (2003) *Theoretical and Applied Genetics* 106 (4): 759-764), mutagenesis breeding (Mullins et al. (1999) *European Journal of Plant Pathology* 105 (5): 465-475; Wu et al. (1996) *Sichuan Daxue Xuebao* (*Ziran Kexueban*) 33 (2): 201-205; LiangHong et al., 2003, extensive screening efforts (Sedun et al. (1989) *Canadian Journal of Plant Science* 69 (1): 229-232; Zhao et al. (2004) *Plant Disease* 88 (9): 1033-1039); and screening for expressed sequence tags (ESTs) (Li et al. (2004) *Fungal Genetics and Biology* 41 (8): 735-753) to name a few. Several spring canola varieties with moderate tolerance to *Sclerotinia* have been developed (Ahmadi et al. (2000) *Seed and Plant* 16 (1): Pe127-Pe129, en14; Ahmadi et al. (2000) Introduction of rapeseed (*Brassica napus* L.), cultivar Esteghlal. *Seed and Plant* 16 (1): Pe127-Pe126, en13; BaoMing et al. (1999) *Chinese Journal of Oil Crop Sciences* 4: 12-14; and Liu et al. (1991) *Scientia Agricultura Sinica* 24 (3): 43-49), however the level of tolerance is low and the lines cannot withstand high disease pressure. Recently, transgenic canola has been developed carrying an oxalic oxidase gene (U.S. Pat. No. 6,166,291 and divisional patents thereof) however there are regulatory and social problems associated with transgenic plants. Accordingly, significant technical human intervention is required to breed canola varieties that are resistant to *Sclerotinia*.

More recently, *Brassica* and canola varieties with high levels of resistance to *Sclerotinia* were developed after a long and intensive breeding program (See, for example, WO 2006/135717, the entire teachings of which are hereby incorporated by reference). This approach is very time and labor intensive, and requires a long time to determine whether the breeding program is successful. The difficulty in breeding for whole plant field resistance to *Sclerotinia* is due, at least in part, to the multigenic nature of this trait.

What is needed in the art and industry is a means to identify genes conferring whole plant field resistance to *Sclerotinia*, using molecular markers. These markers can then be used to tag the favorable alleles of these genes in segregating populations and then employed to make selection for resistance more effective. The present invention provides this and other advantages.

SUMMARY OF THE INVENTION

The present invention provides methods and markers for identifying Quantitative Trait Loci ("QTLs") associated with whole plant field resistance or improved whole plant field resistance to *Sclerotinia* in plants.

A first aspect of the invention features a method of identifying a *Brassica* plant or germplasm that exhibits whole plant field resistance or improved whole plant field resistance to *Sclerotinia*. The method comprises detecting in the plant or germplasm at least one allele of at least one quantitative trait locus (QTL) that is associated with the whole plant field resistance or improved whole plant field resistance to *Sclerotinia*, wherein the QTL is localized to a linkage group selected from N1, N3, N4, N7, N8, N9, N10, N11, N12, N13, N15, N18 or N19, wherein each linkage group comprises at least one marker that is associated with the whole plant field resistance or improved whole plant field resistance to *Sclerotinia* with a statistical significance of $p \leq 0.01$, thereby identifying the *Brassica* plant or germplasm that exhibits whole plant field resistance or improved whole plant field resistance to *Sclerotinia*.

In one embodiment, the QTL is localized to a chromosomal interval selected from: (a) an interval flanked by and including (i) markers CA0614 and PE0177 or (ii) markers AG0093 and AG0482 on linkage group N1; (b) an interval flanked by and including markers CA0410 and AG0023 on linkage group N3; (c) an interval flanked by and including markers BG1442 and BG0106 on linkage group N4; (d) an interval flanked by and including markers AG0510 and CA0105 on linkage group N7; (e) an interval flanked by and including markers CA0837 and BG1286 on linkage group N8; (f) an interval flanked by and including (i) markers CA1034 and AG0441 or (ii) markers AG0378 and KK66 on linkage group N9; (g) an interval flanked by and including markers BG0228 and PE0131 on linkage group N10; (h) an interval flanked by and including (i) markers CA0120 and CA0163 or (ii) markers CA0120 and CA1097 on linkage group N11; (i) an interval flanked by and including (i) markers BG1321 and CA0991 or (ii) markers CA0753 and PE0250 on linkage group N12; (j) an interval flanked by and including markers CA0603 and CA0736 on linkage group N13; (k) an interval flanked by and including markers PE0286 and AG0369 on linkage group N15; (l) an interval flanked by and including (i) markers BG0278 and CA0636 or (ii) markers UB0315 and CA0739 on linkage group N18; and (m) an interval flanked by and including (i) markers CA1107 and CA0221 or (ii) markers UB0307 and KK98G on linkage group N19.

In another embodiment, the QTL is localized to a chromosomal interval selected from: (a) one or more intervals on linkage group N1, flanked by and including markers (i) AG0093 and PE0203, or (ii) BG0111 and BG1392, or (iii) BG1090 and AG0482, or (iv) BG1090 and PE0203, or (v) CA0614 and BG1392, or (vi) BG0988 and AG0482; or (vii) AG0243 and AG0482; or (viii) AG0243 and BG1453; or BG0988; (b) one or more intervals on linkage group N3, flanked by and including markers (i) BG1197 and AG0023, or (ii) CA0410 and BG1368 or (iii) CA0410 and BG1197; (c) one or more intervals on linkage group N4, flanked by and including markers (i) BG1442 and BG0106, or (ii) UB0181 and BG0106; (d) one or more intervals on linkage group N8, flanked by and including markers (i) BG1449 and BG1062, or (ii) CA0837 and AG0328, or (iii) CA0837 and BG1062, or (iv) CA0837 and BG1101, or (v) CA0837 and BG1286, or (vi) CA0837 and BG1449 or (vii) PE0281 and BG0647; (e) one or more intervals on linkage group N9, flanked by and including markers (i) AG0323 and BG0295, or (ii) CA1034 and AG0378 or (iii) BG1123 and AG0441; (f) one or more intervals on linkage group N10, flanked by and including markers (i) BG0228 and AG0047, or BG0255 and PE0131; (g) one or more intervals on linkage group N11, flanked by and including markers (i) BG0031 and BG1149, or (ii) BG0031 and BG1230, or (iii) BG0031 and BG1513, or (iv) CA0120 and CA0328, or (v) PE0283 and CA0163, or (vi) PE0324 and PE0283 or (vii) CA0328 and PE0324, or (viii) CA0226 and BG0713, or (ix) CA0233 and CA1080, or (x) CA0233 and AG0370; (h) one or more intervals on linkage group N12, flanked by and including markers (i) BG1321 and CA0991, or (ii) BG1321 and CA1027, or (iii) BG1321 and PE0133, or (iv) PE0063 and CA0991, or (v) PE0133 and CA0991, or (vi) CA1027 and PE0063, or (vii) CA1027 and UB0331, or (viii) CA0423 and PE0250, or (ix) AG0359 and PE0250, or (x) AG0359 and CA0896; (i) one or more intervals on linkage group N13, flanked by and including markers (i) BG0516 and AG0148, or (ii) CA0488 and AG0148, or (iii) CA0488 and CA0736, or (iv) CA0603 and AG0504, or (v) BG1288 and AG0504; (j) one or more intervals on linkage group N15, flanked by and including markers (i) CA0719 and AG0369, or (ii) PE0091 and PE0187, or (iii) PE0286 and AG0369, or (iv) PE0286 and PE0187, or (v) PE0286 and CA0719; (k) one or more intervals on linkage group N18, flanked by and including markers (i) AG0285 and CA0636, or (ii) BG0278 and CA07739, or (iii) CA0739 and CA0636, or (iv) UB0315 and CA0636, or (v) UB0315 and CA0739; and (1) one or more intervals on linkage group N19, flanked by and including markers (i) CA0552 and CA0221, or (ii) CA1107 and CA0552, or (iii) CA1107 and CA0221, or (iv) CA0221 and KK98G, or (v) UB0307 and BG1241, or (vi) BG1241 and KK98G, or (vii) CA0221 and BG1241.

In a particular embodiment, the QTL is localized to a chromosomal interval on linkage group N1, N9, N11, N12, N18 or N19.

In other embodiments, the marker comprises a polymorphism that identifies the at least one allele of the at least one quantitative trait locus (QTL) as being associated with the whole plant field resistance or improved whole plant field resistance to *Sclerotinia*, and the detecting comprises identifying the polymorphism. The polymorphism may be, for example, a single nucleotide polymorphism (SNP) or a simple sequence repeat (SSR). In another embodiment of the method of the invention, the detecting comprises detecting at least one marker comprising the polymorphism, selected from AG0023; AG0045; AG0047; AG0070; AG0086; AG0093; AG0125; AG0148; AG0171; AG0203; AG0239; AG0243; AG0272; AG0304; AG0323; AG0324; AG0328; AG0359; AG0369; AG0370; AG0378; AG0391; AG0410; AG0441; AG0477; AG0482; AG0504; AG0510; BG0031; BG0106; BG0111; BG0119; BG0181; BG0228; BG0255; BG0278; BG0295; BG0452; BG0516; BG0647; BG0651; BG0713; BG0864; BG0869; BG0988; BG1062; BG1090; BG1101; BG1123; BG1127; BG1149; BG1182; BG1197; BG1230; BG1241; BG1244; BG1286; BG1288; BG1321; BG1368; BG1392; BG1442; BG1449; BG1453; BG1513; CA0105; CA0120; CA0163; CA0221; CA0226; CA0233; CA0328; CA0410; CA0423; CA0456; CA0488; CA0546; CA0552; CA0603; CA0614; CA0636; CA0681; CA0719; CA0736; CA0739; CA0753; CA0834; CA0837; CA0896; CA0991; CA1027; CA1032; CA1034; CA1035; CA1066; CA1080; CA1090; CA1097; CA1107; PE0012; PE0017;

PE0063; PE0091; PE0131; PE0133; PE0177; PE0187; PE0203; PE0250; PE0281; PE0283; PE0286; PE0324; PE0340; PE0355; UB0015; UB0126; UB0163; UB0181; UB0196; UB0307; UB0315; UB0331; KK66; and KK98G.

In another embodiment of the method of the invention, the detecting comprises detecting the polymorphism in at least one marker selected from AG0093; AG0304; AG0378; AG0391; AG0482; BG1149; BG1230; BG1241; BG1453; BG1513; CA0120; CA0221; CA0546; CA0739; CA1027; PE0063; PE0203; UB0163; and UB0315.

In other embodiments, the method comprises detecting two or more markers located in two or more different linkage groups, three or more markers located in three or more different linkage groups, four or more markers located in four or more different linkage groups, five or more markers located in five or more different linkage groups, six or more markers located in six or more different linkage groups, seven or more markers located in seven or more different linkage groups, eight or more markers located in eight or more different linkage groups, nine or more markers located in nine or more different linkage groups, ten or more markers located in ten or more different linkage groups, eleven or more markers located in eleven or more different linkage groups, or twelve or more markers located in twelve or more different linkage groups.

In other embodiments, in the method, the detecting comprises amplifying the marker from genomic DNA of the plant or germplasm and determining if the marker comprises the polymorphism associated with the whole plant field resistance or improved whole plant field resistance to *Sclerotinia*. In other embodiments, the plant is *Brassica napus; Brassica juncea; Brassica rapa; Brassica oleracea; or Brassica carinata*. In other embodiments, the plant is spring canola, winter canola, or semi-winter canola. In another embodiment, the whole plant field resistance or improved whole plant field resistance results from decreased disease incidence compared to a plant lacking the allele of the QTL associated with the whole plant field resistance or improved whole plant field resistance. In another embodiment, the whole plant field resistance or improved whole plant field resistance results from decreased disease severity compared to a plant lacking the allele of the QTL associated with the whole plant field resistance or improved whole plant field resistance. In another embodiment, the plant has whole plant field resistance or improved whole plant field resistance to *Sclerotinia sclerotiorum*.

Another aspect of the invention features a method of introgressing *Sclerotinia* resistance in a second plant by cross pollinating the plant or a progeny identified according to the methods described above with a second plant, wherein the second plant lacks the at least one allele of the at least one QTL detected in the identified plant.

In another aspect, the invention features a method of producing an F1 hybrid seed, wherein the F1 hybrid plant derived from the F1 hybrid seed is resistant to *Sclerotinia*, the method comprising cross pollinating the plant or progeny identified according to the methods described above with a second plant, wherein the second plant lacks the at least one allele of the at least one QTL detected in the identified plant.

In another aspect, the invention features a method of positional cloning of a nucleic acid comprising a quantitative trait locus (QTL) associated with *Sclerotinia* whole plant field resistance or improved whole plant field resistance, the method comprising: providing a nucleic acid from a plant comprising a marker that is associated with *Sclerotinia* whole plant field resistance or improved whole plant field resistance with a statistical significance of $p \leq 0.01$, wherein the QTL is localized to a linkage group selected from N1, N3, N4, N7, N8, N9, N10, N11, N 12, N13, N15, N18 or N19, and wherein the linkage group comprises the marker; and cloning the nucleic acid comprising a quantitative trait locus (QTL) associated with *Sclerotinia* whole plant field resistance or improved whole plant field resistance. (a) an interval flanked by and including (i) markers CA0614 and PE0177 or (ii) markers AG0093 and AG0482 on linkage group N1; (b) an interval flanked by and including markers CA0410 and AG0023 on linkage group N3; (c) an interval flanked by and including markers BG1442 and BG0106 on linkage group N4; (d) an interval flanked by and including markers AG0510 and CA0105 on linkage group N7; (e) an interval flanked by and including markers CA0837 and BG1286 on linkage group N8; (f) an interval flanked by and including (i) markers CA1034 and AG0441or (ii) markers AG0378 and KK66 on linkage group N9; (g) an interval flanked by and including markers BG0228 and PE0131 on linkage group N10; (h) an interval flanked by and including (i) markers CA0120 and CA0163 or (ii) markers CA0120 and CA1097 on linkage group N11; (i) an interval flanked by and including (i) markers BG1321 and CA0991 or (ii) markers CA0753 and PE0250 on linkage group N12; (j) an interval flanked by and including markers CA0603 and CA0736 on linkage group N13; (k) an interval flanked by and including markers PE0286 and AG0369 on linkage group N15; (1) an interval flanked by and including (i) markers BG0278 and CA0636 or (ii) markers UB0315 and CA0739 on linkage group N18; and (m) an interval flanked by and including (i) markers CA1107 and CA0221 or (ii) markers UB0307 and KK98G on linkage group N19.

In another embodiment, the QTL is localized to a chromosomal interval selected from: (a) one or more intervals on linkage group N1, flanked by and including markers (i) AG0093 and PE0203, or (ii) BG0111 and BG1392, or (iii) BG1090 and AG0482, or (iv) BG1090 and PE0203, or (v) CA0614 and BG1392, or (vi) BG0988 and AG0482; or (vii) AG0243 and AG0482; or (viii) AG0243 and BG1453; or BG0988; (b) one or more intervals on linkage group N3, flanked by and including markers (i) BG1197 and AG0023, or (ii) CA0410 and BG1368 or (iii) CA0410 and BG1197; (c) one or more intervals on linkage group N4, flanked by and including markers (i) BG1442 and BG0106, or (ii) UB0181 and BG0106; (d) one or more intervals on linkage group N8, flanked by and including markers (i) BG1449 and BG1062, or (ii) CA0837 and AG0328, or (iii) CA0837 and BG1062, or (iv) CA0837 and BG1101, or (v) CA0837 and BG1286, or (vi) CA0837 and BG1449 or (vii) PE0281 and BG0647; (e) one or more intervals on linkage group N9, flanked by and including markers (i) AG0323 and BG0295, or (ii) CA1034 and AG0378 or (iii) BG1123 and AG0441; (f) one or more intervals on linkage group N10, flanked by and including markers (i) BG0228 and AG0047, or BG0255 and PE0131; (g) one or more intervals on linkage group N11, flanked by and including markers (i) BG0031 and BG1149, or (ii) BG0031 and BG1230, or (iii) BG0031 and BG1513, or (iv) CA0120 and CA0328, or (v) PE0283 and CA0163, or (vi) PE0324 and PE0283 or (vii) CA0328 and PE0324, or (viii) CA0226 and BG0713, or (ix) CA0233 and CA1080, or (x) CA0233 and AG0370; (h) one or more intervals on linkage group N12, flanked by and including markers (i) BG1321 and CA0991, or (ii) BG1321 and CA1027, or (iii) BG1321 and PE0133, or (iv) PE0063 and CA0991, or (v) PE0133 and CA0991, or (vi) CA1027 and PE0063, or (vii) CA1027 and UB0331, or (viii) CA0423 and PE0250, or (ix) AG0359 and PE0250, or (x) AG0359 and CA0896; (i) one or more intervals on linkage group N13, flanked by and including markers (i) BG0516 and AG0148, or (ii) CA0488 and AG0148, or (iii) CA0488 and CA0736, or (iv) CA0603 and AG0504, or (v) BG1288 and AG0504; (j) one or more intervals on linkage group N15, flanked by and including markers (i) CA0719 and AG0369, or (ii) PE0091 and PE0187, or (iii) PE0286 and AG0369, or (iv) PE0286 and PE0187, or (v) PE0286 and CA0719; (k) one or more intervals on linkage group N18, flanked by and including markers (i) AG0285 and CA0636, or (ii) BG0278 and CA07739, or (iii) CA0739 and CA0636, or (iv) UB0315 and CA0636, or (v) UB0315 and CA0739; and (1) one or more intervals on linkage group N19, flanked by and including markers (i) CA0552 and CA0221, or (ii) CA1107 and CA0552, or (iii) CA1107 and CA0221, or (iv) CA0221 and KK98G, or (v) UB0307 and BG1241, or (vi) BG1241 and KK98G, or (vii) CA0221 and BG1241.

In a particular embodiment, the QTL is localized to a chromosomal interval on linkage group N1, N9, N11, N12, N18 or N19.

In other embodiments, the marker comprises a polymorphism that identifies the at least one allele of the at least one quantitative trait locus (QTL) as being associated with the whole plant field resistance or improved whole plant field resistance to *Sclerotinia*, and the detecting comprises identifying the polymorphism. The polymorphism may be, for example, a single nucleotide polymorphism (SNP) or a simple sequence repeat (SSR). In another embodiment of the method of the invention, the detecting comprises detecting at least one marker selected from AG0023; AG0045; AG0047; AG0070; AG0086; AG0093; AG0125; AG0148; AG0171; AG0203; AG0239; AG0243; AG0272; AG0304; AG0323; AG0324; AG0328; AG0359; AG0369; AG0370; AG0378; AG0391; AG0410; AG0441; AG0477; AG0482; AG0504; AG0510; BG0031; BG0106; BG0111; BG0119; BG0181; BG0228; BG0255; BG0278; BG0295; BG0452; BG0516; BG0647; BG0651; BG0713; BG0864; BG0869; BG0988; BG1062; BG1090; BG1101; BG1123; BG1127; BG1149; BG1182; BG1197; BG1230; BG1241; BG1244; BG1286; BG1288; BG1321; BG1368; BG1392; BG1442; BG1449; BG1453; BG1513; CA0105; CA0120; CA0163; CA0221; CA0226; CA0233; CA0328; CA0410; CA0423; CA0456; CA0488; CA0546; CA0552; CA0603; CA0614; CA0636; CA0681; CA0719; CA0736; CA0739; CA0753; CA0834; CA0837; CA0896; CA0991; CA1027; CA1032; CA1034; CA1035; CA1066; CA1080; CA1090; CA1097; CA1107; PE0012; PE0017; PE0063; PE0091; PE0131; PE0133; PE0177; PE0187; PE0203; PE0250; PE0281; PE0283; PE0286; PE0324; PE0340; PE0355; UB0015; UB0126; UB0163; UB0181; UB0196; UB0307; UB0315; UB0331; KK66; and KK98G.

In another embodiment of the method of the invention, the detecting comprises detecting at least one marker selected from AG0093; AG0304; AG0378; AG0391; AG0482; BG1149; BG1230; BG1241; BG1453; BG1513; CA0120; CA0221; CA0546; CA0739; CA1027; PE0063; PE0203; UB0163; and UB0315.

In other embodiments, the plant is a whole plant, a plant organ, a plant seed or a plant cell. In other embodiments, the plant is canola. The plant may be, for example, *Brassica napus, Brassica juncea, Brassica rapa, Brassica oleracea*; or *Brassica carinata*. The plant may be, for example, spring canola, winter canola, or semi-winter canola. In another embodiment, the *Sclerotinia* whole plant field resistant plant is resistant to *Sclerotinia sclerotiorum*.

In another aspect, the invention features a method of making a transgenic dicot comprising a quantitative trait locus (QTL) associated with *Sclerotinia* whole plant field resistance or improved whole plant field resistance, the method comprising the steps of: introducing a nucleic acid cloned according to the method described above into a dicot cell; and growing the cell under cell growth conditions. In one embodiment, the QTL is localized to a chromosomal interval selected from: (a) an interval flanked by and including (i) markers CA0614 and PE0177 or (ii) markers AG0093 and AG0482 on linkage group N1; (b) an interval flanked by and including markers CA0410 and AG0023 on linkage group N3; (c) an interval flanked by and including markers BG1442 and BG0106 on linkage group N4; (d) an interval flanked by and including markers AG0510 and CA0105 on linkage group N7; (e) an interval flanked by and including markers CA0837 and BG1286 on linkage group N8; (f) an interval flanked by and including (i) markers CA1034 and AG0441or (ii) markers AG0378 and KK66 on linkage group N9; (g) an interval flanked by and including markers BG0228 and PE0131 on linkage group N10; (h) an interval flanked by and including (i) markers CA0120 and CA0163 or (ii) markers CA0120 and CA1097 on linkage group N11; (i) an interval flanked by and including (i) markers BG1321 and CA0991 or (ii) markers CA0753 and PE0250 on linkage group N12; (j) an interval flanked by and including markers CA0603 and CA0736 on linkage group N13; (k) an interval flanked by and including markers PE0286 and AG0369 on linkage group N15; (1) an interval flanked by and including (i) markers BG0278 and CA0636 or (ii) markers UB0315 and CA0739 on linkage group N18; and (m) an interval flanked by and including (i) markers CA1107 and CA0221 or (ii) markers UB0307 and KK98G on linkage group N19.

In another embodiment, the QTL is localized to a chromosomal interval selected from: (a) one or more intervals on linkage group N1, flanked by and including markers (i) AG0093 and PE0203, or (ii) BG0111 and BG1392, or (iii) BG1090 and AG0482, or (iv) BG1090 and PE0203, or (v) CA0614 and BG1392, or (vi) BG0988 and AG0482; or (vii) AG0243 and AG0482; or (viii) AG0243 and BG1453; or BG0988; (b) one or more intervals on linkage group N3, flanked by and including markers (i) BG1197 and AG0023, or (ii) CA0410 and BG1368 or (iii) CA0410 and BG1197; (c) one or more intervals on linkage group N4, flanked by and including markers (i) BG1442 and BG0106, or (ii) UB0181 and BG0106; (d) one or more intervals on linkage group N8, flanked by and including markers (i) BG1449 and BG1062, or (ii) CA0837 and AG0328, or (iii) CA0837 and BG1062, or (iv) CA0837 and BG1101, or (v) CA0837 and BG1286, or (vi) CA0837 and BG1449 or (vii) PE0281 and BG0647; (e) one or more intervals on linkage group N9, flanked by and including markers (i) AG0323 and BG0295, or (ii) CA1034 and AG0378 or (iii) BG1123 and AG0441; (f) one or more intervals on linkage group N10, flanked by and including markers (i) BG0228 and AG0047, or BG0255 and PE0131; (g) one or more intervals on linkage group N11, flanked by and including markers (i) BG0031 and BG1149, or (ii) BG0031 and BG1230, or (iii) BG0031 and BG1513, or (iv) CA0120 and CA0328, or (v) PE0283 and CA0163, or (vi) PE0324 and PE0283 or (vii) CA0328 and PE0324, or (viii) CA0226 and BG0713, or (ix) CA0233 and CA1080, or (x) CA0233 and AG0370; (h) one or more intervals on linkage group N12, flanked by and including markers (i) BG1321 and CA0991, or (ii) BG1321 and CA1027, or (iii) BG1321 and PE0133, or (iv) PE0063 and CA0991, or (v) PE0133 and CA0991, or (vi) CA1027 and PE0063, or (vii) CA1027 and UB0331, or (viii) CA0423 and PE0250, or (ix) AG0359 and PE0250, or (x) AG0359 and CA0896; (i) one or more intervals on linkage group N13, flanked by and including markers (i) BG0516 and AG0148, or (ii) CA0488 and AG0148, or (iii) CA0488 and CA0736, or (iv) CA0603 and AG0504, or (v) BG1288 and AG0504; (j) one or more intervals on linkage group N15, flanked by and including markers (i) CA0719 and AG0369, or (ii) PE0091 and PE0187, or (iii) PE0286 and AG0369, or (iv) PE0286 and PE0187, or (v) PE0286 and CA0719; (k) one or more intervals on linkage group N18, flanked by and including markers (i) AG0285 and CA0636, or (ii) BG0278 and CA07739, or (iii) CA0739 and CA0636, or (iv) UB0315 and CA0636, or (v) UB0315 and CA0739; and (1) one or more intervals on linkage group N19, flanked by and including markers (i) CA0552 and CA0221, or (ii) CA1107 and CA0552, or (iii) CA1107 and CA0221, or (iv) CA0221 and KK98G, or (v) UB0307 and BG1241, or (vi) BG1241 and KK98G, or (vii) CA0221 and BG1241.

In a particular embodiment, the QTL is localized to a chromosomal interval on linkage group N1, N9, N11, N12, N18 or N19.

In other embodiments, the marker comprises a polymorphism that identifies the at least one allele of the at least one quantitative trait locus (QTL) as being associated with the whole plant field resistance or improved whole plant field resistance to *Sclerotinia*, and the detecting comprises identifying the polymorphism. The polymorphism may be, for example, a single nucleotide polymorphism (SNP) or a simple sequence repeat (SSR). In another embodiment of the method of the invention, the detecting comprises detecting at least one marker selected from AG0023; AG0045; AG0047; AG0070; AG0086; AG0093; AG0125; AG0148; AG0171; AG0203; AG0239; AG0243; AG0272; AG0304; AG0323; AG0324; AG0328; AG0359; AG0369; AG0370; AG0378; AG0391; AG0410; AG0441; AG0477; AG0482; AG0504; AG0510; BG0031; BG0106; BG0111; BG0119; BG0181; BG0228; BG0255; BG0278; BG0295; BG0452; BG0516; BG0647; BG0651; BG0713; BG0864; BG0869; BG0988; BG1062; BG1090; BG1101; BG1123; BG1127; BG1149; BG1182; BG1197; BG1230; BG1241; BG1244; BG1286; BG1288; BG1321; BG1368; BG1392; BG1442; BG1449; BG1453; BG1513; CA0105; CA0120; CA0163; CA0221; CA0226; CA0233; CA0328; CA0410; CA0423; CA0456; CA0488; CA0546; CA0552; CA0603; CA0614; CA0636; CA0681; CA0719; CA0736; CA0739; CA0753; CA0834; CA0837; CA0896; CA0991; CA1027; CA1032; CA1034; CA1035; CA1066; CA1080; CA1090; CA1097; CA1107; PE0012; PE0017; PE0063; PE0091; PE0131; PE0133; PE0177; PE0187; PE0203; PE0250; PE0281; PE0283; PE0286; PE0324; PE0340; PE0355; UB0015; UB0126; UB0163; UB0181; UB0196; UB0307; UB0315; UB0331; KK66; and KK98G.

In another embodiment, the detecting comprises detecting at least one marker selected from AG0093; AG0304; AG0378; AG0391; AG0482; BG1149; BG1230; BG1241; BG1453; BG1513; CA0120; CA0221; CA0546; CA0739; CA1027; PE0063; PE0203; UB0163; and UB0315.

In another embodiment, the dicot cell is regenerated to form a first plant. In another embodiment, the first plant is crossed with a second plant of the same species. In another embodiment, the dicot is a soybean, sunflower, canola, or alfalfa. In another embodiment, the dicot is canola, for example, spring canola, winter canola, or semi-winter canola. In another embodiment, the dicot is *Brassica napus, Brassica juncea, Brassica rapa,* or *Brassica oleracea.* In another embodiment, the *Sclerotinia* whole plant field resistant plant is resistant to *Sclerotinia sclerotiorum.* In other embodiments the whole plant field resistance results from decreased disease incidence or from decreased disease severity compared to a dicot lacking the QTL.

Another aspect of the invention features a method of identifying a candidate nucleic acid comprising a QTL associated with *Sclerotinia* whole plant field resistance from a dicot, the method comprising: providing a nucleic acid cloned according to the methods described above; and, identifying a homolog of the nucleic acid in a dicot.

Another aspect of the invention features a method of marker assisted selection comprising (MAS) of a quantitative trait locus (QTL) associated with whole plant field resistance to *Sclerotinia*, the method comprising the steps of: obtaining a first *Brassica* plant having at least one allele of a marker locus, wherein the marker locus is associated with the whole plant field resistance or improved whole plant field resistance to *Sclerotinia* with a statistical significance of $p \leq 0.01$; crossing the first *Brassica* plant to a second *Brassica* plant; evaluating the progeny for at least the allele; and selecting progeny plants that possess at least the allele. In one embodiment, the plant is a member of a segregating population. In another embodiment, the marker assisted selection is done via high throughput screening.

Another aspect of the invention features a *Brassica* plant identified by the above method, and progeny thereof, including F1, F2 and F3 progeny.

Another aspect of the invention features an isolated or recombinant nucleic acid comprising a polynucleotide selected from the group consisting of: a sequence selected from any one of marker sequences AG0023 (SEQ ID NO:1); AG0045 (SEQ ID NO:2); AG0047 (SEQ ID NO:3); AG0070 (SEQ ID NO:4); AG0086 (SEQ ID NO:5); AG0093 (SEQ ID NO:6); AG0125 (SEQ ID NO:7); AG0148 (SEQ ID NO:8); AG0171 (SEQ ID NO:9); AG0203 (SEQ ID NO:10); AG0239 (SEQ ID NO:11); AG0243 (SEQ ID NO:12); AG0272 (SEQ ID NO:13); AG0304 (SEQ ID NO:14); AG0323 (SEQ ID NO:15); AG0324 (SEQ ID NO:16); AG0328 (SEQ ID NO:17); AG0359 (SEQ ID NO:18); AG0369 (SEQ ID NO:19); AG0370 (SEQ ID NO:20); AG0378 (SEQ ID NO:21); AG0391 (SEQ ID NO:22); AG0410 (SEQ ID NO:23); AG0441 (SEQ ID NO:24); AG0477 (SEQ ID NO:25); AG0482 (SEQ ID NO:26); AG0504 (SEQ ID NO:27); AG0510 (SEQ ID NO:28); BG0031 (SEQ ID NO:29); BG0106 (SEQ ID NO:30); BG0111 (SEQ ID NO:31); BG0119 (SEQ ID NO:32); BG0181 (SEQ ID NO:33); BG0228 (SEQ ID NO:34); BG0255 (SEQ ID NO:35); BG0278 (SEQ ID NO:36); BG0295 (SEQ ID NO:37); BG0452 (SEQ ID NO:38); BG0516 (SEQ ID NO:39); BG0647 (SEQ ID NO:40); BG0651 (SEQ ID NO:41); BG0713 (SEQ ID NO:42); BG0864 (SEQ ID NO:43); BG0869 (SEQ ID NO:44); BG0988 (SEQ ID NO:45); BG1062 (SEQ ID NO:46); BG1090 (SEQ ID NO:47); BG1101 (SEQ ID NO:48); BG1123 (SEQ ID NO:49); BG1127 (SEQ ID NO:50); BG1149 (SEQ ID NO:51); BG1182 (SEQ ID NO:52); BG1197 (SEQ ID NO:53); BG1230 (SEQ ID NO:54); BG1241 (SEQ ID NO:55); BG1244 (SEQ ID NO:56); BG1286 (SEQ ID NO:57); BG1288 (SEQ ID NO:58); BG1321 (SEQ ID NO:59); BG1368 (SEQ ID NO:60); BG1392 (SEQ ID NO:61); BG1442 (SEQ ID NO:62); BG1449 (SEQ ID NO:63); BG1453 (SEQ ID NO:64); BG1513 (SEQ ID NO:65); CA0105 (SEQ ID NO:66); CA0120 (SEQ ID NO:67); CA0163 (SEQ ID NO:68); CA0221 (SEQ ID NO:69); CA0226 (SEQ ID NO:70); CA0233 (SEQ ID NO:71); CA0328 (SEQ ID NO:72); CA0410 (SEQ ID NO:73); CA0423 (SEQ ID NO:74); CA0456 (SEQ ID NO:75); CA0488 (SEQ ID NO:76); CA0546 (SEQ ID NO:77);

CA0552 (SEQ ID NO:78); CA0603 (SEQ ID NO:79); CA0614 (SEQ ID NO:80); CA0636 (SEQ ID NO:81); CA0681 (SEQ ID NO:82); CA0719 (SEQ ID NO:83); CA0736 (SEQ ID NO:84); CA0739 (SEQ ID NO:85); CA0753 (SEQ ID NO:86); CA0834 (SEQ ID NO:87); CA0837 (SEQ ID NO:88); CA0896 (SEQ ID NO:89); CA0991 (SEQ ID NO:90); CA1027 (SEQ ID NO:91); CA1032 (SEQ ID NO:92); CA1034 (SEQ ID NO:93); CA1035 (SEQ ID NO:94); CA1066 (SEQ ID NO:95); CA1080 (SEQ ID NO:96); CA1090 (SEQ ID NO:97); CA1097 (SEQ ID NO:98); or CA1107 (SEQ ID NO:99); (b) a polynucleotide sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a polynucleotide of (a); and (c) a polynucleotide sequence complementary to the polynucleotide sequence of (a) or (b). In one embodiment, the isolated or recombinant nucleic acid is associated with whole plant field resistance to *Sclerotinia*.

In another embodiment, the isolated or recombinant nucleic acid comprising a polynucleotide is selected from the group consisting of: (a) a sequence selected from any one of marker sequences AG0093 (SEQ ID NO:6); AG0304 (SEQ ID NO:14); AG0378 (SEQ ID NO:21); AG0391 (SEQ ID NO:22); AG0482 (SEQ ID NO:26); BG1149 (SEQ ID NO:51); BG1230 (SEQ ID NO:54); BG1241 (SEQ ID NO:55); BG1453 (SEQ ID NO:64); BG1513 (SEQ ID NO:65); (SEQ ID NO:67); CA0221 (SEQ ID NO:69); CA0546 (SEQ ID NO:77); CA0739 (SEQ ID NO:85); or CA1027 (SEQ ID NO:91); (b) a polynucleotide sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a polynucleotide of (a); and (c) a polynucleotide sequence complementary to the polynucleotide sequence of (a) or (b).

Another aspect of the invention features an isolated nucleic acid molecule for detecting a polymorphism in plant DNA associated whole plant field resistance or improved whole plant field resistance to *Sclerotinia*, wherein the nucleic acid molecule comprises at least 15 nucleotides and is identical to a sequence of the same number of consecutive nucleotides in either strand of the plant DNA in a region where the polymorphism is located, wherein the nucleic acid molecule comprises a sequence that is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical to a marker sequence or a fragment of a marker sequence selected from the group consisting of marker AG0023 (SEQ ID NO:1); AG0045 (SEQ ID NO:2); AG0047 (SEQ ID NO:3); AG0070 (SEQ ID NO:4); AG0086 (SEQ ID NO:5); AG0093 (SEQ ID NO:6); AG0125 (SEQ ID NO:7); AG0148 (SEQ ID NO:8); AG0171 (SEQ ID NO:9); AG0203 (SEQ ID NO:10); AG0239 (SEQ ID NO:11); AG0243 (SEQ ID NO:12); AG0272 (SEQ ID NO:13); AG0304 (SEQ ID NO:14); AG0323 (SEQ ID NO:15); AG0324 (SEQ ID NO:16); AG0328 (SEQ ID NO:17); AG0359 (SEQ ID NO:18); AG0369 (SEQ ID NO:19); AG0370 (SEQ ID NO:20); AG0378 (SEQ ID NO:21); AG0391 (SEQ ID NO:22); AG0410 (SEQ ID NO:23); AG0441 (SEQ ID NO:24); AG0477 (SEQ ID NO:25); AG0482 (SEQ ID NO:26); AG0504 (SEQ ID NO:27); AG0510 (SEQ ID NO:28); BG0031 (SEQ ID NO:29); BG0106 (SEQ ID NO:30); BG0111 (SEQ ID NO:31); BG0119 (SEQ ID NO:32); BG0181 (SEQ ID NO:33); BG0228 (SEQ ID NO:34); BG0255 (SEQ ID NO:35); BG0278 (SEQ ID NO:36); BG0295 (SEQ ID NO:37); BG0452 (SEQ ID NO:38); BG0516 (SEQ ID NO:39); BG0647 (SEQ ID NO:40); BG0651 (SEQ ID NO:41); BG0713 (SEQ ID NO:42); BG0864 (SEQ ID NO:43); BG0869 (SEQ ID NO:44); BG0988 (SEQ ID NO:45); BG1062 (SEQ ID NO:46); BG1090 (SEQ ID NO:47); BG1101 (SEQ ID NO:48); BG1123 (SEQ ID NO:49); BG1127 (SEQ ID NO:50); BG1149 (SEQ ID NO:51); BG1182 (SEQ ID NO:52); BG1197 (SEQ ID NO:53); BG1230 (SEQ ID NO:54); BG1241 (SEQ ID NO:55); BG1244 (SEQ ID NO:56); BG1286 (SEQ ID NO:57); BG1288 (SEQ ID NO:58); BG1321 (SEQ ID NO:59); BG1368 (SEQ ID NO:60); BG1392 (SEQ ID NO:61); BG1442 (SEQ ID NO:62); BG1449 (SEQ ID NO:63); BG1453 (SEQ ID NO:64); BG1513 (SEQ ID NO:65); CA0105 (SEQ ID NO:66); CA0120 (SEQ ID NO:67); CA0163 (SEQ ID NO:68); CA0221 (SEQ ID NO:69); CA0226 (SEQ ID NO:70); CA0233 (SEQ ID NO:71); CA0328 (SEQ ID NO:72); CA0410 (SEQ ID NO:73); CA0423 (SEQ ID NO:74); CA0456 (SEQ ID NO:75); CA0488 (SEQ ID NO:76); CA0546 (SEQ ID NO:77); CA0552 (SEQ ID NO:78); CA0603 (SEQ ID NO:79); CA0614 (SEQ ID NO:80); CA0636 (SEQ ID NO:81); CA0681 (SEQ ID NO:82); CA0719 (SEQ ID NO:83); CA0736 (SEQ ID NO:84); CA0739 (SEQ ID NO:85); CA0753 (SEQ ID NO:86); CA0834 (SEQ ID NO:87); CA0837 (SEQ ID NO:88); CA0896 (SEQ ID NO:89); CA0991 (SEQ ID NO:90); CA1027 (SEQ ID NO:91); CA1032 (SEQ ID NO:92); CA1034 (SEQ ID NO:93); CA1035 (SEQ ID NO:94); CA1066 (SEQ ID NO:95); CA1080 (SEQ ID NO:96); CA1090 (SEQ ID NO:97); CA1097 (SEQ ID NO:98); or CA1107 (SEQ ID NO:99). In one embodiment, the nucleic acid is selected from any of SEQ ID NOs: 126-323.

In another embodiment, the marker sequence is AG0093 (SEQ ID NO:6); AG0304 (SEQ ID NO:14); AG0378 (SEQ ID NO:21); AG0391 (SEQ ID NO:22); AG0482 (SEQ ID NO:26); BG1149 (SEQ ID NO:51); BG1230 (SEQ ID NO:54); BG1241 (SEQ ID NO:55); BG1453 (SEQ ID NO:64); BG1513 (SEQ ID NO:65); (SEQ ID NO:67); CA0221 (SEQ ID NO:69); CA0546 (SEQ ID NO:77); CA0739 (SEQ ID NO:85); or CA1027 (SEQ ID NO:91). In one embodiment, the nucleic acid is selected from any of SEQ ID NOs: 136, 137, 152, 153, 166, 167, 168, 169, 176, 177, 226, 227, 232, 233, 234, 235, 252, 253, 254, 255, 258, 259, 262, 263, 278, 279, 294, 295, 306, or 307.

Another aspect of the invention features a kit for screening a plant or germplasm for a QTL associated with whole plant field resistance to *Sclerotinia*, comprising a container in which is contained one or more of the isolated nucleic acid molecules of claim as described above; and instructions for screening a plant for the QTL associated with whole plant field resistance or improved whole plant field resistance to *Sclerotinia*.

In one embodiment, the further comprises a buffer. In another embodiment, the kit is for use in high throughput screening and comprises at least one component for such use. In another embodiment the kit is for use in high throughput screening in an integrated system.

In another aspect, the invention features a *Brassica* plant that exhibits whole plant field resistance or improved whole plant field resistance to *Sclerotinia*, comprising alleles favorable to *Sclerotinia* whole plant field resistance in at least 1 QTL localized to a chromosomal interval selected from: (a) an interval flanked by and including (i) markers CA0614 and PE0177 or (ii) markers AG0093 and AG0482 on linkage group N1; (b) an interval flanked by and including markers CA0410 and AG0023 on linkage group N3; (c) an interval flanked by and including markers BG1442 and BG0106 on linkage group N4; (d) an interval flanked by and including markers AG0510 and CA0105 on linkage group N7; (e) an interval flanked by and including markers CA0837 and BG1286 on linkage group N8; (f) an interval flanked by and including (i) markers CA1034 and AG0441or (ii) markers AG0378 and KK66 on linkage group N9; (g) an interval flanked by and including markers BG0228 and PE0131 on linkage group N10; (h) an interval flanked by and including (i) markers CA0120 and CA0163 or (ii) markers CA0120 and CA1097 on linkage group N11; (i) an interval flanked by and including (i) markers BG1321 and CA0991 or (ii) markers CA0753 and PE0250 on linkage group N12; (j) an interval flanked by and including markers CA0603 and CA0736 on linkage group N13; (k) an interval flanked by and including markers PE0286 and AG0369 on linkage group N15; (l) an interval flanked by and including (i) markers BG0278 and CA0636 or (ii) markers UB0315 and CA0739 on linkage group N18; and (m) an interval flanked by and including (i) markers CA1107 and CA0221 or (ii) markers UB0307 and KK98G on linkage group N19.

In another embodiment, the QTL is localized to a chromosomal interval selected from: (a) one or more intervals on linkage group N1, flanked by and including markers (i) AG0093 and PE0203, or (ii) BG0111 and BG1392, or (iii) BG1090 and AG0482, or (iv) BG1090 and PE0203, or (v) CA0614 and BG1392, or (vi) BG0988 and AG0482; or (vii) AG0243 and AG0482; or (viii) AG0243 and BG1453; or BG0988; (b) one or more intervals on linkage group N3, flanked by and including markers (i) BG1197 and AG0023, or (ii) CA0410 and BG1368 or (iii) CA0410 and BG1197; (c) one or more intervals on linkage group N4, flanked by and including markers (i) BG1442 and BG0106, or (ii) UB0181 and BG0106; (d) one or more intervals on linkage group N8, flanked by and including markers (i) BG1449 and BG1062, or (ii) CA0837 and AG0328, or (iii) CA0837 and BG1062, or (iv) CA0837 and BG1101, or (v) CA0837 and BG1286, or (vi) CA0837 and BG1449 or (vii) PE0281 and BG0647; (e) one or more intervals on linkage group N9, flanked by and including markers (i) AG0323 and BG0295, or (ii) CA1034 and AG0378 or (iii) BG1123 and AG0441; (f) one or more intervals on linkage group N10, flanked by and including markers (i) BG0228 and AG0047, or BG0255 and PE0131; (g) one or more intervals on linkage group N11, flanked by and including markers (i) BG0031 and BG1149, or (ii) BG0031 and BG1230, or (iii) BG0031 and BG1513, or (iv) CA0120 and CA0328, or (v) PE0283 and CA0163, or (vi) PE0324 and PE0283 or (vii) CA0328 and PE0324, or (viii) CA0226 and BG0713, or (ix) CA0233 and CA1080, or (x) CA0233 and AG0370; (h) one or more intervals on linkage group N12, flanked by and including markers (i) BG1321 and CA0991, or (ii) BG1321 and CA1027, or (iii) BG1321 and PE0133, or (iv) PE0063 and CA0991, or (v) PE0133 and CA0991, or (vi) CA1027 and PE0063, or (vii) CA1027 and UB0331, or (viii) CA0423 and PE0250, or (ix) AG0359 and PE0250, or (x) AG0359 and CA0896; (i) one or more intervals on linkage group N13, flanked by and including markers (i) BG0516 and AG0148, or (ii) CA0488 and AG0148, or (iii) CA0488 and CA0736, or (iv) CA0603 and AG0504, or (v) BG1288 and AG0504; (j) one or more intervals on linkage group N15, flanked by and including markers (i) CA0719 and AG0369, or (ii) PE0091 and PE0187, or (iii) PE0286 and AG0369, or (iv) PE0286 and PE0187, or (v) PE0286 and CA0719; (k) one or more intervals on linkage group N18, flanked by and including markers (i) AG0285 and CA0636, or (ii) BG0278 and CA07739, or (iii) CA0739 and CA0636, or (iv) UB0315 and CA0636, or (v) UB0315 and CA0739; and (1) one or more intervals on linkage group N19, flanked by and including markers (i) CA0552 and CA0221, or (ii) CA1107 and CA0552, or (iii) CA1107 and CA0221, or (iv) CA0221 and KK98G, or (v) UB0307 and BG1241, or (vi) BG1241 and KK98G, or (vii) CA0221 and BG1241.

In a particular embodiment, the QTL is localized to a chromosomal interval on linkage group N1, N9, N11, N12, N18 or N19.

Other features and advantages of the invention will be understood from the detailed description and examples that follow.

DETAILED DISCUSSION

Overview

The present invention relates to the identification of genetic markers, e.g., marker loci and nucleic acids corresponding to (or derived from) these marker loci, such as probes and amplification products useful for genotyping plants, correlated with *Sclerotinia* whole plant field resistance. The markers of the invention are used to identify plants, particularly plants of the species *Brassica napus* (*B. napus*) (canola), that are resistant or exhibit improved resistance to *Sclerotinia*. Accordingly, these markers are useful for marker-assisted selection (MAS) and breeding of *Sclerotinia* resistant plants, and for identification of susceptible plants. The markers of the invention are also used to identify and define nucleic acids that are proximal to and/or chromosome intervals corresponding to, or including, quantitative trait loci associated with *Sclerotinia* whole plant field resistance. Quantitative Trait Loci (QTLs) associated with *Sclerotinia* whole plant field resistance are isolated by positional cloning, e.g., nucleic acids proximal to or of genetic intervals defined by a pair of markers described herein, or subsequences of an interval defined by and including such markers. Such isolated QTL nucleic acids can be used for the production of transgenic cells and plants exhibiting improved resistance to *Sclerotinia*. In addition, QTL nucleic acids isolated from one organism, e.g., canola, can, in turn, serve to isolate homologs of QTLs for *Sclerotinia* whole plant field resistance from other susceptible organisms, including a variety of commercially important dicots, such as soybean, alfalfa, sunflower, flax, beans, (for example, white beans), potatoes, peas and peanuts.

Definitions

Units, prefixes, and symbols are denoted in their International System of Units (SI) accepted form. Unless otherwise indicated, nucleic acids are written left to right in 5' to 3' orientation; and amino acid sequences are written left to right in amino to carboxy orientation. Numeric ranges recited within the specification are inclusive of the numbers defining the range and include each integer within the defined range. Nucleotides may be referred to herein by their one-letter symbols recommended by the IUPAC-IUBMB Nomenclature Commission. The terms defined below are more fully defined by reference to the specification as a whole. Section headings provided throughout the specification are provided for convenience and are not limitations to the various objects and embodiments of the present invention.

The term "*Sclerotinia* whole plant field resistance" or "whole plant field resistance to *Sclerotinia*" refers to the resistance of a plant against the plant pathogen *Sclerotinia*, under field conditions or under extreme disease pressure field research conditions (as described, for example, herein and in WO 2006/135717). It reflects the resistance of the entire plant when exposed to *Sclerotinia* under these conditions. In one embodiment, a plant with *Sclerotinia* whole plant field resistance has a rating of disease development of 5.0 or greater, based on the *Sclerotinia Sclerotiorum* Disease Incidence Severity (SSDIS) rating scale. In other embodiments, a plant with *Sclerotinia* whole plant field resistance has a rating of disease development of 5.5, 6.0, 6.5, 7.0, 7.5, 8.0, 8.5, 9.0 or greater, based on the *Sclerotinia Sclerotiorum* Disease Incidence Severity (SSDIS) rating scale. Ratings of disease development are sometimes expressed in ranges; for instance in a range of 5-6, 6-7, 7-8, 8-9 or in a range of 5-7, 7-9 and so on, or by a number range within integers, such as 5.5-6.5, 5.5-7.5, 6-7.5, 7-8.5, for example. In those instances, a plant with *Sclerotinia* whole plant field resistance has a rating of disease development in the range of at least 5-6, or 6-7, or 7-8, or 8-9, based on the *Sclerotinia Sclerotiorum* Disease Incidence Severity (SSDIS) rating scale.

It will be understood by the skilled artisan that the greater the number (or percentage) of favorable alleles for *Sclerotinia* whole plant field resistance a plant posesses, the greater will be the level of resistance exhibited. This concept can be appreciated by reference to Table 8 herein. In certain embodiments, a plant with *Sclerotinia* whole plant field resistance has a genome containing at least about 50% favorable alleles. In more particular embodiments, a plant with *Sclerotinia* whole plant field resistance has a genome containing at least 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95% or more favorable alleles. The percentage of favorable alleles can also be expressed as a number value. For instance, as shown in Table 8, if a total number of 15 favorable alleles are possible in a certain mapping population, a plant having 12 of those alleles would have 80% favorable alleles. In certain embodiments, the number or percent of favorable alleles in a plant can serve as a rough predictor of the expected level of *Sclerotinia* whole plant field resistance a plant will exhibit.

It will also be understood by the skilled artisan that the QTLs described herein represent regions of the genome comprising genes that contribute to the *Sclerotinia* whole plant field resistance of a plant. Further, each QTL can contribute differently to that resistance level. Thus, breeding efforts are directed to increasing the number of those QTLs, particularly quantitatively significant QTLs, present in the germplasm. Early in a breeding program, fewer QTLs may be present in a particular germplasm, but that number will increase as the breeding program progresses. Thus, in certain embodiments, a plant exhibiting *Sclerotinia* whole plant field resistance may contain at least 6 of the QTLs described herein. More particularly, the plant may contain at least 7, 8, 9 or 10 of the QTLs described herein. Yet more particularly, the plant may contain 11, 12 or all of the QTLs described herein.

In the present invention, the evaluation for whole plant field resistance, using, for example, extreme disease pressure field research conditions, mimicked growers' field conditions and the worst-case field scenario in canola, requiring two fungicide applications to protect the crop from infection from *Sclerotinia*.

The term "*Sclerotinia* improved whole plant field resistance" or "improved whole plant field resistance to *Sclerotinia*" refers to the increase in resistance of a plant against the plant pathogen *Sclerotinia*, under field conditions or under extreme disease pressure field research conditions (as described, for example, herein and in WO 2006/135717). In one embodiment, a plant with improved whole plant field resistance to *Sclerotinia* is a plant having at least one allele of a QTL associated with whole plant field resistance to *Sclerotinia* and having rating of disease development of 5.0 or higher based on the SSDIS scale compared to a plant that does not have the at least one allele. Other embodiments of *Sclerotinia* improved whole plant field resistance parallel those outlined in the description of *Sclerotinia* whole plant field resistance set forth above.

*Sclerotinia* affects many different tissues of a plant. Natural infection by *Sclerotinia* begins with infection of the flower petal. The disease spreads to the leaves once the infected petals fall onto them. Lesions then develop simultaneously on a number of leaves per plant. These lesions further expand to colonize and wilt the leaf with infection proceeding further towards the stem via leaf petioles. The infection then reaches the stem to develop further in the stem causing premature ripening.

A plant with whole plant field resistance to *Sclerotinia* is a plant that is resistant to the pathway of *Sclerotinia* disease development in all tissues of the plant. Accordingly, a plant with whole plant field resistance to *Sclerotinia* can also be termed a plant with "pathway resistance" or "field pathway resistance" to *Sclerotinia*. The screening methods as described herein are used to identify plants with whole plant field resistance to *Sclerotinia*.

These methods are unique compared to other screening methods known in the art for assessing resistance to *Sclerotinia*. Other screening methods known in the art to assess resistance to *Sclerotinia* examine only part of the plant, and these methods take place at growth stages not associated with natural disease development. For example, Zhou et al. (2003, TAG 106: 759-764) performed phenotyping by inoculating the leaf at the seedling stage and by inoculating the stem at the mature plant stage. Zhou et al. (2006, TAG 112:509-5160) phenotyped based on petiole inoculation on a single plant per line, while Bela et al. (17th Crucifer Genetics Workshop (*Brassica* 2010), September 2010, Saskatoon, Canada) phenotyped based on petiole inoculation on 12 plants per line. Yin et al. (2010, Euphytica, online version: DOI 10.1007/s10681-009-0095-1) utilized three inoculation methods: mycelial toothpick inoculation, mycelial plug inoculation and infected petal inoculation onto cauline leaves. While it may be possible to identify one or more QTLs associated with *Sclerotinia* resistance using such screening methods, these screening methods are not as comprehensive as the screening methods to identify whole plant field resistance to *Sclerotinia* as described herein. This means that while these other screening methods may be used to uncover one or a few QTLs associated with resistance to *Sclerotinia* in a particular tissue of the plant, they cannot be used to identify all of the QTLs associated with *Sclerotinia* resistance throughout the entire plant. In addition, screening methods involving a single tissue, rather than the whole plant, will not be able to detect epistatic effects resulting from genes in different tissues working together to influence *Sclerotinia* resistance.

There are a number of advantages to using a whole plant approach to detecting resistance to *Sclerotinia*. First, this methodology most closely resembles the natural interaction between *Sclerotinia* and plants in the field, and should, therefore, be a superior system in which to identify QTLs associated with resistance to *Sclerotinia*. Second, the whole plant approach allows for a larger number of QTLs to be identified relative to other screening methodologies that only examine one plant tissue. Third, this approach permits analyses of epistatic effects, unlike other screening methods. Fourth, this approach allows actual field performance to be predicted from the data.

The term "quantitative trait locus" or "QTL" refers to a polymorphic genetic locus with at least two alleles that differentially affect the expression of a continuously distributed phenotypic trait, for example, whole plant field resistance to *Sclerotinia* or improved whole plant field resistance to *Sclerotinia*. For example, the QTL may have a favorable allele that confers, or contributes to, whole plant field resistance to *Sclerotinia* or improved whole plant field resistance to *Sclerotinia*.

The term "favorable allele" is an allele at a particular locus that confers, or contributes to, a desirable phenotype, e.g., whole plant field resistance to *Sclerotinia* or improved whole plant field resistance to *Sclerotinia*, or alternatively is an allele that allows the identification of plants with decreased whole plant field resistance that can be removed from a breeding program or planting ("counterselection"). A favorable allele of a marker is a marker allele that segregates with the favorable phenotype, or alternatively, segregates with the unfavorable plant phenotype, therefore providing the benefit of identifying plants. Alleles that are favorable for whole plant field resistance to *Sclerotinia* or improved whole plant field resistance to *Sclerotinia* are provided, for example, in Tables 7 and 13.

The term "associated with" or "associated" in the context of this invention refers to, e.g., a nucleic acid and a phenotypic trait or a second nucleic acid, that are in linkage disequilibrium, i.e., the nucleic acid and the trait/second nucleic acid are found together in progeny plants more often than if the nucleic acid and phenotype/second nucleic acid segregated separately.

The term "linkage" is used to describe the degree with which one marker locus is associated with another marker locus or some other locus (for example, a QTL). The linkage relationship between a molecular marker and a phenotype is given as a "probability" or "adjusted probability". Linkage can be expressed as a desired limit or range. For example, in some embodiments, any marker is linked (genetically and physically) to any other marker when the markers are separated by less than 50, 40, 30, 25, 20, or 15 map units (or cM). In some aspects, it is advantageous to define a bracketed range of linkage, for example, between 10 and 20 cM, between 10 and 30 cM, or between 10 and 40 cM. The more closely a marker is linked to a second locus, the better an indicator for the second locus that marker becomes. Thus, "closely linked loci" such as a marker locus and a second locus display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "proximal to" or "in proximity of" each other. Since one cM is the distance between two markers that show a 1% recombination frequency, any marker is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

The term "linkage disequilibrium" refers to a non-random segregation of genetic loci. This implies that such loci are in sufficient physical proximity along a length of a chromosome that they tend to segregate together with greater than random frequency.

The term "genetically linked" refers to genetic loci that are in linkage disequilibrium and statistically determined not to assort independently. Genetically linked loci assort dependently from 51% to 99% of the time or any whole number value there between, preferably at least 60%, 70%, 80%, 90%, 95% or 99%. Loci or alleles that are inherited in this way are said to be linked, and are referred to as "linkage groups".

The "probability value" or "p-value" is the statistical likelihood that the particular combination of a phenotype and the presence or absence of a particular marker is random. The lower the probability value, the greater the likelihood that a phenotype and a particular marker will co-segregate. In some aspects, the probability value is considered "significant" or "non-significant". In some embodiments, a probability value of 0.05 (p=0.05, or a 5% probability) of random assortment is considered a significant indication of co-segregation. However, an acceptable probability can be any probability of less than 50% (p=0.5). For example, a significant probability can be less than 0.25, less than 0.2, less than 0.15, less than 0.1, less than 0.05, less than 0.01 or less than 0.001.

The term "marker locus" is a specific chromosome location in the genome of a species where a specific marker can be found. A marker locus can be used to track the presence of a second linked locus, e.g., a linked locus that encodes or contributes to expression of a phenotypic trait. For example, a marker locus can be used to monitor segregation of alleles at a locus, such as a QTL or single gene, that are genetically or physically linked to the marker locus.

The term "marker" is a nucleotide sequence or encoded product thereof (e.g., a protein) used as a point of reference. For markers to be useful at detecting recombinations, they need to detect differences, or polymorphisms, within the population being monitored. For molecular markers, this means differences at the DNA level due to polynucleotide sequence differences (e.g., SSRs, RFLPs, FLPs, SNPs). The genomic variability can be of any origin, for example, insertions, deletions, duplications, repetitive elements, point mutations, recombination events, or the presence and sequence of transposable elements. Molecular markers can be derived from genomic or expressed nucleic acids (e.g., ESTs) and can also refer to nucleic acids used as probes or primer pairs capable of amplifying sequence fragments via the use of PCR-based methods. A large number of *Brassica* molecular markers are known in the art, and are published or available from various sources.

Examples of markers are provided, in SEQ ID NOS: 1-125. It will be understood by one skilled in the art that a marker of the present invention may comprise the entire sequence of any one of the sequences set out in SEQ ID NOS: 1-125, or a fragment of such a sequence. The fragment can be, for example, the SSR (as set out, for example, in Table 14, or a sequence that flanks (e.g., those as set out as SEQ ID NOS: 126-325) and includes the SSR. It will also be understood by one skilled in the art that the sequences of markers such as those set out in any of SEQ ID NOS: 1-125 or a fragment of such a sequence will have some variation from line to line. Therefore, the markers of the present invention include sequences that have 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a sequence as provided in any of SEQ ID NOS: 1-125 or a fragment thereof.

Markers corresponding to genetic polymorphisms between members of a population can be detected by methods well-established in the art. These include, e.g., DNA sequencing, PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also known for the detection of expressed sequence tags (ESTs) and SSR markers derived from EST sequences and randomly amplified polymorphic DNA (RAPD).

The term "molecular marker" may be used to refer to any type of nucleic acid based marker, or an encoded product thereof (e.g., a protein) used as a point of reference when identifying a linked locus. A marker can be derived from genomic nucleotide sequences or from expressed nucleotide sequences (e.g., from a spliced RNA, a cDNA, etc.), or from an encoded polypeptide. The term also refers to nucleic acid sequences complementary to or flanking the marker sequences, such as nucleic acids used as probes or primer pairs capable of amplifying the marker sequence. A "molecular marker probe" is a nucleic acid sequence or molecule that can be used to identify the presence of a marker locus, e.g., a nucleic acid probe that is complementary to a marker locus sequence. Alternatively, in some aspects, a molecular marker probe refers to a probe of any type that is able to distinguish (i.e., genotype) the particular allele that is present at a marker locus. Nucleic acids are "complementary" when they specifically hybridize in solution, e.g., according to Watson-Crick base pairing rules. Any suitable marker detection technology may be used to identify such a hybridization marker, e.g., SSR technology is used in the examples provided herein.

A "marker allele", alternatively an "allele of a marker locus", can refer to one of a plurality of polymorphic nucleotide sequences found at a marker locus in a population that is polymorphic for the marker locus.

The term "interval" refers to a continuous linear span of chromosomal DNA with termini that are typically defined by and including molecular markers.

The terms "nucleic acid," "nucleotide", "polynucleotide," "polynucleotide sequence" and "nucleic acid sequence" refer to single-stranded or double-stranded deoxyribonucleotide or ribonucleotide polymers, or chimeras thereof. As used herein, the term can additionally or alternatively include analogs of naturally occurring nucleotides having the essential nature of natural nucleotides in that they hybridize to single-stranded nucleic acids in a manner similar to naturally occurring nucleotides (e.g., peptide nucleic acids). Unless otherwise indicated, a particular nucleic acid sequence of this invention optionally encompasses complementary sequences, in addition to the sequence explicitly indicated. The term "gene" is used to refer to, e.g., a cDNA and an mRNA encoded by the genomic sequence, as well as to that genomic sequence.

The term "homologous" refers to nucleic acid sequences that are derived from a common ancestral gene through natural or artificial processes (e.g., are members of the same gene family), and thus, typically, share sequence similarity. Typically, homologous nucleic acids have sufficient sequence identity that one of the sequences or its complement is able to selectively hybridize to the other under selective hybridization conditions. The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences have about at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity with each other. A nucleic acid that exhibits at least some degree of homology to a reference nucleic acid can be unique or identical to the reference nucleic acid or its complementary sequence.

The term "isolated" refers to material, such as a nucleic acid or a protein, which is substantially free from components that normally accompany or interact with it in its naturally occurring environment. The isolated material optionally comprises material not found with the material in its natural environment, e.g., a cell. In addition, if the material is in its natural environment, such as a cell, the material has been placed at a location in the cell (e.g., genome or subcellular organelle) not native to a material found in that environment. For example, a naturally occurring nucleic acid (e.g., a promoter) is considered to be isolated if it is introduced by non-naturally occurring means to a locus of the genome not native to that nucleic acid. Nucleic acids that are "isolated" as defined herein, are also referred to as "heterologous" nucleic acids.

The term "recombinant" indicates that the material (e.g., a nucleic acid or protein) has been synthetically (non-naturally) altered by human intervention. The alteration to yield the synthetic material can be performed on the material within or removed from its natural environment or state. For example, a naturally occurring nucleic acid is considered a recombinant nucleic acid if it is altered, or if it is transcribed from DNA that has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868.

The term "introduced" when referring to a heterologous or isolated nucleic acid refers to the incorporation of a nucleic acid into a eukaryotic or prokaryotic cell where the nucleic acid can be incorporated into the genome of the cell (e.g., chromosome, plasmid, plastid or mitochondrial DNA), converted into an autonomous replicon, or transiently expressed (e.g., transfected mRNA). The term includes such nucleic acid introduction means as "transfection," "transformation" and "transduction."

The terms "SSR" or "simple sequence repeat" refers to a polymorphic locus present in nuclear and organellar DNA that consist of repeating units of 1-6 base pairs in length. Different alleles can have different numbers of the repeating SSR, resulting in different lengths of the alleles, as detectable, for example, by gel electrophoresis after amplification of the allele. For example, a di-nucleotide repeat would be GAGAGAGA and a tri-nucleotide repeat would be ATGATGATGATG. It is believed that when DNA is being replicated, errors occur in the process and extra sets of these repeated sequences are added to the strand. Over time, these repeated sequences vary in length between one cultivar and another. An example of an allelic variation in SSRs would be: Allele A: GAGAGAGA (4 repeats of the GA sequence) and Allele B: GAGAGAGAGAGA (6 repeats of the GA sequence). These variations in length are easy to trace in the lab and allow tracking of genotypic variation in breeding programs.

The term "microsatellite" is an alternative term for SSR.

The term "single nucleotide polymorphism" or "SNP" is a DNA sequence variation occurring when a single nucleotide—A, T, C, or G—in the genome (or other shared sequence) differs between members of a species (or between paired chromosomes in an individual). For example, two sequenced DNA fragments from different individuals, AAGCCTA to AAGCTTA, contain a difference in a single nucleotide. In this case we say that there are two alleles: C and T. Almost all common SNPs have only two alleles.

The term "host cell" means a cell that contains a heterologous nucleic acid, such as a vector, and supports the replication and/or expression of the nucleic acid. Host cells may be prokaryotic cells such as *E. coli*, or eukaryotic cells such as yeast, insect, amphibian, or mammalian cells. The host cells can be monocotyledonous or dicotyledonous plant cells. The dicotyledonous host cell can be, for example, a canola host cell.

The term "transgenic plant" refers to a plant that comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to refer to any cell, cell line, callus, tissue, plant part or plant, the genotype of which has been altered by the presence of heterologous nucleic acid including those transgenic organisms or cells initially so altered, as well as those created by crosses or asexual propagation from the initial transgenic organism or cell. The term "transgenic" as used herein does not encompass the alteration of the genome (chromosomal or extra-chromosomal) by conventional plant breeding methods (i.e., crosses) or by naturally occurring events such as random cross-fertilization, non-recombinant viral infection, non-recombinant bacterial transformation, non-recombinant transposition, or spontaneous mutation.

The term "dicot" refers to the subclass of angiosperm plants also knows as "dicotyledoneae" and includes reference to whole plants, plant organs (e.g., leaves, stems, roots, etc.), seeds, plant cells, and progeny of the same. Plant cell, as used herein includes, without limitation, seeds, suspension cultures, embryos, meristematic regions, callus tissue, leaves, roots, shoots, gametophytes, sporophytes, pollen, and microspores.

The term "crossed" or "cross" in the context of this invention means the fusion of gametes via pollination to produce progeny (i.e., cells, seeds, or plants). The term encompasses both sexual crosses (the pollination of one plant by another) and selfing (self-pollination, i.e., when the pollen and ovule are from the same plant).

The term "introgression" refers to the transmission of a desired allele of a genetic locus from one genetic background to another. For example, introgression of a desired allele at a specified locus can be transmitted to at least one progeny plant via a sexual cross between two parent plants, where at least one of the parent plants has the desired allele within its genome. Alternatively, for example, transmission of an allele can occur by recombination between two donor genomes, e.g., in a fused protoplast, where at least one of the donor protoplasts has the desired allele in its genome. The desired allele can be, e.g., a transgene or a selected allele of a marker or QTL.

The term "extreme disease pressure field research conditions" means controlled disease research conditions as described, for Example, in WO 2006/135717. For example, extreme disease pressure can be generated with the application of *Niger* seed carrier mimicking *Sclerotinia*-colonized petals. Natural inoculum may be present in the field as a backup inoculum. The percent disease incidence of the test plants are adjusted to running checks, and given an SSDIS score of 1 to 9. However, under these extreme conditions plants are more susceptible to *Sclerotinia* for at least the following reasons: (1) under extreme disease pressure field research conditions, the plants are subjected to wetness provided by misting irrigation, which is favorable for *Sclerotinia* development, (2) under extreme disease pressure field research conditions the plants are in a semi-enclosed environment due to the artificial canopy, which ensures continuous moist conditions favorable for *Sclerotinia* development, and (3) under extreme disease pressure field research conditions there are six rows of different test plants in each plot, therefore any one row of test plants having a particular morphological phenotype may be surrounded by two different rows of plants with different morphological phenotypes. Accordingly, any benefits from a morphological phenotype that is less conducive to *Sclerotinia* infection (for example high branching) are decreased because any one row may be surrounded by plants having a different morphological phenotype (for example low branching). In contrast, a plant growing under natural field conditions is (1) not enclosed in an artificial canopy, which ensures continuous moisture and (2) is grown in plots surrounded by plants with the same morphological phenotype, which allows all benefits from the morphology to be expressed. Accordingly, selections having a morphology that is less conducive to *Sclerotinia* infection, for example high branching, perform significantly better under natural field conditions compared to extreme disease pressure field research conditions.

It is well established that generating reliable field data on an annual basis is not common. *Sclerotinia* is a potent disease but it only develops during wet summers with moderate temperatures. A number of issues become critical in screening for *Sclerotinia* resistance in the field in years when the conditions of *Sclerotinia* are sub-optimal. Duration of wetness, water quality, availability of inoculum, and presence of moist or humid microenvironments affect disease development in the crop. Although the methods described are directed to *Brassica*, it is to be understood that the methods may be applied to any plant susceptible to *Sclerotinia* infection via ascospores. This includes sunflower (head rot), safflower (head rot), dry bean (pod rot), dry pea (pod rot), soybean (stem and pod rot), alfalfa (blossom blight), and lettuce (lettuce drop). Bardin and Huang 2001. See also U.S. Patent application publication 2003/0150016 for *Sclerotinia* effects in soybean. The critical issues in the field have been resolved as follows:

(a) Appropriate artificial inoculum for continuum of data collection: Since natural inoculum is not always triggered in the field, an inoculum that mimics infection via petals has been developed. The carrier for the fungus can be *Niger* seed (Guizotia *abyssinica*-Nyer seed) colonized with *Sclerotinia* and distributed at the time of full petal drop.

(b) Water quality and *Sclerotinia*: Initially, ground water was used to irrigate the *Sclerotinia* colonized fields. However, a lack of infection transfer in years with low rainfall and either high or low temperatures was observed. In vitro tests have confirmed that ground water inhibits *Sclerotinia* growth. Through lab and field testing, it was determined that deionizing (DI) water treatment alters the ground water quality sufficiently to prevent inhibition of *Sclerotinia* development. Henceforth, DI water was used to irrigate extreme disease pressure field research plots. In theory, the treated deionized water differs from the original ground water in that the minerals, for example magnesium and calcium (lime), are reduced while the pH is not affected. *Sclerotinia* produces oxalic acid, a diffusible toxin, to aid in the infection process (U.S. Pat. No. 6,380,461). Calcium can bind with oxalic acid to create calcium oxalate. Removal of calcium is very likely the qualitative change in the deionized water that enables growth of *Sclerotinia*. Accordingly, a water source low in minerals or having no minerals, for example reduced or eliminated magnesium and calcium, can be used.

(c) Irrigation operated by leaf-wetness sensors: To enable continuous wetness in the field, leaf wetness sensors (Campbell Scientific) that trigger irrigation only if moisture is lower than a set threshold are used. Optimized irrigation enables disease development and enhances screening for disease resistance. However, excess irrigation may interfere with meaningful evaluation. In particular, in a research setting with rows of unique genotypes in close proximity, lodging of one entry can lead to transfer of the pathogen by plant-to-plant contact and increased disease incidence on a second genotype. Thus the *Sclerotinia* resistance score for the second genotype may underestimate its potential performance in a more homogeneous population. In natural field data trials, excessive irrigation can create a more conducive environment for *Sclerotinia* through an increase in lodging over what is usual for a given genotype. Thus, the performance of the trial entries may be distorted due to excessive irrigation.

(d) Providing an enclosure to help maintain a microenvironment necessary for disease development: To enable development of disease in dry, hot and/or windy seasons, a netting enclosure may be used.

The new methodologies enable controlled disease development, reliable expression of phenotype, and characterization of many different lines under optimal *Sclerotinia* conditions.

Markers

The present invention provides molecular markers genetically linked to quantitative trait loci ("QTLs") associated with whole plant field resistance to *Sclerotinia*. Such molecular markers are useful for identifying and producing dicotyledonous plants, in particular, such commercially important dicot crops as sunflower, canola, alfalfa, and soybean, resistant, or with improved resistance, to *Sclerotinia.*

Genetic mapping of several hundred molecular markers has developed a genetic linkage map covering approximately 1400 cM (centiMorgans) corresponding to the 19 canola chromosomes. Additional details regarding the nature and use of molecular markers are provided below in the section entitled "MARKER ASSISTED SELECTION AND BREEDING OF PLANTS."

Exemplary marker loci associated with whole plant field resistance to *Sclerotinia* are localized to thirteen linkage groups in *Brassica napus*: N1, N3, N4, N7, N8, N9, N10, N11, N12, N13, N15, N18 and N19. These exemplary marker loci delineate chromosomal intervals including Quantitative Trait Loci (QTLs) associated with phenotypic measures of whole plant field resistance or improved whole plant field resistance to *Sclerotinia*. For example, Tables 5 and 11 herein list markers that localize to linkage groups N1, N3, N4, N7, N8, N9, N10, N11, N12, N13, N15, N18 and N19. Additional primers and probes corresponding to these markers or fragments of these markers can be designed based on the sequence information provided herein.

AG0023 (SEQ ID NO:1); AG0045 (SEQ ID NO:2); AG0047 (SEQ ID NO:3); AG0070 (SEQ ID NO:4); AG0086 (SEQ ID NO:5); AG0093 (SEQ ID NO:6); AG0125 (SEQ ID NO:7); AG0148 (SEQ ID NO:8); AG0171 (SEQ ID NO:9); AG0203 (SEQ ID NO:10); AG0239 (SEQ ID NO:11); AG0243 (SEQ ID NO:12); AG0272 (SEQ ID NO:13); AG0304 (SEQ ID NO:14); AG0323 (SEQ ID NO:15); AG0324 (SEQ ID NO:16); AG0328 (SEQ ID NO:17); AG0359 (SEQ ID NO:18); AG0369 (SEQ ID NO:19); AG0370 (SEQ ID NO:20); AG0378 (SEQ ID NO:21); AG0391 (SEQ ID NO:22); AG0410 (SEQ ID NO:23); AG0441 (SEQ ID NO:24); AG0477 (SEQ ID NO:25); AG0482 (SEQ ID NO:26); AG0504 (SEQ ID NO:27); AG0510 (SEQ ID NO:28); BG0031 (SEQ ID NO:29); BG0106 (SEQ ID NO:30); BG0111 (SEQ ID NO:31); BG0119 (SEQ ID NO:32); BG0181 (SEQ ID NO:33); BG0228 (SEQ ID NO:34); BG0255 (SEQ ID NO:35); BG0278 (SEQ ID NO:36); BG0295 (SEQ ID NO:37); BG0452 (SEQ ID NO:38); BG0516 (SEQ ID NO:39); BG0647 (SEQ ID NO:40); BG0651 (SEQ ID NO:41); BG0713 (SEQ ID NO:42); BG0864 (SEQ ID NO:43); BG0869 (SEQ ID NO:44); BG0988 (SEQ ID NO:45); BG1062 (SEQ ID NO:46); BG1090 (SEQ ID NO:47); BG1101 (SEQ ID NO:48); BG1123 (SEQ ID NO:49); BG1127 (SEQ ID NO:50); BG1149 (SEQ ID NO:51); BG1182 (SEQ ID NO:52); BG1197 (SEQ ID NO:53); BG1230 (SEQ ID NO:54); BG1241 (SEQ ID NO:55); BG1244 (SEQ ID NO:56); BG1286 (SEQ ID NO:57); BG1288 (SEQ ID NO:58); BG1321 (SEQ ID NO:59); BG1368 (SEQ ID NO:60); BG1392 (SEQ ID NO:61); BG1442 (SEQ ID NO:62); BG1449 (SEQ ID NO:63); BG1453 (SEQ ID NO:64); BG1513 (SEQ ID NO:65); CA0105 (SEQ ID NO:66); CA0120 (SEQ ID NO:67); CA0163 (SEQ ID NO:68); CA0221 (SEQ ID NO:69); CA0226 (SEQ ID NO:70); CA0233 (SEQ ID NO:71); CA0328 (SEQ ID NO:72); CA0410 (SEQ ID NO:73); CA0423 (SEQ ID NO:74); CA0456 (SEQ ID NO:75); CA0488 (SEQ ID NO:76); CA0546 (SEQ ID NO:77); CA0552 (SEQ ID NO:78); CA0603 (SEQ ID NO:79); CA0614 (SEQ ID NO:80); CA0636 (SEQ ID NO:81); CA0681 (SEQ ID NO:82); CA0719 (SEQ ID NO:83); CA0736 (SEQ ID NO:84); CA0739 (SEQ ID NO:85); CA0753 (SEQ ID NO:86); CA0834 (SEQ ID NO:87); CA0837 (SEQ ID NO:88); CA0896 (SEQ ID NO:89); CA0991 (SEQ ID NO:90); CA1027 (SEQ ID NO:91); CA1032 (SEQ ID NO:92); CA1034 (SEQ ID NO:93); CA1035 (SEQ ID NO:94); CA1066 (SEQ ID NO:95); CA1080 (SEQ ID NO:96); CA1090 (SEQ ID NO:97); CA1097 (SEQ ID NO:98); CA1107 (SEQ ID NO:99); PE0012 (SEQ ID NO:100); PE0017 (SEQ ID NO:101); PE0063 (SEQ ID NO:102); PE0091 (SEQ ID NO:103); PE0131 (SEQ ID NO:104); PE0133 (SEQ ID NO:105); PE0177 (SEQ ID NO:106); PE0187 (SEQ ID NO:107); PE0203 (SEQ ID NO:108); PE0250 (SEQ ID NO:109); PE0281 (SEQ ID NO:110); PE0283 (SEQ ID NO:111); PE0286 (SEQ ID NO:112);

PE0324 (SEQ ID NO:113); PE0340 (SEQ ID NO:114); PE0355 (SEQ ID NO:115); UB0015 (SEQ ID NO:116); UB0126 (SEQ ID NO:117); UB0163 (SEQ ID NO:118); UB0181 (SEQ ID NO:119); UB0196 (SEQ ID NO:120); UB0307 (SEQ ID NO:121); UB0315 (SEQ ID NO:122); UB0331 (SEQ ID NO:123); KK66 (SEQ ID NO:124); and KK98G (SEQ ID NO:125) (sometimes referred to as "the markers exemplified by SEQ ID NOs: 1-125"). contain simple sequence repeat (SSR) polymorphisms or single nucleotide polymorphisms (SNPs) that identify QTLs contributing to *Sclerotinia* whole plant field resistance or improved whole plant field resistance and can be used as markers thereof. It will be appreciated that the number of repeats in the SSR can vary. Favorable alleles that contribute to whole plant field resistance to *Sclerotinia* or improved whole plant field resistance to *Sclerotinia* are provided, for example, in Tables 7 and 13.

It will be noted that, regardless of their molecular nature, e.g., whether the marker is an SSR, AFLP, RFLP, etc., markers are typically strain specific. That is, a particular polymorphic marker, such as the exemplary markers of the invention described above, is defined relative to the parental lines of interest. For each marker locus, resistance-associated, and conversely, susceptibility-associated alleles are identified for each pair of parental lines. Following correlation of specific alleles with susceptibility and resistance in parents of a cross, the marker can be utilized to identify progeny with genotypes that correspond to the desired resistance phenotype. In some circumstance, i.e., in some crosses of parental lines, the exemplary markers described herein will not be optimally informative. In such cases, additional informative markers, e.g., certain linked markers and/or homologous markers are evaluated and substituted for genotyping, e.g., for marker-assisted selection, etc. In the case where a marker corresponds to a QTL, following identification of resistance- and susceptibility-associated alleles, it is possible to directly screen a population of samples, e.g., samples obtained from a seed bank, without first correlating the parental phenotype with an allele.

Linked Markers

Those of skill in the art will recognize that additional molecular markers can be identified within the intervals defined by the above-described pairs of markers. Such markers are also genetically linked to the QTLs identified herein as associated with *Sclerotinia* whole plant field resistance, and are within the scope of the present invention. Markers can be identified by any of a variety of genetic or physical mapping techniques. Methods of determining whether markers are genetically linked to a QTL (or to a specified marker) associated with resistance to *Sclerotinia* are known to those of skill in the art and include, e.g., interval mapping (Lander and Botstein (1989) *Genetics* 121:185), regression mapping (Haley and Knott (1992) *Heredity* 69:315) or MQM mapping (Jansen (1994) *Genetics* 138:871). In addition, such physical mapping techniques as chromosome walking, contig mapping and assembly, and the like, can be employed to identify and isolate additional sequences useful as markers in the context of the present invention.

Homologous Nucleotide Sequences

In addition, AG0023; AG0045; AG0047; AG0070; AG0086; AG0093; AG0125; AG0148; AG0171; AG0203; AG0239; AG0243; AG0272; AG0304; AG0323; AG0324; AG0328; AG0359; AG0369; AG0370; AG0378; AG0391; AG0410; AG0441; AG0477; AG0482; AG0504; AG0510; BG0031; BG0106; BG0111; BG0119; BG0181; BG0228; BG0255; BG0278; BG0295; BG0452; BG0516; BG0647; BG0651; BG0713; BG0864; BG0869; BG0988; BG1062; BG1090; BG1101; BG1123; BG1127; BG1149; BG1182; BG1197; BG1230; BG1241; BG1244; BG1286; BG1288; BG1321; BG1368; BG1392; BG1442; BG1449; BG1453; BG1513; CA0105; CA0120; CA0163; CA0221; CA0226; CA0233; CA0328; CA0410; CA0423; CA0456; CA0488; CA0546; CA0552; CA0603; CA0614; CA0636; CA0681; CA0719; CA0736; CA0739; CA0753; CA0834; CA0837; CA0896; CA0991; CA1027; CA1032; CA1034; CA1035; CA1066; CA1080; CA1090; CA1097; and CA1107; as well as PE0012; PE0017; PE0063; PE0091; PE0131; PE0133; PE0177; PE0187; PE0203; PE0250; PE0281; PE0283; PE0286; PE0324; PE0340; PE0355; UB0015; UB0126; UB0163; UB0181; UB0196; UB0307; UB0315; UB0331; KK66; and KK98G are useful for the identification of homologous nucleotide sequences with utility in identifying QTLs associated with *Sclerotinia* whole plant field resistance in different lines, varieties, or species of dicots. Such homologous markers are also a feature of the invention.

Such homologous sequences can be identified by selective hybridization to a reference sequence. The reference sequence is typically a unique sequence, such as a unique oligonucleotide primer sequence, EST, amplified fragment (e.g., corresponding to AFLP markers) and the like, derived from any of the marker loci listed herein or its complement.

Two single-stranded nucleic acids "hybridize" when they form a double-stranded duplex. The double stranded region can include the full-length of one or both of the single-stranded nucleic acids, or all of one single stranded nucleic acid and a subsequence of the other single-stranded nucleic acid, or the double stranded region can include a subsequence of each nucleic acid. Selective hybridization conditions distinguish between nucleic acids that are related, e.g., share significant sequence identity with the reference sequence (or its complement) and those that associate with the reference sequence in a non-specific manner. Generally, selective hybridization conditions are those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Selective hybridization conditions may also be achieved with the addition of destabilizing agents such as formamide. Selectivity can be achieved by varying the stringency of the hybridization and/or wash conditions. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically a function of post-hybridization washes, with the critical factors being ionic strength and temperature of the final wash solution. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$).

The $T_m$ is the temperature (under defined ionic strength and pH) at which 50% of a complementary target sequence hybridizes to a perfectly matched probe. For DNA-DNA hybrids, the $T_m$ can be approximated from the equation of Meinkoth and Wahl ((1984) *Anal. Biochem.* 138:267-284): $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization and/or wash conditions can be adjusted to hybridize to sequences of the desired identity. For example, if sequences with ≥90% identity are sought, the $T_m$ can be decreased 10° C.

Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. Hybridization and/or wash conditions can be applied for at least 10, 30, 60, 90, 120, or 240 minutes. An extensive guide to the hybridization of nucleic acids is found in Tijssen (1993) *Laboratory Techniques in Biochemistry and Molecular Biology—Hybridization with Nucleic Acid Probes* Part I, Chapter 2 "Overview of principles of hybridization and the strategy of nucleic acid probe assays" Elsevier, New York. General Texts that discuss considerations relevant to nucleic acid hybridization, the selection of probes, and buffer and incubation conditions, and the like, as well as numerous other topics of interest in the context of the present invention (e.g., cloning of nucleic acids that correspond to markers and QTLs, sequencing of cloned markers/QTLs, the use of promoters, vectors, etc.) can be found in Berger and Kimmel (1987) *Guide to Molecular Cloning Techniques, Methods in Enzymology* vol. 152, Academic Press, Inc., San Diego ("Berger"); Sambrook et al., (2001) *Molecular Cloning-A Laboratory Manual*, 3$^{rd}$ ed. Vols. 1-3, Cold Spring Harbor Laboratory, Cold Spring Harbor ("Sambrook"); and Ausubel et al., (eds) (supplemented through 2001) *Current Protocols in Molecular Biology*, John Wiley and Sons, Inc., ("Ausubel").

In addition to hybridization methods described above, homologs of the markers of the invention can be identified in silico using any of a variety of sequence alignment and comparison protocols. For the purposes of the ensuing discussion, the following terms are used to describe the sequence relationships between a marker nucleotide sequence and a reference polynucleotide sequence:

A "reference sequence" is a defined sequence used as a basis for sequence comparison with a test sequence, e.g., a candidate marker homolog, of the present invention. A reference sequence may be a subsequence or the entirety of a specified sequence; for example, a segment of a full-length cDNA or gene sequence, or the complete cDNA or gene sequence.

As used herein, a "comparison window" is a contiguous and specified segment, (e.g., a subsequence) of a polynucleotide/polypeptide sequence to be compared to a reference sequence. The segment of the polynucleotide/polypeptide sequence in the comparison window can include one or more additions or deletions (i.e., gaps) with respect to the reference sequence, which (by definition) does not comprise addition(s) or deletion(s), for optimal alignment of the two sequences. An optimal alignment of two sequences yields the fewest number of unlike nucleotide/amino acid residues in a comparison window. Generally, the comparison window is at least 20 contiguous nucleotide/amino acid residues in length, and optionally can be 30, 40, 50, 100, or longer. Those of skill in the art understand that to avoid a falsely high similarity between two sequences, due to inclusion of gaps in the polynucleotide/polypeptide sequence, a gap penalty is typically assessed and is subtracted from the number of matches.

"Sequence identity" or "identity" in the context of two nucleic acid or polypeptide sequences refers to residues that are the same in both sequences when aligned for maximum correspondence over a specified comparison window.

"Percentage sequence identity" refers to the value determined by comparing two optimally aligned sequences over a comparison window. The percentage is calculated by determining the number of positions at which both sequences have the same nucleotide or amino acid residue, determining the number of matched positions, dividing the number of matched positions by the total number of positions in the comparison window, and multiplying the result by 100 to yield the percentage of sequence identity.

When percentage of sequence identity is used in reference to proteins it is recognized that residue positions that are not identical often differ by conservative amino acid substitutions, where amino acid residues are substituted for other amino acid residues with similar chemical properties (e.g., charge or hydrophobicity) and therefore do not change the functional properties of the molecule. Where sequences differ by conservative substitutions, the percent sequence identity may be adjusted upwards to correct for the conservative nature of the substitution. Sequences that differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller (1988) *Computer Applic. Biol. Sci.* 4:11-17, e.g., as implemented in the program PC/GENE (Intelligenetics, Mountain View, Calif., USA).

Methods of alignment of sequences for comparison are well-known in the art. Optimal alignment of sequences for comparison may be conducted by the local homology algorithm of Smith and Waterman ((1981) *Adv. Appl. Math.* 2:482); by the homology alignment algorithm of Needleman and Wunsch ((1970) *J. Mol. Biol.* 48:443); by the search for similarity method of Pearson and Lipman ((1988) *Proc. Natl. Acad. Sci. USA* 85:2444); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), Madison, Wis., USA; the CLUSTAL program is well described by Higgins and Sharp ((1988) *Gene* 73:237-244); Higgins and Sharp ((1989) *CABIOS* 5:151-153); Corpet et al. ((1988) *Nucleic Acids Research* 16:10881-90); Huang et al. ((1992) *Computer Applications in the Biosciences* 8: 155-65), and Pearson et al. ((1994) *Methods in Molecular Biology* 24:307-331).

The BLAST family of programs that can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, e.g., *Current Protocols in Molecular Biology*, Chapter 19, Ausubel et al., Eds., (1995) Greene Publishing and Wiley-Interscience, New York; Altschul et al. (1990) *J. Mol. Biol.* 215:403-410; and, Altschul et al. (1997) *Nucleic Acids Res.* 25:3389-3402.

Software for performing BLAST analyses is publicly available, e.g., through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see, e.g., Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul (1993) *Proc. Nat'l. Acad. Sci. USA* 90:5873-5877). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences that may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen (1993) *Comput. Chem.* 17:149-163) and XNU (Claverie and States (1993) *Comput. Chem.* 17:191-201) low-complexity filters can be employed alone or in combination.

Unless otherwise stated, nucleotide and protein identity/similarity values provided herein are calculated using GAP (GCG Version 10) under default values.

GAP (Global Alignment Program) can also be used to compare a polynucleotide or polypeptide of the present invention with a reference sequence. GAP uses the algorithm of Needleman and Wunsch ((1970) *J. Mol. Biol.* 48: 443-453), to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 100. Thus, for example, the gap creation and gap extension penalties can each independently be: 0, 1, 2, 3, 4, 5, 6, 7, 8, 9, 10, 15, 20, 30, 40, 50, 60 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see, e.g., Henikoff & Henikoff (1989) *Proc. Natl. Acad. Sci. USA* 89:10915).

Multiple alignment of the sequences can be performed using the CLUSTAL method of alignment (Higgins and Sharp (1989) *CABIOS.* 5:151-153) with the default parameters (GAP PENALTY=10, GAP LENGTH PENALTY=10). Default parameters for pairwise alignments using the CLUSTAL method are KTUPLE 1, GAP PENALTY=3, WINDOW=5 and DIAGONALS SAVED=5.

The percentage sequence identity of a homologous marker to its reference marker (e.g., any one of the markers described herein) is typically at least 70% and, rounded upwards to the nearest integer, can be expressed as an integer selected from the group of integers between 70 and 99. Thus, for example, the percentage sequence identity to a reference sequence can be at least 70%, 75%, 80%, 85%, 90%, 95%, 97%, or 99%. Sequence identity can be calculated using, for example, the BLAST, CLUSTALW, or GAP algorithms under default conditions.

Detection of Marker Loci

Markers corresponding to genetic polymorphisms between members of a population can be detected by numerous methods, well-established in the art (e.g., restriction fragment length polymorphisms, isozyme markers, allele specific hybridization (ASH), amplified variable sequences of the plant genome, self-sustained sequence replication, simple sequence repeat (SSR), single nucleotide polymorphism (SNP), or amplified fragment length polymorphisms (AFLP)).

The majority of genetic markers rely on one or more properties of nucleic acids for their detection. For example, some techniques for detecting genetic markers utilize hybridization of a probe nucleic acid to nucleic acids corresponding to the genetic marker. Hybridization formats include but are not limited to, solution phase, solid phase, mixed phase, or in situ hybridization assays. Markers that are restriction fragment length polymorphisms (RFLP), are detected by hybridizing a probe, which is typically a sub-fragment (or a synthetic oligonucleotide corresponding to a sub-fragment) of the nucleic acid to be detected to restriction digested genomic DNA. The restriction enzyme is selected to provide restriction fragments of at least two alternative (or polymorphic) lengths in different individuals, and will often vary from line to line. Determining a (one or more) restriction enzyme that produces informative fragments for each cross is a simple procedure, well known in the art. After separation by length in an appropriate matrix (e.g., agarose) and transfer to a membrane (e.g., nitrocellulose, nylon), the labeled probe is hybridized under conditions that result in equilibrium binding of the probe to the target followed by removal of excess probe by washing.

Nucleic acid probes to the marker loci can be cloned and/or synthesized. Detectable labels suitable for use with nucleic acid probes include any composition detectable by spectroscopic, radioisotopic, photochemical, biochemical, immunochemical, electrical, optical or chemical means. Useful labels include biotin for staining with labeled streptavidin conjugate, magnetic beads, fluorescent dyes, radiolabels, enzymes, and colorimetric labels. Other labels include ligands that bind to antibodies labeled with fluorophores, chemiluminescent agents, and enzymes. Labeling markers is readily achieved such as by the use of labeled PCR primers to marker loci.

The hybridized probe is then detected using, most typically by autoradiography or other similar detection technique (e.g., fluorography, liquid scintillation counter, etc.). Examples of specific hybridization protocols are widely available in the art, see, e.g., Berger, Sambrook, Ausubel, all supra.

Amplified variable sequences refer to amplified sequences of the plant genome that exhibit high nucleic acid residue variability between members of the same species. All organisms have variable genomic sequences and each organism (with the exception of a clone) has a different set of variable sequences. Once identified, the presence of specific variable sequence can be used to predict phenotypic traits. Preferably, DNA from the plant serves as a template for amplification with primers that flank a variable sequence of DNA. The variable sequence is amplified and then sequenced.

In vitro amplification techniques are well known in the art. Examples of techniques sufficient to direct persons of skill through such in vitro methods, including the polymerase chain reaction (PCR), the ligase chain reaction (LCR), Qβ-replicase amplification and other RNA polymerase mediated techniques (e.g., NASBA), are found in Berger, Sambrook and Ausubel (all supra) as well as Mullis et al. ((1987) U.S. Pat. No. 4,683,202); *PCR Protocols, A Guide to Methods and Applications* ((Innis et al., eds.) Academic Press Inc., San Diego Academic Press Inc. San Diego, Calif. (1990) (Innis)); Arnheim & Levinson ((Oct. 1, 1990) *C&EN* 36-47); *The Journal Of NIH Research* (1991) 3, 81-94; Kwoh et al. ((1989) *Proc. Natl. Acad. Sci. USA* 86, 1173); Guatelli et al. ((1990) *Proc. Natl. Acad. Sci. USA* 87, 1874); Lomeli et al. ((1989) *J. Clin. Chem.* 35, 1826); Landegren et al. ((1988) *Science* 241, 1077-1080); Van Brunt ((1990) *Biotechnology* 8, 291-294); Wu and Wallace ((1989) *Gene* 4, 560); Barringer et al. ((1990) *Gene* 89, 117), and Sooknanan and Malek ((1995) *Biotechnology* 13: 563-564). Improved methods of cloning in vitro amplified nucleic acids are described in Wallace et al., U.S. Pat. No. 5,426,039. Improved methods of amplifying large nucleic acids by PCR are summarized in Cheng et al. (1994) *Nature* 369: 684, and the references therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, Ausubel, Sambrook and Berger, all supra.

Oligonucleotides for use as primers, e.g., in amplification reactions and for use as nucleic acid sequence probes are typically synthesized chemically according to the solid phase phosphoramidite triester method described by Beaucage and Caruthers ((1981) *Tetrahedron Lett.* 22:1859), or can simply be ordered commercially.

Alternatively, self-sustained sequence replication can be used to identify genetic markers. Self-sustained sequence replication refers to a method of nucleic acid amplification using target nucleic acid sequences that are replicated exponentially in vitro under substantially isothermal conditions by using three enzymatic activities involved in retroviral replication: (1) reverse transcriptase, (2) Rnase H, and (3) a DNA-dependent RNA polymerase (Guatelli et al. (1990) *Proc. Natl. Acad. Sci. USA* 87:1874). By mimicking the retroviral strategy of RNA replication by means of cDNA intermediates, this reaction accumulates cDNA and RNA copies of the original target.

Amplified fragment length polymorphisms (AFLP) can also be used as genetic markers (Vos et al. (1995) *Nucl. Acids Res.* 23:4407. The phrase "amplified fragment length polymorphism" refers to selected restriction fragments that are amplified before or after cleavage by a restriction endonuclease. The amplification step allows easier detection of specific restriction fragments. AFLP allows the detection large numbers of polymorphic markers and has been used for genetic mapping of plants (Becker et al. (1995) *Mol. Gen. Genet.* 249:65; and Meksem et al. (1995) *Mol. Gen. Genet.* 249:74.

Allele-specific hybridization (ASH) can be used to identify the genetic markers of the invention. ASH technology is based on the stable annealing of a short, single-stranded, oligonucleotide probe to a completely complementary single-strand target nucleic acid. Detection is via an isotopic or non-isotopic label attached to the probe.

For each polymorphism, two or more different ASH probes are designed to have identical DNA sequences except at the polymorphic nucleotides. Each probe will have exact homology with one allele sequence so that the range of probes can distinguish all the known alternative allele sequences. Each probe is hybridized to the target DNA. With appropriate probe design and hybridization conditions, a single-base mismatch between the probe and target DNA will prevent hybridization. In this manner, only one of the alternative probes will hybridize to a target sample that is homozygous or homogenous for an allele. Samples that are heterozygous or heterogeneous for two alleles will hybridize to both of two alternative probes.

ASH markers are used as dominant markers where the presence or absence of only one allele is determined from hybridization or lack of hybridization by only one probe. The alternative allele may be inferred from the lack of hybridization. ASH probe and target molecules are optionally RNA or DNA; the target molecules are any length of nucleotides beyond the sequence that is complementary to the probe; the probe is designed to hybridize with either strand of a DNA target; the probe ranges in size to conform to variously stringent hybridization conditions, etc.

PCR allows the target sequence for ASH to be amplified from low concentrations of nucleic acid in relatively small volumes. Otherwise, the target sequence from genomic DNA is digested with a restriction endonuclease and size separated by gel electrophoresis. Hybridizations typically occur with the target sequence bound to the surface of a membrane or, as described in U.S. Pat. No. 5,468,613, the ASH probe sequence may be bound to a membrane.

In one embodiment, ASH data are obtained by amplifying nucleic acid fragments (amplicons) from genomic DNA using PCR, transferring the amplicon target DNA to a membrane in a dot-blot format, hybridizing a labeled oligonucleotide probe to the amplicon target, and observing the hybridization dots by autoradiography.

Single nucleotide polymorphisms (SNP) are markers that consist of a shared sequence differentiated on the basis of a single nucleotide. Typically, this distinction is detected by differential migration patterns of an amplicon comprising the SNP on e.g., an acrylamide gel. However, alternative modes of detection, such as hybridization, e.g., ASH, or RFLP analysis are not excluded.

In yet another basis for providing a genetic linkage map, Simple sequence repeats (SSR), take advantage of high levels of di-, tri-, tetra-, penta- or hexa-nucleotide tandem repeats within a genome. Dinucleotide repeats have been reported to occur in the human genome as many as 50,000 times with n varying from 10 to 60 or more (Jacob et al. (1991) *Cell* 67:213. Dinucleotide repeats have also been found in higher plants (Condit and Hubbell (1991) *Genome* 34:66).

Briefly, SSR data are generated by hybridizing primers to conserved regions of the plant genome that flank the SSR sequence. PCR is then used to amplify the nucleotide repeats between the primers. The amplified sequences are then electrophoresed to determine the size and therefore the number of di-, tri-, and tetra-nucleotide repeats. The number of repeats distinguishes the favorable allele from an unfavorable allele. Favorable alleles for whole plant field resistance to *Sclerotinia* or improved whole plant field resistance to *Sclerotinia* are provided, for example, in Tables 1 and 13.

Alternatively, isozyme markers are employed as genetic markers. Isozymes are multiple forms of enzymes that differ from one another in their amino acid, and therefore their nucleic acid sequences. Some isozymes are multimeric enzymes containing slightly different subunits. Other isozymes are either multimeric or monomeric but have been cleaved from the proenzyme at different sites in the amino acid sequence. Isozymes can be characterized and analyzed at the protein level, or alternatively, isozymes that differ at the nucleic acid level can be determined. In such cases any of the nucleic acid based methods described herein can be used to analyze isozyme markers.

In alternative embodiments, in silico methods can be used to detect the marker loci. For example, the sequence of a nucleic acid comprising the marker can be stored in a computer. The desired marker locus sequence or its homolog can be identified using an appropriate nucleic acid search algorithm as provided by, for example, in such readily available programs as BLAST.

QTL Mapping

Multiple experimental paradigms have been developed to identify and analyze QTLs. In general, these paradigms involve crossing one or more parental pairs, which can be, for example, a single pair derived from two inbred strains, or multiple related or unrelated parents of different inbred strains or lines, which each exhibit different characteristics relative to the phenotypic trait of interest. The parents and a population of progeny are genotyped, typically for multiple marker loci, and evaluated for the trait of interest. In the context of the present invention, the parental and progeny plants are genotyped for any one or more of the molecular markers exemplified herein, or homologs, or alternative markers linked to any one or more of the markers exemplified herein, and evaluated for whole plant field resistance, or improved whole plant field resistance to *Sclerotinia*. QTLs associated with *Sclerotinia* whole plant field resistance are identified based on the significant statistical correlations between the marker genotype(s) and the resistance phenotype of the evaluated progeny plants. Numerous methods for determining whether markers are genetically linked to a QTL (or to another marker) associated with whole plant field resistance to *Sclerotinia* are known to those of skill in the art and include, e.g., interval mapping (Lander and Botstein (1989) Genetics 121:185), regression mapping (Haley and Knott (1992) Heredity 69:315) or MQM mapping (Jansen (1994) Genetics 138:871). In addition, the following applications provide additional details regarding alternative statistical methods applicable to complex breeding populations that can be used to identify and localize QTLs associated with *Sclerotinia* whole plant field resistance: U.S. Ser. No. 09/216,089 by Beavis et al. "QTL MAPPING IN PLANT BREEDING POPULATIONS" and PCT/US00/34971 by Jansen et al. "MQM MAPPING USING HAPLOTYPED PUTATIVE QTLS ALLELES: A SIMPLE APPROACH FOR MAPPING QTLS IN PLANT BREEDING POPULATIONS."

Marker Assisted Selection and Breeding of Plants

A primary motivation for development of molecular markers in crop species is the potential for increased efficiency in plant breeding through marker assisted selection (MAS). Genetic marker alleles, or alternatively, identified QTL alleles, are used to identify plants that contain a desired genotype at one or more loci, and that are expected to transfer the desired genotype, along with a desired phenotype to their progeny. Genetic marker alleles (or QTL alleles) can be used to identify plants that contain a desired genotype at one locus, or at several unlinked or linked loci (e.g., a haplotype), and that would be expected to transfer the desired genotype, along with a desired phenotype to their progeny. The present invention provides the means to identify plants, particularly dicots, e.g., *Brassica*, that are resistant, or exhibit improved resistance, to *Sclerotinia* whole plant field resistance by identifying plants having a specified allele, e.g., at one or more of the markers exemplified herein, or other markers within the intervals set forth herein. Similarly, by identifying plants lacking a desired allele of the marker, susceptible plants can be identified, and, e.g., eliminated from subsequent crosses. It will be appreciated that for the purposes of MAS, the term marker can encompass both marker and QTL loci as both can be used to identify plants that are resistant or have improved resistance to *Sclerotinia*.

After a desired phenotype, e.g., *Sclerotinia* whole plant field resistance, and a polymorphic chromosomal locus, e.g., a marker locus or QTL, are determined to segregate together, it is possible to use those polymorphic loci to select for alleles corresponding to the desired phenotype—a process called marker-assisted selection (MAS). In brief, a nucleic acid corresponding to the marker nucleic acid is detected in a biological sample from a plant to be selected. This detection can take the form of hybridization of a probe nucleic acid to a marker, e.g., using allele-specific hybridization, southern blot analysis, northern blot analysis, in situ hybridization, hybridization of primers followed by PCR amplification of a region of the marker or the like. A variety of procedures for detecting markers are described herein, e.g., in the section entitled "DETECTION OF MARKER LOCI." After the presence (or absence) of a particular marker in the biological sample is verified, the plant is selected, i.e., used to make progeny plants by selective breeding.

Plant breeders need to combine disease tolerant loci with genes for high yield and other desirable traits to develop improved plant varieties. Disease screening for large numbers of samples can be expensive, time consuming, and unreliable. Use of the polymorphic loci described herein, and genetically-linked nucleic acids, as genetic markers for disease resistance loci is an effective method for selecting tolerant varieties in breeding programs. For example, one advantage of marker-assisted selection over field evaluations for disease resistance is that MAS can be done at any time of year regardless of the growing season. Moreover, environmental effects are irrelevant to marker-assisted selection.

When a population is segregating for multiple loci affecting one or multiple traits, e.g., multiple loci involved in resistance to a single disease, or multiple loci each involved in resistance to different diseases, the efficiency of MAS compared to phenotypic screening becomes even greater because all the loci can be processed in the lab together from a single sample of DNA. In the present instance, this means that multiple markers selected from among AG0023; AG0045; AG0047; AG0070; AG0086; AG0093; AG0125; AG0148; AG0171; AG0203; AG0239; AG0243; AG0272; AG0304; AG0323; AG0324; AG0328; AG0359; AG0369; AG0370; AG0378; AG0391; AG0410; AG0441; AG0477; AG0482; AG0504; AG0510; BG0031; BG0106; BG0111; BG0119; BG0181; BG0228; BG0255; BG0278; BG0295; BG0452; BG0516; BG0647; BG0651; BG0713; BG0864; BG0869; BG0988; BG1062; BG1090; BG1101; BG1123; BG1127; BG1149; BG1182; BG1197; BG1230; BG1241; BG1244; BG1286; BG1288; BG1321; BG1368; BG1392; BG1442; BG1449; BG1453; BG1513; CA0105; CA0120; CA0163; CA0221; CA0226; CA0233; CA0328; CA0410; CA0423; CA0456; CA0488; CA0546; CA0552; CA0603; CA0614; CA0636; CA0681; CA0719; CA0736; CA0739; CA0753; CA0834; CA0837; CA0896; CA0991; CA1027; CA1032; CA1034; CA1035; CA1066; CA1080; CA1090; CA1097; CA1107; PE0012; PE0017; PE0063; PE0091; PE0131; PE0133; PE0177; PE0187; PE0203; PE0250; PE0281; PE0283; PE0286; PE0324; PE0340; PE0355; UB0015; UB0126; UB0163; UB0181; UB0196; UB0307; UB0315; UB0331; KK66; and KK98G or markers homologous or linked thereto can be assayed simultaneously or sequentially in a single sample or population of samples. Thus, any one or more of these markers, e.g., two or more, up to and including all of the established markers, can be assayed simultaneously. In some instances, it is desirable to evaluate a marker corresponding to each of the linkage groups associated with *Sclerotinia* whole plant field resistance.

Another use of MAS in plant breeding is to assist the recovery of the recurrent parent genotype by backcross breeding. Backcross breeding is the process of crossing a progeny back to one of its parents. Backcrossing is usually done for the purpose of introgressing one or a few loci from a donor parent into an otherwise desirable genetic background from the recurrent parent. The more cycles of backcrossing that are done, the greater the genetic contribution of the recurrent parent to the resulting variety. This is often necessary, because tolerant plants may be otherwise undesirable, i.e., due to low yield, low fecundity, or the like. In contrast, strains that are the result of intensive breeding programs may have excellent yield, fecundity or the like, merely being deficient in one desired trait such as resistance to a particular pathogen (e.g., *Sclerotinia* whole plant field resistance).

The presence and/or absence of a particular genetic marker allele, or a homolog thereof, in the genome of a plant exhibiting a preferred phenotypic trait is determined by any method listed above, e.g., RFLP, AFLP, SSR, etc. If the nucleic acids from the plant are positive for a desired genetic marker, the plant can be selfed to create a true breeding line with the same genotype, or it can be crossed with a plant with the same marker or with other desired characteristics to create a sexually crossed hybrid generation.

As mentioned above, the skilled artisan will understand that the QTLs described herein represent regions of the genome comprising genes that contribute to the *Sclerotinia* whole plant field resistance of a plant. Further, each QTL can contribute differently to that resistance level. Thus, breeding efforts are directed to increasing the number of those QTLs, particularly quantitatively significant QTLs, present in the germplasm. Early in a breeding program, fewer QTLs may be present in a particular germplasm, but that number will increase as the breeding program progresses. Thus, in certain embodiments, a plant exhibiting *Sclerotinia* whole plant field resistance may contain at least 6 of the QTLs described herein. More particularly, the plant may contain at least 7, 8, 9 or 10 of the QTLs described herein. Yet more particularly, the plant may contain 11, 12 or all of the QTLs described herein.

Positional Cloning

The molecular markers of the present invention and nucleic acids homologous thereto, can be used, as indicated previously, to identify additional linked marker loci, which can be cloned by well established procedures, e.g., as described in detail in Ausubel, Berger and Sambrook, supra. Similarly, the exemplified markers, as well as any additionally identified linked molecular markers can be used to physically isolate, e.g., by cloning, nucleic acids associated with QTLs contributing to *Sclerotinia* whole plant field resistance. Such nucleic acids, i.e., linked to QTLs, have a variety of uses, including as genetic markers for identification of additional QTLs in subsequent applications of marker assisted selection (MAS).

These nucleic acids are first identified by their genetic linkage to markers of the present invention. Isolation of the nucleic acid of interest is achieved by any number of methods as discussed in detail in such references as Ausubel, Berger and Sambrook, supra, and Clark, Ed. (1997) *Plant Molecular Biology: A Laboratory Manual* Springer-Verlag, Berlin.

For example, positional gene cloning uses the proximity of a genetic marker to physically define an isolated chromosomal fragment that is linked to a QTL. The isolated chromosomal fragment can be produced by such well known methods as digesting chromosomal DNA with one or more restriction enzymes, or by amplifying a chromosomal region in a polymerase chain reaction (PCR), or alternative amplification reaction. The digested or amplified fragment is typically ligated into a vector suitable for replication, e.g., a plasmid, a cosmid, a phage, an artificial chromosome, or the like, and, optionally, expression of the inserted fragment. Markers that are adjacent to an open reading frame (ORF) associated with a phenotypic trait can hybridize to a DNA clone, thereby identifying a clone on which an ORF is located. If the marker is more distant, a fragment containing the open reading frame is identified by successive rounds of screening and isolation of clones, which together comprise a contiguous sequence of DNA, a "contig." Protocols sufficient to guide one of skill through the isolation of clones associated with linked markers are found in, e.g., Berger, Sambrook and Ausubel, all supra.

Nucleic Acids in Proximity to Markers/Isolated Chromosome Intervals

The present invention provides isolated nucleic acids comprising a QTL associated with *Sclerotinia* whole plant field resistance. The QTL is in proximity to a marker described herein and/or is localized within an interval defined by two markers of the present invention wherein each marker flanks the QTL. Such nucleic acids and/or intervals can be utilized to identify homologous nucleic acids and/or can be used in the production of transgenic plants having whole plant field resistance to *Sclerotinia* conferred by the introduced QTL. The nucleic acid and/or chromosome interval comprising a QTL is isolated, e.g., cloned via positional cloning methods outlined above. A chromosome interval can contain one or more ORFs associated with resistance, and can be cloned on one or more individual vectors, e.g., depending on the size of the chromosome interval.

It will be appreciated that numerous vectors are available in the art for the isolation and replication of the nucleic acids of the invention. For example, plasmids, cosmids and phage vectors are well known in the art, and are sufficient for many applications (e.g., in applications involving insertion of nucleic acids ranging from less than 1 to about 20 kilobases (kb). In certain applications, it is advantageous to make or clone large nucleic acids to identify nucleic acids more distantly linked to a given marker, or to isolate nucleic acids in excess of 10-20 kb, e.g., up to several hundred kilobases or more, such as the entire interval between two linked markers, i.e., up to and including one or more centiMorgans (cM), linked to QTLs as identified herein. In such cases, a number of vectors capable of accommodating large nucleic acids are available in the art, these include, yeast artificial chromosomes (YACs), bacterial artificial chromosomes (BACs), plant artificial chromosomes (PACs) and the like. For a general introduction to YACs, BACs, PACs and MACs as artificial chromosomes, see, e.g., Monaco and Larin (1994) *Trends Biotechnol.* 12:280. In addition, methods for the in vitro amplification of large nucleic acids linked to genetic markers are widely available (e.g., Cheng et al. (1994) *Nature* 369:684, and references therein). Cloning systems can be created or obtained from commercially; see, for example, Stratagene Cloning Systems, Catalogs 2000 (La Jolla, Calif.).

Generation of Transgenic Plants and Cells

The present invention also relates to host cells and organisms that are transformed with nucleic acids corresponding to QTLs and other genes identified according to the invention. For example, such nucleic acids include chromosome intervals, ORFs, and/or cDNAs or corresponding to a sequence or subsequence included within the identified chromosome interval or ORF. Additionally, the invention provides for the production of polypeptides corresponding to QTLs by recombinant techniques. Host cells are genetically engineered (i.e., transduced, transfected or transformed) with the vectors of this invention (i.e., vectors that comprise QTLs or other nucleic acids identified according to the methods of the invention and as described above) that include, for example, a cloning vector or an expression vector. Such vectors include, in addition to those described above, e.g., an *agrobacterium*, a virus (such as a plant virus), a naked polynucleotide, or a conjugated polynucleotide. The vectors are introduced into plant tissues, cultured plant cells or plant protoplasts by a variety of standard methods including electroporation (From et al. (1985) *Proc. Natl. Acad. Sci. USA* 82; 5824), infection by viral vectors such as cauliflower mosaic virus (CaMV) (Hohn et al. (1982) *Molecular Biology of Plant Tumors* (Academic Press, New York, pp. 549-560); Howell U.S. Pat. No. 4,407,956), high velocity ballistic penetration by small particles with the nucleic acid either within the matrix of small beads or particles, or on the surface (Klein et al. (1987) *Nature* 327; 70), use of pollen as vector (WO 85/01856), or use of *Agrobacterium tumefaciens* or *A. rhizogenes* carrying a T-DNA plasmid in which DNA fragments are cloned. The T-DNA plasmid is transmitted to plant cells upon infection by *Agrobacterium tumefaciens*, and a portion is stably integrated into the plant genome (Horsch et al. (1984) *Science* 233; 496; Fraley et al. (1983) *Proc. Natl. Acad. Sci. USA* 80; 4803). The method of introducing a nucleic acid of the present invention into a host cell is not critical to the instant invention. Thus, any method, e.g., including but not limited to the above examples, which provides for effective introduction of a nucleic acid into a cell or protoplast can be employed.

The engineered host cells can be cultured in conventional nutrient media modified as appropriate for such activities as, for example, activating promoters or selecting transformants. These cells can optionally be cultured into transgenic plants. Plant regeneration from cultured protoplasts is described in Evans et al. ((1983) "Protoplast Isolation and Culture," *Handbook of Plant Cell Cultures* 1, 124-176 (MacMillan Publishing Co., New York); Davey ((1983) "Recent Developments in the Culture and Regeneration of Plant Protoplasts," *Protoplasts*, pp. 12-29, (Birkhauser, Basel)); Dale ((1983) "Protoplast Culture and Plant Regeneration of Cereals and Other Recalcitrant Crops," *Protoplasts*, pp. 31-41, (Birkhauser, Basel)); and Binding ((1985) "Regeneration of Plants," *Plant Protoplasts*, pp. 21-73, (CRC Press, Boca Raton)).

The present invention also relates to the production of transgenic organisms, which may be bacteria, yeast, fungi, or plants, transduced with the nucleic acids, e.g., cloned QTLs of the invention. A thorough discussion of techniques relevant to bacteria, unicellular eukaryotes and cell culture may be found in references enumerated above and are briefly outlined as follows. Several well-known methods of introducing target nucleic acids into bacterial cells are available, any of which may be used in the present invention. These include: fusion of the recipient cells with bacterial protoplasts containing the DNA, treatment of the cells with liposomes containing the DNA, electroporation, projectile bombardment (biolistics), carbon fiber delivery, and infection with viral vectors (discussed further, below), etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, a plethora of kits are commercially available for the purification of plasmids from bacteria. For their proper use, follow the manufacturer's instructions (see, for example, EasyPrep™, FlexiPrep™, both from Pharmacia Biotech; StrataClean™, from Stratagene; and, QIAprep™ from Qiagen). The isolated and purified plasmids are then further manipulated to produce other plasmids, used to transfect plant cells or incorporated into *Agrobacterium tumefaciens* related vectors to infect plants. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or preferably both. See, Giliman & Smith ((1979) *Gene* 8:81); Roberts et al. ((1987) *Nature* 328:731); (Schneider et al. (1995) *Protein Expr. Purif.* 6435:10); Ausubel, Sambrook, Berger (all supra). A catalogue of Bacteria and Bacteriophages useful for cloning is provided, e.g., by the ATCC, e.g., *The ATCC Catalogue of Bacteria and Bacteriophage* (1992) Gherna et al. (eds) published by the ATCC. Additional basic procedures for sequencing, cloning and other aspects of molecular biology and underlying theoretical considerations are also found in Watson et al. (1992) *Recombinant DNA*, Second Edition, Scientific American Books, NY.

Transforming Nucleic Acids into Plants

Embodiments of the present invention pertain to the production of transgenic plants comprising the cloned nucleic acids, e.g., chromosome intervals, isolated ORFs, and cDNAs associated with QTLs, of the invention. Techniques for transforming plant cells with nucleic acids are generally available and can be adapted to the invention by the use of nucleic acids encoding or corresponding to QTLs, QTL homologs, isolated chromosome intervals, and the like. In addition to Berger, Ausubel and Sambrook, useful general references for plant cell cloning, culture and regeneration include Jones (ed.) ((1995) *Plant Gene Transfer and Expression Protocols—Methods in Molecular Biology, Volume* 49 Humana Press Towata NJ); Payne et al. ((1992) *Plant Cell and Tissue Culture in Liquid Systems* John Wiley & Sons, Inc. New York, N.Y. (Payne)); and Gamborg and Phillips (eds) ((1995) *Plant Cell, Tissue and Organ Culture; Fundamental Methods* Springer Lab Manual, Springer-Verlag (Berlin Heidelberg New York) (Gamborg)). A variety of cell culture media are described in Atlas and Parks (eds.) (*The Handbook of Microbiological Media* (1993) CRC Press, Boca Raton, Fla. (Atlas)). Additional information for plant cell culture is found in available commercial literature such as the *Life Science Research Cell Culture Catalogue* (1998) from Sigma-Aldrich, Inc. (St Louis, Mo.) (Sigma-LSRCCC) and, e.g., the *Plant Culture Catalogue* and supplement (1997) also from Sigma-Aldrich, Inc. (St Louis, Mo.) (Sigma-PCCS). Additional details regarding plant cell culture are found in Croy, (ed.) ((1993) *Plant Molecular Biology* Bios Scientific Publishers, Oxford, U.K.)

The nucleic acid constructs of the invention, e.g., plasmids, cosmids, artificial chromosomes, DNA and RNA polynucleotides, are introduced into plant cells, either in culture or in the organs of a plant by a variety of conventional techniques. Where the sequence is expressed, the sequence is optionally combined with transcriptional and translational initiation regulatory sequences that direct the transcription or translation of the sequence from the exogenous DNA in the intended tissues of the transformed plant.

Isolated nucleic acids of the present invention can be introduced into plants according to any of a variety of techniques known in the art. Techniques for transforming a wide variety of higher plant species are well known and described in the technical, scientific, and patent literature. See, for example, Weising et al. (1988) *Ann. Rev. Genet.* 22:421-477.

The DNA constructs of the invention, for example, plasmids, cosmids, phage, naked or variously conjugated-DNA polynucleotides, (e.g., polylysine-conjugated DNA, peptide-conjugated DNA, liposome-conjugated DNA, etc.), or artificial chromosomes, can be introduced directly into the genomic DNA of the plant cell using techniques such as electroporation and microinjection of plant cell protoplasts, or the DNA constructs can be introduced directly to plant cells using ballistic methods, such as DNA particle bombardment.

Microinjection techniques for injecting e.g., cells, embryos, callus and protoplasts, are known in the art and well described in the scientific and patent literature. For example, a number of methods are described in Jones (ed.) ((1995) *Plant Gene Transfer and Expression Protocols—Methods in Molecular Biology, Volume* 49 Humana Press Towata N.J.), as well as in the other references noted herein and available in the literature.

For example, the introduction of DNA constructs using polyethylene glycol precipitation is described in Paszkowski, et al. (*EMBO J.* 3:2717 (1984)). Electroporation techniques are described in Fromm, et al. (*Proc. Nat'l. Acad. Sci. USA* 82:5824 (1985)). Ballistic transformation techniques are described in Klein, et al. (*Nature* 327:70-73 (1987)). Additional details are found in Jones (1995) and Gamborg and Phillips (1995), supra, and in U.S. Pat. No. 5,990,387.

Alternatively, *Agrobacterium*-mediated transformation is employed to generate transgenic plants. *Agrobacterium*-mediated transformation techniques, including disarming and use of binary vectors, are also well described in the scientific literature. See, for example, Horsch, et al. (1984) *Science* 233:496; and Fraley et al. (1984) *Proc. Nat'l. Acad. Sci. USA* 80:4803 and reviewed in Hansen and Chilton (1998) *Current Topics in Microbiology* 240:22 and Das (1998) *Subcellular Biochemistry* 29: *Plant Microbe Interactions* pp. 343-363.

The DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616. Although *Agrobacterium* is useful primarily in dicots, certain monocots can be transformed by *Agrobacterium*. For instance, *Agrobacterium* transformation of maize is described in U.S. Pat. No. 5,550,318.

Other methods of transfection or transformation include (1) *Agrobacterium rhizogenes*-mediated transformation (see, e.g., Lichtenstein and Fuller (1987) In: *Genetic Engineering*, vol. 6, PWJ Rigby, Ed., London, Academic Press; and Lichtenstein; C. P., and Draper (1985) In: *DNA Cloning*, Vol. II, D. M. Glover, Ed., Oxford, IRI Press); WO 88/02405, published Apr. 7, 1988, describes the use of *A. rhizogenes* strain A4 and its Ri plasmid along with *A. tumefaciens* vectors pARC8 or pARC16 (2) liposome-mediated DNA uptake (see, e.g., Freeman et al. (1984) *Plant Cell Physiol.* 25:1353), (3) the vortexing method (see, e.g., Kindle (1990) *Proc. Natl. Acad. Sci., (USA)* 87:1228).

DNA can also be introduced into plants by direct DNA transfer into pollen as described by Zhou et al. ((1983) *Methods in Enzymology*, 101:433); Hess ((1987) *Intern Rev.*

Cytol. 107:367); and Luo et al. ((1988) *Plant Mol. Biol. Reporter* 6:165). Expression of polypeptide coding genes can be obtained by injection of the DNA into reproductive organs of a plant as described by Pena et al. ((1987) *Nature* 325:274). DNA can also be injected directly into the cells of immature embryos and the desiccated embryos rehydrated as described by Neuhaus et al. ((1987) *Theor. Appl. Genet.* 75:30); and Benbrook et al. ((1986) in *Proceedings Bio Expo* Butterworth, Stoneham, Mass., pp. 27-54). A variety of plant viruses that can be employed as vectors are known in the art and include cauliflower mosaic virus (CaMV), geminivirus, brome mosaic virus, and tobacco mosaic virus.

Regeneration of Transgenic Plants

Transformed plant cells that are derived by any of the above transformation techniques can be cultured to regenerate a whole plant that possesses the transformed genotype and thus the desired phenotype. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al. ((1983) *Protoplasts Isolation and Culture, Handbook of Plant Cell Culture* pp. 124-176, Macmillian Publishing Company, New York); and Binding ((1985) *Regeneration of Plants, Plant Protoplasts* pp. 21-73, CRC Press, Boca Raton). Regeneration can also be obtained from plant callus, explants, somatic embryos (Dandekar et al. (1989) *J. Tissue Cult. Meth.* 12:145; McGranahan, et al. (1990) *Plant Cell Rep.* 8:512) organs, or parts thereof. Such regeneration techniques are described generally in Klee et al. ((1987)., *Ann. Rev. of Plant Phys.* 38:467-486). Additional details are found in Payne (1992) and Jones (1995), both supra, and Weissbach and Weissbach, eds. ((1988) *Methods for Plant Molecular Biology* Academic Press, Inc., San Diego, Calif.). This regeneration and growth process includes the steps of selection of transformant cells and shoots, rooting the transformant shoots and growth of the plantlets in soil. These methods are adapted to the invention to produce transgenic plants bearing QTLs and other genes isolated according to the methods of the invention.

In addition, the regeneration of plants containing the polynucleotide of the present invention and introduced by *Agrobacterium* into cells of leaf explants can be achieved as described by Horsch et al. ((1985) *Science* 227:1229-1231). In this procedure, transformants are grown in the presence of a selection agent and in a medium that induces the regeneration of shoots in the plant species being transformed as described by Fraley et al. ((1983) *Proc. Natl. Acad. Sci. (U.S.A.)* 80:4803). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Plants for the transformation and expression of whole plant filed resistance to *Sclerotinia* associated QTLs and other nucleic acids identified and cloned according to the present invention include, but are not limited to, agronomically and horticulturally important species. Such species include primarily dicots, e.g., of the families: Brassicaceae, Leguminosae (including pea, beans, lentil, peanut, yam bean, cowpeas, velvet beans, soybean, clover, alfalfa, lupine, vetch, lotus, sweet clover, *wisteria*, and sweetpea); and, Compositae (the largest family of vascular plants, including at least 1,000 genera, including important commercial crops such as sunflower).

Additionally, targets for modification with the nucleic acids of the invention, as well as those specified above, plants from the genera: *Allium, Apium, Arachis, Brassica, Capsicum, Cicer, Cucumis, Curcubita, Daucus, Fagopyrum, Glycine, Helianthus, Lactuca, Lens, Lycopersicon, Medicago, Pisum, Phaseolus, Solanum, Trifolium, Vigna*, and many others.

Common crop plants that are targets of the present invention include soybean, sunflower, canola, peas, beans, lentils, peanuts, yam beans, cowpeas, velvet beans, clover, alfalfa, lupine, vetch, sweet clover, sweetpea, field pea, fava bean, broccoli, brussel sprouts, cabbage, cauliflower, kale, kohlrabi, celery, lettuce, carrot, onion, pepper, potato, eggplant, and tomato.

In construction of recombinant expression cassettes of the invention, which include, for example, helper plasmids comprising virulence functions, and plasmids or viruses comprising exogenous DNA sequences such as structural genes, a plant promoter fragment is optionally employed to direct expression of a nucleic acid in any or all tissues of a regenerated plant. Examples of constitutive promoters include the cauliflower mosaic virus (CaMV) 35S transcription initiation region, the 1'- or 2'-promoter derived from T-DNA of *Agrobacterium tumefaciens*, and other transcription initiation regions from various plant genes known to those of skill. Alternatively, the plant promoter may direct expression of the polynucleotide of the invention in a specific tissue (tissue-specific promoters) or may be otherwise under more precise environmental control (inducible promoters). Examples of tissue-specific promoters under developmental control include promoters that initiate transcription only in certain tissues, such as fruit, seeds, or flowers.

Any of a number of promoters that direct transcription in plant cells can be suitable. The promoter can be either constitutive or inducible. In addition to the promoters noted above, promoters of bacterial origin that operate in plants include the octopine synthase promoter, the nopaline synthase promoter and other promoters derived from native Ti plasmids. See, Herrara-Estrella et al. ((1983), *Nature,* 303: 209). Viral promoters include the 35S and 19S RNA promoters of cauliflower mosaic virus. See, Odell et al. ((1985) *Nature,* 313:810). Other plant promoters include the ribulose-1,3-bisphosphate carboxylase small subunit promoter and the phaseolin promoter. The promoter sequence from the E8 gene and other genes may also be used. The isolation and sequence of the E8 promoter is described in detail in Deikman and Fischer ((1988) *EMBO J.* 7:3315). Many other promoters are in current use and can be coupled to an exogenous DNA sequence to direct expression of the nucleic acid.

If expression of a polypeptide, including those encoded by QTLs or other nucleic acids correlating with phenotypic traits of the present invention, is desired, a polyadenylation region at the 3'-end of the coding region is typically included. The polyadenylation region can be derived from the natural gene, from a variety of other plant genes, or from, e.g., T-DNA.

The vector comprising the sequences (e.g., promoters or coding regions) from genes encoding expression products and transgenes of the invention will typically include a nucleic acid subsequence, a marker gene that confers a selectable, or alternatively, a screenable, phenotype on plant cells. For example, the marker may encode biocide resistance, particularly antibiotic resistance, such as resistance to kanamycin, G418, bleomycin, hygromycin, or herbicide resistance, such as resistance to chlorosluforon, or phosphinothricin (the active ingredient in the herbicides bialaphos or Basta). See, e.g., Padgette et al. (1996) In: *Herbicide-Resistant Crops* (Duke, ed.), pp 53-84, CRC Lewis Publishers, Boca Raton ("Padgette, 1996"). For example, crop selectivity to specific herbicides can be conferred by engineering genes into crops that encode appropriate herbicide metabolizing enzymes from other organisms, such as microbes. See, Vasil (1996) In: *Herbicide-Resistant Crops* (Duke, ed.), pp 85-91, CRC Lewis Publishers, Boca Raton) ("Vasil", 1996).

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed. In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype. Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing a polynucleotide of the present invention can be screened for transmission of the nucleic acid of the present invention by, for example, standard immunoblot and DNA detection techniques. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then be analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

One embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Back-crossing to a parental plant and out-crossing with a non-transgenic plant are also contemplated.

High Throughput Screening

In one aspect of the invention, the determination of genetic marker alleles is performed by high throughput screening. High throughput screening involves providing a library of genetic markers, e.g., RFLPs, AFLPs, isozymes, specific alleles and variable sequences, including SSR. Such libraries are then screened against plant genomes to generate a "fingerprint" for each plant under consideration. In some cases a partial fingerprint comprising a sub-portion of the markers is generated in an area of interest. Once the genetic marker alleles of a plant have been identified, the correspondence between one or several of the marker alleles and a desired phenotypic trait is determined through statistical associations based on the methods of this invention.

High throughput screening can be performed in many different formats. Hybridization can take place in a 96-, 324-, or a 1524-well format or in a matrix on a silicon chip or other format.

In one commonly used format, a dot blot apparatus is used to deposit samples of fragmented and denatured genomic DNA on a nylon or nitrocellulose membrane. After cross-linking the nucleic acid to the membrane, either through exposure to ultra-violet light or by heat, the membrane is incubated with a labeled hybridization probe. The labels are incorporated into the nucleic acid probes by any of a number of means well-known in the art. The membranes are washed to remove non-hybridized probes and the association of the label with the target nucleic acid sequence is determined.

A number of well-known robotic systems have been developed for high throughput screening, particularly in a 96 well format. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; ORCA™, Beckman Coulter, Fullerton Calif.). Any of the above devices are suitable for use with the present invention. The nature and implementation of modifications to these devices (if any) so that they can operate as discussed herein will be apparent to persons skilled in the relevant art.

In addition, high throughput screening systems themselves are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate or membrane in detector(s) appropriate for the assay. These configurable systems provide high throughput and rapid start up as well as a high degree of flexibility and customization. The manufacturers of such systems provide detailed protocols for the use of their products in high throughput applications.

In one variation of the invention, solid phase arrays are adapted for the rapid and specific detection of multiple polymorphic nucleotides. Typically, a nucleic acid probe is linked to a solid support and a target nucleic acid is hybridized to the probe. Either the probe, or the target, or both, can be labeled, typically with a fluorophore. If the target is labeled, hybridization is evaluated by detecting bound fluorescence. If the probe is labeled, hybridization is typically detected by quenching of the label by the bound nucleic acid. If both the probe and the target are labeled, detection of hybridization is typically performed by monitoring a color shift resulting from proximity of the two bound labels.

In one embodiment, an array of probes is synthesized on a solid support. Using chip masking technologies and photoprotective chemistry, it is possible to generate ordered arrays of nucleic acid probes. These arrays, which are known, e.g., as "DNA chips" or as very large scale immobilized polymer arrays (VLSIPS™ arrays) can include millions of defined probe regions on a substrate having an area of about 1 cm$^2$ to several cm$^2$.

In another embodiment, capillary electrophoresis is used to analyze a polymorphism. This technique works best when the polymorphism is based on size, for example, AFLP and SSR. This technique is described in detail in U.S. Pat. Nos. 5,534,123 and 5,728,282. Briefly, capillary electrophoresis tubes are filled with the separation matrix. The separation matrix contains hydroxyethyl cellulose, urea and optionally formamide. The AFLP or SSR samples are loaded onto the capillary tube and electrophoresed. Because of the small amount of sample and separation matrix required by capillary electrophoresis, the run times are very short. The molecular sizes and therefore, the number of nucleotides present in the nucleic acid sample are determined by techniques described herein. In a high throughput format, many capillary tubes are placed in a capillary electrophoresis apparatus. The samples are loaded onto the tubes and electrophoresis of the samples is run simultaneously. See, Mathies and Huang (1992) Nature 359:167.

Integrated Systems

Because of the great number of possible combinations present in one array, in one aspect of the invention, an integrated system such as a computer, software corresponding to the statistical models of the invention, and data sets corresponding to genetic markers and phenotypic values, facilitates mapping of phenotypic traits, including QTLs. The phrase "integrated system" in the context of this invention refers to a system in which data entering a computer corresponds to physical objects or processes external to the computer, e.g., nucleic acid sequence hybridization, and a process that, within a computer, causes a physical transformation of the input signals to different output signals. In other words, the input data, e.g., hybridization on a specific region of an array is transformed to output data, e.g., the identification of the sequence hybridized. The process within the computer is a set of instructions, or "program," by which positive hybridization signals are recognized by the integrated system and attributed to individual samples as a genotype. Additional programs correlate the genotype, and more particularly in the methods of the invention, the haplotype, of individual samples with phenotypic values, e.g., using the HAPLO-IM$^+$, HAPLO-MQM, and/or HAPLO-MQW$^+$ models of the invention. For example, the programs JoinMap® and MapQTL® are particularly suited to this type of analysis and can be extended to include the HAPLO-IM$^+$, HAPLO-MQM, and/or HAPLO-MQM$^+$ models of the invention. In addition there are numerous e.g., C/C++ programs for computing, Delphi and/or Java programs for GUI interfaces, and Active X applications (e.g., Olectra Chart and True WevChart) for charting tools. Other useful software tools in the context of the integrated systems of the invention include statistical packages such as SAS, Genstat, and S-Plus. Furthermore additional programming languages such as Fortran and the like are also suitably employed in the integrated systems of the invention.

In one aspect, the invention provides an integrated system comprising a computer or computer readable medium comprising a database with at least one data set that corresponds to genotypes for genetic markers. The system also includes a user interface allowing a user to selectively view one or more databases. In addition, standard text manipulation software such as word processing software (e.g., Microsoft Word™ or Corel Wordperfect™) and database or spreadsheet software (e.g., spreadsheet software such as Microsoft Excel™ Corel Quattro Pro™, or database programs such as Microsoft Access™ or Paradox™) can be used in conjunction with a user interface (e.g., a GUI in a standard operating system such as a Windows, Macintosh or Linux system) to manipulate strings of characters.

The invention also provides integrated systems for sample manipulation incorporating robotic devices as previously described. A robotic liquid control armature for transferring solutions (e.g., plant cell extracts) from a source to a destination, e.g., from a microtiter plate to an array substrate, is optionally operably linked to the digital computer (or to an additional computer in the integrated system). An input device for entering data to the digital computer to control high throughput liquid transfer by the robotic liquid control armature and, optionally, to control transfer by the armature to the solid support is commonly a feature of the integrated system.

Integrated systems for genetic marker analysis of the present invention typically include a digital computer with one or more of high-throughput liquid control software, image analysis software, data interpretation software, a robotic liquid control armature for transferring solutions from a source to a destination operably linked to the digital computer, an input device (e.g., a computer keyboard) for entering data to the digital computer to control high throughput liquid transfer by the robotic liquid control armature and, optionally, an image scanner for digitizing label signals from labeled probes hybridized, e.g., to expression products on a solid support operably linked to the digital computer. The image scanner interfaces with the image analysis software to provide a measurement of, e.g., differentiating nucleic acid probe label intensity upon hybridization to an arrayed sample nucleic acid population, where the probe label intensity measurement is interpreted by the data interpretation software to show whether, and to what degree, the labeled probe hybridizes to a label. The data so derived is then correlated with phenotypic values using the statistical models of the present invention, to determine the correspondence between phenotype and genotype(s) for genetic markers, thereby, assigning chromosomal locations.

Optical images, e.g., hybridization patterns viewed (and, optionally, recorded) by a camera or other recording device (e.g., a photodiode and data storage device) are optionally further processed in any of the embodiments herein, e.g., by digitizing the image and/or storing and analyzing the image on a computer. A variety of commercially available peripheral equipment and software is available for digitizing, storing and analyzing a digitized video or optical image, e.g., using PC (Intel x86 or pentium chip-compatible DOS™, OS2™ WINDOWS™, WINDOWS NT™ or WINDOWS95™ based machines), MACINTOSH™, LINUX, or UNIX based (e.g., SUN™ work station) computers.

Kits

Kits are also provided to facilitate the screening of germplasm for the markers of the present invention. The kits comprise the polynucleotides of the present invention, fragments or complements thereof, for use as probes or primers to detect the markers for *Sclerotinia* whole plant field resistance or improved whole plant field resistance to *Sclerotinia*. Instructions for using the polynucleotides, as well as buffers and/or other solutions may also be provided to facilitate the use of the polynucleotides. The kit is useful for high throughput screening and in particular, high throughput screening with integrated systems.

EXAMPLES

The following experimental methods and results provide additional details regarding specific aspects of protocols and procedures relevant to the practice of the present invention. The examples, which are provided without limitation to illustrate the claimed invention, involve the application of protocols well known to those of skill in the art, and detailed in the references cited herein. Examples 1-6 describe analyses of one *Brassica napus* mapping population. Examples 7-10 describe analyses of a different *Brassica napus* mapping population.

Example 1: Mapping Population #1

The parents used for the mapping population were 04DHS11418 (a *Sclerotinia* resistant double haploid deposited as ATCC Accession No. PTA-6778) and PHI2004HS1 (a non-resistant spring canola DH line polymorphic to the resistant line, selected for having a similar agronomic phenotype with consistent high susceptibility in the same testing environment where the 04DHS11418 line was selected for resistance) (see Table 2). These lines were used to develop a double haploid mapping population consisting of 186 progeny.

TABLE 2

| Measuring field performance under extreme disease pressure (research trials) | | | | |
|---|---|---|---|---|
| Rating SSDIS** | Category | Disease incidence SSDI %* | Spring Checks | Mapping Parents |
| 1.0 | Highly susceptible | ≥80 | 44A89 | |
| 1.1-2.0 | Susceptible | 79-70 | 46A65 = 2 | PHI2004HS1 |
| 2.1-3.0 | Moderately | 69-60 | 46A76 = 3 | |
| 3.1-4.0 | susceptible | 59-50 | | |
| 4.1-5.0 | Moderately | 49-40 | | |
| 5.1-6.0 | resistant | 39-30 | | |
| 6.1-7.0 | Resistant | 29-20 | | 04DHS11418 |
| 7.1-8.0 | | 19-10 | | |
| 8.1-9.0 | Highly resistant | 9-0 | | |

*SSDI % *Sclerotinia sclerotiorum* Disease Incidence %. SSDI % is UNSSDI (where UNSSDI is the percentage of plants in a population infected with *Sclerotinia*) rating adjusted for a deviation from the expected mean of checks 04DHS11418 (25%) and PHI2004HS1 (75%) as described on Table 4. This rating is used only under controlled extreme disease pressure field research conditions. It is calculated by multiplying the observed SSDI % by Factor X, where Factor X is the factor that brings the average SSDI % of the appropriate checks to 50%. Adjustment for severity is not done.
**SSDIS *Sclerotinia sclerotiorum* . SSDIS is the UNSSDI rating adjusted for a deviation from the expected mean of checks 46A65/46A76 for spring canola under extreme disease pressure This rating is used only under controlled extreme disease pressure field research conditions. It is calculated by multiplying the observed UNSSDI by Factor X, where Factor X is the factor that brings the average SSDI % of the appropriate checks to 50%. Adjustment for severity is done after incidence adjustment.
UNSSDS is a rating of the extent of disease development on an affected plant. Two scales are used in the invention. The Pioneer SSDS scale ranges from 1 (dead) to 9 (no disease) and the Public scale ranges from 0 (no disease) to 5 (dead) plant. For details of the Pioneer SSDS scale, see Table 15 of WO 2006/135717. The Public scale is provided as follows: 0 = no disease; 1 = superficial lesions or small branch affected; 2 = large branch dead; 3 = main stem at least 50% girdled; 4 = main stem girdled but plant produced good seed; 5 = main stem girdled, much reduced yield.

Both parents have good standability. Therefore, standability or lodging resistance is fixed, thus eliminating this variable in the mapping process. The choice of a highly susceptible line resulted in a population without transgressive segregation (i.e., all resistance came from 04DHS11418 and no DH progeny lines were more resistant than the resistant parent). Over a period of four years, the population was phenotyped in the field and genotyped with SSR molecular markers. Phenotyping was carried out as described in WO 2006/135717, the entire teachings of which are hereby incorporated by reference.

Example 2: RNA Expression Profiling

RNA expression profiling experiments were carried using 04DHS11418, PHI2004HS1, resistant and susceptible bulks (comprised of susceptible and resistant double haploid (DH) progenies). Intact leaf tissues (not inoculated) were used, as well as leaf tissues sampled 6, 24 and 48 hours after leaf inoculation with mycelium. RNA expression profiling was performed by probing the different bulks with a chip consisting of *Brassica* (85,820) and *Arabidopsis* stress-related (17,617) nucleic acid sequences. A number of genes related to *Sclerotinia* disease resistance or to pectin (these genes are associated with cell wall integrity) were upregulated when inoculated with mycelium at 6, 24 and 48 hours. A summary of the results can be found in Table 3. Some of these genes were sequenced in the resistant and susceptible lines to find any SNPs. These SNPs were then added to the genetic map (termed KK).

TABLE 3

| Number of disease related genes upregulated at different time treatments. | | | | | | | | | | |
|---|---|---|---|---|---|---|---|---|---|---|
| | Pectin-Related Gene Sorting | | | | | Disease Resistance-Related Gene Sorting | | | | |
| Treatment | Total | 1 Set | 2 Set | 3 Set | 4 Set | Total | 1 Set | 2 Set | 3 Set | 4 Set |
| 6 Hour Treatment | 25 | 13 | 4 | 7 | 1 | 19 | 11 | 4 | 3 | 1 |
| 24 Hour Treatment | 65 | 21 | 38 | 6 | 0 | 48 | 38 | 9 | 0 | 1 |

TABLE 3-continued Number of disease related genes upregulated at different time treatments.

| Treatment | Pectin-Related Gene Sorting | | | | | Disease Resistance-Related Gene Sorting | | | | |
|---|---|---|---|---|---|---|---|---|---|---|
| | Total | 1 Set | 2 Set | 3 Set | 4 Set | Total | 1 Set | 2 Set | 3 Set | 4 Set |
| 48 Hour Treatment | 60 | 53 | 5 | 2 | 0 | 52 | 43 | 6 | 3 | 0 |
| Total | 150 | 87 | 47 | 15 | 1 | 119 | 92 | 19 | 6 | 2 |

Example 3: *Sclerotinia* Screening

Disease Scoring

The plants of the double haploid mapping population created as described in Example 1, were rated for disease as described in Table 4. The unadjusted parameters (e.g., UNSSDI and UNSSDS) showed year to year variatation due to environmental variation such as positional variation in the field and weather conditions. Such variation would be expected by one skilled in the art.

Example 4: Genetic Mapping and QTL Analysis

Genetic mapping and QTL analysis were performed using JoinMap v3.0 (Van Ooijen, J. W. and R. E. Voorrips, 2001 JoinMap® 3.0, Software for the calculation of genetic linkage maps. Plant Research International, Wageningen, the Netherlands). The Kosambi centiMorgan function was used. A QTL was declared if its LOD score exceeded the threshold of 2.0.

TABLE 4

Field-collected *Sclerotinia* parameters UNSSDI and UNSSDS and their relationship to derived parameters SSDI %, SSDIS (research data) and SSFS (natural/research data).

| Trait | UNSSDI Disease Incidence | UNSSDS Disease severity of affected plants | SSDI % Based on adjusted UNSSDI under extreme disease pressure field research conditions | SSDIS Based on adjusted UNSSDI and UNSSDS under extreme disease pressure field research conditions | SSFS Field severity based on both UNSSDI and UNSSDS used in natural field conditions or research |
|---|---|---|---|---|---|
| Scale | 0-100% | Pioneer SSDS scale 1 = dead 9 = no disease Public scale 0 = no disease 5 = dead plant | 0-100% Conversion of UNSSDI and adjustment for checks' UNSSDI | 1-9 Conversion of UNSSDI and UNSSDS adjustment for checks' UNSSDI and UNSSDS | 0-100% % field impact - quantifies damage in the field irrespective of disease pressure |
| Usage Adjustments Hypothetical Examples (HE): Different combinations of disease incidence and disease severity | General N/A | General N/A Pioneer SSDS scale / Public scale | Pioneer only Adjusted to checks *assuming checks do not deviate for UNSSDI | Pioneer only Adjusted to checks **assuming checks to do not deviate for UNSSDI and UNSSDS | General Unadjusted |
| HE 1 | 80 | 1 | 5.0 | *80 | **1.0 (80) | 80 |
| HE 2 | 80 | 5 | 2.0 | 80 | 2.6 (64) | 32 |
| HE 3 | 50 | 5 | 2.0 | 50 | 5.0 (40) | 20 |
| HE 4 | 30 | 7 | 1.0 | 30 | 7.3 (17) | 6 |
| HE 5 | 10 | 8 | 1.0 | 10 | 8.5 (5) | 2 |

UNSSDI is the percentage of plants in a population infected with *Sclerotinia*.
UNSSDS is a rating of the extent of disease development on an affected plant. Two scales are used in the invention. The Pioneer SSDS scale ranges from 1 (dead) to 9 (no disease) and the Public scale ranges from 0 (no disease) to 5 (dead) plant. For details of the Pioneer SSDS scale, see Table 15 of WO 2006/135717. The Public scale is provided as follows: 0 = no disease; 1 = superficial lesions or small branch affected; 2 = large branch dead; 3 = main stem at least 50% girdled; 4 = main stem girdled but plant produced good seed; 5 = main stem girdled, much reduced yield.
SSDI % is UNSSDI rating adjusted for a deviation from the expected mean of checks 04DHS11418 (25%) and PHI2004HS1 (75%) as described on Table 4. This rating is used only under controlled extreme disease pressure field research conditions. It is calculated by multiplying the observed SSDI % by Factor X, where Factor X is the factor that brings the average SSDI % of the appropriate checks to 50%. Adjustment for severity is not done.
SSDIS is UNSSDI rating adjusted for a deviation from the expected mean of checks 04DHS11418 (25%) and PHI2004HS1 (75%) as described on Table 4. This rating is used only under controlled extreme disease pressure field research conditions. It is calculated by multiplying the observed UNSSDI by Factor X, where Factor X is the factor that brings the average SSDI % of the appropriate checks to 50%. Adjustment for severity is done after incidence adjustment.
SSFS is a measure of both disease incidence and severity under natural disease pressure in the field. It is calculated as follows: SSFS = [SSDI % × SSDS(0-5 scale)] ÷ 5

Genetic Mapping

Genetic mapping has placed 351 molecular markers to 19 linkage groups (Lg) that correspond to 19 canola chromosomes and public linkage group nomenclature. The linkage map covers ~1400 cM.

QTL Analysis

QTL analysis using simple interval mapping and composite interval mapping (CIM) (Zeng (1994), Genetics 136: 1457) identified 7 linkage groups (N1, N7, N9, N11, N12, N18 and N19) contributing to whole plant field resistance to *Sclerotinia*. In addition, regions identified by interval mapping as being associated with *Sclerotinia* resistance were confirmed by single-factor analysis of variance (PROC GLM, SAS Enterprise Guide 4.2) on *Sclerotinia* parameters at the P≤0.01 significance level. These QTLs are identified in Tables 5 and 6 below. As shown by the "Phenotypic Variation Explained" values in Table 6, some QTLs had a larger effect on *Sclerotinia* resistance than others.

Genetic mapping and QTL analysis were performed using JoinMap v3.0 (Van Ooijen, J. W. and R. E. Voorrips, 2001 JoinMap® 3.0, Software for the calculation of genetic linkage maps. Plant Research International, Wageningen, the Netherlands). The Kosambi centiMorgan function was used. A QTL was declared if its LOD score exceeded the threshold of 2.0. LOD stands for logarithm of the odds (to the base 10).

TABLE 5

Markers significantly associated with *Sclerotinia* resistance at P ≤ 0.01.

| Linkage Group | Marker | Map Position (cM) | Parameter | Year |
|---|---|---|---|---|
| N1 | AG0093 | 48.1 | UNSSDS | 2008 |
| | AG0243 | 52.2 | UNSSDS, SSFS, SSDIS | 2008 |
| | BG1453 | 52.8 | UNSSDS, SSDIS | 2008 |
| | UB0163 | 54.3 | SSFS, SSDIS | 2008 |
| | AG0391 | 55.4 | UNSSDS, SSFS, SSDIS, SSDI % | 2008 |
| | AG0045 | 55.7 | SSFS, SSDIS | 2008 |
| | AG0304 | 56.4 | SSFS, SSDIS | 2008 |
| | PE0203 | 57.2 | SSDIS | 2008 |
| | BG0119 | 58.6 | SSFS, SSDIS | 2008 |
| | BG0988 | 60.3 | SSDI % | 2005 |
| | | | UNSSDS, UNSSDI, SSFS, SSDI % | 2008 |
| | AG0482 | 66.1 | UNSSDS, SSFS, SSDIS, SSDI % | 2005 |
| | | | SSFS, SSDIS | 2006 |
| | | | UNSSDS, UNSSDI, SSFS, SSDIS, SSDI % | 2008 |
| | | | UNSSDS, SSFS, SSDIS | Across years |
| N7 | AG0510 | 0.0 | UNSSDS, UNSSDI, SSFS, SSDIS, SSDI % | 2007 |
| | | | UNSSDS, UNSSDI, SSFS, SSDIS, SSDI % | Across years |
| | CA0105 | 0.5 | UNSSDS | 2006 |
| | | | UNSSDS, UNSSDI, SSFS, SSDIS, SSDI % | 2007 |
| | | | UNSSDS, UNSSDI, SSFS, SSDIS, SSDI % | Across years |
| N9 | AG0378 | 0.0 | UNSSDI, SSFS | 2006 |
| | | | UNSSDI | Across years |
| | KK66 | 4.0 | UNSSDI | 2006 |
| | | | UNSSDI | Across years |
| N11 | CA0120 | 21.9 | UNSSDS | Across years |
| | CA0233 | 28.8 | UNSSDS | 2006, Across years |
| | | | SSFS | 2007 |
| | CA0226 | 30.7 | UNSSDS | 2006, Across years |
| | CA0546 | 30.7 | UNSSDS | 2006 |
| | | | SSFS | 2007 |
| | | | UNSSDS, SSDIS, SSFS | Across years |
| | BG1149 | 30.8 | UNSSDS | 2006, 2007, Across years |
| | | | SSFS | 2007, Across years |
| | CA1080 | 30.8 | UNSSDS, SSFS | 2006 |
| | | | SSFS, SSDIS | 2007 |
| | | | UNSSDS, SSFS, SSDIS | Across years |
| | BG1230 | 31.3 | UNSSDS | 2006 |
| | | | UNSSDS, SSFS | Across years |
| | AG0370 | 31.3 | UNSSDS | 2006 |
| | | | UNSSDS, SSFS | Across years |
| | BG0713 | 31.7 | UNSSDS | 2006, Across years |
| | | | SSFS | 2007, Across years |
| | BG0869 | 32.9 | UNSSDS | 2006, Across years |
| | BG1513 | 33.3 | UNSSDS | 2006, Across years |
| | BG0181 | 33.4 | UNSSDS | 2006, Across years |
| | CA1097 | 36.2 | UNSSDS, SSFS | 2006 |
| | | | UNSSDI, SSFS | 2007 |
| | | | UNSSDI, SSFS | 2008 |
| | | | UNSSDS, SSFS, SSDIS | Across years |
| N12 | CA0753 | 60.5 | UNSSDS | 2005, Across years |
| | CA1027 | 78.9 | UNSSDS, SSFS | 2005 |
| | | | UNSSDS, SSFS, SSDIS, SSDI % | 2006 |
| | | | UNSSDS | Across years |
| | PE0063 | 79.3 | UNSSDS, SSFS | 2005 |
| | | | UNSSDS, SSFS, SSDIS, SSDI % | 2006 |
| | | | UNSSDS, SSFS | Across years |

TABLE 5-continued

Markers significantly associated with *Sclerotinia* resistance at P ≤ 0.01.

| Linkage Group | Marker | Map Position (cM) | Parameter | Year |
|---|---|---|---|---|
| | UB0331 | 83.1 | UNSSDS, SSFS | 2005 |
| | | | UNSSDS, SSFS, SSDIS, SSDI % | 2006 |
| | | | UNSSDS | Across years |
| | CA0681 | 84.7 | UNSSDS | 2005 |
| | | | UNSSDS, SSFS, SSDIS, SSDI % | 2006 |
| | | | UNSSDS, SSFS | Across years |
| | AG0359 | 93.0 | UNSSDS, UNSSDI, SSFS, SSDIS, SSDI % | 2006 |
| | | | UNSSDS, SSFS, SSDIS, SSDI % | Across years |
| | CA0423 | 95.6 | UNSSDS | 2005 |
| | | | UNSSDS, UNSSDI, SSFS, SSDIS, SSDI % | 2006 |
| | | | UNSSDS, SSFS, SSDI % | Across years |
| | AG0086 | 96.1 | SSFS | 2005 |
| | | | UNSSDS, UNSSDI, SSFS, SSDIS, SSDI % | 2006 |
| | | | UNSSDS, SSFS, SSDIS, SSDI % | Across years |
| | CA0896 | 96.4 | UNSSDS, SSFS, SSDIS, SSDI % | 2006, Across years |
| | PE0250 | 96.6 | SSFS | 2005 |
| | | | UNSSDS, UNSSDI, SSFS, SSDIS, SSDI % | 2006 |
| | | | UNSSDS, SSFS, SSDIS, SSDI % | Across years |
| N18 | UB0315 | 34.8 | UNSSDI, SSDI % | 2008 |
| | CA0739 | 42.2 | UNSSDI, SSDI % | 2008 |
| N19 | UB0307 | 30.1 | UNSSDS, SSFS, SSDIS, SSDI % | 2005 |
| | | | UNSSDI, SSFS, SSDIS, SSDI % | 2006 |
| | | | UNSSDI, SSFS, SSDIS, SSDI % | Across years |
| | CA0221 | 31.6 | UNSSDS, SSFS, SSDIS, SSDI % | 2005 |
| | | | SSDIS | Across years |
| | BG1241 | 32.3 | UNSSDS, SSFS, SSDIS, SSDI % | 2005 |
| | | | UNSSDI, SSFS, SSDIS | Across years |
| | KK98G | 41.8 | UNSSDS, UNSSDI, SSFS, SSDIS, SSDI % | 2005 |
| | | | UNSSDI | 2006 |
| | | | UNSSDI, SSFS, SSDIS, SSDI % | Across years |

TABLE 6

QTLs associated with *Sclerotinia* whole plant field tolerance.

| Linkage | Parameter | Year | QTL interval | LOD score | Phenotypic variation explained (%) |
|---|---|---|---|---|---|
| N1 | SSDI %, SSDIS, SSFS, UNSSDS | 2005 | BG0988-AG0482 | 3.2 | 7.9 |
| | SSFS, SSDIS | 2008 | AG0243-AG0482 | 2.4 | 16.5 |
| | UNSSDS | 2008 | AG0243-BG1453 | 2.4 | 16.6 |
| | SSDI % | 2008 | BG0988-AG0482 | 2.6 | 17.8 |
| | SSDIS | across years | BG0988-AG0482 | 2.2 | 5.5 |
| N7 | SSDI %, SSDIS, UNSSDS | 2007 | AG0510-CA0105 | 3.4 | 8.7 |
| | SSDIS | across years | AG0510-CA0105 | 2.3 | 5.7 |
| N9 | UNSSDI | 2006, across years | AG0378-KK66 | 3.4 | 8.3 |
| N11 | UNSSDS | 2006 | CA0226-BG0713 | 3.4 | 7.7 |
| | SSFS | 2007 | CA0233-CA1080 | 2.2 | 5.5 |
| | SSFS, UNSSDS | across years | CA0233-AG0370 | 3.3 | 7.9 |
| N12 | SSFS | 2005 | CA1027-PE0063 | 2.3 | 5.7 |
| | UNSSDS | 2005 | CA1027-UB0331 | 3.0 | 7.1 |
| | SSDI %, SSDIS, SSFS, UNSSDS, UNSSDI | 2006 | CA0423-PE0250 | 4.4 | 10.3 |
| | SSDI % | across years | CA0423-PE0250 | 2.5 | 6.0 |
| | SSDIS, SSFS | across years | AG0359-PE0250 | 2.7 | 6.4 |
| | UNSSDS | across years | AG0359-CA0896 | 3.9 | 9.2 |
| N18 | SSDI %, UNSSDI | 2008 | UB0315-CA0739 | 3.2 | 22.2 |
| | SSDI %, UNSSDI | across years | UB0315-CA0739 | 2.4 | 17.2 |
| N19 | SSDIS, SSFS | 2005 | CA0221-KK98G | 2.6 | 6.3 |
| | SSDIS | 2006 | UB0307-BG1241 | 2.1 | 5.0 |
| | SSDI %, SSFS | across years | BG1241-KK98G | 2.2 | 5.4 |
| | SSDIS, UNSSDI | across years | CA0221-BG1241 | 2.4 | 5.7 |

Additional information about the SSR markers flanking the seven QTLs associated with whole field plant resistance to *Sclerotinia* are shown in Table 14 in Example 12. The forward and reverse primer sequences for each marker are also provided. "Repeat" indicates the SSRs or SNPs associated with each marker. The positions of the SSRs and SNPS are shown in the sequence information located at the end of the specification.

Additional information about the alleles and allele size of each SSR marker flanking the 7 QTLs associated with whole plant field resistance to *Sclerotinia* is provided in Table 7.

TABLE 7

The alleles and allele size of each SSR marker flanking the seven *Sclerotinia* (SCL) QTLs.

| Linkage Group | Marker | Allele | Allele Size | Favorable allele for SCL |
|---|---|---|---|---|
| N1 | AG0093 | a | 221 | |
| | AG0093 | b | 223 | yes |
| | AG0243 | a | 177 | |
| | AG0243 | b | 182 | |
| | AG0243 | c | 193 | |
| | AG0243 | d | 189 | |
| | AG0243 | e | null | yes |
| | BG1453 | a | 120 | |
| | BG1453 | b | 122 | |
| | BG1453 | c | 130 | |
| | BG1453 | d | 132 | yes |
| | BG1453 | e | 134 | |
| | BG1453 | f | 146 | |
| | BG1453 | g | 148 | |
| | BG1453 | h | 152 | |
| | BG1453 | i | 154 | |
| | BG1453 | j | 156 | |
| | BG1453 | k | 172 | |
| | BG1453 | l | 142 | |
| | BG1453 | m | 138 | |
| | BG1453 | n | 158 | |
| | BG1453 | o | 162 | |
| | BG1453 | p | 144 | |
| | BG1453 | q | 136 | |
| | BG1453 | r | 176 | |
| | BG1453 | s | 114 | |
| | BG1453 | t | 160 | |
| | UB0163 | b | 111 | |
| | UB0163 | c | 129 | yes |
| | UB0163 | e | 107 | |
| | UB0163 | f | 117 | |
| | AG0391 | c | 139 | |
| | AG0391 | a | 127 | yes |
| | AG0045 | a | 168 | |
| | AG0045 | b | 170 | yes |
| | AG0304 | a | 163 | |
| | AG0304 | b | 226 | |
| | AG0304 | c | 229 | yes |
| | PE0203 | a | 205 | |
| | PE0203 | b | 209 | yes |
| | PE0203 | c | 211 | |
| | PE0203 | d | 203 | |
| | PE0203 | e | 207 | |
| | BG0119 | a | 270 | |
| | BG0119 | b | 252 | yes |
| | BG0988 | a | 184 | |
| | BG0988 | b | 208 | |
| | BG0988 | c | 200 | yes |
| | BG0988 | d | 190 | |
| | BG0988 | e | 208 | |
| | BG0988 | f | 186 | |
| | AG0482 | a | 277 | yes |
| | AG0482 | b | 280 | |
| | AG0482 | c | 283 | |
| | AG0482 | d | 286 | |
| | AG0482 | e | 271 | |
| N7 | AG0510 | a | 272 | |
| | AG0510 | b | 278 | |
| | AG0510 | c | 282 | yes |
| | CA0105 | a | 152 | yes |
| | CA0105 | b | 170 | |
| N9 | AG0378 | a | 275 | |
| | AG0378 | b | 281 | yes |
| | AG0378 | c | 290 | |
| | AG0378 | d | 293 | |
| | AG0378 | e | 284 | |
| | AG0378 | f | 312 | |
| | AG0378 | g | 299 | |
| | AG0378 | h | 296 | |
| N11 | CA0120 | a | 138 | |
| | CA0120 | b | 160 | |
| | CA0120 | c | 172 | yes |
| | CA0120 | d | 163 | |
| | CA0120 | e | 169 | |
| | CA0233 | a | 298 | yes |
| | CA0226 | a | 229 | |
| | CA0226 | b | 250 | yes |
| | CA0226 | c | 252 | |
| | CA0226 | d | 221 | |
| | CA0226 | e | 344 | |
| | CA0546 | a | 110 | |
| | CA0546 | b | 120 | |
| | CA0546 | c | 123 | |
| | CA0546 | d | 146 | yes |
| | CA0546 | e | 149 | |
| | CA0546 | f | 126 | |
| | CA0546 | g | 144 | |
| | CA0546 | h | 112 | |
| | BG1149 | a | 260 | yes |
| | BG1149 | b | 266 | |
| | BG1149 | c | 263 | |
| | CA1080 | a | 300 | |
| | CA1080 | b | 303 | |
| | CA1080 | c | 306 | |
| | CA1080 | d | 325 | |
| | CA1080 | e | 336 | |
| | CA1080 | f | 339 | yes |
| | CA1080 | g | 342 | |
| | CA1080 | h | 345 | |
| | CA1080 | i | 348 | |
| | CA1080 | j | 351 | |
| | CA1080 | k | 354 | |
| | CA1080 | l | 357 | |
| | CA1080 | m | 333 | |
| | CA1080 | n | 330 | |
| | BG1230 | a | 252 | |
| | BG1230 | b | 288 | yes |
| | AG0370 | a | 283 | yes |
| | AG0370 | b | 290 | |
| | AG0370 | c | 298 | |
| | AG0370 | d | 316 | |
| | AG0370 | e | 287 | |
| | BG0713 | a | 222 | |
| | BG0713 | b | 226 | yes |
| | BG0713 | c | 228 | |
| | BG0713 | d | 216 | |
| | BG0869 | a | 212 | |
| | BG0869 | b | 216 | yes |
| | BG1513 | a | 164 | yes |
| | BG1513 | b | 214 | |
| | BG1513 | c | 216 | |
| | BG0181 | a | 210 | |
| | BG0181 | b | 216 | yes |
| | CA1097 | a | 245 | |
| | CA1097 | b | 248 | yes |
| | CA1097 | c | 251 | |
| | CA1097 | d | 260 | |
| | CA1097 | e | 239 | |
| N12 | CA0753 | a | 214 | |
| | CA0753 | b | 216 | |
| | CA0753 | c | 281 | yes |

TABLE 7-continued

The alleles and allele size of each SSR marker flanking the seven Sclerotinia (SCL) QTLs.

| Linkage Group | Marker | Allele | Allele Size | Favorable allele for SCL |
|---|---|---|---|---|
| | CA0753 | d | 291 | |
| | CA0753 | e | 218 | |
| | CA1027 | a | 297 | yes |
| | CA1027 | b | 300 | |
| | CA1027 | c | 303 | |
| | CA1027 | d | 306 | |
| | PE0063 | a | 114 | |
| | PE0063 | b | 126 | yes |
| | UB0331 | a | 123 | |
| | UB0331 | b | 126 | yes |
| | CA0681 | a | 264 | |
| | CA0681 | b | 266 | yes |
| | CA0681 | c | 268 | |
| | CA0681 | d | 276 | |
| | AG0359 | a | 306 | |
| | AG0359 | b | 330 | yes |
| | AG0359 | d | 315 | |
| | AG0359 | f | 312 | |
| | CA0423 | a | 195 | |
| | CA0423 | b | 201 | |
| | CA0423 | c | 204 | |
| | CA0423 | d | 207 | yes |
| | CA0423 | e | 210 | |
| | AG0086 | a | 238 | |
| | AG0086 | b | 226 | yes |
| | AG0086 | c | 232 | |
| | CA0896 | a | 254 | yes |
| | CA0896 | b | 266 | |
| | CA0896 | c | 260 | |
| | PE0250 | a | 239 | |
| | PE0250 | b | 245 | yes |
| | PE0250 | c | 269 | |
| N18 | UB0315 | a | 127 | |
| | UB0315 | b | 131 | yes |
| | UB0315 | c | 133 | |
| | CA0739 | a | 220 | |
| | CA0739 | b | 222 | |
| | CA0739 | c | 232 | |
| | CA0739 | d | 234 | yes |
| | CA0739 | e | 240 | |
| | CA0739 | f | 224 | |
| | CA0739 | g | 236 | |
| | CA0739 | h | 242 | |
| N19 | UB0307 | a | 120 | yes |
| | UB0307 | b | 126 | |
| | UB0307 | c | 134 | |
| | UB0307 | e | 108 | |
| | CA0221 | a | 271 | |
| | CA0221 | b | 253 | yes |
| | CA0221 | c | 265 | |
| | BG1241 | a | 370 | |
| | BG1241 | b | 329 | yes |

Example 5: Validation of the 7 QTLs Associated with Whole Plant Field Resistance to *Sclerotinia*

Simulated validation of the 7 QTLs associated with whole plant field resistance to *Sclerotinia* was performed on 16 *Sclerotinia*-resistant and 10 *Sclerotinia* susceptible breeding lines from Pioneer Hi-Bred's spring canola program under extreme disease pressure field research conditions. This allowed the development of extreme disease conditions every year, regardless of the natural environment.

Referring to Table 8 below, each resistant line was genotyped for SSR markers flanking the seven QTLs identified. In Table 8, the first digit in the QTL group refers to the linkage group and the second digit refers to the QTL number on that linkage group. The number above the marker names represent the positions (in centiMorgans) of the marker on the linkage group. Each allele was denoted as i) present only in resistant lines (noted as * in Table 8), ii) present only in susceptible lines (noted as * in Table 8), or iii) present in both resistant and susceptible lines (noted as  in Table 8). The total number of favorable alleles were added for each breeding line by assigning either 1) (allele present only in resistant line), 0.5 (allele is present in both resistant and susceptible) or 0 (allele present only in susceptible line). The percentage of favorable alleles in the resistant lines ranged from 63-90% and only 13-47% in susceptible breeding lines. This correlation indicates that the markers flanking the seven QTLs identified as being associated with *Sclerotinia* in breeding populations can be used to select for individuals that had the highest number of favorable alleles in breeding populations. Those individuals with the highest percentage of favorable alleles would be selected as good candidates for *Sclerotinia* resistance.

TABLE 8

Comparison of allele scores among three groups: sources of *Sclerotinia* resistance, elite lines with *Sclerotinia* resistance, and elite lines susceptible to *Sclerotinia*. (First number in QTL name refers to linkage groups and second number refers to QTL number on that linkage group

| | | *Sclerotinia* QTLs and Flanking SSR Markers | | | | | | | |
|---|---|---|---|---|---|---|---|---|---|
| | | Scl_1.1 | | Scl_7.1 | | Scl_9.1 | | Scl_11.1 | |
| | | 60.3 | 66.1 | 0 | 0.5 | 0 | 28.8 | 30.8 | 31.3 |
| | SSDIS | BG0988 | AG0482 | AG0510 | CA0105 | AG0378 | CA0233 | BG1149 | AG0370 |
| Sources of *Sclerotinia* Resistance | | | | | | | | | |
| WC-865 | 5.5 | A* | b,d* | a,b** | a* | a** | +* | a,c* | d* |
| 04DHS11418 (Mapping Parent) | 6.5 | C** | a,b* | a,c* | a* | b* | +* | a* | a* |
| SC-1068 | 6.8 | C** | a,b* | a,c* | a* | d*** | +* | a* | a* |
| SC-1349 | 7.2 | C** | b,d* | a* | | d*** | +* | a* | a* |
| SC-182 | 6.0 | C** | b,d* | a,c* | a* | b,d* | +* | a* | d* |

TABLE 8-continued

Comparison of allele scores among three groups: sources of *Sclerotinia* resistance,
elite lines with *Sclerotinia* resistance, and elite lines susceptible to *Sclerotinia*. (First number in
QTL name refers to linkage groups and second number refers to QTL number on that linkage group

| | | | | | | | | | |
|---|---|---|---|---|---|---|---|---|---|
| Elite lines with SCL resistance | | | | | | | | | |
| SC-391 | 5.0 | C** | b,c,d* | a,b** | a,b** | b,d* | +* | **** | a* |
| SC-631 | 6.0 | C** | b,d* | a,b** | b*** | b* | +* | **** | a* |
| SC-613 | 5.0 | C** | a,b,c** | c** | a* | b* | +* | a,c* | a* |
| SC-940 | 6.0 | C** | b,d* | a,b** | b*** | b,d* | +* | a* | a* |
| SC-942 | 5.0 | B* | b,d* | c** | a* | a** | +* | a* | b** |
| SC-1023 | 5.0 | D*** | b,c** | a* | a* | b* | +* | a* | a* |
| SC-1178 | 5.0 | B* | d** | a,c* | a* | a** | .*** | b*** | b** |
| SC-1179 | 6.0 | B* | b,d* | c** | a* | b* | .*** | c*** | b** |
| SC-1180 | 6.0 | B* | b,d* | a* | a* | b* | +* | a* | b** |
| SC-1284 | 6.0 | B* | b,d* | a,c* | a* | a** | +* | a* | b** |
| SC-1285 | 7.0 | B* | b,d* | b** | b*** | b* | +* | a* | b** |
| Elite susceptible lines | | | | | | | | | |
| SC-067 | 1.0 | C** | b,c* | a,b** | b*** | d*** | .*** | b*** | b** |
| SC-062 | 2.0 | C** | **** | b** | b*** | a,d*** | +* | a* | b** |
| SC-004 | 2.0 | C** | b,c** | a,b** | b*** | d*** | .*** | b*** | b** |
| SC-101 | 3.0 | D*** | a,b,c** | a,b,c*** | a,b** | a** | .*** | c*** | c*** |
| SC-105 | 2.0 | C** | b,c** | a,b** | b*** | d*** | .*** | c*** | a* |
| SC-112 | 2.0 | E*** | d** | b** | b*** | a** | .*** | b*** | b** |
| SC-129 | 2.0 | D*** | b,c** | c** | a* | d*** | .*** | c*** | c*** |
| SC-139 | 1.0 | C** | b,c** | a,b** | b*** | a** | .*** | b*** | b** |
| SC-412 | 1.0 | C** | b,c** | a,b,c*** | a* | d*** | +* | c*** | b** |
| PHI2004HS1 (MappingParent) | 1.5 | D*** | b,c** | a,b** | b*** | d*** | .*** | c*** | c*** |

| | | *Sclerotinia* QTLs and Flanking SSR Markers | | | | | | | | |
|---|---|---|---|---|---|---|---|---|---|---|
| | | Scl_12.1 | | | Scl_18.1 | | Scl_19.1 | | | |
| | SSDIS | 93 AG0359 | 96.1 AG0086 | 96.6 PE0250 | 34.8 UB0315 | 42.2 CA0739 | 30.1 UB0307 | 31.6 CA0221 | Number of favorable alleles | Percent favorable alleles |
| **Sources of *Sclerotinia* Resistance** | | | | | | | | | | |
| WC-865 | 5.5 | **** | a* | a,b* | a,b* | e* | a,c** | a,b* | 12.5 | 83% |
| 04DHS11418 (Mapping Parent) | 6.5 | b** | a,b** | a,b* | c* | a,d* | a* | a,b* | 13.5 | 90% |
| SC-1068 | 6.8 | b** | a* | a,b* | c* | a,d* | a,c** | b,c** | 12.0 | 80% |
| SC-1349 | 7.2 | b** | a,b** | a,b* | c* | d* | a* | a,b* | 12.5 | 83% |
| SC-182 | 6.0 | b** | a,b** | a,b* | c* | a,d* | a* | a,b* | 13.5 | 90% |
| Elite lines with SCL resistance | | | | | | | | | | |
| SC-391 | 5.0 | b,d** | a,b** | a,b* | b** | c,d* | a* | a,b* | 11.0 | 73% |
| SC-631 | 6.0 | b,d** | a,b* | a,b* | b** | a,c* | a* | a,b,c* | 11.0 | 73% |
| SC-613 | 5.0 | a,b* | a* | a,b* | b** | a,d* | a,c* | b,c** | 12.0 | 80% |
| SC-940 | 6.0 | b,d** | a,b** | a,b* | b** | d* | a* | a,b* | 11.5 | 77% |
| SC-942 | 5.0 | b** | a,b** | a,b* | b** | c* | a* | a,b,c* | 120 | 80% |
| SC-1023 | 5.0 | b** | a,b** | a,b* | b** | d* | a,c** | b,c** | 11.0 | 73% |
| SC-1178 | 5.0 | b** | a,b** | a,b* | b** | c* | a* | b,c** | 9.5 | 63% |
| SC-1179 | 6.0 | b** | a,b** | a,b* | b** | c* | a* | a,b* | 10.5 | 70% |
| SC-1180 | 6.0 | b** | a,b** | a,b* | b** | a,d* | a* | a,b* | 13.0 | 67% |
| SC-1284 | 6.0 | b** | a,b** | a,b* | b** | a,d* | a* | a,b* | 12.5 | 83% |
| SC-1285 | 7.0 | b** | a,b** | a,b* | **** | a,c* | a* | a,b,c* | 11.0 | 73% |
| Elite susceptible lines | | | | | | | | | | |
| SC-067 | 1.0 | a,d*** | b,c*** | b,c*** | b** | a,e*** | a,c** | b,c** | 3.5 | 23% |
| SC-062 | 2.0 | b** | a,b** | a,b* | a*** | g*** | a,c** | a,b* | 7.0 | 47% |
| SC-004 | 2.0 | b** | a,c*** | a,b,c*** | b** | g*** | a,c** | b,c** | 4.0 | 27% |
| SC-101 | 3.0 | b** | a* | b*** | a*** | a,e** | a* | a,b* | 5.0 | 33% |
| SC-105 | 2.0 | b,d** | a,b** | a,b* | b** | **** | a,c** | a,b* | 6.5 | 43% |
| SC-112 | 2.0 | b** | a,b** | a,b* | b** | **** | a* | b,c** | 6.0 | 40% |
| SC-129 | 2.0 | b** | a,b** | a,b* | b** | d* | a,c** | b,c** | 6.5 | 43% |
| SC-139 | 1.0 | b** | a,b** | a,b* | a*** | g*** | a* | b,c** | 5.0 | 33% |
| SC-412 | 1.0 | b,d** | a,b** | b*** | a*** | **** | a,c** | b,c** | 5.5 | 37% |
| PHI2004HS1 (MappingParent) | 1.5 | a*** | b,c*** | a,b,c*** | b** | a,e*** | a,c** | b,c** | 2.5 | 16% |

*allele combination present only in resistant lines
**allele combination present in resistant and susceptible lines
***allele combination present only in susceptible lines
****undetermined Example 6: Introgressing *Sclerotinia* Resistance from Spring *Brassica napus* to Winter *Brassica napus*

The *Sclerotinia* resistant source 04DHS11418 was crossed to winter canola lines in bi-parental, 3-way or complex crosses (as shown, for example, in Table 9). The F1 cross was then backcrossed to an elite susceptible parent. At the BC1F1 generation, approximately 500 progeny (minimum number required to identify at least one individual with all favorable alleles present) were generated for each cross and submitted for marker analysis using the markers identified as being associated with *Sclerotinia* in spring canola. Each individual sample was examined for presence of the favorable alleles from the *Sclerotinia* resistant line 04DHS11418. The percentage of favorable alleles present in each sample was calculated and the top three from each population were used to cross back to the recurrent parent. This process was repeated again at the BC2 stage. In addition, selections were intermated to develop populations in which individuals could be identified with homozygous desirable *Sclerotinia* alleles.

Example 7: Mapping Population #2

The parents used for the mapping population were 06DSB13911 (a *Sclerotinia* resistant double haploid) and PHI2008HS1 (a susceptible spring canola DH line polymorphic to the resistant line, selected for having a similar agronomic phenotype with consistent high susceptibility in the same testing environment where the 06DSB13911 line was selected for resistance) (see Table 10). These lines were used to develop a double haploid mapping population consisting of 187 progeny.

TABLE 10

Measuring field performance under extreme disease pressure (research trials)

| Rating SSDIS** | Category | Disease incidence SSDI %* | Spring Checks | Mapping Parents |
|---|---|---|---|---|
| 1.0 | Highly susceptible | ≥80 | 44A89 = 1 | |
| 1.1-2.0 | Susceptible | 79-70 | 46A65 = 2 | PHI2008HS1 |

TABLE 9

Example of introgression of *Sclerotinia* resistance into winter *B. napus* using marker-assisted selection

| | Sample Name | N9 AG 0378 | N7 AG 0510 | N7 BG 1439 | N18 CA 0739 | N18 UB 0315 | N1 AG 0482 | N1 BG 0988 | N11 AG 0370 | N19 BG 1241 | N12 AG 0359 | N12 CA 0423 | Number of favorable alleles | Percent favorable alleles |
|---|---|---|---|---|---|---|---|---|---|---|---|---|---|---|
| | | | | | | Example Set 1 MAS Results | | | | | | | | |
| Female | 04DHS11418 | b | a, c | a, b | a, d | c | a, b | c | a | d | b | b, d | | |
| Male | WC-058 | b | a, b | a | g | a | d | a | d | e | a | a, e | | |
| | WC-022 | b | a, b | a | g | a | d | e | a | e | a | e | | |
| | WC-663 | b | a, b | a | c, g | a | d | a, e | d | e | a | d, e | | |
| | 09-CMAS-01-1641 | b, d | b | a, b | a, d, g | a, c | b, d | c, e | a | d, e | a, b | b, d, e | 9.5 | 86.4 |
| | 09-CMAS-01-1737 | b, d | a, b | a, b | a, d, g | a, c | a, d | c, e | a | d, e | a, b | b, d, e | 9.5 | 86.4 |
| | | | | | | Example Set 2 MAS Results | | | | | | | | |
| Male | 04DHS11418 | B | a, c | a, b | a, d | c | a, b | c | a | d | b | b, d | | |
| | WC-058 | D | a, b | a | g | a | d | a | d | e | a | a, e | | |
| Female | WC-227 | D | a, b | a | d | a | d | b | a | d | a | a, e | | |
| | 09-CMAS-01-715 | b, d | a, b, c | a, b | a, d | a, c | a, b, d | c, e | a | d | a | a, b, d, e | 10.0 | 90.9 |
| | 09-CMAS-01-929 | b, d | a, b | a, b | a, d | a, c | a, b, d | c, e | a | d | a, b | a, b, d, e | 10.0 | 90.9 |
| | | | | | | Example Set 3 MAS Results | | | | | | | | |
| Male | 04DHS11418 | B | a, c | a, b | a, d | c | a, b | c | a | d | b | b, d | | |
| | WC-058 | D | a, b | a | g | a | d | a | d | e | a | a, e | | |
| Female | WC-063 | D | a, b | a | d | a | d | a | c, d | d | a, c | d, e | | |
| | WC-457 | D | a, b | a, b | c | a | b, d | a | c, d | e | a | d, e | | |
| | WC-227 | D | a, b | A | d | a | d | e | a | c, d | a | a, e | | |
| | 09-CMAS-01-1205 | b, d | a, b, c | a, b | a, d | a, c | a, b, d | a, c | c, d | d | a, b | a, b, d, e | 9.5 | 90.5 |
| | 09-CMAS-01-1234 | b, d | a, b | a, b | a, d | a, c | a, d | c, e | a | d, e | a, b | b, d, e | 9.0 | 85.7 |
| | 09-CMAS-01-1241 | b, d | a, b, c | a, b | a, d | a, c | a, d | c, e | a | d, e | a, b | d, e | 9.0 | 85.7 |

TABLE 10-continued

Measuring field performance under extreme disease pressure (research trials)

| Rating SSDIS** | Category | Disease incidence SSDI %* | Spring Checks | Mapping Parents |
|---|---|---|---|---|
| 2.1-3.0 | Moderately | 69-60 | 46A76 = 3 | |
| 3.1-4.0 | susceptible | 59-50 | | |
| 4.1-5.0 | Moderately | 49-40 | | |
| 5.1-6.0 | resistant | 39-30 | | |
| 6.1-7.0 | Resistant | 29-20 | | |
| 7.1-8.0 | | 19-10 | | 06DSB13911 |
| 8.1-9.0 | Highly resistant | 9-0 | | |

*SSDI % *Sclerotinia sclerotiorum* Disease Incidence %. SSDI % is UNSSDI (where UNSSDI is the percentage of plants in a population infected with *Sclerotinia*) rating adjusted for a deviation from the expected mean of checks 06DSB13911 (15%) and PHI2008HS1 (75%). This rating is used only under controlled extreme disease pressure field research conditions. It is calculated by multiplying the observed UNSSDI % by Factor X, where Factor X is the factor that brings the average SSDI % of the appropriate checks to 45%.
**SSDIS *Sclerotinia sclerotiorum*. SSDIS is the UNSSDI rating adjusted for a deviation from the expected mean of check parents for spring canola under extreme disease pressure. This rating is used only under controlled extreme disease pressure field research conditions. It is calculated by multiplying the observed UNSSDI by Factor X, where Factor X is the factor that brings the average SSDI % of the appropriate checks to 45%. Adjustment for severity is done after incidence adjustment.
UNSSDS is a rating of the extent of disease development on an affected plant. Two scales are used in the invention. The Pioneer SSDS scale ranges from 1 (dead) to 9 (no disease) and the Public scale ranges from 0 (no disease) to 5 (dead) plant. For details of the Pioneer SSDS scale, see Table 15 of WO 2006/135717. The Public scale is provided as follows: 0 = no disease; 1 = superficial lesions or small branch affected; 2 = large branch dead; 3 = main stem at least 50% girdled; 4 = main stem girdled but plant produced good seed; 5 = main stem girdled, much reduced yield.

Both parents have good standability. Therefore, standability or lodging resistance is fixed, thus eliminating this variable in the mapping process. The choice of a highly susceptible line resulted in a population without transgressive segregation (i.e., all resistance came from 06DSB13911 and no DH progeny lines were more resistant than the resistant parent). Over a period of three years, the population was phenotyped in the field and genotyped with SSR molecular markers. Phenotyping was carried out as described in WO 2006/135717, the entire teachings of which are hereby incorporated by reference.

Example 8: *Sclerotinia* Screening

Disease Scoring

The plants of the double haploid mapping population created, as described in Example 7, were rated for disease as described in Table 4 of Example 3. The unadjusted parameters (e.g., UNSSDI and UNSSDS) showed year to year variation due to environmental variation such as positional variation in the field and weather conditions. Such variation would be expected by one skilled in the art.

Example 9: Genetic Mapping and QTL Analysis

Genetic mapping and QTL analysis were performed using JoinMap v3.0 (Van Ooijen, J. W. and R. E. Voorrips, 2001 JoinMap® 3.0, Software for the calculation of genetic linkage maps. Plant Research International, Wageningen, the Netherlands). The Kosambi centiMorgan function was used. A QTL was declared if its LOD score exceeded the threshold of 2.0. LOD stands for logarithm of the odds (to the base 10).

Genetic Mapping

Genetic mapping has placed 278 molecular markers to 19 linkage groups (Lg) that correspond to 19 canola chromosomes and public linkage group nomenclature. The linkage map covers ~1100 cM.

QTL Analysis

QTL analysis using simple interval mapping and composite interval mapping (CIM) (Zeng (1994), Genetics 136: 1457) identified 12 linkage groups (N1, N3, N4, N8, N9, N10, N11, N12, N13, N15, N18 and N19) contributing to whole plant field resistance to *Sclerotinia*. In addition, regions identified by interval mapping as being associated with *Sclerotinia* resistance were confirmed by single-factor analysis of variance (PROC GLM, SAS Enterprise Guide 4.2) on *Sclerotinia* parameters at the P≤0.01 significance level. These QTLs are identified in Tables 11 and 12 below. As shown by the "Phenotypic Variation Explained" values in Table 12, some QTLs had a larger effect on *Sclerotinia* resistance than others.

TABLE 11

Markers significantly associated with *Sclerotinia* resistance at P ≤ 0.01.

| Linkage Group | Marker | Map Position (cM) | Parameter | Year |
|---|---|---|---|---|
| N1 | CA0614 | 8.2 | UNSSDI | 2010 |
| | | | UNSSDS, SSFS, SSDIS | 2009 |
| | BG0111 | 10.9 | UNSSDI, SSDI % | 2010 |
| | BG1392 | 22.7 | UNSSDS, SSFS, SSDIS | 2009 |
| | | | UNSSDI, SSDI %, SSDIS | 2010 |
| | BG1182 | 35.6 | UNSSDS, UNSSDI, SSFS, SSDIS | 2009 |
| | | | UNSSDI, SSDI % | 2010 |
| | BG1090 | 41.9 | UNSSDS, UNSSDI, SSFS, SSDIS | 2009 |
| | | | UNSSDI, SSDI % | 2010 |
| | AG0093 | 46.3 | UNSSDS, UNSSDI, SSFS, SSDIS | 2009 |
| | | | UNSSDI, SSFS, SSDI %, SSDIS | 2010 |
| | BG1453 | 53.1 | UNSSDS, UNSSDI, SSFS, SSDIS | 2009 |
| | | | UNSSDI, SSFS, SSDI %, SSDIS | 2010 |
| | PE0017 | 53.5 | UNSSDS, UNSSDI, SSFS, SSDIS | 2009 |
| | | | UNSSDI, SSFS, SSDI %, SSDIS | 2010 |
| | AG0391 | 56.9 | UNSSDS, SSFS, SSDIS | 2009 |
| | | | UNSSDI, SSFS, SSDI %, SSDIS | 2010 |
| | AG0304 | 56.9 | UNSSDS, SSFS, SSDIS | 2009 |
| | | | UNSSDI, SSFS, SSDI %, SSDIS | 2010 |
| | UB0163 | 57.0 | UNSSDS, UNSSDI, SSFS, SSDIS | 2009 |
| | | | UNSSDI, SSFS, SSDI %, SSDIS | 2010 |
| | PE0203 | 57.5 | UNSSDS, SSFS | 2009 |
| | | | UNSSDI, SSFS, SSDI %, SSDIS | 2010 |

TABLE 11-continued

Markers significantly associated with *Sclerotinia* resistance at P ≤ 0.01.

| Linkage Group | Marker | Map Position (cM) | Parameter | Year |
|---|---|---|---|---|
| | AG0482 | 68.5 | UNSSDI | 2010 |
| | PE0177 | 73.6 | UNSSDS, SSFS, SSDIS | 2009 |
| | | | UNSSDI | 2010 |
| N3 | CA0410 | 0.0 | UNSSDS, SSDIS | 2009 |
| | | | UNSSDI, SSFS | 2011 |
| | BG1368 | 2.2 | UNSSDS, SSFS, SSDIS | 2009 |
| | | | UNSSDI, SSFS | 2011 |
| | BG1197 | 37.3 | UNSSDS, SSFS, SSDIS | 2009 |
| | | | UNSSDI, SSFS | 2011 |
| | | | UNSSDI, SSDI % | 2010 |
| | AG0272 | 40.1 | UNSSDS, SSFS, SSDIS | 2009 |
| | | | UNSSDI, SSDI % | 2010 |
| | AG0023 | 40.1 | UNSSDS, SSFS, SSDIS | 2009 |
| | | | UNSSDI, SSDI % | 2010 |
| N4 | BG1442 | 0.0 | UNSSDS, SSFS | 2009 |
| | | | UNSSDS, UNSSDI, SSFS, SSDI %, SSDIS | 2010 |
| | | | UNSSDI, SSFS, SSDI %, SSDIS | 2011 |
| | UB0181 | 3.9 | UNSSDS, SSFS, SSDIS | 2009 |
| | | | UNSSDS, UNSSDI, SSFS, SSDI %, SSDIS | 2010 |
| | UB0126 | 10.3 | UNSSDS, SSFS, SSDIS | 2009 |
| | | | UNSSDI, SSFS, SSDI %, SSDIS | 2011 |
| | | | UNSSDS, UNSSDI, SSFS, SSDI %, SSDIS | 2010 |
| | AG0477 | 10.8 | UNSSDS, UNSSDI, SSFS, SSDIS | 2009 |
| | | | UNSSDS, UNSSDI, SSFS, SSDI %, SSDIS | 2010 |
| | | | UNSSDI, SSFS, SSDI %, SSDIS | 2011 |
| | BG1127 | 11.0 | UNSSDS, SSFS, SSDIS | 2009 |
| | | | UNSSDS, UNSSDI, SSFS, SSDI %, SSDIS | 2010 |
| | | | UNSSDI, SSFS, SSDI %, SSDIS | 2011 |
| | AG0125 | 14.2 | UNSSDS, SSFS, SSDIS | 2009 |
| | | | UNSSDS, UNSSDI, SSFS, SSDI %, SSDIS | 2010 |
| | | | UNSSDI, SSFS, SSDI %, SSDIS | 2011 |
| | BG1244 | 15.0 | UNSSDS, SSFS, SSDIS | 2009 |
| | | | UNSSDS, UNSSDI, SSFS, SSDI %, SSDIS | 2010 |
| | | | SSFS | 2011 |
| | AG0239 | 15.2 | UNSSDS, SSFS, SSDIS | 2009 |
| | | | UNSSDS, UNSSDI, SSFS, SSDI %, SSDIS | 2010 |
| | | | SSFS | 2011 |
| | AG0203 | 16.1 | UNSSDS, SSFS, SSDIS | 2009 |
| | | | UNSSDS, UNSSDI, SSFS, SSDI %, SSDIS | 2010 |
| | | | SSFS | 2011 |
| | BG0106 | 18.5 | UNSSDS, SSFS, SSDIS | 2009 |
| | | | UNSSDI, SSFS, SSDI %, SSDIS | 2010 |
| | | | SSFS | 2011 |
| N8 | CA0837 | 0.0 | UNSSDS, UNSSDI, SSFS, SSDI %, SSDIS | 2009 |
| | BG0647 | 3.1 | UNSSDS, UNSSDI, SSFS, SSDIS | 2009 |
| | | | UNSSDI | 2011 |
| | AG0070 | 3.1 | UNSSDS, UNSSDI, SSFS, SSDIS | 2009 |
| | | | UNSSDI | 2010 |
| | | | UNSSDI | 2011 |
| | PE0281 | 3.2 | UNSSDS, UNSSDI, SSFS, SSDI %, SSDIS | 2009 |
| | | | UNSSDI | 2011 |
| | AG0324 | 4.6 | UNSSDS, UNSSDI, SSFS, SSDI %, SSDIS | 2009 |
| | BG1101 | 7.3 | UNSSDS, UNSSDI, SSFS, SSDI %, SSDIS | 2009 |
| | | | UNSSDI, SSFS, SSDI %, SSDIS | 2010 |
| | AG0328 | 15.6 | UNSSDS, UNSSDI, SSFS, SSDIS | 2009 |
| | BG1449 | 25.9 | UNSSDS, SSFS, SSDIS | 2009 |
| | | | UNSSDI, SSFS, SSDI %, SSDIS | 2010 |
| | BG1062 | 25.9 | UNSSDS, SSFS, SSDIS | 2009 |
| | | | UNSSDI, SSFS, SSDI %, SSDIS | 2010 |
| | AG0410 | 30.3 | UNSSDS, SSFS, SSDIS | 2009 |
| | BG1286 | 33.2 | UNSSDS | 2009 |
| N9 | CA1034 | 0.0 | UNSSDS, UNSSDI, SSFS, SSDIS | 2009 |
| | | | UNSSDI, SSFS, SSDI %, SSDIS | 2010 |
| | CA0834 | 0.0 | UNSSDS, UNSSDI, SSFS, SSDIS | 2009 |
| | | | UNSSDI, SSFS, SSDI %, SSDIS | 2010 |
| | AG0378 | 0.1 | UNSSDI | 2009 |
| | | | UNSSDI, SSFS, SSDI %, SSDIS | 2010 |
| | BG1123 | 33.4 | UNSSDI, UNSSDS, SSFS, SSDIS | 2011 |
| | AG0323 | 45.8 | UNSSDI, UNSSDS, SSFS, SSDIS | 2011 |
| | BG0295 | 49.5 | UNSSDI, UNSSDS, SSFS, SSDIS | 2011 |
| | AG0441 | 66.6 | UNSSDI, UNSSDS, SSFS, SSDIS | 2011 |
| N10 | BG0228 | 0.0 | UNSSDS, UNSSDI, SSFS, SSDIS | 2009 |
| | PE0355 | 5.1 | SSFS | 2009 |
| | AG0171 | 7.1 | UNSSDS, SSFS | 2009 |

TABLE 11-continued

Markers significantly associated with *Sclerotinia* resistance at P ≤ 0.01.

| Linkage Group | Marker | Map Position (cM) | Parameter | Year |
|---|---|---|---|---|
| | BG0651 | 13.6 | UNSSDS, SSFS | 2009 |
| | BG0255 | 17.9 | UNSSDS, SSFS | 2009 |
| | | | SSDI % | 2011 |
| | AG0047 | 19.9 | UNSSDS, SSFS | 2009 |
| | | | SSDI % | 2011 |
| | UB0196 | 29.4 | SSDI % | 2011 |
| | UB0015 | 29.5 | SSDI % | 2011 |
| | PE0131 | 36.8 | SSDI % | 2011 |
| N11 | CA0120 | 20.6 | UNSSDS | 2010 |
| | BG0452 | 32.8 | UNSSDS | 2010 |
| | | | UNSSDS, UNSSDI, SSFS, SSDIS | 2011 |
| | BG0031 | 34.1 | UNSSDS, UNSSDI, SSFS, SSDIS | 2009 |
| | | | UNSSDS, UNSSDI, SSFS, SSDI %, SSDIS | 2010 |
| | | | UNSSDS, UNSSDI, SSFS, SSDIS | 2011 |
| | CA1035 | 37.5 | UNSSDS, SSFS, SSDIS | 2009 |
| | | | UNSSDS, UNSSDI, SSFS, SSDI %, SSDIS | 2010 |
| | | | UNSSDS, UNSSDI, SSFS, SSDIS | 2011 |
| | CA0546 | 37.5 | UNSSDS, SSFS, SSDIS | 2009 |
| | | | UNSSDS, UNSSDI, SSFS, SSDI %, SSDIS | 2010 |
| | | | UNSSDS, UNSSDI, SSFS, SSDIS | 2011 |
| | CA1032 | 37.5 | UNSSDS, SSFS, SSDIS | 2009 |
| | | | UNSSDS, UNSSDI, SSFS, SSDI %, SSDIS | 2010 |
| | | | UNSSDS, UNSSDI, SSFS, SSDIS | 2011 |
| | BG1149 | 37.8 | UNSSDS, SSFS, SSDIS | 2009 |
| | | | UNSSDS, UNSSDI, SSFS, SSDI %, SSDIS | 2010 |
| | | | UNSSDS, UNSSDI, SSFS, SSDIS | 2011 |
| | BG1230 | 39.1 | UNSSDS, SSFS, SSDIS | 2009 |
| | | | UNSSDS, UNSSDI, SSFS, SSDI %, SSDIS | 2010 |
| | | | UNSSDS, UNSSDI, SSFS, SSDIS | 2011 |
| | BG1513 | 42.0 | UNSSDS | 2009 |
| | | | UNSSDS, UNSSDI, SSFS, SSDI %, SSDIS | 2010 |
| | | | UNSSDS, UNSSDI, SSFS, SSDIS | 2011 |
| | CA0328 | 42.3 | UNSSDS | 2010 |
| | | | UNSSDS, UNSSDI, SSFS, SSDIS | 2011 |
| | PE0324 | 49.1 | UNSSDS | 2010 |
| | | | UNSSDS, UNSSDI, SSFS, SSDIS | 2011 |
| | PE0283 | 53.1 | UNSSDS, UNSSDI, SSFS, SSDI %, SSDIS | 2009, 2010 |
| | CA0163 | 56.6 | UNSSDS, UNSSDI, SSFS, SSDIS | 2009 |
| | | | UNSSDS, UNSSDI, SSFS, SSDI %, SSDIS | 2010 |
| N12 | BG1321 | 0.0 | UNSSDS, UNSSDI, SSFS, SSDIS | 2009 |
| | | | UNSSDI, SSDI % | 2010 |
| | | | UNSSDI, SSDI % | 2011 |
| | PE0133 | 19.9 | UNSSDS, SSFS, SSDI %, SSDIS | 2009 |
| | | | UNSSDI, SSFS, SSDI %, SSDIS | 2010 |
| | | | UNSSDI, SSDI % | 2011 |
| | CA0456 | 21.2 | UNSSDS, SSFS, SSDIS | 2009 |
| | | | UNSSDI, SSFS, SSDI %, SSDIS | 2010 |
| | | | UNSSDI, SSDI % | 2011 |
| | PE0063 | 27.2 | UNSSDS, SSFS, SSDI %, SSDIS | 2009 |
| | | | UNSSDI, SSFS, SSDI %, SSDIS | 2010 |
| | | | UNSSDI, SSDI % | 2011 |
| | CA1027 | 27.2 | UNSSDS, SSFS, SSDI %, SSDIS | 2009 |
| | | | UNSSDS, UNSSDI, SSFS, SSDI %, SSDIS | 2010 |
| | | | UNSSDI, SSDI % | 2011 |
| | BG0864 | 28.9 | SSFS, SSDIS | 2009 |
| | | | UNSSDI, SSFS, SSDI %, SSDIS | 2010 |
| | | | UNSSDI, SSDI % | 2011 |
| | CA1090 | 28.9 | SSFS, SSDIS | 2009 |
| | | | UNSSDI, SSFS, SSDI %, SSDIS | 2010 |
| | | | UNSSDI, SSDI % | 2011 |
| | CA0991 | 28.9 | SSFS, SSDI %, SSDIS | 2009 |
| | | | UNSSDS, UNSSDI, SSFS, SSDI %, SSDIS | 2010 |
| | | | UNSSDI, SSDI % | 2011 |
| N13 | CA0603 | 0.0 | UNSSDI, SSFS, SSDI %, SSDIS | 2010 |
| | BG1288 | 2.9 | UNSSDI, SSFS, SSDI %, SSDIS | 2010 |
| | | | UNSSDI, SSFS, SSDIS | 2011 |
| | CA0488 | 11.9 | UNSSDS, SSFS, SSDIS | 2009 |
| | | | UNSSDI, SSFS, SSDI %, SSDIS | 2010 |
| | | | UNSSDS, SSFS, SSDIS | 2011 |
| | PE0012 | 13.1 | UNSSDS, SSFS, SSDIS | 2009 |
| | | | UNSSDI, SSFS, SSDI %, SSDIS | 2010 |
| | | | UNSSDS, SSFS, SSDIS | 2011 |

TABLE 11-continued

Markers significantly associated with *Sclerotinia* resistance at P ≤ 0.01.

| Linkage Group | Marker | Map Position (cM) | Parameter | Year |
|---|---|---|---|---|
| | PE0340 | 13.5 | UNSSDS, SSFS, SSDIS | 2009 |
| | | | UNSSDI, SSFS, SSDI %, SSDIS | 2010 |
| | | | UNSSDS, SSFS, SSDIS | 2011 |
| | BG0516 | 22.1 | UNSSDS, SSFS, SSDIS | 2009 |
| | | | UNSSDI, SSFS, SSDI %, SSDIS | 2010 |
| | | | UNSSDS, SSFS, SSDIS | 2011 |
| | AG0504 | 42.8 | UNSSDS, UNSSDI, SSFS, SSDIS | 2009 |
| | | | UNSSDI, SSDI %, SSDIS | 2010 |
| | | | UNSSDS, SSFS, SSDIS | 2011 |
| | AG0148 | 55.5 | UNSSDS, UNSSDI, SSFS, SSDIS | 2009 |
| | CA0736 | 65.8 | UNSSDS, SSFS | 2009 |
| N15 | PE0286 | 0.0 | UNSSDS, SSFS, SSDIS | 2009 |
| | | | UNSSDI, SSDI %, SSDIS | 2010 |
| | | | UNSSDI, SSFS, SSDI %, SSDIS | 2011 |
| | PE0091 | 6.7 | UNSSDS, UNSSDI, SSFS, SSDIS | 2009 |
| | | | UNSSDI, SSFS, SSDI %, SSDIS | 2010 |
| | | | UNSSDI, SSFS, SSDI %, SSDIS | 2011 |
| | PE0187 | 15.2 | UNSSDS, UNSSDI, SSFS, SSDIS | 2009 |
| | | | UNSSDI, SSFS, SSDI %, SSDIS | 2010 |
| | | | UNSSDS, SSFS, SSDI %, SSDIS | 2011 |
| | CA0719 | 24.8 | UNSSDI, SSFS, SSDIS | 2009 |
| | | | UNSSDI, SSFS, SSDI %, SSDIS | 2010 |
| | | | UNSSDI, SSFS, SSDI %, SSDIS | 2011 |
| | AG0369 | 43.9 | UNSSDI, SSFS, SSDI %, SSDIS | 2009, 2010 |
| N18 | BG0278 | 12.9 | UNSSDI, SSFS, SSDIS | 2009 |
| | CA0739 | 21.6 | UNSSDS, UNSSDI, SSFS, SSDI %, SSDIS | 2009 |
| | | | UNSSDI, SSDI %, SSDIS | 2010 |
| | UB0315 | 27.0 | UNSSDS, UNSSDI, SSFS, SSDI %, SSDIS | 2009 |
| | | | UNSSDI, SSFS, SSDI %, SSDIS | 2010 |
| | | | SSDI % | 2011 |
| | CA0636 | 32.4 | UNSSDS, UNSSDI, SSFS, SSDIS | 2009 |
| | | | UNSSDI, SSDI % | 2010 |
| | | | SSDI % | 2011 |
| N19 | CA1107 | 0.0 | UNSSDS, SSFS, SSDI %, SSDIS | 2010 |
| | CA0552 | 16.1 | UNSSDS, SSFS, SSDIS | 2009 |
| | | | UNSSDI | 2010 |
| | CA1066 | 19.7 | UNSSDS, SSFS | 2009 |
| | BG1241 | 27.6 | UNSSDI, SSFS, SSDIS | 2009 |
| | | | UNSSDI, SSFS, SSDI %, SSDIS | 2010 |
| | CA0221 | 29.7 | UNSSDS, SSFS, SSDIS | 2009 |

TABLE 12

QTL interval, LOD score and explained phenotypic variation of QTLs associated with *Sclerotinia* whole plant field resistance or improved whole plant field resistance

| Linkage Group | Parameter | Year | QTL Interval | LOD Score | Phenotypic Variation Explained (%) |
|---|---|---|---|---|---|
| N1 | SSFS, SSDIS | 2010 | AG0093-PE0203 | 2.9 | 7.8 |
| | SSFS, SSDIS | 2009 | BG0111-BG1392 | 3.5 | 8.4 |
| | SSDI % | 2010 | BG0111-BG1392 | 2.8 | 7.4 |
| | UNSSDI | 2010 | BG1090-AG0482 | 5.0 | 11.5 |
| | UNSSDI, UNSSDS, SSFS, SSDIS | 2009 | BG1090-PE0203 | 3.9 | 10.5 |
| | SSDI % | 2010 | BG1090-PE0203 | 4.7 | 11.1 |
| | UNSSDS | 2009 | CA0614-BG1392 | 5.5 | 13.0 |
| | UNSSDI | 2010 | CA0614-BG1392 | 3.2 | 12.5 |
| N3 | UNSSDS, SSFS, SSDIS | 2009 | BG1197-AG0023 | 4.0 | 9.6 |
| | UNSSDI, SSDI % | 2010 | BG1197-AG0023 | 2.2 | 5.4 |
| | SSFS, SSDIS | 2009 | CA0410-BG1368 | 2.8 | 6.7 |
| | UNSSDI, SSFS | 2011 | CA0410-BG1197 | 2.9 | 3.9 |
| N4 | UNSSDS, SSFS | 2009, 2010 | BG1442-BG0106 | 6.3 | 14.7 |
| | UNSSDI, SSDI %, SSDIS | 2010 | BG1442-BG0106 | 8.1 | 18.5 |
| | UNSSDI, SSFS, SSDI %, SSDIS | 2011 | BG1442-BG0106 | 7.6 | 11.1 |
| | SSDIS | 2009 | UB0181-BG0106 | 3.4 | 8.1 |
| N8 | UNSSDI | 2010 | BG1449-BG1062 | 2.3 | 6.0 |
| | SSDI % | 2009 | CA0837-AG0328 | 2.3 | 6.5 |
| | SSDIS | 2009 | CA0837-BG1062 | 6.6 | 15.1 |

TABLE 12-continued

QTL interval, LOD score and explained phenotypic variation of QTLs associated with *Sclerotinia* whole plant field resistance or improved whole plant field resistance

| Linkage Group | Parameter | Year | QTL Interval | LOD Score | Phenotypic Variation Explained (%) |
|---|---|---|---|---|---|
| | UNSSDI | 2010 | CA0837-BG1101 | 2.3 | 5.6 |
| | UNSSDS, SSFS | 2009 | CA0837-BG1286 | 7.5 | 17.2 |
| | UNSSDI | 2009 | CA0837-BG1449 | 3.7 | 10.5 |
| | UNSSDI | 2011 | BG0647-PE0281 | 2.3 | 2.6 |
| N9 | UNSSDS, SSFS, SSDIS | 2009 | AG0323-BG0295 | 4.5 | 10.6 |
| | UNSSDI, SSDI % | 2010 | AG0323-BG0295 | 2.9 | 6.9 |
| | UNSSDI, SSFS, SSDI %, SSDIS | 2010 | CA1034-AG0378 | 5.3 | 12.2 |
| | UNSSDI, UNSSDS, SSFS, SSDIS | 2011 | BG1123-AG0441 | 3.2 | 5.7 |
| N10 | UNSSDS, SSFS | 2009 | BG0228-AG0047 | 3.3 | 7.9 |
| | SSDI % | 2011 | BG0255-PE0131 | 3.0 | 4.3 |
| N11 | SSFS, SSDIS | 2009 | BG0031-BG1149 | 4.4 | 10.5 |
| | UNSSDS | 2009 | BG0031-BG1230 | 4.1 | 10.5 |
| | UNSSDI, SSDI % | 2010 | BG0031-BG1230 | 3.4 | 8.5 |
| | SSFS, SSDIS | 2010 | BG0031-BG1513 | 5.3 | 12.2 |
| | UNSSDS | 2010 | CA0120-CA0328 | 5.4 | 13.9 |
| | UNSSDI, SSFS, SSDIS | 2009, 2010 | PE0283-CA0163 | 5.2 | 12.2 |
| | UNSSDS | 2009 | PE0283-CA0163 | 5.2 | 12.3 |
| | SSDI % | 2010 | PE0283-CA0163 | 2.4 | 5.6 |
| | SSDI % | 2009 | PE0324-PE0283 | 2.2 | 5.4 |
| | UNSSDS, UNSSDI, SSFS, SSDIS | 2011 | CA0328-PE0324 | 5.8 | 7.2 |
| N12 | SSFS, SSDIS | 2009 | BG1321-CA0991 | 5.1 | 13.8 |
| | UNSSDI, SSDI % | 2010 | BG1321-CA0991 | 4.6 | 11.6 |
| | UNSSDS | 2009 | BG1321-CA1027 | 3.7 | 10.2 |
| | UNSSDI | 2009 | BG1321-PE0133 | 2.7 | 6.5 |
| | UNSSDI, SSDI % | 2011 | BG1231-PE0133 | 4.1 | 6.6 |
| | SSDI % | 2009 | PE0063-CA0991 | 2.0 | 5.0 |
| | SSFS, SSDIS | 2010 | PE0133-CA0991 | 4.9 | 12.2 |
| N13 | UNSSDI | 2009 | BG0516-AG0148 | 2.9 | 9.7 |
| | SSFS, SSDIS | 2009 | CA0488-AG0148 | 7.3 | 21.7 |
| | UNSSDS | 2009 | CA0488-CA0736 | 9.8 | 27.3 |
| | SSDI %, SSDIS | 2010 | CA0603-AG0504 | 7.3 | 17.3 |
| | UNSSDS, SSFS, SSDIS | 2011 | BG1288-AG0504 | 4.6 | 6.8 |
| N15 | SSDI % | 2009 | CA0719-AG0369 | 2.7 | 8.5 |
| | SSFS | 2010 | PE0091-PE0187 | 4.2 | 10.0 |
| | UNSSDI, UNSSDS, SSFS, SSDIS | 2009 | PE0286-AG0369 | 7.1 | 17.8 |
| | UNSSDI, SSDI %, SSDIS | 2010 | PE0286-PE0187 | 7.4 | 17.2 |
| | UNSSDI, SSFS, SSDI %, SSDIS | 2011 | PE0286-CA0719 | 8.7 | 12.1 |
| N18 | UNSSDS, SSFS, SSDIS | 2009 | AG0285-CA0636 | 8.4 | 20.0 |
| | UNSSDI | 2009 | BG0278-CA0779 | 6.6 | 16.4 |
| | SSDI % | 2009 | CA0739-CA0636 | 2.9 | 7.0 |
| | UNSSDI | 2010 | CA0739-CA0636 | 3.3 | 8.0 |
| | SSDI % | 2011 | CA0739-CA0636 | 2.7 | 4.1 |
| | SSDI % | 2010 | UB0315-CA0636 | 2.6 | 6.4 |
| N19 | SSDIS | 2009 | CA0552-CA0221 | 2.9 | 9.8 |
| | UNSSDI, SSFS, SSDI %, SSDIS | 2010 | CA1107-CA0552 | 2.8 | 8.0 |
| | UNSSDS, SSFS | 2009 | CA1107-CA0221 | 4.3 | 13.5 |

Additional information about the SSR markers flanking the twelve QTLs associated with whole field plant resistance to *Sclerotinia* is shown in Table 14 of Example 12, where exemplary sets of forward and reverse primer sequences for each SSR are also provided. "Repeat" indicates the SSRs or SNPs associated with each marker. The positions of the SSRs are shown in the sequence information located in Example 12. Additional information about the alleles and allele size of each SSR marker flanking the 12 QTLs associated with whole plant field resistance to *Sclerotinia* is provided in Table 13.

TABLE 13

The alleles and allele size of each SSR marker flanking the twelve *Sclerotinia* QTLs. as well as favorable allele for *Sclerotinia* (SCL) resistance.

| Linkage Group | SSR Marker | Allele Name | Allele Size (bp) | Favorable Allele for SCL Resistance |
|---|---|---|---|---|
| N1 | CA0614 | a | 160 | |
| | CA0614 | b | 178 | yes |
| | CA0614 | c | 188 | |
| | CA0614 | d | 196 | |
| | BG0111 | a | 141 | yes |
| | BG0111 | b | 146 | |

TABLE 13-continued

The alleles and allele size of each SSR marker flanking the twelve *Sclerotinia* QTLs. as well as favorable allele for *Sclerotinia* (SCL) resistance.

| Linkage Group | SSR Marker | Allele Name | Allele Size (bp) | Favorable Allele for SCL Resistance |
|---|---|---|---|---|
| | BG0111 | c | 147 | |
| | BG0111 | d | 144 | |
| | BG1392 | a | 251 | yes |
| | BG1392 | b | 257 | |
| | BG1182 | a | 299 | |
| | BG1182 | b | 301 | |
| | BG1182 | c | 303 | yes |
| | BG1182 | d | 347 | |
| | BG1182 | e | 345 | |
| | BG1090 | a | 268 | yes |
| | BG1090 | b | 272 | |
| | AG0093 | a | 221 | |
| | AG0093 | b | 223 | yes |
| | BG1453 | a | 120 | |
| | BG1453 | b | 122 | |
| | BG1453 | c | 130 | |
| | BG1453 | d | 132 | yes |
| | BG1453 | e | 134 | |
| | BG1453 | f | 146 | |
| | BG1453 | g | 148 | |
| | BG1453 | h | 152 | |
| | BG1453 | i | 154 | |
| | BG1453 | j | 156 | |
| | BG1453 | k | 172 | |
| | BG1453 | l | 142 | |
| | BG1453 | m | 138 | |
| | BG1453 | n | 158 | |
| | BG1453 | o | 162 | |
| | BG1453 | p | 144 | |
| | BG1453 | q | 136 | |
| | BG1453 | r | 176 | |
| | BG1453 | s | 114 | |
| | BG1453 | t | 160 | |
| | PE0017 | a | 81 | yes |
| | PE0017 | b | 84 | |
| | PE0017 | c | 78 | |
| | PE0017 | d | 87 | |
| | AG0391 | a | 127 | yes |
| | AG0391 | b | 130 | |
| | AG0391 | c | 139 | |
| | AG0304 | a | 163 | |
| | AG0304 | b | 226 | |
| | AG0304 | c | 229 | yes |
| | UB0163 | b | 111 | |
| | UB0163 | c | 129 | yes |
| | UB0163 | e | 107 | |
| | UB0163 | f | 117 | |
| | PE0203 | a | 205 | |
| | PE0203 | b | 209 | |
| | PE0203 | c | 211 | yes |
| | PE0203 | d | 203 | |
| | PE0203 | e | 207 | |
| | AG0482 | a | 278 | |
| | AG0482 | b | 281 | |
| | AG0482 | c | 284 | |
| | AG0482 | d | 287 | yes |
| | AG0482 | e | 272 | |
| | PE0177 | a | 197 | |
| | PE0177 | b | 199 | yes |
| | PE0177 | c | 201 | |
| | PE0177 | d | 205 | |
| N3 | CA0410 | a | 140 | |
| | CA0410 | b | 142 | yes |
| | CA0410 | c | 148 | |
| | CA0410 | d | 154 | |
| | BG1368 | a | 128 | yes |
| | BG1368 | b | 131 | |
| | BG1197 | a | 262 | |
| | BG1197 | b | 267 | yes |
| | BG1197 | c | 272 | |
| | BG1197 | d | 286 | |
| | AG0272 | a | 151 | yes |
| | AG0272 | b | 157 | |
| | AG0272 | c | 163 | |
| | AG0023 | a | 128 | |
| | AG0023 | b | 131 | yes |
| | AG0023 | c | 139 | |
| | AG0023 | d | 145 | |
| | AG0023 | e | 148 | |
| N4 | BG1442 | a | 232 | yes |
| | BG1442 | b | 238 | |
| | BG1442 | c | 250 | |
| | BG1442 | d | 258 | |
| | BG1442 | e | 266 | |
| | BG1442 | f | 242 | |
| | BG1442 | g | 254 | |
| | BG1442 | h | 230 | |
| | UB0181 | a | 147 | |
| | UB0181 | b | 283 | |
| | UB0181 | c | 369 | |
| | UB0181 | d | 379 | yes |
| | UB0181 | e | 275 | |
| | UB0181 | f | 285 | |
| | UB0181 | g | 289 | |
| | UB0126 | a | 216 | yes |
| | UB0126 | b | 220 | |
| | UB0126 | c | 230 | |
| | AG0477 | a | 268 | |
| | AG0477 | b | 276 | |
| | AG0477 | c | 278 | |
| | AG0477 | d | 289 | yes |
| | AG0477 | e | 292 | |
| | AG0477 | f | 285 | |
| | BG1127 | a | 284 | |
| | BG1127 | b | 290 | |
| | BG1127 | c | 304 | yes |
| | BG1127 | d | 306 | |
| | BG1127 | e | 292 | |
| | BG1127 | f | 294 | |
| | BG1127 | g | 302 | |
| | AG0125 | a | 212 | |
| | AG0125 | b | 238 | |
| | AG0125 | c | 255 | |
| | AG0125 | d | 264 | yes |
| | AG0125 | e | 267 | |
| | AG0125 | f | 225 | |
| | BG1244 | a | 247 | |
| | BG1244 | b | 284 | yes |
| | BG1244 | c | 275 | |
| | AG0239 | a | 295 | |
| | AG0239 | b | 311 | |
| | AG0239 | c | 314 | yes |
| | AG0203 | a | 206 | |
| | AG0203 | b | 209 | |
| | AG0203 | c | 215 | |
| | AG0203 | d | 221 | yes |
| | AG0203 | j | 213 | |
| | AG0203 | k | 203 | |
| | AG0203 | l | 227 | |
| | BG0106 | a | 216 | |
| | BG0106 | b | 286 | |
| | BG0106 | c | 310 | yes |
| | BG0106 | d | 288 | |
| | BG0106 | e | 276 | |
| | BG0106 | f | 284 | |
| | BG0106 | g | 280 | |
| N8 | CA0837 | a | 257 | |
| | CA0837 | b | 269 | |
| | CA0837 | c | 253 | yes |
| | CA0837 | d | 279 | |
| | CA0837 | e | 283 | |
| | BG0647 | a | 247 | yes |

TABLE 13-continued

The alleles and allele size of each SSR marker flanking the twelve *Sclerotinia* QTLs. as well as favorable allele for *Sclerotinia* (SCL) resistance.

| Linkage Group | SSR Marker | Allele Name | Allele Size (bp) | Favorable Allele for SCL Resistance |
|---|---|---|---|---|
| | BG0647 | b | 250 | |
| | BG0647 | c | 259 | |
| | BG0647 | d | 272 | |
| | BG0647 | e | 275 | |
| | BG0647 | f | 244 | |
| | AG0070 | a | 270 | yes |
| | AG0070 | b | 274 | |
| | AG0070 | c | 272 | |
| | PE0281 | a | 179 | |
| | PE0281 | b | 209 | yes |
| | PE0281 | c | 211 | |
| | PE0281 | d | 213 | |
| | PE0281 | e | 233 | |
| | PE0281 | f | 221 | |
| | PE0281 | g | 215 | |
| | PE0281 | h | 236 | |
| | PE0281 | i | 203 | |
| | PE0281 | j | 194 | |
| | PE0281 | k | 206 | |
| | PE0281 | l | 249 | |
| | AG0324 | a | 226 | yes |
| | AG0324 | b | 229 | |
| | AG0324 | c | 244 | |
| | BG1101 | a | 210 | |
| | BG1101 | b | 219 | yes |
| | AG0328 | a | 222 | |
| | AG0328 | b | 228 | yes |
| | AG0328 | c | 255 | |
| | AG0328 | d | 258 | |
| | AG0328 | e | 267 | |
| | AG0328 | f | 270 | |
| | AG0328 | g | 279 | |
| | AG0328 | h | 276 | |
| | AG0328 | i | 281 | |
| | AG0328 | j | 273 | |
| | AG0328 | k | 287 | |
| | BG1449 | a | 132 | |
| | BG1449 | b | 134 | |
| | BG1449 | c | 158 | |
| | BG1449 | d | 160 | yes |
| | BG1449 | e | 164 | |
| | BG1449 | f | 156 | |
| | BG1449 | g | 170 | |
| | BG1062 | a | 188 | |
| | BG1062 | b | 210 | |
| | BG1062 | c | 212 | yes |
| | BG1062 | d | 186 | |
| | BG1062 | e | 214 | |
| | BG1062 | f | 216 | |
| | BG1062 | g | 224 | |
| | BG1062 | h | 208 | |
| | BG1062 | i | 196 | |
| | BG1062 | j | 176 | |
| | BG1062 | k | 206 | |
| | BG1062 | l | 218 | |
| | BG1062 | m | 202 | |
| | BG1062 | o | 182 | |
| | BG1062 | p | 222 | |
| | AG0410 | a | 322 | |
| | AG0410 | b | 325 | |
| | AG0410 | c | 328 | yes |
| | AG0410 | d | 334 | |
| | AG0410 | e | 337 | |
| | AG0410 | f | 331 | |
| | BG1286 | a | 156 | |
| | BG1286 | b | 159 | |
| | BG1286 | c | 162 | yes |
| | BG1286 | d | 165 | |
| N9 | CA1034 | a | 275 | yes |
| | CA1034 | b | 290 | |
| | CA1034 | c | 293 | |
| | CA1034 | d | 306 | |
| | CA1034 | e | 309 | |
| | CA1034 | f | 321 | |
| | CA1034 | g | 299 | |
| | CA1034 | h | 284 | |
| | CA1034 | i | 278 | |
| | CA1034 | j | 315 | |
| | CA1034 | k | 296 | |
| | CA1034 | l | 324 | |
| | CA1034 | m | 327 | |
| | CA1034 | n | 287 | |
| | CA0834 | a | 274 | yes |
| | CA0834 | b | 289 | |
| | CA0834 | c | 292 | |
| | CA0834 | d | 301 | |
| | CA0834 | e | 304 | |
| | CA0834 | f | 307 | |
| | CA0834 | g | 298 | |
| | CA0834 | h | 319 | |
| | CA0834 | i | 283 | |
| | CA0834 | j | 313 | |
| | CA0834 | k | 295 | |
| | CA0834 | l | 277 | |
| | CA0834 | m | 286 | |
| | CA0834 | n | 325 | |
| | CA0834 | o | 322 | |
| | AG0378 | a | 275 | |
| | AG0378 | b | 281 | |
| | AG0378 | c | 290 | |
| | AG0378 | d | 293 | yes |
| | AG0378 | e | 284 | |
| | AG0378 | f | 312 | |
| | AG0378 | g | 300 | |
| | AG0378 | h | 295 | |
| | BG1123 | a | 202 | |
| | BG1123 | b | 216 | |
| | BG1123 | c | 220 | yes |
| | BG1123 | d | 252 | |
| | BG1123 | e | 254 | |
| | BG1123 | f | 256 | |
| | BG1123 | g | 222 | |
| | BG1123 | h | 226 | |
| | BG1123 | i | 234 | |
| | BG1123 | j | 258 | |
| | BG1123 | k | 218 | |
| | BG1123 | l | 224 | |
| | BG1123 | m | 264 | |
| | BG1123 | n | 248 | |
| | AG0323 | a | 210 | |
| | AG0323 | b | 216 | yes |
| | AG0323 | c | 219 | |
| | AG0323 | d | 231 | |
| | AG0323 | e | 213 | |
| | AG0323 | f | 222 | |
| | AG0323 | g | 201 | |
| | AG0323 | h | 228 | |
| | AG0323 | i | 195 | |
| | BG0295 | a | 286 | yes |
| | BG0295 | b | 288 | |
| | BG0295 | c | 283 | |
| | AG0441 | a | 292 | yes |
| | AG0441 | b | 301 | |
| | AG0441 | c | 283 | |
| N10 | BG0228 | a | 137 | yes |
| | BG0228 | b | 143 | |
| | BG0228 | c | 146 | |
| | PE0355 | a | 217 | |
| | PE0355 | b | 223 | yes |
| | PE0355 | c | 225 | |
| | PE0355 | d | 237 | |
| | PE0355 | e | 229 | |

TABLE 13-continued

The alleles and allele size of each SSR marker flanking the twelve *Sclerotinia* QTLs. as well as favorable allele for *Sclerotinia* (SCL) resistance.

| Linkage Group | SSR Marker | Allele Name | Allele Size (bp) | Favorable Allele for SCL Resistance |
|---|---|---|---|---|
| | AG0171 | a | 241 | |
| | AG0171 | b | 245 | yes |
| | AG0171 | c | 247 | |
| | BG0651 | a | 230 | |
| | BG0651 | b | 245 | |
| | BG0651 | c | 253 | |
| | BG0651 | d | 256 | yes |
| | BG0651 | e | 269 | |
| | BG0651 | f | 248 | |
| | BG0651 | g | 251 | |
| | BG0651 | h | 275 | |
| | BG0651 | i | 272 | |
| | BG0255 | a | 180 | |
| | BG0255 | b | 183 | |
| | BG0255 | c | 186 | yes |
| | AG0047 | a | 293 | yes |
| | AG0047 | b | 311 | |
| | AG0047 | c | 319 | |
| | UB0196 | a | 281 | |
| | UB0196 | b | 287 | |
| | UB0196 | c | 293 | |
| | UB0196 | d | 295 | yes |
| | UB0196 | e | 283 | |
| | UB0196 | f | 275 | |
| | UB0196 | g | 271 | |
| | UB0196 | h | 277 | |
| | UB0196 | i | 265 | |
| | UB0196 | j | 289 | |
| | UB0015 | a | 241 | |
| | UB0015 | b | 243 | |
| | UB0015 | c | 253 | yes |
| | UB0015 | e | 251 | |
| | UB0015 | f | 255 | |
| | PE0131 | b | 144 | |
| | PE0131 | c | 148 | yes |
| | PE0131 | d | 152 | |
| | PE0131 | e | 150 | |
| | PE0131 | f | 154 | |
| N11 | CA0120 | a | 138 | |
| | CA0120 | b | 160 | |
| | CA0120 | c | 172 | yes |
| | CA0120 | d | 163 | |
| | CA0120 | e | 169 | |
| | BG0452 | a | 197 | |
| | BG0452 | b | 209 | yes |
| | BG0452 | c | 212 | |
| | BG0452 | d | 215 | |
| | BG0452 | e | 221 | |
| | BG0452 | f | 194 | |
| | BG0452 | g | 191 | |
| | BG0031 | a | 225 | |
| | BG0031 | b | 228 | |
| | BG0031 | c | 237 | yes |
| | CA1035 | a | 255 | |
| | CA1035 | b | 258 | |
| | CA1035 | c | 282 | |
| | CA1035 | d | 294 | |
| | CA1035 | e | 297 | yes |
| | CA1035 | f | 285 | |
| | CA1035 | g | 306 | |
| | CA1035 | h | 300 | |
| | CA0546 | a | 110 | |
| | CA0546 | b | 120 | |
| | CA0546 | c | 123 | |
| | CA0546 | d | 146 | yes |
| | CA0546 | e | 149 | |
| | CA0546 | f | 126 | |
| | CA0546 | g | 144 | |
| | CA0546 | h | 112 | |
| | CA1032 | a | 203 | yes |
| | CA1032 | b | 211 | |
| | BG1149 | a | 260 | |
| | BG1149 | b | 266 | yes |
| | BG1149 | c | 263 | |
| | BG1230 | a | 252 | |
| | BG1230 | b | 288 | yes |
| | BG1513 | a | 164 | yes |
| | BG1513 | b | 214 | |
| | BG1513 | c | 216 | |
| | CA0328 | a | 237 | |
| | CA0328 | b | 240 | |
| | CA0328 | c | 252 | yes |
| | CA0328 | d | 255 | |
| | CA0328 | e | 258 | |
| | CA0328 | f | 234 | |
| | CA0328 | g | 264 | |
| | PE0324 | a | 258 | |
| | PE0324 | b | 270 | yes |
| | PE0283 | a | 149 | yes |
| | PE0283 | b | 167 | |
| | PE0283 | c | 173 | |
| | PE0283 | d | 176 | |
| | CA0163 | a | 311 | |
| | CA0163 | b | 317 | yes |
| N12 | BG1321 | a | 197 | yes |
| | BG1321 | b | 200 | |
| | BG1321 | c | 330 | |
| | PE0133 | a | 131 | |
| | PE0133 | b | 141 | |
| | PE0133 | c | 147 | yes |
| | PE0133 | d | 153 | |
| | PE0133 | e | 133 | |
| | CA0456 | a | 179 | |
| | CA0456 | b | 185 | yes |
| | PE0063 | a | 114 | yes |
| | PE0063 | b | 126 | |
| | CA1027 | a | 297 | |
| | CA1027 | b | 300 | yes |
| | CA1027 | c | 303 | |
| | CA1027 | d | 306 | |
| | BG0864 | a | 169 | yes |
| | BG0864 | b | 175 | |
| | BG0864 | c | 185 | |
| | BG0864 | d | 191 | |
| | BG0864 | e | 193 | |
| | BG0864 | f | 197 | |
| | BG0864 | g | 195 | |
| | BG0864 | h | 187 | |
| | CA1090 | a | 282 | |
| | CA1090 | b | 288 | yes |
| | CA1090 | c | 292 | |
| | CA1090 | d | 295 | |
| | CA1090 | e | 279 | |
| | CA0991 | a | 162 | |
| | CA0991 | b | 165 | yes |
| N13 | CA0603 | a | 179 | |
| | CA0603 | b | 182 | yes |
| | BG1288 | a | 199 | |
| | BG1288 | b | 205 | yes |
| | CA0488 | a | 202 | |
| | CA0488 | b | 217 | |
| | CA0488 | c | 237 | |
| | CA0488 | d | 231 | yes |
| | CA0488 | e | 234 | |
| | CA0488 | f | 240 | |
| | PE0012 | a | 115 | |
| | PE0012 | b | 134 | yes |
| | PE0340 | c | 279 | yes |
| | PE0340 | d | 281 | |
| | PE0340 | e | 277 | |
| | PE0340 | f | 255 | |
| | PE0340 | g | 257 | |

TABLE 13-continued

The alleles and allele size of each SSR marker flanking the twelve *Sclerotinia* QTLs. as well as favorable allele for *Sclerotinia* (SCL) resistance.

| Linkage Group | SSR Marker | Allele Name | Allele Size (bp) | Favorable Allele for SCL Resistance |
|---|---|---|---|---|
| | BG0516 | a | 165 | yes |
| | BG0516 | b | 170 | |
| | BG0516 | c | 179 | |
| | BG0516 | d | 154 | |
| | BG0516 | e | 182 | |
| | BG0516 | f | 173 | |
| | BG0516 | g | 158 | |
| | AG0504 | a | 320 | |
| | AG0504 | b | 332 | yes |
| | AG0504 | c | 338 | |
| | AG0148 | a | 268 | |
| | AG0148 | b | 272 | |
| | AG0148 | c | 280 | yes |
| | AG0148 | d | 286 | |
| | CA0736 | a | 324 | yes |
| | CA0736 | b | 474 | |
| N15 | PE0286 | a | 186 | |
| | PE0286 | b | 194 | yes |
| | PE0091 | a | 152 | |
| | PE0091 | b | 164 | |
| | PE0091 | c | 176 | |
| | PE0091 | d | 180 | yes |
| | PE0187 | a | 176 | |
| | PE0187 | b | 178 | |
| | PE0187 | c | 180 | |
| | PE0187 | f | 182 | yes |
| | PE0187 | i | 184 | |
| | CA0719 | a | 300 | |
| | CA0719 | b | 304 | yes |
| | AG0369 | a | 180 | |
| | AG0369 | b | 184 | yes |
| | AG0369 | c | 186 | |
| N18 | BG0278 | a | 239 | |
| | BG0278 | b | 241 | yes |
| | CA0739 | a | 220 | |
| | CA0739 | b | 222 | |
| | CA0739 | c | 232 | |
| | CA0739 | d | 234 | yes |
| | CA0739 | e | 240 | |
| | CA0739 | f | 224 | |
| | CA0739 | g | 236 | |
| | CA0739 | h | 242 | |
| | UB0315 | a | 127 | |
| | UB0315 | b | 133 | |
| | UB0315 | c | 131 | yes |
| | BG0278 | a | 239 | |
| | BG0278 | b | 341 | yes |
| | CA0636 | a | 257 | |
| | CA0636 | b | 263 | yes |
| N19 | CA1107 | a | 225 | |
| | CA1107 | b | 228 | yes |
| | CA1107 | c | 328 | |
| | CA1107 | d | 216 | |
| | CA0552 | a | 192 | |
| | CA0552 | b | 195 | yes |
| | CA0552 | c | 204 | |
| | CA0552 | d | 207 | |
| | CA1066 | a | 196 | |
| | CA1066 | b | 217 | |
| | CA1066 | c | 232 | |
| | CA1066 | d | 235 | |
| | CA1066 | e | 238 | |
| | CA1066 | f | 241 | yes |
| | CA1066 | g | 244 | |
| | BG1241 | d | 329 | yes |
| | BG1241 | e | 370 | |
| | CA0221 | a | 253 | yes |
| | CA0221 | b | 265 | |
| | CA0221 | c | 271 | |

Example 10: Introgressing *Sclerotinia* Resistance from Spring *Brassica napus* to Winter *Brassica napus*

The *Sclerotinia* resistant source 06DSB13911 is crossed to winter canola lines in bi-parental, 3-way or complex crosses. The F1 cross is then backcrossed to an elite susceptible parent. At the BC1F1 generation, approximately 800-1000 progeny (minimum number required to identify at least one individual with all favorable alleles present) are generated for each cross and submitted for marker analysis using the markers identified as being associated with *Sclerotinia* in spring canola. Each individual sample is examined for the presence of the favorable alleles from the *Sclerotinia* resistant line 06DSB13911. The percentage of favorable alleles present in each sample is calculated and the top three from each population are used to cross back to the recurrent parent. This process is repeated again at the BC2 stage. In addition, selections are intermated to develop populations in which individuals can be identified with homozygous desirable *Sclerotinia* alleles.

Example 11: Use of *Sclerotinia* Resistant Lines for Hybrid Seed Production

*Sclerotinia* resistant lines with scores of 5 and higher for SSDIS are selected for use in hybrid seed production and hybrid testing. Production of these seeds can be done according to methods known to the skilled person and are described, for example, in WO 2006/135717.

Example 12: Marker Sequences Containing Polymorphisms, and Exemplary Primers

Set forth below is sequence information for markers of QTLs significantly associated with *Sclerotinia* whole plant field resistance at $P \leq 0.01$, as set forth in the foregoing examples. In the sequences, n=an unknown nucleotide; underlined sequences indicate the primer sequences from Table 14 below and sequences in brackets indicate polymorphic regions (SSRs, SNPs).

AG0023

(SEQ ID NO: 1)

CGAATTCGCCCTTCTCTTGCTTAGATCTGGACTAACTACTTCnnAAAGAAAACATTnnnTTAATGTTTAT

GTCGAATGTCATTTATGCTGAACAAAATAACCTTGAAAATATGTTCTGTAGGCTAAAGTTGGGAGAGAGA

AGGAGGTTGAAGAGATTTTGTCAAGATTGCGAGGAGAAAATTCTGATGTATCAGATGAGGCAGGAGAGAT

-continued

ATTAGTAAGCATATATATGCATGAATAATCATATGATCAATGTATATATTTTTTACTTCACAATATTTTG

ATGATCATCAGGCATATACAGAACATGTTAAACAACAAGGAGATGATCGCGGTTTCCTCAAGTTGTTTCA

GCGAAAATACGCGTTCTCACTTACTGTAATT[CTTCTTCTTCTTCTTCTTCTTCTTTTTCTTCTTCTTCT

TCTTCTT]TAATAACCCGTTTGGTTTACACAGATTGGAGTTGTTCTTATAGCTTTGCCTCAACTTGGAGG

TCTTAGTGGTTATTCTTTTTACACTGAGTCCATTTTCATATCTACAGGTAnnnTAACTCTTACTTCTTCA

ACAAAATCTTGATTTTTATATATTTATTTACCGTAACGATAATTGTTGATAATTACGnnnATCAGGTGTA

TCGAGTGATGTTGGATTCATATCGACATCTATAGTTC

AG0045
(SEQ ID NO: 2)
ACGAATTCGCCCTTCTCTTGCTTAGATCTGGACTAnnnnnTGATTTGCCCGCTATGTTCGACGGGTGGAG

ATTTTAGTTTTACTTCCTCGATCTGATTGTATGGGTTGGGAGTAGGGTCTAATATATCAACTGCGAGTGT

ATGTTCGTTTCCTCCTCAGTTTCGAAGTTGGGTTCTTATGTGTTTAGCCTAAGnnnCTGTGAnnnGnTAG

TTTTTTTTTAATCAGTTCCAACAGGATTCATTTCAGGnnnTTGGAACTTGTGTATATGTGTTAGCCTGAG

ATCTCTGTAGTGTCCGGAAATGATATTTnnnnATTATCATTAATTTAGTTCGAAGnATGAAGCTCAGTGT

TGTTGGACTTGTGTATATGGAGCTCGAAGAGTGAAGCTCAGTGCGTTTTCATCTGAGGATGATGATGATG

GAGCTAATGTGCTGAGCAATGAGAACTCGAGATGATAAGGCTTGAGGGACATGCCAGTGAGT[GAAGAAA]

CCGTCGGGCTATAGCTTAGT[GAAGAAGAAGAAGAA]GAGCTCGTGGAGTGATCAAATTTGCAGGTATG

CCCAAACTTGCCAATCCCACATTGTGGAGAATGGCTGCATTTTTACCACAAAGCTGTTTCTGTGGAGCCA

AAAATGAATGGAGGATAGTAAAACAGAACGTCATAATCAAATCAAGAAATTTTAACTTTTTTTGTCAGCA

CAAATTTnnnCTTTATCTTTAATTATTTAC

AG0047
(SEQ ID NO: 3)
CGAATTCGCCCTTCTCTTGCTTAnnnnCTGGACTAACAACAATTCCAAAATACTAATTCACAAACTTTGT

TTACAATCCAAAGAAAATCCGCTCTTTTGAAGCGCGGATCAAGATCTAGTGTTATAATATATCTAGAACA

TGGGAGTTTGGTCCAATGAACTACTGTATAGTTCTATCGAAATTTTTGAGTGATAAGATTGAAGCTCCAG

CACTCACTTATCTATTTGAGAAGCAAATAATAGAAAAAGAAGTAGATTTGAGGAAGAGATGATGGAGTTG

AACAAGGAGCTTTAAGATTTGAGTTCTGACAGTGTAGAAGCTGCAATACTGAGGCACCAAGGAAGAAAT

[CATCATCATCATCATCATCATCATCAT]CAAGAATTAGTTTCAGTTCATATCCACAACCATTTTTTCTTT

CAAAGAAATTTGCTGGTAGTAATTTTGAAGTTGTAAATTTTACATTTTCAGTGTTTCATTTTTCTCACGT

TTTCTTAATAATTGTTTACTTGCCAAATGATTCCATCACTTGGAAACTCACTATTGTTTGACATTTTGGT

GTGCTTAAGTGACTCTTTTCGAGTATTCATACATTATAGAAATTGTTTGGGACAACAGGTAAGAATTGCT

TGGCACAAGTAATGGCATCCCTCCCTGCAAATATATATAAATATTACAGTTGTCCTGGAACTTTTnnnnT

CTATCCTCTGCTGACAGGATGAGATATATGCATATAGAATATTAACTTCnnTCnGCCCGTATGTTCATGG

ATGnnnAGCTCCAT

AG0070
(SEQ ID NO: 4)
CGAGGAGTTGAATGACCCTGACTGTACTTTGGCCTCGAGACAGTCCCATCAAGAATAATTTACTGGGTCG

ATTTTTATTTTTAATTCTGGTCGAGCCAACTCCGAACTGGTCGAGCGGGATTTTTTAATTCTGGTCGACC

AAAATCATATCCGCTCGTGAGGGTCTTTACAACCACCATCACCACACTCGGACGATCACCCCACCACCAC

TTGGACGA[CCACCACCACCACCA]CCGGCGGCTCGGCTAGCTCTCGGGGGGCTCGCGGCGAG[GAGAGA]

GGAAGATATCCNACGGAAAGAGAAAAGAGAGG[GAGAGAGAGAGAGA]GGCGTGAGAGAAGAAGAGAGA

AAAGGAAAAGAGAAGCTTGACGGCTAGGGTTTCCTAGTCTCTATAAATTCCTGCAGAGCTTCACTCAAGT

TTCAGAATGAGAGAAGAGTAAGAGGAGGCAGCTTCATTTATAGAAACAGGAGGAAACCCTAGGTCATTTA

CCCTAATGGGCTGCAGTCTTAATGGGCTCTCCTTAAGAAAATTTTGGGCTAGGAACCGGGACGTTACAAT

-continued

AATGCTTCTTATGAATATGTCTGAGTAGTTCTTTTGTTAGATTTAGGGTTCTTCAAGGGGTGAATTATGG

TTTGCTANATTTATATTGTTGTTTGTGTGATTT

AG0086

(SEQ ID NO: 5)

GCTCGCCGACTTCGGAGTCGCCTCGCCGCTCGATATCCCTTTCAGCCTCGCCTCCATCTCTTTTCCCCAA

ACTCTAGGCTGTTGCTGTTGCGTCGCCGCCGCCGCCGCCGTGGCTGTTATCGAGCTATTTGATCTACCGT

ACAGCATTTTAAACCGTTGATCAGATTCGGGATCAGACTTTGTCGTCACCGGAGGGCTCTTGATCGGCGG

TTGCACTTCCCCCTCCGTACACGGCGTACAATGTCGGTAAGCACCGGAAGCTTTCAGAGCCATATCTTTG

AGCTGAGAATGAATTTACGAAAATACCCTTGATCAGTATAGAGAATGACAAGAGGTGGAGGATGAGCAAA

[GAGAGAGAGAGAGAGAGA]AGTCTACCTGAGATGTTAGAGATTTGGCTTGCTTGGAATCCGGATCGT

CGGGTTGACCCGAGGTTTCATCGCCGGCTCGCTTCGAACGAGCTATACAAGTCAGCATTTTCCGGCAGCT

GCTGTTTCTTGGTAATGTGATTTTGTTTCTTCTCTTTTTGGATACG[GAGAGA]CAGTAGATGCTGTCAG

TTTCTAACTTTGGTTTGTGTTGTGTGTTTGGTCATGGTGCTCTTTTTATGTTTTATACTCACTTTACCAN

NGAAAACGGTTCCATTTTTTTAA

AG0093

(SEQ ID NO: 6)

TAGGAGATGAGATGTACTGTTGCTTAGGGCTCTTATTTCTCTTGAAACTAGAATAAGCTGCCATCGGGTC

GGTGTAATAATCAAACCTTGGCTTATCATACGATTCCTGCTGATGTATGGATGCTTCAGCCAAGGGATTT

GAGAGGTGACTTGTGTTCATAGAGGTTCCAAGCTCTGTAGAACCATCATTCTCTG[CAGCAGCAGCAGCA

GCAG]CTTCCATCCGCATTGCTTTTAGCATTT[CTTTTCTTTT]CTCTGAATCTTCCATTACTGCTCAGC

TTCAAAGCTAATCAACTACAAAAATATAAACTTTTTTTCGAAATTATCAATCGAATCGCACCAAAAGAGC

TAAGATCTCCACGCGAGAACAATCTAACTAACCCTAAACCCCCAAATTATCCCAAACTCTGTACGGATAC

TCAAATTGGAAAAGCGAAATTGAGAGGATGCTAACCTTGGTTTACTCAACTTCTTCACTTCCTGGTCGCC

AGAGGTAGAGGATGAATGACAAGTGAAAACCCAGAACACGATGATGACGACAACNAAGCCTCCACAAATA

AATATAANACCCGGTTCGTGTTCGACCGTGTTTTTCCNATTAAAACCGTTTACGGCGATNAGAATCATA

AACCAAATACGATNATCACGAAGGGTGACGATTAANACGAGACTTCCCAAAACCGGTTCGT

AG0125

(SEQ ID NO: 7)

CTGTTGAGGGGAGGAAACAAGAGCCTGGGAGGAGAACTCCTTGCTGGGGAAGACGAGATCATTCTCCTCA

GAGGCAATGGATTCACCTAAGACCACAGCGTTTAACTGAGAGATCTTGCCGGCACCTGAGGGTAGCAGAG

ACATGGACTCCACATGCCTTAGGTGATTGGATGACATTGTCTTACACCGGAGAAGTTTGTCCAACGGAGA

TGATCTGCCACACCCTTACAAGTCAGATGTCATTTGAATAAAATTTAAAACAAACCACAAATGTCTTTT

TGACTTATTTATCAAAACTGCCTAAACCCCAAACCCAAT[CATCATCATCATCATCATCAT]AACCATAT

TCATCAATCATTCTATCATTATTGTCATCATTGGATCAGATTATTCATTCACCTTTGAGAAGCCGGAAGA

ATCCGAGATCCAAGTGATCCGCTTGTTTTCAGATCCTGAAGAAACAAAAACAGATCANAGGCGAATATTC

TTTTTTGATTACNATCAGATCATAAGAAGAAGAANAGATTGAAACTTTCGTANACCCAAAACATATCATT

ATGACNAAAGATCACATCTTTAACTCCNATGATCCCTAAGATTCGACTTACAGGTCGAGAACGAAGAGAG

GAAATTTTTGAAAAATTGTAAGAAGGGGCG

AG0148

(SEQ ID NO: 8)

CTTGAGAGAGAGATTGAAAGTGAGCTGCGCCAAGAACCAAAACGGACATATCACAAGGCTTACTTTAGCA

ACACGCATCCTTGTCCAACGTCCCTTCTCATCTAAACCTTTAGCACAAATCTCACCACTAACATCAAGCT

CTACACTTTCCACACCAGATTCAATCCCACTACCATCTCCCTCCTCTTCTCTAACAACAACCCCTGATCC

TTCAGACACATCTGACA[CCACCACCACACCACCTCCTCCT]AGCAAAACATCCTTCTGTGACTCAGCCG

-continued

ACTCCTGCAAATGAGACCTTTTGCTTCTCCGAAACAGTATACTCCCATACGCATCTGCTAAATA<u>CGACC</u>

<u>GATCTCGAAGAGAGGAA</u>GGTTAGTCCAGATCTAAGCAAGAGAAGGGCGAATTCGCGGCCGCTAAATTCAA

TTCGCCCTATAGTGAGTCGTATTACAATTCACTGGACCGTCGTTTTACAACGACATGACTGGGAAAACCC

TGGCGTTACCCAACTTAATCGCCTTGCAGCACATCCCCCTTTCGCCATCTGGCGTAATAGCTAACAGGCC

CGGACCGATCGCCCTTCCCAACAGTTGCGCAGCCTATACGTACGGCGGATTAAGGTTTACACCTATCAGA

GAGAGAGCCGTTATCGTCTGTTTGTGGATGTACAGAGTGATATTATTGACACGCCGGGG

AG0171

(SEQ ID NO: 9)

CACTTTGCATAAATACTTTTACGAGCAATTTTAAAAAAAAATTCTAAAAATGTCTATTATTTGTGGACTT

GGAATAGCCGTTTATCTGCTTTGATTTTGTCGTTTCTTAAATCAAAGTCCTAATCAGGGTCCTTATATAA

GATCAGTCCTCTAGAATCTGAATAGCTTTTTAAGACAAAAAAAAAACAAAACAGATTAGAGTCCGAATC<u>G</u>

<u>GACTCGAACATCTCCAATTTAACT</u>TCTATCTTTTTTTTTCTAAAATAAAATGTAAAATAAAAATATTTT

AATTGTATGAAAAATTGCATTCAATAGCTAAAAAAAAATAAAAATTCAATACATAACTAAAATCCCACTT

T[CTCTCCTCTTTTCTCTTCCTATCTCTCTCTTCTCTCTCT]AAAAATCTAATTTTTCTTTTTTTTC

TGGTTATTCCCTAAAT<u>AAGCCCTAATTGTATTCTATTTTC</u>ACTCTAAAAAATAGCTTGATTTTATAAATA

GAATAATTCATTTGTTTTTTAAAAATAAATTATCATTAGAATATAATTTAACTTTATTATAAAATTATT

CTCTTTTAGAGCAAAAAAATAAAATAAACCATTAGAAATTGTTTTAGAGAAATCATCAGTCAAAATCTCA

CNNNTTCCACTATTTAGTTTCATCTCTNNNGCAATCAGACGTAAGAACACAAAAACATATGTTAT

AG0203

(SEQ ID NO: 10)

CAGCCATTCTCTATGGCCTTGGTGACCATGGAGATCAAGTGCCTTAACAGCAACCGGTTGGGCTTCTAAA

CCCGGTTTAACCTTGTCATCAATGAACCCTTTGTAAACTGGCCCAAACCCTCCTTCTCCCAGCATGTTAC

TTCTTGAGAAATTATGCGTAATAACTCTCAGCTCAGACAAGGTGAACATACGAAGCTTTTGAGATGTGGA

GGAGTTTGAGAGGTCATCCATGACCGACATGGGCGAGCTTGGATCACTTATGTCCGATAACGACAGCCTC

TTGATCACCGGACAAGTTCTTATTTTCATT<u>GCGTTGCCCCTCTCCTCTACTT</u>CGTATCTACTCGCGTTCT

TTGTCCTGTAACATCCTAAAAACAGAGATGTCAATGATGT[CTTCTTGTTCTT]GGTTACTGCCATTTT

[CTTCTTCTTCTTCTTCTTCTTCTTCTTCTTCTTCTTCTTCTTCTT]CAACTTTTTGGAGAA

AATGGAAGATAGATAGTGTTTTACT<u>CTTTTTGATGTATCTTTTGTAGATTGCG</u>TNNNNNTNNNAATTAAG

GGTGTTTTAGTTAACCTACTTGTCTTCAAAGTCCTGTATTTATAGNGGTTGTTGTGTCTTATTCGTAGTG

ACTACCTTGGAACTTTCTNNNGACATATACTGTN

AG0239

(SEQ ID NO: 11)

AAGCAACCTACGGTGTTCTCTTATTACCGAGTGCTATTAGGCTTGTCTTAATGTCCTAAACAATTACGTT

TTTACTTTGAATGTGAACCTGCTCTTGAACGAAATATCTTCATGACTTCATATCATTTGTTTAATTCTAC

TACTGTCTGGTTAAAAATGGTTGTATGTTGCATATATTGCTATTTTAACCACATGT<u>AAGAAAAGAGAAAC</u>

<u>GATCCCACG</u>TTTATACTCAAATTCAAGAATCCAACACAAATCCTCTCACAATTCTATTAGATTGGAAGAA

AGAAACTCATAAAATAATTATAAATAACAAAAGGACAAGTAAATAGAGTCTATCTGGAACATAAAAACAC

TAACGGGTCTTGTGGGGTTTACAGA[TTTTCTTCTTTCTCTTCTTGACAGATTTGGGTGTCTTGTTCTTC

CTAGCCTCTCTCTTCTCTTCTTTTACTTTCTTCTTGAGCTCTTTCCTTGCTGCTTTCTTGTCTT]CAN<u>GA</u>

<u>CCCAACTCCTCTTCACTCTCA</u>CTTCCACTTTCCTCTTCTTCNNNNTCACTTTCTTCTTCTCCTTCTCCTT

TTTCTTCCTCTTTTCCCTCTTCAACATCAACCTTTACTNNCTGCTCATCTACTTTAGGANNNCATCCTTA

NNN

AG0243

(SEQ ID NO: 12)
TTTAGAATCAACACAAGACATAGNCAANTTGATTTTGGCTACTGGGTATTAATAATCCCCAAAATCACAT

CCTTCAAACCGAACGAACAATCAACAAGAAAATAAGAGCTACGATTCAGAAAAAGCCTATGATCAAAACG

CCTAAAATAACNNNAAAAAAAANNNGGAGCAATTTTAAACAAATGGAATTGAATAGTATGAGATGAGATGA

GAAACAAAAGAGAAAGCAGTGTGCATAGATCATCAGGGAAGCTAACCTGAAATGATTTGTT<u>GATTGGGGG</u>

<u>ATGAGATTGTTGG</u>AAGGGGACAGAGA[GAAGAAGAA]GGTTTGCTTGAAGACTCGAAAATTAAAGCTTGT

TAAG[GAAGAAGAA]GAG[GAAGAAGAA]GAGGATATAAATTGACATGGACCTATTAAATGCCCATTTTG

TTCTGNTTATTTACTTAAGATTGCCACTA<u>TGACCTTTGACTTTTGGACGGC</u>GNNTGTAGCTAAGCTACTG

TTTCTTCATTAATCACGCTTGCCATGATTAGTTTTTTTTTCCTCCTATAGNNTTCATANNTAGCCCGAA

ATTACTGACTTTTATGAGATAAAGATCGTATTTTTTATTTCTTANNGTTTAATACCCT

AG0272

(SEQ ID NO: 13)
CTACTTCCAAAAGAAAACATTAAATTAATGTTTATGTCGAATGTCATTTATACTGAACAAAATAACCTTG

AAAATATGTTCTGTACGCTAAAGTTGGGAGAGAGAAGGAGGTTGAAGAGATTTTGTCAAGATTGCGAGGA

GAAAATTCTGATGTATCAGATGAAGCAGGAGAGATATTAGTAAGCATATATATGCATGAATAATCATATG

ATCAATGTATATATTTTTTACTTCATAATATTTTGATGATCATCACGCATATACAGAACATGTTAAACAA

CAACG<u>AGATGATCGCGGTTTCCTCAAG</u>TTGTTTCAGCGAAAATACACGTTCTCACTTACTGTAATT[CTT

CTTCTTCTTCTTTTTCTTCTTCTTCTTCTTCTTCTTCTT]TAATAACCCNNNTGGTTTACACAG

AT<u>TGGAGTTGTTCTTATAGCTTTGCCTC</u>AACTTGGAGGTCTTAGTGNGTATTCTTTTTACACTGAGTCCA

TTTTCATATCTACAGGTAAAATAATTCTTCTTCTTNNNCAAAATATTGATTTTTATATATTTATTTACCT

TAACGATAATTGTTGATAATTACNNNNATCACGTGTATCGAGTGATGTTGGATTCATATCGACATCTATA

GTTCNNNNNTTACCGATTTCGAGTGACCTTGTTTAGAGTTC

AG0304

(SEQ ID NO: 14)
ACAAACATAATTGCAATTAAACGGATAGTAAGGGTCACAGATCACACAATACTGCATCGAAGTTTTGTCA

TCAACACAAGTGCGCATCGTTTCATTCTTTTCTTTCTTCCGGCTTACCTGAGCCCGGCCGTGGCACAATC

TTCTTCAACAGACAGCGTTTAAATAAAACTTAACTTGGTAGGGCTGAGGATTCAAGAATCATTTCTTGTA

ATTCACTGGCACATCGTCGTCATCTTCTTCAAGATCACTAAACGTTACATCTTCATCCTCATCCACAA<u>CA</u>

<u>TGTTTGGTTGCTACGGTGGA</u>GCTAACAGTTCCTGCATTATCTTCATCCTTCAACCAATCATCAA[CATCA

TCATCATCATCATCAT]CGACTTGAACGTCAATAACTCTAGGTGAAGATCCAGTGACTGGCTTGTCATGG

GGCGCTGGTGCTGGTTTTTCTTCAATCACAGGCTTGTCAACAACTTGTATCTCCTTGCTCTCGATT<u>GGGT</u>

<u>GCTTCTCCGTCTCAACCTC</u>NNNTGTATCACTCAAATGTATTGTTTCCANNNAGATGNANTTGACTGNNNC

TGGTGAAGACACAGTAAGTGGTTCCTCATTGGCA

AG0323

(SEQ ID NO: 15)
AATCATCCTAAATTTACCTAACCCATGGATTCAAAAGGTAACTAACTACTCGCTAATAGACATGATAAAC

CCAAAACCAATAGTGATTGAAGGTTAATCATGATTAGTGATCAAGATAATCCAATAAACACAAGACAAAG

ATGAAAAGAGGCTAAAGATTGAATCTTTCACCAAAATATGTTCATGTCTAGAGAAAACAAGATAGATCCT

AAGAATCTAACAATACTAAAAGCATGATAGTAAGCCCTCTAAGCGTGTCCACGTAAGTTAATATATTCAG

CTAATCAGAGATTACTAGCTATTTTGCCATGTCATAACAATTTTAAGTC<u>GACCAATACAAAAACCGGGCA</u>

<u>A</u>GGCGTCTGGGCCATTAGTAATATCCAGTGGCCAATACGAAACCCATCTCATTAATATCAAATCTCCAAT

GAAAGCCATTATCGTGGCGACTCTTCTTTTT[CATCATCATCATCATCCTCATCATCATCATCATCATCA

TCAT]CGCTTGGGATCACAACAATTTCCTGTT<u>AGCACAACCCACTCTCCATCAA</u>TCAATCAGGGTCTTTA

-continued

CTACTCTTTTCATGCTTTCGTNTCAACTCCCTTTGTTTATCCTCCTATATAAATCATTGAATATCNNNAT

TTTGATCCAAG

AG0324

(SEQ ID NO: 16)

TA<u>GTCTCACCAACTCCAAACTTGTTAA</u>CATCTGAAGGAGTCTGAATATTCTCCTCCT[CATCATCATCAT

CATCATCATCATCATCATCATCAT]CACAATCAACAACTTCAACCTTCTTCTTATTGTTATCATCATCCTTTA

CTAATTTCTCCTCATCACAATCAATAACTTCAATGACTGAATCTTGAGAAACTGCTTCTTCTTCTTC

CTCCAAATCGATAAA<u>CTCTTTATCTTTGGTAAGGAACCTG</u>AAGGCATTCAAAGCCGATCTCTTGGCGTTA

TCATACTCGCGAGTGAAAAGCTCCCCCTTCTCGCAGCAATCGTTAGGCTTAGCCGTGGGTGATCCTCCGT

ATATAAGGTTCGCTCTGCTANNAGCGTGGATTGCTCGTCTAAGTGGAGTTTTGGCGTCGGGATACCTCGA

AATCCTCGAAGATGGCTTGTTGGGATCCTGAGACATGGTTCCGAAGGAGAATCTGCGTTTCTTCGGAGCT

TGGAAGTAGGGCGAATGTCAGCGGAATTGGGCGGTGGAAGGGTGGTTGGAGTATAAGGAATCTTCGCTGC

GCTTGCGATTGATGGCGACNGCGCTCATTTNNNGAGTCGATCACTGAACCCTANNGATTGGGAGATCGAC

GNNNGGAGAGGAACCATAAGAGTNGAGA

AG0328

(SEQ ID NO: 17)

TTGCCAAAACATTTAACCAGGTGAGCACTTAAACTCTTGTCTGGCCCAAAAAAAAAAGAGTGAGACTGTA

TAGAGGATCAAGCCAACAGTAGATGAGGAAGAGGAAGGCCATGTAATCTCTAATCCACAACGATCTTGAT

TACCCATATAGGTCCATTGACTTTGAATCTTAATTTCAGAACATCAACAAATCTTCATCTTTACTAAAAT

TACAAAAAATCTTTTAACTTTTTAATTTTTGAAAAAAATACATATACACACATACAGCTAGTCTCTTACG

AAACACTACACAACTAGATAACTCCAAACATTTACAACTGAAAGTTTATCAGCTTGGAAAATCATCACTC

AGATTTCTTGTGGAACTTCACGGAGTCTATCAAGTGTATTAACAATCTCACTCAGACAAGCGATG<u>AGCTC</u>

<u>GTCTCCTTGCTGTCTCA</u>CAAACTTTAACTTGTCCTCAATGCCAACATCATCCTCTGTTTCACTTCCATTT

GCTAGATTTCTCCCGACTATTGCATGTATCATGTCAGCTTTCTCACCTAGCTTTGCTTCCAACGCTTTAA

CCTCTTCTTCTATGCTCATCGTTT[CTTCCTCTTCTTCTTCTTCTTCTTCTTCTTCTTCTTCTTCTTCTT

CTT]CTACATCANNNGAAATTTCTAC<u>CACCGGCTTCTTCTTCACTTCC</u>ATGGTTTTATTCTTCTGATGGN

NNGCTTTTGCACG

AG0359

(SEQ ID NO: 18)

CTCTTGCTTAGNTCTGGACTAACCCATATCCGAAAAGNTTCGAGGACCGACTCGAAAACCCAACCCGAAG

ATCTGCACGCCTAGGCCTAGTTTACAAGCAAGCCTACCAAAATATGTCAACTCGTTAAAAGCCTTTTAAC

CTGTCTGGTTCGGTGCACGGTTCAATTCCCGGTTTAGTTGTAACCGGTTTGTGAT<u>TGCTCAAAACCCTAG</u>

<u>TCGTCACC</u>CTTTTTTATCATTATTGTGAACAAGTAGTCACCTCTACAAGTAAAACCTTAAACCCTATTGA

GCGAGTAGCAGAGCGCAGCAAGAAGAAACAAAACCAAAATATGAGACCACCACGTGGCGGCGGAAGCTTC

AGAGGAAGAGGAGGAAGAGATGGCAGCGGACGCGGAGGTGGCGGACGTTTTAATCGTGGAGGTGGCCGCT

TT[GGTGGTGGTGGTGGTGGT]GGCTGGCGTGACGAAGGACCTCCCGACCAAGTCGTNNNTTCGTTTTCT

C<u>TCCTCTCTTGGTTTTCGCTCTCA</u>CTTTACAGCTCAAGCAGAAGTCTTTATTAACAAAAGTTGTCACCTT

TGACAAATTAGTCTTATCCCTTTGTTAGAGTCATCTTTAAGTTAAAGGTATAAACTTTGTGAAGTTATTC

GTTATGACAAAGTTTCTTTCTTTCGTTGGGTTATAACAGAAGTTGCAACGTTTGTTCATGCTNN

AG0369

(SEQ ID NO: 19)

TTTTGAAGGAGGTTGCTTGGGTGATTTTTGATGAGATTCATTACATGAAGGATAGGGAGAGAGGGGTTGT

TTGGGAGGAGAGTATTATTTTCTTGCCGCCTGCTATTAAGATGGTTTTTCTTTCGGCCACGATGTCTAAT

GCTACTGAGTTTGCGGAGTGGATTTGCTATCTGCATAAGCAGCCGTGTCACGTGGTGTATACGGACTTTA

GGCCCACGCCTCTGCAGCATTATGCTTTTCCTATGGGTGG<u>GAGTGGGCTGTACCTTGTAGTTGA</u>TGAGAA

-continued

TGAGCAGTTTAGAGAGGCTAATTTCATTAAGATGCATGATACTTTCCCAAAACCAAAATCTGAGGGGAAA

AAGAGTGCAAATGGCAAATCA[GGTGGTAGGGGCGGCGCTAAAGGTGGTGGCGGCGGC]GGTGGTGATTC

TGATGTTTACAAAATTGTAAA

AG0370

(SEQ ID NO: 20)
TAAAAAATACCTTAAATATATAAAAAATCTATCTTTGTCGAACAAGTAAAAAATTTAAAACATCTTACTT

TTGGAAACGAGGGAATATGATATTTTGGAATGAATCAAAATTGACAATCACCTTGTATAGAACCCATAGG

TTCGTGGATTCGCGGTCCTCACCACTAATAGGTTGGACCTGGTTAAGAATCCTTGCACACAGAAATAAAC

TTAACCATTGCCGCCTTACATTGTATTCCAAATTTGTTAATTACCGGCCAACAACACAATTATGTTATCT

CCATTATTACAACCACCCGCCGCAATAATTATCTCAATCA[GTTTTGTTTTGTTTT]TATTTATATTCAA

ACGGAATATCGTTATTTAATTATTAGAGCTTTAAATAATCTATATAAAGTCCATACAATTTTTGTTTATG

GAAATAGACACTACAAACGCGTATTTTCAGTTTTTTTTTCATATGGAGAGAACTACCAATCAGTTGAAAG

AAAAAAGAGAACTACCAATCTACCATATAATATAAAAACAATAATAGTATTAAAAAAAGGAGAGGGCAAC

GGAACGGGACGGAAGAGAATGGAAATGGTTACGTTTATAATAGCAATGATCTGTTGAACAGCTTATGACA

CCTCACTCTGCGCTTGCTTCCATTCCTCATCTCTCTCTCTCTNNNAACTCTCTACGAAACCCTACCTT

CTTCN

AG0378

(SEQ ID NO: 21)
TACAAGACAGACGGACATAATAAGAAGAAATGCAAATAGACAAGTCCTGAGAGAGAGTATCCAAAATAGA

GATTTTAAAATCTGTCACTAACTTTTAGGCATAGCTTGTTTAGTTCGCTTAGTCCCTCCTTTCTTCACAA

AACCAAAACCAAAAAAAAAAAGATGAGAGAGAGCAGTTTGTTGATAAAGAAGCAAATGAAATGTAACTTA

CTTTTCTACCGGCGGTGGTGGTTGCTGGTGGAGTTGCTGCTGCAATTGAGTAACGTCACAACAAAAAGGA

AGATGGAAATGAAAAAAAGGAGGATTCAATGGATATCAACAAAAACGTGTTAGAAAGACTCACCACTCTG

TTGAGCTTCACCACCTTGGCTGCCTCCTCTTCTCGTCGGGGTCTACACATTTCAATAGATTCGTCAACAA

CAGTAACGAGATTGCGTCGAAACCTAACTCAGAAAAAAAAAGAGATGACGTACCGCACTCGGACCTG[CC

GCCGCCGCCGCCG]AAGATGAAGCAGTCGCATCTACAAATTTCAGATGCCAAATTAGGGTTTAACCTAGA

AAATAAAATATCAATAAGGCAAAGAGAGAGAGAGAGAGTACTAGTTGGATTGCGATCT

AG0391

(SEQ ID NO: 22)
GTCTTCTCACGGCCGTACGGATAACGCCGTGAAAAACCACTGGAACTCGACGCTCAAGAGGAAATGCTTA

GGCGGCGGTGGAGATGGTAATCTCATTGTGATGAGGAC[GGAGGAGGAGGAGGA]TCAGGATCGGCGGAA

GAAGAGGAGATCGGTGAGCTCTGAGTCTGCTACTCCGGTGGACACTGGGTTGTACATGAGCCCGGAGAGT

CCCACCGGAATCCCATCTCCGCCGTCTCCGGTTGATGCTCAGCTTTTAAAACCAATGGCGATGCCGTCAC

CGGTGGAAATGTCTTCGGTGGAGGAGGATCCGACAGCGTCATTGAGCCTGTCACTGTCACTTCCTGGTCC

TGATGTCAGACAGGAGTTGAAGAACGCGGGTTCGAAACACAACTCGTTGCTGTTTCCCCGGTTTGGGAGT

CAAATGAAAATTAATGTTGAGGAGAGAGGAGAAGCACGTGTTGGACATAAAGCTGAGTTTTTGACGGTGG

TGCAAGAGATGATTAAGGTGGAAGTGAGGAGTTATATGGCGGAGATGCAAAAAAATAGCGGTGGTGGCGG

TGGTGAATTCATCGTCAGTGGTTTTTATGATGCCGGCAACGGCGGTTTCAGGGATAGTGGG

AG0410

(SEQ ID NO: 23)
AAAAGGAAAGTTTAAGACTTTAAGCTTTACCTGATGATCCATATCGGGGAAAATCGCGGCGAGGTGATCG

AGGAGAAGC[GAGGAGGAGGCAGGAGGAGGAGGA]GGGGGAAAACGCGGCGGAGAAGAGGATGAGAAGTA

ACGGAGTTTCTTGGAGACGGGAGGGGAAGAAGCGGCGGACAAATCCTCGAACAGAGATCTCTTGCTACCG

CAAACAATCGCAGACATGTTATCTGCTTCCACCTTCTTTTTCTTCTTCTTTCTTCCTTCCTTCAGATCTC

```
                                      -continued
AACCTTTCCTTTTTGTTTGGTTTTTTTTTTCCTTTTT]CCTCTAATCCATCTCTGATCTGTTTCTGTCG

GAAACCAAGCAAAAAAAGTCAAAACACATCGGATCTTCTTCCGCATCTAAATAGATCCAACAACCCGGA

CTCGGATTCAAAT

AG0441
                                                           (SEQ ID NO: 24)
AAAAGACGTTGACTTGATTTGATATGCCATAGAGCTAAACCCTAATTGAATTTCAATCAATTAGGGGTAA

AGATCTCTCAATCTACGAACAAAAGATCTAATATTTACAGTCAAAATCTACGGAAAACACAAAGAAAAGG

CTTACGGCGACTGGGCTGCGAGGAGCGCGATTCTGATTACGGATCGGCATCTTCCGATTCTGGATCCGAG

CTAGGCGATACGAAAGATGATTTCTTCCGGAAACCTCCGATTGAGTAACAAGAATCTCGACAGAAGTTGT

TTCTTCTCAGTTAGAGAGAAGAGATTAGGCTTCGGCCCTTTTTGTGATTTTGAGAAGGAT[GAGAGAGAG

AGAGA]GT[GGAGGAGGAAGGAGGAGGAGGAGGAGGAGGA]GCCTTTGTTATTTTGAAAGTTTGAAAATA

GATCTTGAGAATAATTGTAACGTTACTCTTGGTCCTCTATATGCTTATTTATTTATTCCACTAATACTTT

ATAAGGTATATGGGCTTTATATGGACTATAATCTCGGCCCATCTATGTTAAACTAATCCGTAATTTTCTT

GGTTTTTTTTAAACTTGCGCGCTCCTTAATTTGAAT

AG0477
                                                           (SEQ ID NO: 25)
ACTTTTTATAACCGACACTTAAATCAAAACTTGAAAAATAGCATCAATTAGATTTGTAACGGAGTATCAT

CAATCATCAAGAAACAACAATCTTGTAGGTGAGTAAATAAAAGATACCGTGAATAATGTCAACAATCGTA

ATCTCATACCACTAATACGTAATTAAAGAAAATAATCATATAATTAGGGAGATAATGTTGGGAATCTTAA

TCGTATAATCAGAAGCGTATTCATTTCATTACAAATTGATTCTCTTGTCATTTGTTATAT[AATAATAAT]

AAAAAAAACGTTAAATCAATTCAAACTAAACCTT[CTCTCTCTCTCTCTCT]TTCTATTTCGCTCAT

CATCATTTTATCTGATGAATACGCCCAATTGAAATCCTTTCCTTATCAACTCAAATTGAGTTTTCAAAAT

TATTCAATTTTCGGATCTCCGTAGATTTGCTCGGCGGAGGAGGAGGAAGGATGGCTCAGTTGGCGGCGGC

GGCGGGGAGGAGAATAGGGGATTACGCGGTGGGAAGACAAATCGGGTCGGGTTCGTTTTCGGTGGTGTGG

GAAGGGAGGCATCTGGGAGATGGAAACGTGGTTGTAATCAAGGAGATAGCCATGGCGAGGCTTAGTAAGA

AGTTGCAAGATAGTCTCATGTCCGAGATTATCATCTTGAGGAA

AG0482
                                                           (SEQ ID NO: 26)
ACCCAAACGAATTGCTCTGTCCGTAGAAAGAACAGGCTCGGGAGCTGAGT[GGTGGTGGTGGTGGT]GGA

GAAGCGACGGTGGACCATCCGGGAACGAGTGCAGCGAGAGACGGAGATCTTGACTCGGAGGAGCTTCCGT

CGAGGAGCCAACCACCGGGAAAAACGACTCCGAATCCATCGACGGCGGAAGAAAACTCGGAAGCTCCGCC

ACTCCGTCGAATCCACCGGACCGTGCACCACCGAACTGAAGCTGTTCCCGCTG[CGGCGGCGGCGG]CGA

CGGAGATATTTTAGTTTTGGCGGCGGTTCTTCTCGGTTTAGCGTTTGCGGCGGCGTTGCGAACAGCGTCG

GCGGGACTCCACGGAGGAAGCTGAGCGAGCTCGTCGATGGAAGTCTGAGCCTTTCTGATCAGCCAGTCAA

CGGCTTTGCTCGGTCGGTCGAAGCCAAGGCGGTCTTGAACGTCGTAGAACTGAATCGCCGTGTGAGCCGA

TAGCCTCACGCGCCGGTCACGTGGCCCTTTGGCCGTGCAGACTTTGCTGTGCCGGTCTTTTCTCCCCGTC

GACCGCACAATGTGACCTCCTTGCACCTCCACTATCTCGTCTGACGCAGCGCGGTGCCTCATTGAAGAAG

GCNGNNNGGGTTGAGGGGTGGAGGAAGTGGTGAGCTTCGTCGTGGTCGTCTGCCATTGGTTGAGCATAC

AG0504
                                                           (SEQ ID NO: 27)
ACAACTTTGAAGTGTGAATAGAGTAAAAGATTCAATCTTTCATATCAAAAGACTAACCTAGACTCGAACT

CACGGATCTCAGCAAGTTCTTTCCCCATCAAATCCACCCACTGCACCTTCTTCTTCTTCTCCCTTCTCTC

ACCATCCTCTGAATCTAAAGTTTCCTTTTTTAGACTACTCTTCAGGATCTCTCCATTACTTTGACCTTCC

TCTAAGGCACAATCTTCTTCCTTTCCCTCTTCTTCTGTTCCCTCATTCACCAAACTATCAACGTGATCAA

CAACTTCCTCTACTTGTGCATCAACATACTGAT[CATCATCATCACCGTCAT]CAACAACCGAAGAGACT
```

-continued

TGA[GGAGGAGGAGGAGGAGGAGGAGGAGGA]GTGTCCTCCAATTTCAGAGAACCAGA<u>TGCGTAGATGTG</u>

<u>AGGAGAAGGC</u>TTACAGAAGCAGATGAAAGAAGGGCACTGGATCTTACAAAGCAAAACCCTCATCAAAACA

TATGTTCCAATCATCAACCAATTCAACAAGATCTCTTTTGTCTTTGGCAAAGTTAGAAACTTTGTGTGCC

CATTGATATGCCCAGATTGAGAAAAGGAAACACTTTTGATTTCTGAATAAAAAGTAGAAACAGAGCAGCA

AAGAAGTTAGTATATATCTCTCGTCTTGGATAGAATCCAAAGACCATAAATAACGAGTTGATCAGATGAN

NNAGCAGACAAA

AG0510
(SEQ ID NO: 28)
ACTGGTCTCAATGGAGGTGGTGGAGGAGGAGGAGGAAGAATACGACTGGAATCTCTTTTAGACCTTGTAG

AGAGTTAAAAGATAGTTTTAAGAAACAAATGTCAATCTCTCAAAATAGGAATACTATACTCTTTACCTGT

GAGATAGCTGAGCAAAATCA<u>TCATCTGATTCATCGTCATCATC</u>ATGATTGATGCTGACAAGTTGAGCT[G

GAGGAGGAGGAGGAGGAGGA]GCTGTTGCACCGCCTCCATTTGAAGGAACAGAGGCGATATCGTCATGAC

GCTGAAGAACACGCTGCAAGTTATCGTTCAATGCTAATCCCTGGCACAGAAGCTCCTCGTCTCTGAAGAA

AAGAAACATCATCAAAAGGGGATGAAACATCAGGTGAT[GAAGCAAGAAGAAGAAGAA]AACTCA<u>CGTGG</u>

<u>TGGTGTTGACAAGAGTCAT</u>CACACGTTTCTGATAGGT

BG0031
(SEQ ID NO: 29)
C<u>GAGGAAGCAT</u>[AGGAGGAGGAGGAGG]AAGCAGTTTGAGTGTTTGGAGGAGATGCCTGAGG[AGAGAGA

G]GAAGGGAGGGAGTCGGACGAAGGCGTGTGTTTTGCACGTGCAGCGGAGGAGAATCCGGATCCGAAGA

CGGAGAGGGAGAGTGGGAGTCGGTGGAATGGACGGCTGAGATGGAGGCGGAGGCTGAGGGAATGGGATGG

GCCGTTG<u>ATTTGGGGATTTGGGTTATGT</u>GTTTAGGTGTGGGCTACTTGGTGTCCAAAGCCTCAACTAAAA

CCTTGAGAGGTGGAGGAAGGAGAAGAAGATCAAAAAGTTTCTTTTAGAGTTCTCTGTAATCAGTCAGTCT

AGTTGTTCAATAACGTTCTAATGTAATAGTACAGATCAATAAACCATAAATGTAAAACAATCCATGATTT

TGAATACCAAGAGTCGCACGAGTTCCATTTTATTTGAGAGCATAGAACAATAAACTTTCTCCTCTGACCT

GATGAACTAAGGCAAGTTCATGCAAGAATCTAATGAATGCAAGCAATCAAGTACGTCAAATCATATTGCA

TTTACAAATTATACAAATACACAAAGGATCCAAAAGTGCCTTCTCCCTTTTCTTACTAACAATAATAAT

AATGCAGCAAAAAGGAATAAAAGTTTATCAAAAACGTGTGATGATAATTCAATGTAAATAAGCAAATATG

TGGAGAGCT

BG0106
(SEQ ID NO: 30)
GTAGCCTTGTGTGAGTTGGAACCAGACTTTCCTGTTTCCCTGCCTTGTCTCAAGGTTATGCATTTAGAGA

GAGTTATAGCTAACCTTGAGAGGCTTATAACTAGCTGCCCTGTTCTTGAAAAGTTAACCATAATCAGGGA

TTCTTTTGAAGTTCT<u>CGAAATTATGTGTGTGCGCTCC</u>AAGTCTTTAAAAAGTTTGGCTCTACTGATTGAA

GCTTCTGATACTGATCTCTTAGAAGATCACGATTTGGAGATCGATGCCCAAAGCTTGAGCGTATGAGTC

TCTGTGATCACTTATCCAGAAGCATCGTTATACACAGTATTGCTCCCTCTGCAGTGGTACAGATCGATGT

TAACTTTAAT[AGGGAGGG]TGGTGATACATTATTGGACCAA[GATGATGATGATGATGATGATGAT]

TCCAAGAGAACTA<u>TGATCCGTAATTTCCTAACCGGG</u>ATATCCACAGTCAGCCTCATGAAGATCTCCTCT

GATACTCTACAGGTAC

BG0111
(SEQ ID NO: 31)
GTAATCATTTCTTTGTTATCTCTCTTTCCATGATCGTCCGTCCAAGAGATATGTAATTGGCGTTGTTTGA

TTCTGCAATCCGTACAATCCATTTCTAGCTGTTAATCTGAATATAGCCATCTTATTAGACTGAAATCTAA

GCGCCTGGATGGGGTGGTTTTATTTT<u>TCATTTGACTTTTGGCGTTTGG</u>TTTTCAGATCTTTAAGATAT[G

ATGATGATGATGATGATGATGAT]GAAAATGATGAGATTTAGATTTTACTG[ACCACC]CTTTTTTTTTT

-continued

TTTGTCTTTACGTTTCTTTCAGCTCAATTCAGAGAAGAGCCCTTTTCAACGTACTTATGCAGCTCAGGTA

AATTTCATGTTTATCTGACACTTGTCTAGTAATGTGTGATACAATCTAAGAATGTAAATCTTACAATTGT

GATAAAAATATTCTCTCTCGTGTTTAGATAAAAAGATGTGGAGAGATGGCAC

BG0119

(SEQ ID NO: 32)

GTGCGGGTTCGAGCAGCTCTCAGCGCTCGCGGAGGGAGGCATGAACGTGGCCAGGCTCAACATGTGCCAC

GGCACTCGCGACTGGCACCGTGACGTCATCCGCAGCGTCAGGAGGCTCAATGAGGAGAAAGGATTCGCGG

TCGCGATCATGATGGATACCGAAGGTAGCGAGATTCACATGGGAGATCT[CGGCGG]CGAGGCCTCGGCT

AAAGCAGAGGTTCCTTCCTCTTCTTGAAATCTT[GATGATGATGATGATGATGATGAT]GCAT[GTTGTT]

AATCAGATTATTGGATATAATCCGGTTTAGTTAGAGACCGGTTTAGTTAG[ATTAATTA]TGGTTAAGT

TTCTTTTTGCTTAATCATGTATATAAAGAAATGTTAACACAGATGAGGTTTTTGTAGGATGGTGAGGTTT

GGACGTTTACCGTTAGAGCTTTTGATTCGTCTCGTCCTCAACGTACCATTAGTGTGAGTTATGATGGTTT

CGCTGAAGGTAATGTGTCTTTTTTTTTTGTGTTATGAAAGCATCAAGTGGATGTGAGTATGAGATGGGGA

TCGATTTTTTTTTTTTTTGTGATTTCAGATGTAAGAGTTGGTGATGAGCTTCTTGTTGATGGTGGAAT

GGTTAGATTTGATGTGATTGAGAAGATTGGTTCCGATGTGAAGTGTCTGTGTACTGACCCTGGGCTGTTG

CTTCCTCGAGCTAACTTGACTTTCTGGAGAGATGGGAGTCTTGTAC

BG0181

(SEQ ID NO: 33)

GTAACATATACAAATACTTCTAGGAATCAATCGAAATATATATTTCATATCGCAATTTCACAATACTGTT

GAACTTACAAACGTGTATAATTACACCATTTTTTTACACAAAATCTTTAACATGTCGATTTCTTATACCA

TTTGTAATTAACTCAACATATTTTTTTAACTAAATCAGCCTCGCCAATTTGTGTTGGTTTACGGAACCGG

TACAAATATTGTTGGCCTGGCCGTTATTAATTTCAAATGATTGATTCATAGGTAACATGAGAAGTTTGGA

GAGCTTACTAACGAAAGCAGGAGCGGAGACATTGCCATTGGCAGAGCAACGAAGTACGCCTTGAATATTG

ATGAGACCTAAAATGCCTCCAAGGAC[ACCACCACCACC]AAGAATCCCACCAAGGCCACCATTACCAAG

AAGCCCCCCTACTAGGCCACCATTACCAAGAAGGCCACCTAGGCC[ACCACCACC]AAGAAGGCCACCTA

GGCC[ACCACCACCACCACCACCACCACCACC]AAGAAGGCCACCTAGACCCCCAAGCTGAGCCTTA

ACCATTGGAGACACCATCACGAGACACACGAAGATCAGTGAGAAGGTTATGCGTTTGTTCTCAAGCATTG

TCATGTTCTTGG

BG0228

(SEQ ID NO: 34)

GTATCTATCTCCTCTTGCCTAAATCACACCATGACTGACTTTCCCAAAATAACCTAGAGATCCAGAAAGA

ACGGAGGAAAGAAAGAAAAAATGGAGGAGACGAAGCCATTGGTAGGGAACCATCCCCAGCAAC[AGCAGC]

AG[CAACAACAACAACAACAGCAG]CTCCTGTATCAACACCAATTACAACAGAGACAGCAACAGAT

GCTTCTATTACAGCAGTTGCAGAAACAGCAACAACAACAAGCCGCCATGTCTAGGTTCCCCTCCAACATC

GACGTTCATCTCCGACCTCCAGGGTCAATCCAGACCCGACCAATTGTTCCCCCTCAGCAGCAGAACCCTA

ATCCCAACCCTAGCTTGGGACAGCCTACACCGAATCTTCAGCAGCAGCAGCAGCAGCAACAGCAGGT

TGTAGCGAGTCAGCAGATGCTGCAGCAGCAACAACAGCAGCAGCAGAAGTTGATGCGTCCTTTGAAT

CACATCGAGCTTCAATTCGCTTATCAGGACGCTTGGCGTGTCTGCCACCCTGATTTCAAGCGACCTTTCT

CTTCTCTCGAAGACGCTTGCGAAAGGTTCAGTTCTAATTTTATCTAATTACATTTGTCTTTTTGAGATA

TTTCCTTAAATAAAATCGGTTATAGACAATCTCATCCGTTCAATCTTATTTCAGGCTATCGTGTGATATA

TGCATACGGGTCTTGTGATCTTTGAAATGAAACATTGATCTGTTAATGACTTACTTACTGGTCATATCTG

CAACTTGTATGTTCTTCTTTAGTTCGTGTTTGGTATTATGGTGATGATATCTGTTAGCCTTTTCGTTAAT

TTCTATACTTCTTTTCATTGATATTGTTTGTGTTAGATCCAATAGATCCTGCTTCTTTTGGTGTTCGTGC

GAAACTTAAATCTCTTTCTGAGTTTAGTGTGGTTGATTTTATATTATTTTTGTCATCTAATGTGGTTGAT

-continued

TTAGAATTACAAAACTTTGTGATTGTTTCCTATTTTAGTATAACCACCTGATTCACTGATACTGATAATT

ATTCCCTGACTTTTATATTTATGCTAAAAGTTTACAACTTTACATTAGCATATTATTGGTTTTATTGAT

ACATTTGTTGCCTTGATTGAACATTTCTGTATATTGTTTGTTTTATCTTACCTCATAC

BG0255

(SEQ ID NO: 35)

CTAGTGGCTACAAATCCAACTGTCGGTTCTCACTTGGGAGACCCAGGTTTGGATCTATCAAGTTTAAAAA

T<u>CCAAACTCAGCACAGCCTTTCA</u>TTTCTGAAACAAGAAAAGAGATG[GAAGAAGAA]GATCAAGAAGCCA

AAAGCATCGGTTTCAGGGAG[GAAGAAGAAGAAGAAGAA]GATTAT[GATGAT]GGAGCTAAGGGTATTG

ATCTAGAAGGAGAAGAGAAGAAGCATATATGCTGTGAATGTGGCAAACGTTTCAAGTCAGGCAAGGCGTT

AGGTGGCCATAAAAGGATCCATGTGCTCGAAACTCGCAAATTCTCAATGGTGAGACCGAAGATGGTGGTG

ACGTCTGGTGCGGTTGCGGTTGCGGTTGGTAGATCTGATGAGCAGAGAGATGATTTCGAAGTTGATTGCT

GTGTTTGTCATAAGAAGTTTACATCGATGAAGGCTTTGTCTGGACACATGAGGTTTCATCCAGACAGAGG

ATGGAAAGGTGTTTTGCCTCCTCATCATCCACTTGATGATCATCATGGTGGGGAGTTTATAAGCTCCGAT

TACGATGATGATGCTGATTATGATTATCATGAGGATGATGATTATGAGAACTCGGAGTTATGGGATATTA

ATCGTTGGGAATTGGACAACGTGGTTGACCTTAAGGACTCGATCAAAGAAGGATGGACGGTGACAGGAAA

GAGAGGAAGGAGAAGTGCTTTGAAGATTGATGAACCTGATGATATTGATGCTAAGGATCTATTGTTCTTA

GCTACTACAGCAGAATCTGTCGATGCTGCAGAGACTTGTTGTGATTCGCTTTTGGGGAAGAGATGATGA

TGAAGAAGAGGAAAAAGAAGAAGAAAAGATTGTCTGAGATGGAGAAAGAGTCATCATCTAGTCATGGTCA

TCATCAGCTTGAGGTTGGTGATGCTGCTGAGGGAGGTGGCGGTGCAC

BG0278

(SEQ ID NO: 36)

GTATATGTCTTTGGTTATTTTTTTGGTATCCAAATAACCGTAAATAAAAATTAAAAATGGCCCGTTTTC

CCTCGGATAAAAAAATTGTAGAGTTTAAATCATGTCTTTTAAAACCATGGGAGCAAAATCAAAGGAAGAG

AGAAGATAAATTAAATGGT<u>GGCTGTTCAGTTGTTTAGCTGGA</u>AGACATTGATTCTTCTACCTTCACAAGC

TTCAAGACATAAGGGTTTCACTTCTTTTAACAGGTTTTTAATCTGT[CTTCTTCTTCTTCTTCTTCT

TCTTCTTCTTCTTCTTCTTCTTCTTCTTCTTCTTCTTCTTCTTCTTATTATTATTATTATT]AT

AATAGTTTCAAGTTTCTGAAAAACAATTGATTCCATGGTGGTGCATGTGTTTACAAGATATCTCACTGA

AAATTAACTTTGTTGCAGAACATTGAGTTT<u>GCACTCTCTGCCTTCAAATGGG</u>ATTGATTCTTTTAGATCC

CGAGGTGAGGAGGCTCTGAAACACATTCCACGTCTTAATGTCCTTCCTCTCAACAAAGACTCATACTTTC

ATACTATCATATTTTCATAATTTCATTATTACAGGAACCTTCAGAGTCAAATCTCAAAAGACAGGAGACA

CAGAGTCATCTACTTCCAACTTGAATCAACCTAATGATTTAAAATCCAAATTCCATAAGGTGCGTGTGTG

TCATGCATGTCTTTACTTTTTTTATCTAATGATTTACTTAATGCTTTATGTTATAATCTTTCTTAATATA

CATATCTGCAGAGTCTCCAATATAAACTTGTACTAGGATGCATCCCACTGTATGCGGTATCGAGAATTGT

ACAAAAGATCATTCATGGGCTTCCACTCCACATTCAGAACTCAGTAGGGGCTGGCTTGCCTTTTGCTTGT

GCATCAGACTCTCTGAATAAACCATCTTTAAGTGGTATCAAATGGAGTCTTGCAAGGTTCTTTTTCCTGT

TCAATATTCGGCTCGAGAAGAACGTTGCTAC

BG0295

(SEQ ID NO: 37)

CTGTTCCGTTTAACTATGCTCGCACCTCCATTATCTCTCCTCTTTCATAACTCTCTCTCCTCCTTCTTTC

TTCTC<u>CACATCTCTCCGATTTCATCGC</u>TAGAATTCTCCACCGATTCTTAAGGTATGTTTTATCTTCACTT

CAACTCTTGTCGGAATTCACTCTCCTTGCCTGTCTGAAACTTTCCATTTGCAGATCTGTAAAACTTTCTA

TTTGTGTTTCCTCCTTTCCGTAGATCGAGAAGAAACGATGACTTCAACGG[AGGGAGGG]ATACGATCCC

TCTTGTCTC[TCCTCCTCCTCCTCCTCC]TTCTCTTATCCATAACCACTCTAATCTCAGCCGCTGACTAC

-continued

ACACCCACCGACAAAATCCTCTTAAACTGCGGCGGCTCCTCCGACCTAACCGACACAGATAACAGAACAT
GGATCCCCGATGTCAAATCCAAGTTCCTGTCTTCCTCCGGAGACTCCAAAACATCCCCCGCCGCAACACA
AGACCCCTCCGTCCCCACCGTCCCTTACATGTCCGCCAGAATCTTCAGATCTCCCTTCACTTACTCCTTC
CCGGTCGCCTCAGGTATTGGTTCAATCCTGGTTTAGTAATTGTACTTTGGTTTACTCATTTCCGGTTTAC
TAAACACTTTTCCCTATCACAGGTCGCAAGTTCGTGCGTCTCTACTTCTACCCCAACTCCTACGACAGCC
TCAACGCAACCAACTCCCTCTTCTCCCTCTCCTCAGGACCCTACACTCTTCTCAAAAACTTCAGCGCCGC
TCAAACCTCCCAGGCGTTGAACTACGCTCACATCATCAAAGAGTTCGTAGTCAACGTCGAAGGTGGGACC
TTAAACATAACCTTCACACCAGAGTCAACGCCTTCTAACGCCTACGCCTTCGTCAACGGTATCGAAGTAA
CTTCGATGCCTGATATCTACAGTAGCGCCGACGGGACGTTGACCGTTGTAGGGACTTCTAGTGGCGTCAC
GATCGATAACACCACCGCTCTCGAGAATGTCTACAGGCTCAACGTCGGCGGGAACGACATCTCTCCTTCT
GCTGACACCGGTTTGTTTAGGTCTTGGTACGATGATCAGGATTACATCTTCGCCGCGAGTCTCGGTATCC
CCGAGACA

BG0452
(SEQ ID NO: 38)
GGTCTGAGATATATCCTCGAGGGTTGTCCTAAACTAGAGAAGCTTGGGATCAGGGACAGTCCCTTTGGTG
ATGTTGGACTGCGCTCTGGGATGCATAGGTATAACGACATGAGGTTTGTTTGGATGTCGTCATGTCGGTT
ATCCCGGGGAGCCTGCAGGGACATTGCTCATACTCTGCCTAGTG[TGGTGGTGG]AGGCGTTTGGGTCA
[GATGATGATGATGATGATGAT]GACGAAGACGACAATGCAGATTATGTGGAGACGTTGTACATGTATCGG
TCCCTTGATGGCCCAAGGAAGGATGCTCCAAAGTTTGTAACAATTTTATGAAGACAAGCTTAGAGAAAGC
AGGAGCTGAAGTAGAAGAGAATGTGTGTTTGTATGATTGTTTGTACCATTTGATTTGATTGGCTCCCCTC
TGTTTTTGGATTTGTCTTGTACCAAGAAAGAGTGAAGAGTCAGTGAAGAAAGAGGTTGTTTGTGGAAGTC
AAAGAATGAAACTTTTATTATTTGTGTGTAATCAAGAATATGATTTTACAGCCATTTCACGATTATTTTT
GTCTACAAGAAGTATTGGTTATACATTACATTATAAGATCTTCACCAATCTTGACTTCGTCCTCCATCAG
CAGATGCTCTAAGGTGTCGATGAAAGCAGTAACTTTCTCCAAGCTCTTCTCATCAAGCCTTGGGACCGTG
TGGCCCTTGGGATGATGGACCACCACCGGATTCTTGAAGGAATCTATCAGCTCAGTTCCGTAAGGTTTCA
AAAAATCAGTCTCTCCTGCAAAGAAAAAACTCATTTTTCACATTGAAATTTGCAAACCAGATATACAATT
TAGTAGGTCATCAAATTACCTAGAAAGTGGAGGGAGGGAATGTCCATGGTAGACGAATACGCATCCTTCG
CCACCTTGGTGGATTTGAACATAGCTCCTCCAATAATTATGATAAACTTGATCTTTGGTACTTTCTGGAG
TGCAATTCCCTGCAATATAAAATATAATTCTAAGATAATGTAATGCGATTTCCCAACGCAAAAGCAACAC
TACTGACGTACCTTAGCTTGCAGTCCTGGTAATCCTCCAGACAATATTGCACCCTGCAAAATTAACATAG
AGATATATTATTAGATCTTATATAAGAAACTGTTAAATGAGAAATGAAGCAATTTTGTAATTAGAGTACC
TGAGAAAAGCCAATGAGACCATCAAAGGGACCAAGCTCGATCATACGATCCTCTAAATACTCCAAACATT
TCTCGAAATTCG

BG0516
(SEQ ID NO: 39)
GATGTGTTCTTCATTGTATCTAGCAGAAGCTTGGTCAACAGAAAATGGCCTGAAACAT[GATGATGATGA
TGATGATGATGATGAT]GAGACTATAAAACTTAGGACAAAGGTA[TAATAA]TC[TTGGTTTGGT]T
TCTCTTAGCTCACCTAGATGGTTAGTTGCGAATTGCAGCTCAATATTGTCCTTAGAGAGCATGAAAGGAC
ATGCCATTACCCCAGCGTTGTTGCTAACAAGATTTGAGAGATTACAAAACATTAAAACCGTCACAAAACA
CTAGACATGAACTACTGTGTTTCGAGAGCTTACATCAAGATGTTTAGTGGAAGACCAGTAGATTTGTAGT
CAGATGCAAATCTCCTGACAGATTCAATTGAGCTGAGATCTAACTCCATGACGTCGAGTTTAGCACCAGG
GACTTGATTGAGGATATCTTGCTTAACTTTAGCACCGGAGACAGTGTTCCTCACCGCCATAACC

BG0647

(SEQ ID NO: 40)
GCACATATGTCCGCACCTGTACAAAACCGCCTCGACCTGCGTTTCGTCGCAGACGCAGCATTTGCGTTTC

ATTGGGTTTTCTCTGTAAACCGATTGTTGCAAGCTCGCGTTAGCATCCAAACACGTTTTGACAGAATCTC

GTAGTAAGGACATTTCTTGTTGAAGCTGTTGGATCTGTGTTCTCATATCGGTTATCAGCTCCATTTCCTG

AAAACGTTTTAAAGCGGTTCAAAGATTTTACTATTCTACTAGTTGGGGTTTGCGAGTTTTCTATGCAATA

ACAAGAAATCGAAAATTACTTACATGTGAAGGAGGATTGTGAACAGACAAGACAGGAGTGGAAGTTACTT

CGGTGTCTTGACAACTCCATGATCCTGCAGGAGACGATGCAAAGATGGGCGAAGAAGACGATCTGCTTGA

GTCATCTCTATCGTTTTGTTCTTCACCTTCCGTTGATGGCTCTTCTTCAGTTTCCTCCGCAGTGTCATCT

CTATGTTCTTCCT[CTTCTTCTTCTTCTTCTTCTTCTT]GTTGCAATTCCCATGATTCAGAATGCTTTTT

CGAATGTGTCTGCAGACGAGACATCATGAGCCTATCGATCTGATCTCGTAACCCGCTCTCGAGAAAGTCT

GTCACTGTTCTTCTGTAATAGCAAGAAAATATTTATCTTCTTAGTTAATGGTTTAACAAATAAGAAAAGG

GATTTGTTGAATCGATGTTGCGTACCGCTCAAGGAGTCT

BG0651

(SEQ ID NO: 41)
AATGCATAACAAAAGATTTGAACCCGGGTCTTTGGTCAAACAATAATCATCCTAAATTTATGCTAATAGT

GATTCTTTTGTTAGCCACTGAACACAAACTCT[CTTCTTCTTCTTCTTCTTCTTCTTCTTCTTCTT]CCT

CTTTCCTCTGCACTCTCTCCGACACAAGACGGCGGTCAACGGAGTCCTTGTCGGTCAAATGATCCCTAAG

GACGAAGGAGGAGTTGTGGAGATTTCCGATTCTGTTCCGCTCTTTTGCTCCAACCTCGCTCTCCTTCCTC

CTCTCTAGATCTCGCTCATCATGGTCGCTCTCACTACATAAGTTTTTGAAATTGAATATTGAAAAACTTA

GGATCTGAGTGCACTGTTGCGAATTCTCAATATTGTTGTTCTGTAGCTGTGTTTGGGAGAGAGGCAGTGT

CTGTAATAC

BG0713

(SEQ ID NO: 42)
ACGGTTCAGCACAGTAAAAAAAAAGTTTTTTTGACTTTTTTTTCTTTGACCGCCAAAGAAGACGAAAATG

AGTCTTTGAGAAAATCACAAAAAAGAAGAAGAAGAAAAATGAATCCTTTTTGTTTCTTCTGCACAGAATC

TTCTT[CTCTCTCTCTCTCTCTCTCTCTCTCTCTCTCTCTCTCTCTCTCTCTCTCTCTCTCTCTCTCTCT

CTCTCTCTCTCTCTCT]TTCTTGAGGTTTCTTTTCCTCCACGATTCCTCGTCCCTCTTGCTTCTGTGT

GATCGATTTTGGTGAAATTGAGCTGAGTGTATCTGTCCGCCGAGGCCTTTTGTTCACTGTTCAATTCAAC

ATCAGATCAATTTTAGGGGCTTTCAGTCAAAGATCGCTGCTTTGGTGTAAGTTTGAATTTGGGTAACTGA

ATGAATGTGATCTTTGGTTCCAGTTCATGTAATTATGTTTGATTGACTGGGAAAGTATCATCCTTTATTA

CGGATTGTAAACATTTAAGGTTGAATCTTAACATTAGCACCATTTGGATTCGAATTTGTTTGGTGGGTTT

GGCTTTAGATCCATAAGCAAGCTTATGAGCTCTTAAAGTTATGTTGTTTTTTTTGCTTAAGCCATTCAA

ACTGATGAGATATACTCTCTTTGTCTTGCTTCCTAGGTTTGTGATTTTAGTATAGAATCCTGTTATCATG

GATGAACACAATAGGAATCCATTTGCAAGTGCAAGCGGAAGAGCAAGTGGAAGTACAAGTGTGAGTTCCA

ACTCCAGTTTTAGTAGCAGCGTGGCGGATACAGAGGATGATCAAACCATTGC

BG0864

(SEQ ID NO: 43)
TGCAAAGGAAGCAGGTGTAGCAGCTCAAGCTTATGAAGCTCTAAAGACACTGAGAGAAAAAAAAACATCT

GCAAAGTGGTAAACAAACTCTTCTTATTTCACACAACACATGGTAAAGAAAATACTTTTTCATGGAGAAT

AAGAAGAAGAAGAAGCTAAATGCGTTGCGTTGCAGGTG[GAGAGAGAGAGAGAGAGAGAGAGAGAGAG

AGAGAGAGAGAGAGAGAGAGAGAGAGAGAGAGAGAGAGAGAGAGAGAGAGAGAGAGAGAGAGAGAGAGAG

AGAGA]AGCGCATAAGTAGTGTTTGTGTGTTGGTGATTTTCTATTTGGAAACTCTTTTGTAAGCAATAAT

CTCAGATGCTAAAGCCATTGTATTTATTGCTCACTTCATTTTACAGCCAAACTAAGTTTTAAAAACTGAA

-continued

AATATAAAACGCTAAAATTTTCTTTGGTTGACATCAGCATAAATATAAATTTAGCTTACTCCCTCGATTCA

ACAATACAAAAAAAACGACATAAGTTTGAGTTTACATGCTTTCAACCAATAAAATGGAACTCTTTATCAT

AAAATAACAGTCAACGTATTATTAAGTCCAAACCACCACAAACCAATATTTGCACAAATAAAAGTTTCCA

ACCTTAGCTGCCACTATAAAGTTATAAACCACCATCCAAAGTCCATTATTTTAAGATAGATTTCGTACGG

TAC

BG0869
(SEQ ID NO: 44)
TCGTATAAAATAAAATTCTGAACAAAAATAATTATATAATTTCAAATTGCGGCTCAAAATCTATTATTTT

TAAAAACTCAACAAAATTGTATATGGGCCGATGAAGCCCAAGTATTTTAATTACCGTAAAGGAGGGTTTG

AGTCGGCCACAAATCAAGGAATTATTTC[CTCTCTCTCTCTCT]CCTGTGACGAGTTG[CTCTCTCTCTC

TCTCTCT]CGTCTCGTCCGCGCTCCGAAGAAATTTCACAGATTCCTGTCATGTCTTCCGGCGGAAACTCT

ACCCTCTCCAACGTCGAAAAGATGTTCTTCTGTTACCAGTGCAATCGCACAGTCACCATCTCAATCTCCT

CCTCCTCCGACGATCCTTTCTGCCCTCGCTGCTCCGGTGGGTTTCTAGAAGAATACGACGAGCCAAACCC

TAATCCGCCCCCAAATCTCAACCCTCTCGGTTTCCTCCCCATGGCCGATCCTTTCTCCACCCTGCTCCCG

CTCCTATTCGGCTCCTCCTCCTCTCCTCCTTCCTCCACGAACCAGAGCTTCTTCGGCCAGAATCAGCACC

CTCCTCGCGGCGGAGCTTTCGATCCGGTGTCGTTTCTCCAGAACCATCTCCAGCACCTGCAATCCAGCGG

CACTCACGTCCAGTTCGTGGTGGAGGATCATCCCTCGGATCCGTTTGGCCGGATGCCGGGGAACATGGGG

GACTACTTCTTCGGCCCTGGCCTCGAGCA

BG0988
(SEQ ID NO: 45)
AACGGTTTTGTATAAATAGTATATTCTATATATGTATGCATATAATCTTTTTTCGTAACTTAAAAGGATT

AAACCGGATTTATTAAAGACACAAATCTAACTTCCAGATGAGAGGTGCAATACACATATGGATTATTTTC

CAGATATTTAAATGGACCATAAATATAGACCCATAACCGCGTGGCCACATATGGAACTAATGATTTCGCA

CTAGAAGGGAATCGATTCCTGACCTGAACCAACAGGACAATTCCTCCTCTAGCGGAAACCATTAAGCCAC

CACAACATGGTTTTAAACAAAAAATTGTACGCATCTGCGTGGCTTACTATTAAAACATCTCTATCTCTCT

CTTAAAATACATCAAGAGTATAATGAGAGATATCTCAGTTTCATGTAGTAAGACAAAACCCAAGACTCCA

ACCGGAAAATTCCAACCCTAAGAGGCAAACTAAATTTCATTGTACAATAAAATAATTAATGCTATTCAGT

TTTCTAAAAGCAGATTTAAGTCTCTAACTCCAATTTTCCAT[CTCTCTCTCTCTCTCTCTCTCTCTCT

CTCTCTCTCTCTCTCTCTCTCTCTCTCTCTCTCTCTCTCTCTCTCTCTCTCTCTCTCTCTCTCTCTCT

CT]AAATCCCCACTAGGATTATGGGAACTCACGTCCTCGTTTAATGCGATTCATGACTCCTCAAAGCCCA

GCATTCCCACTCTGCAAATTACTAGTACCTCTTAGTCTTAATTACCATTTGACCAATCT

BG1062
(SEQ ID NO: 46)
GTAATGCGGCAGGACAGCCCTCCTCGGAGTCCACTTCATGGAGGAGCATACTATTCATCCAGTGATGATG

ATAACCACTCCACCTACCTCTTCCCAGAAATTGGCACCCCAACTCGTTCCATCCCAGTCTCCGCCAACAC

CACTGTATGAAT[CTCTCTCTCTCTCTCTCTATCTCTCT]TTCACCATTGTTTTTATGATCTTATGGACC

TTAATAAATAAACATATGCAGCCTGTTCACCACAACTACCAAATCATTGCGGTGGAAACCTACGAGCAAG

AGAAGCAGTACGAGCCACCGGAGCTAGCGGACGAGTCACAGAGCTTCTCGATCCAGGAGATCGCCAAAAT

GCGAGGACTCAAGGAAGAGAGCCAATCGATGATCTCCGAGTCCTAC

BG1090
(SEQ ID NO: 47)
GTGAAACCGGTTCTGGAGAACTCTAAGGTTGTTTTGAAAGATCGCAAAAGAGAGTGGAAGCGGAATTAGG

GTTCTGGTTATGGCAAGGAGATGAACCGGAAGGAGGTACGAATCCTTTGGGAAGCATAACAGAAAACGTA

TCCGGTCGGACCGGTCGGTTAAAACCGTTACTGTTTTTCTTGGTCATCATCTTGAAGTAGTTGGCACGGT

GACGAAGACCACGGCGACGAATGCTATGGCGGTAGTAGTAGTAGTGATGGTTGTAACGAAGACGACGGTG

-continued

CTGATCACGTTGCCGCGGGTTCAAGATAAACGGCGTCATTTTCTTGATGTAGACGAGTTGGTGCGGTGAT

TCGTCG<u>CCGTTGAGGTAGGTTTCTGCCTTTT</u>GTGTAGATACTCTTGTTTCTTGATTCGATAATGATGAGG

ATGATGATGATGGCGATGATGGTAAT[GATGATGATGAT]GGTGAGATAGGGAAGACGAGAATGAGAATG

AGAGAGATGATGAAGCATTTGACAAGGTTGTGTTTCATCAAAACATCCATTGCGATT[GAGAGAGAGA]G

GGAGTAGGACTTTTGGTTTAATAGAGAGAGGGAGAGTAAAGATGAAA<u>CAAAAAGATGTGAGCGAGGCAAC</u>

TATAACAAATCTTGGTATGGCGTCTAAATAATTCGTTTAGTTATTCGAATTTTAATTAATTTTAGTATGA

TTTTTGATTGCGTATAATTTGGAAATTAGTTGGGCTTTTTGTTGGTCTGAGGC

BG1101

(SEQ ID NO: 48)
C<u>ACATGCTTGTGGATAAAT</u>[<u>CATCAT</u>CATCATCATCATCATCAACATCATCATCATCATCATCAT]CAAT

ATCAAATATATGGTAAGTCCATTTTCATTTAGCTTTCAGTAAAACTGTTAATCTATGCATTCGATAATTA

AGAGAATCAAACGAATTGTGTTTGCAACATTATAATTAATGGTTGAAATTCATTAAGAATA<u>TTTAGTTTG</u>

<u>GGTTTTCTCATTTTC</u>ATACAAACATTATCCATGCATACGGTTGGTCATTAGGTTTTGAAAATATATGAAA

TCAGAAACATTTTAATTTTTTTAATGTAATTTGAAAGCATACAAGTTATGTATATTAACTTTGTGTAAT

TTGAAAGCATACAACTTATGTATATTAACTTTTCAAAATTTGGACTATAAATAAATATTTCTTTGATCTG

CCCAAAATCACAAAAGATTCTTTTACAAGATAAACTGTATCTTTTACTCTCTTTTTTGTCAATACTGTAT

GTTTCACTTGTCACGAATTTGCATTCAAATAACTATGTAGCAGCACATTATGATAAAGTTGGAAGTGTAT

GAATAAATTGATAATGTAGATTGTAGGGTGAGAAGTTAAAAAAAATGAGTAATTTTTAGGGGCCAAATGT

ATTTTCGTATAAATTAAGGGTGGAAACATGAAAATTAGATTTTTATGTCCGAACTACCCACTGACTTGT

CCGAAGTCCGT

BG1123

(SEQ ID NO: 49)
GTTCAAAGGCATATTTATATTATATTTAAATTGGGACCAAGATTTGCTTTGGGACAAGCTGTGCCCCACG

ACTTTCTCGCTAGTGCTCTCTGGTCGCTTCTCCTTCTAGAGACCAACCATTTCCACCAACTCCGTTTTCA

GTTCACACCATGCCCACCACTGCATCAGTTAGTTGATATGAGCCCAACTTCTTTCTTCACTGTTTAACAA

AATGGACTGGTCAACACAGTCTCTGTCACACCCGAGAATTCTAATGTGGTGGACACAATCTTCACT<u>AGGC</u>

<u>CACCTTTTGTCACCAGTC</u>TCTCTCTCTCTTTTCCTGTTTTGATCCTTCCATAAGATTAAACCTTTATGGT

TACTACCATATTATAACGATCTCGGTGGTGGTAGCGTAGCCCAAAGATGATGATCCGAAACTGAATGTAA

ACTATGTACCAAA[GAGAGAGAGAGAGAGAGAGAGAGAGAGAGA]GG[GAGAGAGAGAGAGAGAGA

GAGAGAGAGAGA]GTAATAATTAAAAC<u>AAATGGGACAAATTAACCCCCC</u>

BG1127

(SEQ ID NO: 50)
<u>CCGCCATAACAAAAATCTTCCC</u>ACAAGCGTGTAGAGATCTG[GAGAGAGAGAGAGAGAGAGAGAGA]GCT

TTCAAGTGATTAAATCCAAAAGTAATAAAGAGAAGACGGAGAAACTAAAGTGACGCGCCCCCTTCCTAAC

GGATTATATTTATTTTATTCTTATATATTTATGGGCTTATTGCAGCAATAGCCATATTTGAAATGAAAAT

TAAGAGAGTAGCCATGATGTTGACATAATGTACTCACTGTCTTTTTACAATTTTACTA<u>GCCGGTTATACC</u>

<u>TTTGTAGGAAACAG</u>GTTCCCAGTTCCTTTAACTAAAGTAAACGATGTGGTGATTTACTGACCCATAGTAA

CAATGAGAGTATTTTAGCAACGCCTAAAATTAAAATGAAAGGAAGGAAAACATTCTATAGAGATGAAAAT

ATAAAAAAACAGAAGTGTAAAAGAAAGAACGTTACAAACGGAGAATGCATGGATCGTAATGCTGATGCC

AAAATATGGAAATAGTTCCACTTCAAATAGAATACACATAGTATAACAATAGTTTAAAGTTTGTCACCGC

TATGTCATATGAGAATATTTTCCATTCTATCGGATATAGATCAGTTTATATTTACTAATATAATCAC

-continued

BG1149

(SEQ ID NO: 51)
GTAGAGTGATAAGAGAACATCTTGTCTGACTCATGCTTCTTTTCTGCTATGTTAGGCTATTGCTCTTAAT

GATCTGCCTTCCACTAACGTATCGAGACTGGGGCTTGCTCTTAACTTATCTCTTTTCTACTATGAGACTC

TCATATCAACTAAAGCTGCGCGTAAGATCGCAAAGGCGGTATGTTGTTGCTTTCTCTCATTTAGTATTTT

GGTTTATGTTATGCGATTATCATCTATTCTCCCAGATGCTCTGTTTGATAAAACTTAATGCTTTTCTTTC

TTTTTTTTTGTTCTGACAATCGTTACTGTTCAATTGTATTCATATTGTGGCATAAATATGTATAT<u>GTTGC</u>

<u>TACACTTCCCTGTGGGTG</u>TGCAATCTTCATATGATATAGTAATGGTTTGCAGATTGCTTATCATTTGGAA

GATAGATATTGTAATTGATTATGATGATGATGTGCATAATTTGGAAAGTAGAGCCTATCGTTATTCCCTT

ACACTAATGGAATTATATATTGATGATGTTCCAAATTTTTTAAATATGATGAATT[GATGATGATGATGA

TGATGAT]GGTAGGCTTTCGAAGCGTCAATAAC<u>AGAAATGCACGCAGTGAGAGAGG</u>AATCATACGAGCAA

ACTGCATTGATCACGAATCTTATCCTTGACCGTATCACCCCTCTGG

BG1182

(SEQ ID NO: 52)
GTGTTTCTAAGCACTTTTTTTTTATAATCAAATCACATACAGCAAACATAAACATGAGTCTCAGCTTCAA

GAGCCAATGAAATTAGCTTCCTTTATAATATTCAAGAACTAACCAGTTTCACTTCTACTAATCCT<u>CGGCG</u>

<u>CACTGATGATGTTTCTA</u>ACTAAATTGGATACTAAAGAACGTAGCTTTTCACCTCGAATCAAACAACTTGA

AAACCAAAACAATCTAAACGAAATTTCATAACCTAAGGAGGATCGGAAACTAAAATTTCTACATCGGAAT

CGAATCGACGCGAAGTGAAACGAAGATCGAT[AGAGAGAGAGAGAGAGAGAG]GACTCACTCGCCAGGAG

AAGACATGTTCGTCGATTTCGAAGATCCGATTGATTCAGAAGCGGAGAACAATCCAAGTTTTTTATTGAG

AG<u>AGCACCGAACAAACTCTCTCCC</u>TAGAACGTTCCTTCCCAGCTTCTCTACAAATCACTTGTTCCGCGAC

TGCGTATCTTATCCAATCATGTCTTGCCACG (SEQ ID NO: 53)
BG1197

BG1197

(SEQ ID NO: 224)
GAACATCCTGCTGTTTCAGTTCTATTTTTCTTGTGTAGTCAAAAAGACATTATTACCCCATTGGAAATTA

CAACAACACATTAG<u>TTGTGAGCGCCAAGATAAGGCT</u>AAAGACGTAAAAACGCTCTGAGTATTCATTCTTT

CAGGTCAGGTTCAGAAACTAGTTTCGTTT[CATTTCATTTCATTTCATTTCATTT]CATCCACCTCCTCT

TCACTTGAGAAGTTCTGTCTTTTGCGATCCTTGTCATTTTTGTAAAGGTGAGTCGATCTATATATGGTCA

CTAGTATTCTGGAAATGATGCTATTTTAATACTCAGTTCGAACATTCTGTTATCAAATCCGGTTCTAGTT

<u>AGTTGTTCGCGGGATAGGGTTT</u>GCTTGAGATCATTTCGCTTCTTTATTTTTTTTAATGTCACTGATGGAT

CTGGTAATCTTCCTTATCGAATTAGGAAAATGAATCTGTATTAAGTGGACTAATCTCAAATCTAGGTAAA

AAAAATGGAGGAGGAGGAGGAGGAGAAGGAGTTGGCGATTTCAGAGCCAAAGTATGGAGCATGTCTGGT

GGGCCTTACTGTAGGCCCAAGCACTGGCGTCGCAACACCGCCTTTGCAATGCTCGGCGTTTTCCTTGTCT

GCATCCCCATTGCCATGAAGTCTGCCGAGCTCGAGG

BG1230

(SEQ ID NO: 54)
AGAGAGACCTCCAGTCACCTCGTCTCTTC<u>AGGCCTCTTGTGTTTCCTCCAAC</u>TTCCTTTACCAAAAAAAA

ACAAATCAAAATCAGATTCAAAGGAGAGAAAGAGAGAGGGAGAGAGCACTACAAGAGTGGAAAAGAAGAG

AATCAGGTCGTG[GAGAGAGAGAGAGAGATGG]CG[GATGGTGGTGG]TGATGAATCTGAGATGCGATGG

TGGTCGTGATGAATCTGAGATGC[GATGGTGGTGG]TGAGGAATGATGGCGGATGGGAAAGATGGC[GAT

GGTGGTGGTGG]TGACGAGTGAATGAGCGG[TGGTGGTGG]TGACGAGTGGGAGG<u>AGAGATGGCGGTAGT</u>

-continued

<u>GGTG</u>GTGGTGGTGATGAGGAGGTCAAACCTGATGGATTGGAGGAGAAAAGGAGGCGTCACAAAGAGAGAG

AGAGAGATTTGTGTGTTAGGTTAAAGATTGCACATTCAGAAATGTGCTTAGACAATGATCTGAAGTGGTC

TTGGTCGAGGTAGTCCGTACATGTCCGTACACAGTGC

BG1241
(SEQ ID NO: 55)
GGATGGGATGAGTCAGCTGCTGGTGATAGGCCCAGTCGAGTTTCAGTTTGGGACATTGAACCAGTTTTAA

CTCCTTTCTACATATGTCCTCCTCCATTTTTTCGACCTCGGTTTGCTGGACAACCAGGAATGCCAGGTAA

AGTCTTTGTACAGTTTCATTTTGCACATCATCTTTGAATCTCCTTAGAGATGGCAATTCTGGTGGTCTTG

CAGATGATGGGACTGACATGGAGTCTGCGTTGAAGAGAGCAATGCCGTGGCTTGACAATGGCCTAGAGAT

GAAGGACCCTTCCAGTACGATATTTCCTGGTCTGAGTTTAGTTCAGTGGATGAGTATGCAACAGCAGAAC

GGCCAGGTCCCTTCTGCCGCTGCACAGCCTGGTTTCTTCCCGTCAATGCTCCCTCCAACCGCGGCTCTGC

ACAACAATCTTGGCGGGGCTGATGATTCCTCAAAGTTACTGAGCTTTCAGGCGCCTCCAGGGGGGTTTC

CTCATCAAACCTCCAAT<u>TTAACAAACCGAATCCGCAAGC</u>GGCAATGTCCCAGTTACCTCAGCCACCAACT

ACGTTGTCCCAACAACAGCAGCTGCAGCAGTTGTTGCACTCCTCTTTGAACCATCAGCAGCAGCAGCAAT

CACAGCCTCAGCAACCACAGTCGTTGCAGCAACAACAACAACCGCAATCCCTGC[AACAACAAC]AATCA

CTG[CAGCAGCAACAAC]AATCACTACTG[CAGCAGCAGCAGCAACAAC]AATCTCTGCAG<u>CAGCAGCAG</u>

<u>CAACAACAATC</u>TCTGCAGCAA

BG1244
(SEQ ID NO: 56)
ATGATGATGAAATAGCTCTGAAGAAGAAGTTAATTAAGGAATTGTTGCTGTCTAATTAGGTGTTCTTGTT

GTTTGGTTAATTATGTTTGGTTCTCGGATTTGAAAGCTCTGTTAAAGAGCTTCAGTTTTAACTTTAATTA

TCGGATTTGAAAGCTCTGTGAAGAGCTTTATTTTTCACTTTATCTGTAATTGTTCTCCTGTTCTTGATGA

TATAAATATTTAAGTTGTTCTTGTGTTGTTCAGTTATATTTACAGTTGTTGTTTATGATATATCATGTT

TCTTTGTCTTGTAGAGAAGTCACGGAGTCCACAGAGATGCTTGGACTGAAGGGAGTCACGGAGTCCACAG

AGAGATGTCATGTACCATGTCTTGTAGTGTGCAGGGTCTGTAACGAGTCACGGACCATGTGTTTGTATGT

GTCAGTATGTGTTTGTACGTGTCTTGTATGTGTCACAGAGTCCATGTTTTTGTTTGTGTCTGTATGTGTT

TGTATGTGTCGATGTCTTGTAGTCACGGACAGTATTTTTGTAGTCACGGACTTTTACCAAACTCATCTTC

TATTTATAACATCAATCTCATCTTCTATTTATATCAACCTTCTCTCTCGAAACATATA<u>CAACGAACTCTT</u>

<u>CTTCTCTGCTTTACA</u>ACAACAAACT[CTTCTT]CT[CTTCTT]AACAACAACAAACT[CTTCTT]ACCAT

ATTTATATTTTTCCCCTTATTATAAACACCAAAACCATCTTTATAAAAACTTTATATGG[CTTCTTCTT]

CTC[ATGATGATGATG]CGTTTG[ATGATG]CATTTG[ATGATG]TTTTTG[ATGATG]TCTATGATCA

ATATTTTGATCAAGCATT<u>TGAGAATTTGACCATTTGTCGTGA</u>TCAAGAAGAACGAAGAAAGAAAAGAAAA

AAACGAGCGTATATCGAAAGACATCGTGAGGAA

BG1286
(SEQ ID NO: 57)
A<u>GTCCGAGACAGAGTATGCTA</u>[AGC]AGCAGCAGCAGCAGCAGC]TGAATACTGCATATGATGCGTCACAG

ACAAATGCTCAGAATCAGATGCAGAATCTTGCTTCTTTATCAAATGTGATGGTAAGCTACATGTGCATTA

TTCA<u>TATTTGAAGTGATCCACCAATGA</u>CATTCTCCAATGGCATTGCTAACATTGGTACTTTGTTTGTGTG

TTTTTGACTCAGCAGGGATATCCACACTCAGATCCCAACAGTTTATTGGCACAAAACGCTAGGGAGCTTG

AGTTCCAGTATTCCAATTTTGCACAGTCTATGCAGTCAAGAAATAGCAATAATGCTTCTTCACTTGGTGG

TCAAAGCATTTCCATGCCAGAGGTAAATAACCACTTTTGTCTTCTTTTTTTTAAGAAACACAAGATGTC

TTGTTAATTAGGTTTTGCTCGACTATGGAGTGATCTATATGTATCCAAATCTATACAACAAGAGGAATTT

ATATGATTTTGATTATATATTTTCTTACATTGTAGGCGCCCCGAGGCAGTGGAATCCAAGCGACGCAGCA

AAACTTACAAGGTGCTAATATCGCCACTGGACCAGCACTTCCTCAACAGCTT

BG1288 (SEQ ID NO: 58)

ATAAGCATACCAATGAAGATATCAAAGAATGCAATATGTATGTTTTGTGTTGTGAAAGCTAAAGGATTCT

ACTTTATTTGTGTTGAGTGATGGTTCTTTAGTTTGGTGTTAATGTCTTGTGAATTGTGTTTGGCAGGTAC

AAGCTAGGTTTTTGTCCCAACGGTCCTGATTGTCGGTACAGGCACGCGAAGCTGCCTGGACCGCCGCCTC

CAGTTGAGGAAGTTCTTCAGAAGATACAGCAGCTGACTTCGTATAATTACGGGCCTAATA<u>GATTCTATCA</u>

<u>GCCACGGAACGC</u>TGCTCCGCAGTTGGGAGATAGTAATAAGCCTCAGGTGCAAGTTCAGACGCAAGAGGCG

GGTAACTTGC[AGCAGCAGCAGCAGCAGCAGCAGC]AACAACCTCAGCAGTCACAACATCAGGTCAGCCA

GACTCAGACACAAAACACTGCTGACCAAACGTCTCATCCTT<u>TGCCTCGTGGGGTAAATAGG</u>TGTGTTCAG

AGTTTCTAAAGTTTTTAATTGGGTTGTGTAAACTATGCTTCTGTATATCTGTCAAGACATTGTTTATTG

BG1321 (SEQ ID NO: 59)

ATGAAGATTGATGTATATTCGAATTTATAAAGTCTACGTTTAGTAAAGGTATACAAATCAGAGGTCTGAA

TTTGTTCAACTTCCTCCTCATTCCCCCATCCCCAAAAGAATCCGAGTTTTTTTGGATCAAGCCTATATAG

ATCCAAAAACCAACATAATGGCCCATTAAAGA<u>TGCATAGACTCGAACCAAACCG</u>GATTAATACACTGCGG

GTGAAACCGGTTTGGGAATTTTCACAATTGACTGAAGAATCAGGGTTTAAGGAGAAGTCACAGACCCAGG

[AAGAAGAAGAAGAAGAAGAAGAAGAAGAAGAAGCAGAAG]AATGGAGTCAGAGCACCAAACGA

TGGAACAGTTCCTACGATGGG<u>CAGCAGAGCTTGGCGTATCAG</u>ATTCCATCGATCCTTCTCGATCTCAAGA

TTCATGTCTCGGCCATTCCCTTTCCGTCGCCGACTTCCCTCTCGCCGGCGGGTGCGTAGAAACAAAAATC

ACATCTTTTTATCATTCAAATTCCTAAACTTTTTCGACCATTGATGGGAAACTAGGAGAGGGTTGGGGGC

TGTT

BG1368 (SEQ ID NO: 60)

CTTCAAGTTTCTATTATTATCAGTTCAGGAAGTGACACTCACTAGACCAACAGAAGAAGAAAAAAATCAA

CATACAGAAAACAGATAAGCACTGCTCATATTAATCATGAATCGTTCAACAAATTTGATCCGAACATTAC

AGAAACTATACGTGTTTGATCCAACAACGAAAGGAGCACAAACAAAATGAGATCAATACGATCGTTCTTC

ATTGTCGTTCTATTACAAAACTGTGCTTGCTTTGTTGGTTCGAACTCGAACATACAACAACATAGATAGT

TATGTCGGGATATACTTATTTATATTTAGATTTAATTATGGATAACGACGGCGAGAGATTCTCGGCGACG

GAATATCAACTGTTTCGCGATGAATGCTTCGATCGTTTTCTGAAACTCTTCGTTTGTCAGATTATCCTCC

GGAAACGGCACTTCTTCGCACGACG<u>CGACGGTTTCACGGCACT</u>TCTCCGTCTCCGATCGCCGGAGCGTAG

GTTTCGTCACCGTCTCCGGACTCTGTTTCGCAGAGATTTCCGTTTTGCTTCTTTTATAGACCTT[CGTCG

TC<u>GTCGTCGT</u>]CGGAGGATGATCATTCGTCGATTC

BG1392 (SEQ ID NO: 61)

CTCAATCTTTGTGTGGGTGGAGCAATACATAAATTTTGTGTGGTTGGAAGGTTATGAAATGAAACTTTTA

GTGGAAACGTGAATAGATCATCCAACTTATTTTGTGTGTTTTAAGAAAGATTAGATGAATTTGACTCAGC

TCATTGGAGAGAGAGAGAGAGAGAGAGAGAGGCTTCACAGAGCCCATCGAATCCTATGCGCGTGTGAA

AAGCACGATCCAATCACGAAGCTAAAATCTTCAGCTTCGTTGTATAAAAAAAACTTATTGAAACAAACCT

CAAATTCCAATTACACCCTTGACAGCGATACACACTCTCTCTCTCTCCAACTAAAACATATCTGGAAATT

ATAAATAAAATTTATACTTTATCTGGTAACCCATCAAATAAAGCTATTAGTCACATAATAGATGACAAAA

AAAAAACAAATAAAGAAAATTTAGGAAACAAATCTACTGAGATTAGGCTGTAAATCATACGTATATCTTT

CCCGTATACAGAGTGCCGTTTTAAGTATAATGTCGACACGTGTCGGTCAGAG<u>GCTCGGCTTCCAAGGGTA</u>

-continued

<u>AGAT</u>TGTAAAATCACGATCGTCATCTCTCTTTAAGAATTTCCAGAGTGCT[GAGAGAGAGAGAGAGAGAG

AGAGAGAGAGA]GGTGCTTTCCCATAGCCATTCACGTC[GAGAGAGAGAGAGAGAGA]GGAAGGAGATGG

AGGATATACAGGAGGAAGAGAACGGTACGGACGAGGAGGTGCTGGGATCGAGCTTGACCATGGAGAAAGT

<u>GGCGGCAGCTAAGCAGTACATC</u>GAGAATCACTACAAAGCTCAGAATAAGAACATTCAGGAGAGGAAAGAG

AGGTATTATAAATCGTCTCTTTCGTTGAGTGAGAGATTTGAGATTTGGAATATCGTTTTTTTTTAGAGAC

TAGTTAGGGCGAAATTAGTTGCGTGAGCTTTGATTAGTCTCTCGTATTTGATGATAATCATGGT

BG1442

(SEQ ID NO: 62)
GAACAATAACCTGATCAAGGCTCTGCTCAGCTGCTTTACGCTCGTCGGGATTGGGACTGCAAGCAGCCGC

AGCGATGATTACTGCCAGGTTAGACAGATCCATCGGGAAAATTCAGCAACAGATTCTCCGAGGAATAGTC

GGCGTGTCAAGAATTTTCCGGTGAATCGAAGAGG<u>CGAGGAGGAAGAAGATGACCGA</u>CGAAGACGAGGACG

AG[GAGAGAGAGAGAGAGAGAGAGAGAGAGAGAGAGAGAGA]GGTATAAGAAGGAAGGTCTAAGCTAGGGTTTT

AATGTATGGTTCGTTGGTCTGTTATGGTAAGTCTATCGCACGCACGCGCGTGGTAAAAAAGTGAAAAAAA

AGAAAAATCGACGTGAGACACGATACACAACCCAGACTTGCCTGGACCTCTAGTCACCT<u>ATTTATTTTCA</u>

<u>CCGCCTGCTCGT</u>TTAGTTAGTTACGGTCAATCGATTGACTTTTGGTTATTTTCTATGTGTTTTCAATATA

ATCAAATTCAAATGATTTTTTAATCAAATCAAATGTAAATAATAAATAATAAAAATCCAAATGGAATTAA

TTAGTTTAAACTTATTAAACTATTTTGTCATCTTTTTAGTTATTTAAGAATTATATTAAAACTTGTAAAA

TTCTAGTTACAAATATAATTTAATGCATAAATCTAATGAATTTGGGAGAAAATAG

BG1449

(SEQ ID NO: 63)
GGTTTCCGCCGCAATGATTTGGT<u>AGTTGTGGTGAACAGGCTGCAT</u>ATGTTTATTTATTAAGGTCCATAAG

ATCATAGAAACAATGGTGAAA[GAGAGAGAGAGAGAGAGAGAGAGAGAGAGAGAGAGAGAGA]TTCATAC

AGTGGTGTTGGCGG<u>AGACTGGGATGGAACGAGTTGGG</u>GTGCCAATTTCTGGGAAGAGGTAGGTGGAGTGG

TTATCATCATCACTGGATGAGTAGTATGCTCCTCCATGAAGTGGACTCCGAGGAGGGCTGTCCTGCCGCA

TAACGTAGCCATCTGGCTCATACATTGCTTCCATTTGCTCATCATTATGATTGTTGCTGCGACGGTCAGG

CTGCGATTTGTTTAGGAGAGCTGATTATTTATTGTCAAGAATATGTTTTATCACTAGAGAAGCTCAGG

CTTGAGAATGTTGTTTGAGTACCGTTCTGTATTGTTGTGGTGGTGGCGAACGGGTCGCAGCTGGATGAAA

TGGGCTTGGTGGAGAGCTGTTTCGTGGTGTTACTTCGCCGTCTCGCTCATACACTTCCTCGGATTGCTGA

TTATCAGGGTGGTTTCTACGACGATCAGGCTGTTAGAATTAGAATAACGAACTTTATTGTCAGGTTAAGT

GAATCACTTTATCTGTTTCTGGAAAATAAGGCTGAGTTTTATGGTACCGTTCTGTATGGTTGTGGTGGTG

GTGGCGAACGTCTTGCGGCTGGATGAAAGGGGCTCGGTGGAGAGCTGGTTCGTGGTGTTACCTCGCCG

BG1453

(SEQ ID NO: 64)
AGTGCTTTAGGAGAGGAGGATCTTGATACAAAATTGTTCTCAAGAATTGAGAAGAGGAAGAAGAAAAAAG

GGTATTAAAAGGAAGAAGAGGAGGGCTTTATTAATCATGTATTGCTAAAGAGGAAGATGAGGAACTCA<u>TC</u>

<u>ACCTTCCTTCCTTCAATGGC</u>AATGAAATGAAAA[GAGAGAGATATGAATGAGAGA]GTGAGTGAAAAA[G

AGAGAGAGAGAGAGAGAGAGAGAGAGAGAGAGAGAGAGAGA]GTTGGGTCTACCAT<u>GA</u>

<u>AAAGCAGAGGAGGTGGGTCA</u>AAGCAAAAGTTTTCGACTCTTTTTTAGGGCTTTTCAATTTCCTTTTTTT

CTTTACTTTCCATGTTTGTATATTTCCCAAAACTCGAATTCATACACAAGTATCTCGGGAAAACGGCTTA

TTCATGCCCGAACTAGGGGTTGCTGAGAGAATACATACCTCAACTTTTACTGCAAGTCGAAACATAC

BG1513

(SEQ ID NO: 65)
ATAGGTTCTGTGTCGTAACCATTAGAGTCTTAAAACCGTCAATTTCGATTCTCACATCCAAAAGGTTTTA

ACATTTATATATAGTAAGATGGGTAAAGTTTGTAACCGCTCGTGTATAAAAATCAGGTTTACGAAAAT

CGCATTACTTTTGATTTTCTGATCGAAACAGAGCTTCGAAAAGGAACTACTACGCAGTAAATAAACTTAC

TTGAAGAAACGAAACTTACTTCGAAAAGGAATTACTTTC<u>TGAAGGTTGCGATAGCGAAGAG</u>AAACTT[GA

GAGAGAGAGAGAGAGA]GCGAGCGAGAGAGATATGAGAGTGATACCGCGGCGGAAATGAAGAAAAAAAA

AAAGGTTTAGGGTTTAACGACGACTGTTGCAAGTTGTAACCTTTGACTTGTTTTTTTTAATAAATCTTT

TTTTCTTTAAATTAAAAGAATAAACTCTAGAGTGGAAACCCCCTGATAAGTAATAATGTTTCAGTTCCGA

CCCCAAAGTAAAGTTTCAAATAATTTAACCCAACTTTATTGTAAATAAAAAAAATATTTCGATGAAACGA

ATATGTGCAAAATTTCATATATCCATAATTCATTACGATGTGTTTTATCAAAAAAAAAATCTTTT

CA0105

(SEQ ID NO: 66)

GGTTAGTCATCCAAGAACAGAAAAATCTCTAAAGAAAACAAACAAACCTTGATGTAATAAGCCTTGCGAA

TCTCTTCCTCAGAAGCGGAGGGAGTGACACCAAGAACATCATAATATAC<u>TGTTTCCTTCACCATGATCGG</u>

<u>AT</u>CAAAGCAAGAGATGTAACTTTTTTGTGTAGATAAGAAAATAAAGGTTGGTTTTGTGGATTGTGTGTGA

AGCTTTTAGGAGATATGGG[GAAGAAGAAGAAGAAGAAGAAGAAGAAGAAGAAGAA]GTT<u>GGGACACAAG</u>

<u>AGAGGTAGGGTGTG</u>TGATCTGCTTGAAGAAGCAAATAAAGAGATGTCTTTACAGTTATGCACTTTTGATT

TAATAAATAAAAAACTTTATAGCGGGGAGGCTACACTACACTTTCACCATCTCTTTTTAACTGTCCACTC

AATTGCTTTATTGATCTCATGCCTCCTTTTTTATTATTCCATTGCTTTTCTGTATTGTTGAACATACTGA

AGAAAAAGAAGATGATGATTTTTGCAATACGATTGTGATCTGGTGTATCTTATCATTTAGCCAAATGGAT

ATTAAGTTGGAAAAAAATTCAAAAATATAGGTCCTACCGGGAGTCGAACCCAGGTCGCTGGATTCAAAGT

CCAGAGTGCTAACCACTACACCATAGAACCTTGTTGTCTTAACTTTACTTTATTTATTTATAATGAAACA

TTATAT

CA0120

(SEQ ID NO: 67)

TTTAAGCCAAAATGTCATAACACAACAAAATGAGACAATAATAACATTACTGTAACAAATACATAGTTTC

TAATTAGAACAAAG<u>ACTAAACCAGACCAAGAGAAAAGTCG</u>ACAACAACTTTTAACTCTGTCCTT[CCACC

ATCATCATCATCATCATCATCATCATCATCATCATCATCA]TCCTCATAACTTATTGTTGTACCAGAACA

CACCTTTCTTCT<u>CACCTTGCCTATCCGGTTCAACA</u>TAGATACACTCCTTCGCCTCCCTCCACATCGCCTT

AACCACCGGCGTTCCATCAAACTGGTAATACTCTCCAAGTATCGGCTTTATCGCCTTGGTCGCTTCCATC

GCGTTATAATGCGGCATCGTCGAGAACAGATGATGCGCCACGTGCGTGTCCGTGATGTTATGAAACACCT

TGTTCAAGATTCCATAGTCTCTATCCACAGTAGCCAAAGCTCCTCTCAACCAATCCCACTCCGAAGAATA

TAGTGAGGCAGCGAAGGGTGCGTGTGCTGCAAGTAAGTGATCAAGACGAGGAAACAGTTGACAATCATAA

GCGGAACTCCGTAGACACAGACCATCGAGGCCACTCCTCGCGAACCAGCGTAGCGGTAGAGACCGTAACA

TACGGAGAGGACGCCAGCGTCAGAGATGTATATCTGGAGACGCTCGCGGTCGTTGTAGATGGGAGCGTTC

GGGTGGAAATGGCAAGCGAAACCGTCGCTGTAAGGTCTTCCAGAGACGTTGAAGGCTAAGTACAACGGCC

AGCCGAGCGTGAACTGGACGGTTAGCATCACCGTGCGTCCTAGCGGG

CA0163

(SEQ ID NO: 68)

TGAGCTATTAAAACTACATTATCTTAACGTCATATCAATTTGACATTTGCTTAATATTCATTTTCTTAGA

ACCGCTTGTCAAAAGCTTTCCCAGTTTTCCATTAACTAAAGAATGCTATCAGGAGAAGTTTCTGAAATTA

GATCATCATCATCATCATTTCTTAGCAACTTTTCTGAGATTGAGATCATATATTATCATCA<u>CCATCATCA</u>

<u>CCACCACCATCAT</u>CATAATCATATTTGCTTAGCAAATTTTTCTAAGAATCGTATATTATAACCACAAAAT

CTATATTTACTAACTTACAAGATAGATCCCATAAATTTATAACATTCTGCGATTACTCATTCCCTATATA

AATAACGTTCCATCTATTATATCCTACATTAT[CATCATCATCATCAT]CACCATCACAAT[CATCATCA

T]CACCATCACAATCATCACCATCACAGTCATCATTTTTTCATAGCAAACTTACAATTCGAAGAAACGAG

CGCCAAA<u>ACATCCGACCTTCTCCAGCAAG</u>ACTGAATCCAAAAATCCGAAATCGACAACATCTCCAGCTCA

-continued

TCACGAACCCTAGGCAGCCACACCCGCACGAATTCGACATCGGTAAGGTACAATTCGTCGGAATCGTCTT

CGACCAAGTCGTCGAACGACATCCCGCTGAGCGCCTTATCAACCCCAACCGATATGACCCTAACGTTGCG

AGAATCTTCGATCAGATTCCTGAAGACCGTCTTGAACGGCGTGACGGAGGTCGAGCGCGATTTGGAGTAC

CGTGACAACGTGCATAGG

CA0221

(SEQ ID NO: 69)
TGTTCCTCTGTTTCTTCAACCTCAAAAGCTCTTTCCACAGAACAGTGCAGTTCGGTGGACGA<u>GGAGAAGG</u>

<u>GTCGTCGTCAAGAAA</u>CCAGCTTCCTCTGTTATTATTCTCCTGCTCCTTGGTGCTGTTGTAACAGTCTCC

TCTTTCTTAACTCTACGAT[CTTCTTCTTCTTCTTCTTCTTCTT]CTACTACTTCTACTTCGTCTACGTC

GACGACTTTTGTTTTCAAGGTAACGTTTTGAAGCTTCTCCGAGTGTTTGGCTTGCCAGAAAGGAAGCAGC

TTTCCTTCGGAGAACAGCTCGTCTGCGGCGG<u>TGAGCATCGTTTGTGTGTTCGA</u>CAGAAACTCAAAGTCTC

CAGCTTTCACTTGTTCTTCTTTTCCCCTTAGGAGATTCTCAGGGTTGATGCAGATGTAGTCTCCCTCGCT

GTCTGATGATGACAGATCGGCGGAGAAGGAAATGCGAGGTCCTTCCGTCGTGAAAACCATCGTAGCCTCC

GCCGTTTCCGCTACTACCATGATCGTACAAATGTGTAGTTATGAAGTGAAAGACAAATCAAGTGGA

CA0226

(SEQ ID NO: 70)
TCTTAAATTTAAATTCTATTCCTCAAACACTAAATCTTAAATCTACACTCTATATCTAATACTCTATACC

ACAAATTTAAACTCTATATACAAAATCATAAACTCAATCTTTACAAACTTATAATAGAAACTTTAAATTT

AAACCTAAGTATATTATAAAACTCAAATTATATACTTAATCCTAAATCTTAACCCTAACTCATAAACCAC

ATATTTCATAAAATATTAAATCTTAATTTTTAAATAAATTATAGTTCCATAAATAAATTAAAATTTCAAA

TAAAAATTTAGATTTTAAATTTGAAATTATGATATCAAAGTATTTAAAACTTAAATAATTTTTATAATA

GCTATAAATAAATAAGAAGATAATTTGTATTGTTTTTTTATACCATTGATTGATTTGAATCAAAGACTCA

AGATAGCTCTTGTATCTATTTTCGCCTTTTTTTCTTATCGGTAGTTGTTGTTTATGG<u>CATGGATCACCTG</u>

<u>CACCCTTAG</u>ATAATATTGAACCAGAGATTAATTGTTCTTTTATTCTTTTTTTTTAATTTACTTTTCTCA

GATCTACGAAA[GAGAGAGAGAGAAGAGA]TGGAGTTCAAGGTAGAGAAGGAGAACGCGACGGCTGTTCG

TC[ACCACCACCACCACCACCACCACC]ATCGTTCGTCACTACCACCTTCGCTTCTC<u>AGATACGTCT</u>

<u>TCACCGGAGTCGCC</u>AGAACCACCGTCACGCTCGTCATAACCAACATCGCTCGTTCCCACAACCACCGCCA

TCTCTCCCATCAGCCATCGCTCGTCACCACCACATCACTTCTCAGATCCGTCTTCACCGGAGTCGCCACC

ACAACCGTCACGCTCCTCATAA

CA0233

(SEQ ID NO: 71)
TTTTTTTGGTTCTTTTAACTTTTAATAATTAATTCAATAATCTGTAACCTCTCTATGTATCTCTTCCTCA

TTGTATCTGATTGAGTTTGAATCAGTTTTTGAGCAGGACGTGGTGATGCCAGAAGATCTAGCGAATGTCC

TTAGGACAGCGAAAGAGATTGTCGTTGCCACAGTCCTTCCCGTCACACTTTGCTTTTTGTACATCTCTAT

GCCTTGACGCCGCCGTAGGAACACGCTATCAAAGCTTGCGGGGTTGGAGGGAGCTCGACGACGGAGGA<u>GG</u>

<u>CAAGCATGGTCTCGTCAGATA</u>CAACAGAGTCAGCATTATCTCAACATTCCGGTCATGTAAGCGGTGTAGT

CGTTTATACAAATTTGATTTTCAGATCTGAGATTCGCTTTTTGACTTTACAGTTTTTGTGTATATTTTTG

TAGGATAGGATGAAGGG[GAAGAAGAAGAA]GGAGGAGACGAAGACGAGAGGCTGTGTGGTTGGCGTCAG

TTATAT[CACCACCACCACCACCACCAC]TACCGTCACGCTTGTCACCACCATGCTCCTTTCCATTC

<u>GAGGCGGCTGGAATCTTTTTTTTTCTAGGTTTAGA</u>

CA0328

(SEQ ID NO: 72)
ATGGTACAAACAATCATACAGACACGCATTCTCTTCTAGTTCAGCTGCTGCTTTCTCTAAGCTTGTCTTC

ATAAAATTGTTACAA<u>ACTTTGGAGCATCCTTCCTTGGG</u>CCATCAAGGGACCGATACATGTACAACGTCTC

CACATAATCTGCATTGT[CGTCTTCGTCGTCGTCGTCGTCTTCGTCGTCGTCATCATCAT]CTGACC

-continued

CAAACACCT[CCACCACCA]CACTAGGCAGAGTATGAGCAACATCCCTGCAGGCTCCCCGGGACAACCTA

CATGACGACATCCAAACAAACCTCATCTCGTTATACCTATGCA<u>TACCAGAGCGCAGTCCAACATC</u>ACCAA

AGGGACTGTCCCTGATCTCAAGCTTCTCTAGTTTAGGACACCCCTCGAGGATATATCTCAGACCCATGTC

ACTGTCCCTGCAAAAGCTACAGATAGAGTACGTATCAGTTTCCCATACTCTCCTATAAGGCTAAAGGCT

TGGTCCGTTAGTAATCCAGATACTGCAAGCCTGGTTAGCTTCTTGCAGTTTTTAACAATGGCGCCAAATC

CATCGTCCATTGGCTTCCTTGTCACGTGGTCAGGCCTATGGCGACCCATTATGCAAAGCCTAAACACGGT

AAGCTGGGGACAGTTCTCAGACATGGCTGTCACAGCTACATTTGTCATCCGCTGGCAGAAGTAGAGAATA

GACTCAAGTTTCTTACAACCTTTCTGAAATTGCTTGGAGGCCTAATCCCGAGACAGGACCTTCACTGTCT

TCACTAGGATCCAAAGGGAAAATCCCTAGCTCACGGAGCTCCTTGCATG

CA0410
(SEQ ID NO: 73)
CGCCGCGTCTCCTCACTCTCCGGATTACTCTCCGTCTGAATCCTCTCCTTCTCGCTCGCGATCTCCCTCT

CCTCCTTCCCGCGACGCTCCCTACCGTCTCCGATCGAAAGCCGCCGCCGCCTCCGCGAATCAAGGAGCTG

GTGGTAATCCATCGGGAAGCCGTACTACTAGGAGCCGTCAACAAGCTGGGAACATCCGTACGTTCGCCGA

TCTGAACCGTTCCCCCGCTGACGGCGCGGATAGTGATTCCGACGAAGGCCAAGAGTACTATACTGGTGGA

CAGAGGAGGTAAAATTGTGTTTATATTGAATGATCATAAACTGAGTAATGTGGAATCATGGAGAATTGTG

CTATTGATTGTTTGTGTTGGCTTCTCTTTAGCTAATGGATTGGGCCTTGTGTGTTTAGTGGGATGATGGT

TCAAGATCCTACTAAGAAAGCAAAAGATGTTGATGCACTCTTTGAGCAAGCTAGGCTTTCAGCTGTGGAC

AGGC<u>CTGTTGAGCCATCGAGATCAGC</u>TTCTACAAGCTTCACTGGAGCTTCTAAGATGTTATCTGGTGAGC

CTGTTCCCTCTGCTACTCCT[CAGCAGCAGCAGCAGCAG]CAAGACCAGCCTCAGTTGG<u>TTATGCACACC

ATCACTTTCTGG</u>

CA0423
(SEQ ID NO: 74)
CCCTATTTCGCTGAATCTGCTTTCTAACCCTAATTTTCTCGATTTTTCTGCTCAAGCGTGTTGGCAATGT

CGGAGGACATGGTGATGCATTTCTCCTC<u>AATTCCTCCAATCAGTCCGATCACTCCCTGC</u>CCGACAAAAT

CGCGAAGCTCGAGGCTCGCTTGACCGGCAAAACCGCCTCCTCCGCCAAGCCGCAGCCTC[AGCAGCAGCA

GCAGC]TCTCCGTCTGGTCATCTGCTTCCGCCCCTGCCAAAGTCGCGGCGGGTTCGTCGGATGTCTCTAT

CAGTGA<u>TTCCGACGACGAGGTAACTTCC</u>GATGATTTTTTTTATTATTTTTTTTTTAAGATTTGATGTC

TAATAGTATTCTCGTTGTTACTACTGTCTCAGAACACAGGAGATTTCCTGATCCGAGCAAATACCAAGAA

GCGCCAGAAAGTTCAAGACTTTAACAACAACAACTCCACTCTTGTTGATCATGCTGAGGTAGTGAATTTT

CAGTTTAAATATCGATCTTTTCGTCCCTTGCCTGGTTCGTAGTTATATTGATATGGTAACTAAGGTTGTG

CGATACTGAAACAATCTGATATGATGCAAGTTTTGTATTCCCTTTTGATGAATTATTATAATGTCGAAAT

TGAAGCCGCAAGAGGCAGCATATGATGGAAGGAAAAACGACGCTGAGAACCAGACAGGCGTCGATGTGAG

TAAGAAGAAGCAAGGTCGAGGTCGAGGTTCATC

CA0456
(SEQ ID NO: 75)
<u>CTTCTGTTAGAATTCTACCG</u>[TTGTTGTTGTTGTTGTTG]TCTTGGTTGTCTTAGAAGC[TCAATCA

A]CGCCTCCGCCTTTAGCTTAGCTCGACTCTTACTACTCTGCGACAAAG[CCACCA]CAGGAGCAATCGC

ACCTTCTCGCGCCACCATGGTTCGATAC<u>ACCACACT</u>[CTCCTC]<u>ACAAAGCT</u>GCAGCAATATCGACACGC

CCATCTCCTTCTGCCTCTGCGTTCCCACCTCCACTATCTCCACAAGCACCGGAACTCCTCCTTCCTCCAC

CACCGCCGGCTTCGACTCCGGCGCCGACATCAGCAGATTCATCACGTACGCCGATTTATCCACCATGTTC

GAATCGAAATCCGCCATCAGCTCCACGAGCGGCTTCATAACTCCCGATTCCACGGCCCTGGTCTTGTTCT

CCTTGGCCGAGCAGAGCGAGTAAAGAGCCGTCGCCGCGTCCTTCTTCCCCCTGAACCCGCCGGTTTCCAG

```
AAGGTTCACCAAGTGAGGAATCGCTCCGGATCTCCCGATCGCGATCTTGTTGTCTTCGATCTGCGATAGG

CGGAGGAGAGCGCAGGCGGCGTTCTCTTTCGCCGTCGGCGTTCCCGATTTCAAAACCCTAACGAGCGGTT

TAATCGCGCCGGAGGAAGCGATCAGCTCCTTGGTCTCGTCGCAGAGGGAGAGGTTCAGCACAGCGGTG
```

CA0488
(SEQ ID NO: 76)
```
GCCAAGCTCTCCGACTTGTCACCGGTGCCAAGAAGCAGCCACTGAGAAAATAAAACTCATTCAAGATTCA

AAATCCTTGTGTGCTTCTTCAATGCCATTTTAGTTTGACTTCTTCATTTGCTACAGTTCATTAGTTATTT

CCTTATTTGCAAAAGAGCCCTCGAGTTTGTTAGAAACGTGAAATAAAGCCATTAAATACCAATTCCCTCC

ACTTTGAAGGGGTTTTGAATATCTTTCCCTCGACTCCAAAATCCTCGCCGGCGATAAGCAAACCCTAGAT

TCGATTCGCCGTCTGTTCATCCAGCAATGTCGTCGTTCAATCCATTCTCTACCCCACAGCGACATCAGCA

GACGCCTCAGCCGCAGAGCATCTCCTTCTTCTCGCCACCGCAGAGCACTCC[CTTCTT]CTCTCAACTG

[CAACAA]CAGCAAACGCCGTCGTTTCAGCCGCACCAGTTCCAGCAG[CAACAACAACAACAACAACAA]

AGTCAGCAGCAGCTGTATTTGTTCACGAACGATCAAGCTCCGGCGAGTTACAGCACCGAATGGGAGTGAT

CTTTCATCCGATTCTCAGAAACTTCTCCTTGAGATTGAGTATTGCTCTTCTTTC
```

CA0546
(SEQ ID NO: 77)
```
ATCAAACCATAGAAATACATGACTTACTACATTCACTCATCTGTGTTGGAAAACTTTTCAAATTTATTAT

ATCTTAATTTATATTATTTACAAATGTTTATAATTGCATGATTTCAATTATCCCCATCACAACATATTT

TAAAAAATTTAAAAATTATTTTTAAGATATACAATATGAGAAGATTTTCAGAAGGCTTCTATGAGTATGT

TCTTAAAAATACATTCTATTTTTTTTTTTGGTCTAATGGACTATTTATAATTTCAGTAGCATTTTAGAT

TAATTTTGCATTTGATCCATGAGGTATATCTTTGTGTTTAAAACCAAGTTTTAGGTTATATTTGGAAATT

TCCTCTTGATAGTTTGAAGGTTTGAAGTTTTGATGCGGATAGCAATGGATAATAAAACGGATTTTGGATC

TAGGACAATAATTCGTCCATCTCCTACGTGGGGTCTTTAGTGATAATGAAAAAACTCTTCTGGTAAAAAC

AAAATGTTTTAATAAATATGGGGCTCATCCATAAGTGAAAAATACCTCTCTTCTTCACTGCAAATGAATT

ATAAACCCCTTCCTTATCCACACACACACAGACTTGTTCGCTCTCTTAAACCCCT[GAAGAGGAAGAAGA

AGAAGAAGAAGAAGAAGAAGAAGAAGAAGAA]GGCGAATCATGCAGATTTGCCAAGCAGCGGTAACC

TTCACCTTCACGAACCCAACAAACCCTAATTTCTGCAAACCCAAACCTCTCTTCCCAAGCTTCCAACCCC

CTCGCCGCGTCGCCTTGCCGCCATGCCGTGGCTTCAGCTCCGACGAGTTCCCCGTCGACGAAACCTTCCT

CGAGAAATTCGGACCCCAGGACAAAGACACAGAGGACGAAGC
```

CA0552
(SEQ ID NO: 78)
```
GATTTAAAATGACAATTTTTTATTGGTTGGTTCCGCTAGGGGGTGAACCAAGAATAACT[CTTCTT]TTA

TTTCTACGTTCTCATTCTTTT[CTTCTTCTTCTTCTTCTTCTTCTTCTTCTTCTT]CTACGATTTTTAATT

TCATTCAATGAAACAACAAAGTAGATCTGATTTTTATTTGAGTTTGGGTCCAAGAAGTGAAGAAAAATAT

TGGAGAGGAGGATCGACGCCTCTGTTCAATAGCCATGGAAACTCTGTACGCTTCCTCTCAAGCTCCGTGG

AGAAGAATACCAGGAAGACGGCGAGCAAGCTCCGTGGAGAAGAAGACCACGAAGACGGCGAGCGACTATG

AAGGTGGCTGGATGCAACGACAAGTACGCCTCATCTCTGAAGCTTGACTCTCAAATCCCACAGCGAAGAA

GAAGAATCAAGGCGGATGTGAAGAGCATAGAAGAGACAACGACGAAGGTGGTGGTGGGGCTGGTGAGGAC

TGGAAGATGAAGAAGACCACGTAGGTGGTGCCATGGTGGTGTGCGGCGGCGTACAAGATGAAGAAGACGA

CATATGGTAGTTAATTAGAAATTAGGTTTAAGCTTGGTTTAGGGTTTTGGTTTATTTGGTTTGGTTTTAG

TACTTTTTTATCTAATTAGATTTTTTTAATATTTTTGTAAAACAATTAA
```

CA0603
(SEQ ID NO: 79)
```
CATCATCATCCATTCATCATCATCATCATCATCATCATCATCATCAGCCACCTTTCTACTTTGTCTGTTT

CACAACTGCCCAATCTACCTCCCAAAGTCGTCTCTTCCATGTGATACACTTCGCTTGGCTTCTTCTGCCT
```

-continued

TTAGCTGTTCCCGTCTCAACGTTCGTACGTTAAAGGTAAAGT[CTTCTTCTTCTTCTTCTTCTTCCCTT]
ACGTATTTTCGTTTTCCATCTAAAGATTCATTCTCTCCTCCGAGTTTCGTCCCCTGTCTACTCTGTTTCT
GTGATGTTGACCTCTCTCTTAAGCTGATCTGATATGTGTTCTTCTTCCTCTTTGATGCTTCTGTCTCTGT
AATTCTTTGACTACTTTAGATATTTTATCTTATGGGTTTCATTAAACTCGCACAAAGCTCGTGACTTTGA
GTTATATAACCAGTTCAGCTCTATTAAAGTTTTCTTGTAGACCAAACACTCATGAGTTACAGTGTCTTGT
TCTTAATCTTCCTTTTGACTATTTTATGAAAAGTTCTTGATCTTCGTTACTTTTCAATAGTCTGATTC

CA0614
(SEQ ID NO: 80)
CGAGGGACACGAGGATAGGACCTGGGATGCCTTGAGTGCAGGCTGTGCAGCACCATAGGCGGGCACCTTT
TTAATATTGTATGTTGTAATATTTCATCTAAAATTATAAGATAATAGGGTATACATAACTTATTTGCGTG
TAAATAGATCTCATTTCTACATTTGAGAATCATGAAAAATATATATGTTCCAAGTGGTTCTGCAATGTGT
TAAA[TATATATATATATATATATATATATA]GATATTATTTTCAATTAATATACTCACAAAGTTGGTTA
TGACTTATAGTACAAAACAAATGTGGAGTTCATTAACTACACGAAACCCATTTGTCCACAATATTGAAG
TAGTCTTTTGTGATGATTGACATAAATTCTCATTTTAATTGCCCTTTATTGGGATAGCTGACAACAACAA
AATAAGTAATTCTTTTCAGATTTGAGAAAATTTCAACTACATATGTAAACAATTCAAAGAACATAAATAT
AATAAGAAATGTGCACAAAAAAAATATAGAGATATATAAGAAATAGGTAAATGAGGCCAAAGATTGTTG
TTATATAGAAAGCAAGTCACTGCATCATAATATCATGTGGTGGTTCAACTTTATGACGATAGTGAATAGG
TCCTCTCTTACGCCTTGAGATTTTGTTTCCGTTGAAGCTGCAGATAACACACCTACACCTATATCTTGGA
TGATAGTGATGATGATAATTATGATGATGAGGATGATGACGCAAGTGATGATGGTTTTTCCTAAGAGCGC
AACAAACCGAGCTGTCTGATACC

CA0636
(SEQ ID NO: 81)
CTCGGAAGAACGAATCGGGTCAGCTCAATGCTCCATCGGGTCAACCTTATCTCTACTCGGATCTCTCTCT
CGGGTCGAACTTCACTTGCGCGACGCGAAGCTCGAACAGCTCTGTGACTTGCTGGGGAGGAGGAGCGGAG
AGGTTCAACAATGTAACCGAAAAGATCTCATTCGAGTCAGTTACATCCGGGTCGGGTCTAATCTGCGGGT
TGATATCCGGTAACCTCTCGGTCATGTGTTGGAGCCCTAATAACTTCTCAAGAATCTTCCTTCCTTTCCC
AGATATCTTACCAGGTCCTTGCGTTGAATCATCTATTTGCAAATGTGGTGTGTATCCACGATCTGATCAG
CTATGCTCCGGCTCGGGTTCGATCTGCAGCAAATGCAAAATCTCA[CCTCCTCCACAACCACCATCACCA
CCACCACCACCA]CCGTCAGATTCATCTCCATCTCCATCTCCGCCGCCGTCGAAGGCGTTAACGAGAGGA
TTACTAGCGTTTGCGATCGTTGGATCAGTAGGAGCGTTTGCAGGGATATGCAGTGTGGTGTACTGTTTGT
GGACCGGAGCTTTCTTGGGGAAAGAGAAAGTTCATAACTCGGTTCAACCGACGATAACCCGCGGCGGTTC
GAGTACCCGGTCAAGCAGCTCGCCGCCTTCTCGGTCCTTGACGAATAGACGTCAGGGATCGAGAATATTT
TCGATGAGAA

CA0681
(SEQ ID NO: 82)
TATACTGCTAACTATTTACATGTAAAATCTCTGTCAATTATCTTTTCCTATTCTATACAATTTTCCACAG
TTATTTTTGTAGTTCTGTTGCTGAACTTGAAGCTGAGTTTGTGGTGAAGAAACAATAACACCAAACACAG
CATATCACCTCCTTCCTTCTTCTAATGCATCTCTTCTCCTCTTCAACCCCACACTGGATGCGAACCTGTT
GTTCTTGCTTCAATCGTTTGAGCTTGGATTTTTTCAATCTCCATCTCCCCTCCTCTTCCACCAACATTAC
TCTCTTCATCCCCATCCAATACCAACTTCTCAAACCTACACTGTTTTGTTGCAAAACACACAGTCTCAGC
CACATCATTAAAAAAAAGGAAGAGG[AAGGAAGGAAGGAAGG]AAAGTTTTACATTTTCACATTCCCATA
AGGGTAGGTGAGACGGCTGATACATTCGCAACTCTGTTTGAGACACGTACAGCTGATGGTTGTTATCCAC
CACACGAGGGGCCTTTCCTTTCTTAGTTGCTTTCCACGGCTCCTCAGCACTCTGCTTTATAACAACCTCC

-continued

GGAAACACGTTACTTCCAGAACCCGAAGTTGATCCACCTCCTCCATATACGTCACTCTGCTGATCTTGCA

TCTCTCTTCTAGATCGGTTCTGGACCATGTACCACCTTCGTATCCTCACAACCGGTCCTTCAGTCTCTGC

ACCAGACTCGGAATCAATCCCCGTCATCACAAAGCCTCACCACCATCCCCAGCCTTCAACGCGTACTGTG

TCATACATCCAGAAGGAGCAAAAACAGTAGATTCCTCGTTACGCTATTATCAGAAGCAGTA

CA0719
(SEQ ID NO: 83)
GCTACATATGTCCCTAAAGAGTGAAACTAAAGCGAATTGCGAGGATTATTGAACAAGTTTCCTTCCAACT

TTCTAACGAATCAGCCATCATAGTAGCTCGCAATCAACATTTAGTTTCTGGGAAGATGAACAAACACAAA

TTACCCAAGAACACGAGACACCCAGAACATAAACAAAATCAAATACATCATGAATCCGATTAAAAAGAAC

GAAGATGGAGCAAAGTACCTTTTCTCGATTCGACTTGGAGAGAAACTCGAACGAAAGGGAATAAAACCCG

AGGAGTGACTTAATTGGGTCACATAATTTTGTTAACCGGAAAGTTA<ins>CCGAACCGGAATCATACAGCTCGT</ins>

<ins>TGTGTAGT</ins>[GGTTGGTTGGTTGGTT]TTACAACTTCCACAGACTAAAAATGACATGAAAAATTAATCAAT

TATTTACCTGAAATGTACGATTAGCCAACAATTAGTTCTGTTATTCATAACAAAAGAAAACATTTTAATT

ACAGAGGTGAACGTATCCTAAAGAGAAATCTTTTTTTTCAAAACAATTAAACTTCCATTCATTAACATTA

ACCATCGCAAATACAAATCAAGGTCCAATCACACATATACGACTCAGACTCA<ins>GGATCTGACTGGTTCAAA</ins>

<ins>CGCAGC</ins>

CA0736
(SEQ ID NO: 84)
GCTTTTATCCCGGTTTAATAACTTTGAAATTCAATCCATCGACGTGGTCGGTTCATGGTCGAACCAATTA

CTGGACCCAACCCGACTATACAACCGGTTCATGGTCGAACCCGGTCCAACCATCGGGTCGGTCCGGTTTT

AAAAACACTGCTCTAAATGGAAAAATATAGTCCTTTTTAACTATTGTTTAATTCAAAATCTGTTGACTAT

AGTGATGGATAATACAATTTATATGGGATTTGAATTTATGTATTAGATGTAAAAATTGAAAAGAAAACA

TATTATATACGCTCTACGAGCTTTTTAAATAGATTTATTGGACCTAAGTATTTCATAAGTTTTGAAAACA

TGGGCTTACAAAACCTTTTTAACGATGTTCAA<ins>CCCGGGCTTAGACAAACTTTATGAG</ins>ATCACGGCTAGGC

CTTTGAGTGCTATTATTTTATTTTATTTATTTCTTGAATTTTAGGGATTAATAAATGTGAGAAGGAGTAG

ATAGTACATAATTAGAGATTGATGGAACAAATTGCAATAATTTAAAAGTAAAAGGATTTAAAATGCAAAA

AAAAATATGAGGACACATGTCAACAAACCCTCCTTCTATATGTCATAAGAAGGGAAAAAATCAACTTTAT

ATAT[ATAGATAGATAGATA]GATATGTATAATTTGGGATAAAAGTCGGTATAGCCG<ins>TACAGGCGTTTGT</ins>

<ins>GCGATCAAT</ins>CGGTCATCAACTAAACAAAATTTTAAAATGATTTTTTAAACAAAAAAAAATATTATTTAAT

ATTTATTAAATAATTTGCAATTTTTAATAAAAAATAGTTTTCATATGGGATAAAATTTATCAATCTCATC

TACTATATAAA

CA0739
(SEQ ID NO: 85)
GATCTTATCACCAAATTTTATATTGTCACGTTTAAGTATATCTTTCGTAGAAACATATTTTCCTCGAAAT

GAAACTATATGATATAATATTTTTTTTGTCTAAACATTTTTATACT<ins>AAAAACTGATAAGATTATTGTTGG</ins>

<ins>TAAC</ins>TACAATTATATTTACCTTGATAAATATATAAAG[ATATATATATATATATATATATATGTATGT

ATGTATGTATGTATGTAT]ATATATCATCTTTTATTGAATTTGGATAATAGCAGATTAATTAATATTTTT

TAGATAATGATAATATATAATTAAATTTTGATTTACTCAATTATTATT<ins>TATGCAAGTTTAACTTTTATTT</ins>

<ins>TTGGG</ins>TGATTTATTATTGTATATGAATATATAAATATATTATGAATAAATATAATTATCTAATTATTAAG

CATTATAAATATAATTATTCATTAAATGTAAAATGACTCTAATTACTCTAGTTTTTAATGCGATAGTTCA

GATCAAAAATATCAATCAGAAACTAATAATATCACAATTTTATATTAGAGTATATTTGTTTAATTAACTA

ACTAATACAATCTGTGAATTTGTATCATTACCAGAAACAACCAATTGAGCAAGTCGGTTAAAAAGTTCAT

GCCATGTTTTAATTTTTGAGCTCATACATTTTTCATTTACTCAGGATTCAC

-continued

CA0753 (SEQ ID NO: 86)
GAGTATCAGCTCTACAACATCGTCCGGAAGCAATTGCAACTCTTCGCGATGCCTTTTCAGTGTTCTTGTT

TTGAACGGAAACATCCTTCTCGTCCTCGTCGTCTCTAAATTTTATTGAATTTGATCAACAGATCTGATAT

ATATATATAGATACAGGCAGCTAAGGAATCTGGAAACACAAAAAAAAAAAAAAGAGAAAATTTCCTCTCC

GTTTAAGTAAGATTTCCTTTTTTGAATTTAAACAGAATCGAAACATCAAATC[TAATAATAATAATAA]T

ACAAAT[ATACATACATACATAC]ATATTACCTCAGACTCAGGCAATGAACAAGCCTTTTCTAATCCTCA

GGAATCATCCA[TCTCTCTCTCTCTCTCTC]GTTTTGTTTGTGAGCATCGATG[CGGCGGCGG]CGCT

TAGACAAAGACATCTCATCGGGACGCCTCTTTTACAACTCCTCCTCCTGTCTTCTTTTGGGCTTTCTGTA

AGGCCCGACCCGGTTTCCCTTAACGCCGGTACGTCCTTAGTTCGCTTACCTCGACCAAACTGGCCCTATC

CGAATTTATTCTCTTAACTTAGGATTATTATGCAATTTTCCTCTAAGAGGTTCAGTTCAGTACACAAGGT

TCGCTAAGTCTAATCCAGCAACTTAGCAGTCTACTAGTAATCGCAGCATAATGAACATGTACCTACTGCC

TCTGTACTTTGGTATCTGATAATCCATCCATACACTCCTTCA

CA0834 (SEQ ID NO: 87)
GCCATTTTCCTGATTCGAATCCAGATACTGCATAATAAATTTGAGAATAATAATCACTTTTTATTCACTG

CGACATTGTAAGAGTGACTGTTATTCATAAGGCTGTTACTGTTAGGGTCGAAGGCAACTATTATTCTTTT

TTTTGTTAAAGCCTTTATTCTTTCTTTTTCTTTTGAATCTTTAGTTCGTAAATATTCTCTTTCATATTC

ATAAAAAATACACAACACAACATATGTATTACTATTAGAGGCATAACCATTAACATTGGATTTATTGAGG

TTAGTAATTATTATGGTTGTTTGACAACAAAAAAAAAAAGTAATTTTTTTTGAGCAAACAAAAGTAATT

ATCTGACAATAGTAGAAACTAAAAAATGCAACCATGCAATACGTGGTTTTATAATCATTCTATTGTTAAA

TATGATGAT[AATAATAATAAT]GAT[AATAATAATAATAATAATAATAATAATAATAATAATAAT]

ATTACAGAATGTTGATGTAATAAACAAAAATAGTTTGTTAGCTAACGCCTCAGATCGATCAATGAGTAAT

TCATTCAGTTACCACATAAAGAAACAAATAAAAACTATGATAAAAAAGTTTTGACATCATTTTTTATTGA

CATGTCAATATGTGATAATACACTCTCTGCAGCAGTGACAACAAATACTACAAAC

CA0837 (SEQ ID NO: 88)
TTGGAGTCCTCCGACTTGGTCTTGATACAAGATTGTGAGGAAATCACTGTCCGTGTGTGGCATCAAACCA

TACACCTCCGATGGTTTCGGACATGGTGGATAACGGTTCATCCTTAGATAACATGTGTTTCGCACACAGG

TTTTTTTGAAGAAACTTGATTTCCGTCCTGATTTCTCTGCAAGGACCTCTGCCAATGAATATGCCAGAGC

CTCGGATTCTGAAGCAAAATTTTCCATTGTTGAGCTGCGATATAAAATGTACATATTATAACTAAGGTTA

ATTTATTATAGAGACAAATAAATCATGTTAAATAAATTAGGTGAAATAATTGCGAAAGCCATGAACCTTT

CTTGTTCCTTTTGTTTAATCCAAGCCATGAATTGTTCATTTGTTTTAACGTAGAATTGCTAAGATTTTTT

TTTTTGTAAACCATGAATTGAAGTTATGATAAGAAAAGAAATGGAAAAT[ATTATTATTATTATTAT

TATTATT]TAATGGTAGAATGATATAGTATAAATAATTATTTCACGGTAATTATTTGATTTGGTAGAAAA

TTGCGGAAATTATTTGATTTGCTGATTTTTTTTGTGAAGAACAAAATTCACCTAACAAAAGAAACACGTA

AGATTATTTGTTATTTGTGGTACATAT

CA0896 (SEQ ID NO: 89)
TAAATTTACATGTAAATTACCACGAAACATTTTCTTTGTAACTTTACTACGACCTTACTACGAAATTCAG

TTTTGTCGTAAAATCGTAGTAATTTTCTCGTAAATTTACGAGGAATATATTTCCTCGTAATTTTTCCTTG

TTATAGGCATGTTTTCTTGTAGTGTTTATGTTGCCGTTGTTCTGACCACGATAGTTATGATACCTTTGTG

ATTTTCTGGTCACATATTCACTTAATTATTTTGTATGCTGACATACCTCATGGGAGGTTCGCTTGATATA

AATCATCACTTACAAACAAAAAATATTCATAAAAAAAAATATTCACACGTTTACAAAATCAAAAGAGTT

-continued

ATATATAAATAGCTAT[AATAATAATAAT]GATACTAATATTAATAACAGT[AATAATAATAAT]GTTTA
GAAAGCTAAACAACAAGGATTAGAACATGTATTTTTACAATTGCAAAAACAACAACAAAGTCGTAGCTTA
GGACATTTAAAACAAGA<u>TGACCATTTGATCTTGCAGTTGC</u>AGCTGCAACATGAGCTCTTCTTATTAAGAC
ATGATGGTCGACTGCAACTGCGGAAACATGTGGGTATGCAACAACATAAGTCCGGACAAGAACAACAGCA
ACCTAGGAAGCATGAACAGCTCGGGCAGCTCAGGCATTTGGGGCAGCTCGGTTTCGGGCAACAACAGCTG
TTTGAGCAGCAGGACCCGTTGCAGCATTTGGAACAACGCAGCTACAACATGTGGAAGTGCAGCATTTTGG
CTTCCTCAGATGGCACGAACACTCGGGTCGG

CA0991

(SEQ ID NO: 90)
GGCCGACGGCGATCTGTATCATCGCCCTGTGGTGGAATTCCTCCTCCGAGGGTATAGAAGGAAGCTAACT
TGGTCTGCTTGTGAAGCTAAAATGAAAGGCTCGAATTTGTTGTACCTTCGTCCACCGTTGACATCAATAA
CACCGAATTTCTTAGACCGAACACCTCTGTTGACGACGGGGCAATGGAATGTATGAAAAACTTAAGGCAG
TTTCAGGTTACGTTTGCAATGGATTATTCTCAATTGGTGAAGATGGTTTTCTGAACCAGATGAATGACCA
GCATTTGAAAGCTACCTGGAAGATATTAAGCTTTTGCGACGAAGTTTCGTCAACTCAGATATTATTCATG
TTCATAGGGCGGAGAACATAAGGGCGGATAGCTTGGCACACGTAGTACTCAGAAACAACCGTCTTTCGTC
GTGCATATGGACGCAGAGTTGC<u>CACATTGGTTTACAGAGTCTACATGAG</u>TCTGTAAATATTTGCTGTTAA
[AATAATAATAATAATAATAAT]ATATATCTGTCTATCAATTTTTAAAACACAATAAGTTTACGGTATAT
TTTTCATTGAATAGAT<u>TGTTTTCAACTTTCACATGTATTTGT</u>ATCTTCTTCTATATATATATTTTCAGAT
TATTATTTCATTATTANAATCGTAACAATATGTATAAAAATTAGTAAAATATTGTTTTGTTGTCATATTC
AAAGATA

CA1027

(SEQ ID NO: 91)
AGCGGCGATCTGATTCTCGCCCTGTGGTGGATTCTTCTTTCTTTAGTCTTTCCATTATTCTATGACGGTG
TAATTCCCTATATATAAAAGGCTCCTTATATTTATGAATAATATAGAAACATAGATTTCATTACGACTAT
ATTATTAGTATA<u>TCAGTCTAGGCGTTTACCAATACC</u>AATATACTTAATATATTTAGTATAATATCTTATG
ATTTACAATTATTTTCATATGATTTTGTACTATAATATGTCAATTATTATAATTTATAAAAAACTT[ATT
CATTATTTATTATTATTATTATT]ATAAACCTACAACCTTTCAACTTAATTAGAATTCACAACCTTTAGA
ATTAATTGAGATTCTTATTATTAATAGATATTATAATCTTTTAAATGGTATATAAGATAATCACCACGGT
ACTAGAAAGCC<u>TAGAGCCAAAGCACCGCCTAAG</u>CCGCCGCCTAGAACAATTACCTAATTTAAAGAAAAAC
TAATACTTATATTTGATTTTGAAATTTTATTAAACTTTGCAAAAAAAGAAGAAGATGGAAACATGTTAGA
AACATATATCCAAATATAAAAATATAAGAATAATTTTATAAAAATTAATGATTAAAAACATATGCAAGAT
TTCGTATGAAAAAACTATTCTGCACAAAAATAATTTATAATATTAGTTTAATATTTACATATTTC

CA1032

(SEQ ID NO: 92)
NGGCGACGGCGATTGATTCTCGCCCTGTGGTGGAATTCCAGTTTGACCAGGACTGTCGTAAGCTTAGTTT
AATTTCACCAGCAGACACCGACTCAATAGCACCCTGGAAAAAACACACTCAAACCAGAAGCAAATGAACT
ATAATAGTCCAAGTAGAAGAAACACAATCAATCATCCAAGAAAGATACTACTACATCACCAACAATACT
GCTAGATAATGTAAAAAATGGACAGAAGAAATAAAACTACACTGGTCTTCCACCGAAAGAGTCCAAATAG
AAACACAAGGAATAAAGCAAAAGAAAACTAAAATTACCATAGCACTAGCAAGATAATGTAAAAACCTACA
TTGATCTTCTACAGAAGCAGTTTGTTTTATTTTTTCTCCGTTTAGAGAATTTTGGGGTGCTTCTCACCTT
A<u>TTGAACTTGACGACGACATCCC</u>TGAGGCATTTCCAACCGCCAAAACGGAACACAACAGATGCTCCCAGC
ACTCGGCTAAGAATCCATGCAAAGAATCTTGAACAGAGTCTGGAGAGTCAAAATG[AAATAAATAAATAA
ATATAATAATAATAATAATAAT]AAGACCACTATAGCAGCATAG<u>TCCAGCAGCTAAATCATGCAAT</u>CTCA

```
GCTACTGAAGGAAATTAGAGAATGTGCAAACCGAACTANAATCATCACTAGAACTAACTCACACGAAGAT

CATCCACAAGACCATGGAAAGAATCAGGAAC

CA1034
                                                      (SEQ ID NO: 93)
AACGGAGACTGATATCTCGCCCTGTGGTGGAATTCTCTGACAATAGTAGAAACTAAAAAATGCAACCATG

CAATACGTGGTTTTATAATCATTCTATTGTTAAATATGATGAT[AATAATAATAATGATAATAATAATAA

TAATAATAATAATAATAATAATAATAAT]ATTACAGAATGTTGATGTAATAAACAAAAATAGTTTGT

TAGCTAACGCCTCAGATCGATCAATGAGTAATTCATTCAGTTACAACATAAAGAAACAAATAAAAACTAT

GATAAAAAAGTTTTGACATCATTTTTTATTGACATGTCAATATGTGATAATACACTCTCTGCAGCAGTG

ACAAACAAATACTACAAACTCTTATTTTTAATCGTTCAAAGATAAGAGTCTATACTAGTAGACTAGAAAG

TGGGGGGAAACAAATAAATTTAGGAGGATTCATTGACAATTTAAGAAGACATTTTTGATACGCCTCGTCT

TATTAGAATTGGGAATGGCCTATGGAGAGGATATGAATGTGATGGGCATAGTGATAAGGTAGAGGAGATA

ATGCAGAAAAGCGAGAAGAAGAATCTTAAACTATCATTTATGAATTATGAGTTAACCTCAGAAAGCCAGT

TTACAAAAAAAAAAAATTATGATATCTCCACTCGTTTCTATTAACTTATTCCTCCATGATTGGTCGTTTT

TGTAAACTTCTGATGATTC

CA1035
                                                      (SEQ ID NO: 94)
AGCGGAGATTGATTCTCGCCACTGTGGTGGAATTCAGTAGCTATGTGCTATTAGTGCATTGATTGTTCTT

TTGTGTGGTGTAATAGACACCTGTTTGTTCCATGCTAGAGCTAGGCCTAAATTTTTGTAGTGCTATTAAC

TAAGTCAGTGGTTTGTGGTTTAGCATCCCATACCTCACTGAGTGACTCCCTTATTGCTCACCCCTCCTTC

GTTCTCCCAGGTGAGACCGACAATCATGAGTGATTTTATCGGATTGGTACTTTTGAGCTTTTATCGTTAC

TGAGCTTTTAGACCTTTGGACTTTTATCTTTTATGCTATTTCATATTTCAGACTTTCGGTTTTATATTGC

TATCTATATTTCAGATGTTATCGGACCTTCTGATATTGACTTTTGTATTATGAAGTGGAG[ATTATTATT

ATTATTATTATTATTATTATTATT]ACTAGATTCCTTTTCCGCGCTACGCGCGGATAGTATCTTATA

AATTTTAAATTTATTTTAAAAAAAAAAATATTTAAAGTTTAATTTACATTATTTTATACCAAAAATCAC

AAATATGGCTAAGAATTGGTTGATTTTATTTGTGATTTTTTGACAATATTAAATTGATTTATTTATTGCT

CATAGTTAACAGATTTGTTTGATTGGTTTTCAGTTCATAGTAATGTATAGTATTATATTTGGTGAGTGTA

TATA

CA1066
                                                      (SEQ ID NO: 95)
TCTCAGCGCTGAGCTCCATGTGGTGGAATTCATCCTAAATCTCTTTGATGCGATTGATCTCTTTTATAAC

TCATTTTGACTCTTTTGGAATTGGAAGAGATGGACTGGACGGCTATTGCAAAGCCTTTGGAAGAGATGCA

AAGGAGCTGGCTATTGCAATCTTCTACGCTCAAGAATAAGAAGACATATGTCAAGAAGAAGAAGATATAT

GCCTGGACTCTTGCCTTCATCGGCGTACTTGTGGTTATTGCATTTAGTTTGAACATAAAGCTCTTAGGGG

CTCATGCATAACGCTTTCTTAATTAGCTCTGTTTTTTCCAACTGATGTTTACTCTTTCTGAT[ATTATTA

TTATTATTATTATT]AATTGTTAGTTGCTGTTGACCGGTTGAGGCTGTTTTTGAGCCCTGGATATCTTTC

TGAGTTGAGAAAAATTTCATAACCAAATCGAGATTGTTATGTGCTCTTTCTTGCCTCCTTTCAACAAGTT

TAATAGAACCAAAGGCAAATAGTTTGTCTTTATTCTATACTAGGATTGCGAATCCCCGCGGTCCGCGGGG

AAAAAAAGATGTTTACCGCAAAAAAAATGATGTTAAAACTTAAATGTAATAGTAAAATTTTAGTTTGTA

ACAATCAACCGGTTGAATGGTTAATAATCAAATATTGCAATGTTAACTATTAAAAATTACAGTGGAACAT

TTAAAAGTTGTGAATATTTATATAAAA
```

CA1080

(SEQ ID NO: 96)

AGCGGCAATTGTATCTCGCCCTGTGGTGGAATTCTGTGATGATCAAAAACAAGTTTCAATCCAAATATCC

TGATTTTGCAAATTATTTGACAAAATCCACATCTCTAATGGTGTTAGAACACTAATAAG[ATTATTATTA

TTATTATTATTATTATTATTATTATTATTATT]AACAGTCTTTCCAAAATAAATGATTGATAAAATA

TTGAAAAAGAAGGCAAAGAAGAGGTTGAGAAACAATTCTTATTTCAAAATTTTACAAAAATACAAATTGT

TCGCGTAACATTTTCATTTTCTATTTAGTTTAATTTTTGTCATTTAAAATTATCTTGTTGGTGTTGTTGG

CGTAAGCCCAAAACCGATGTAGCCTACACTGGGCCAATCTCCTGCGCAAGCCCAAGACATAAAGCATTAG

GGTTTTGTTGCTAGCTCATATGTAAACAAAACTTAAGCTATCTTGTTGCCTAAGGTTTTAAGTTTTCTAA

GATACAAAGCTTGTACATACACAAGCTAGATCATAGTTGTGATCACCTCTGTACTCTCTTATTCATAGTG

AAGTTTGGGAGGACAGTCTCCCACGAGACGTACCGGTTAGAGGCCGGGAACTCGTTAAATTGTGTGTGTT

CTTATTGCTTTAGTTTAATCTCTTCTTAAACAACCATAAGCATGATAAGAACTAGTTA

CA1090

(SEQ ID NO: 97)

GGAAACGGCAGTCTGATATCATCGCCACTGTGGTGGAATTCTAACATAACATATGATTGATAGTACATTG

TATATTCTAATTCAAATTAAAAAATATAAATATACAAATATAAATCACCAATATAGTATTTTTACATATT

AATTTTATAATGCTTTATTCTAATATTTTCTTATACCTACTTATTAATTTTTAACTTATTAATTCTAATC

AATGGTCTATTCTGTATTTATTCTCATAAAGAGAAAATAAAGATCTACCAGAAATTGATATTTATGTACA

TTCATTACATGTACAGTAATAAGACCCACATAATCATTTTGTTTTAGCTATGGCTCGTGTTAGGAAAAAT

CTATAAGATGTATCTAATAGTGTGTTGCAATACTAGACTACCAGTTGATCCAGTTGTTTCAAATAATTAG

TTATGTTTCGGAAACTTTGTAGATTGGCTTATTTTCCATGCAGCTTTTTGTTACGACAGAACAAATTACG

CATAAACCTTTAGGCTGAGCAAAGTTGATGACTTTAACCAAGATTGAGTCTTGAATATGTGTCATTACAT

CGAAATATCGAATGTTAAAAATA[TAATAATAATAATAATAATAATAATAA]CAATAACGGGTTCAT

ATATCATTACAATTATAACGTAATAGCTGAAAATTCAAAATTGACTAAAATAATATTATGACCCGTCCCT

TTTTATGGTTCCCCCGTTCGTGTATTTGCATTGTTGGCCGTTGGTGATCCCATGNCGCACTTACCCTCCA

AGTCTTCA

CA1097

(SEQ ID NO: 98)

TCTGGAGCTGAAGTCCATGTGGTGGAATTCTGATTTTTGAAAAAATTAAGCGTTATTTTTGTGATTTTTG

ACTTTGAGTGCTAATTTGGAAACAAAAACTTGATTTAGAGATATTTTTGTCTTTTTTTCTTCTCCAAGCG

TGTATCTTTATTTTTATTTTTTATAATTAAACAGGCGGCTTTTTATCCTAATTCAATTCAGGTGGGGTTT

TGTTCTTTTACACATGTCAATTTTGTTCTTTTAATGGTAAAAATTTAAGATAAATTATAAACTGAACCGG

AATCGCAATTGGTAATAAACTGAACAAAATTCCTAATAAGATATATTCCTGAAAAAATCCCCGGAAGATT

TTGATACGTATTAAAATCATATTAAGTTTGAAATATCAAGTTTTATATAATAAGATATACATTATATGCA

ACATCTTTGAATAACTCTCAACCTTTTGGTCATATCACAATAAAGTGGTGGAGCTTTTTCCAGTTACTGA

TGAATGAGTTAAAAAGTACTTAAGTTGCAATAATCTATTCATATTCCATGATCAAAAGCTCTTACAAGAA

ACAAAAGATTACATGAAAATGTCCAAAAGGGTACTTT[ATTATTATTATTATTATTATTATTATT]ATCA

GGATTGAGACCCACGTATACGTAATAAGAAAATATATAACTAATAGCGAATGCTACCTTATGTCATATAC

ACGTAAACACATCCCACTGGTCTTGGCAACACAAGGTGTCATCCTTCTCTTAAACATTCAAC

CA1107

(SEQ ID NO: 99)

AGACGGAAATCTGATATCATCGCCACTGTGGTGGAATACTAAACAAGGCATATAGCATAATATTATTTCA

TGATATAAAAGCAAAAAAAAAATAGAATAATTAAATATACAATAAAAAAAATAAACAATAACTAAATATA

CAATAGCAAAAATGAAAAAAACTAAATGAAACATCTATCTGAAAAATGTATAATAAATAAATAATAAGTA

-continued

AATATATAATATGAGAAATAAAAATATTACACTAAATATCTATCGTAATATTAAAATAAAAATGGAGGTG

GAGGCGTTAATATGGGCAATGGAGTGTATGAGGAATTTGCGTCAGTTTCATGTCACGTTTGCAACAGATT

TTCCTCAATTGGTGAAGATGGTTTGAGAACCAGAAAAATGACCAGCATTTGAAAGTTATCTAGAAGACAT

CAAGATTTTGAAAGAAAGTTTCATCAACTCAGAGATCATTCATGTACCTCGGACGGAGAATTTAAGAGCG

GAGAGTCTAGCACGTAGTGTCAAAAAACATTTGTCTTTCATCGTTCACATGGATTTAGAGTTACCAGTTA

GGTTTACAAAGTCGGTATGAGTCTGTAAAAGTCGATTACAA[AATAATAATAATAATAATAATAATAATA

ATAAT]AAGTAAATATATGATACAAAAAATAGAAAACTACATTGAAAATGTGTAGTAAAATAAATAATA

AATAAATATAAAATATGATGACAAAAAAATGACAAAAAGTAAATATAAAATATAACAT

PE0012 (SEQ ID NO: 100)
ATACGCCAAGCTTCAATCAAAGGAGGGAAGTGGTGAGAATACAAACCTAGCCTTATTCTCTCTATGTATC

TTCCTCAACTCTGCATCTTCCAACTGTGCCTGAAAAAGAAAAGCAAAACCCATTAGACGCTAAGCTAAT

GCAATTTCGAGTTTAATGTTTCAGCTTAATCCACATAAAGACGGAAACATACCTGCTCCTGGGTGAATTC

CTCCGGTGCACCGTCGGAGTCTGAATCGGAGTTGTGATCTTTGTTATCCGACATCTGATTATTAT[CTTC

TTCTTCTTCTTCTTCTTCTTCTT]CGTTGCTTTCTTCTCCCTCAGACGACACACACTANGGTTTAAC

GGCTCTTCAGTTTCTCAAAAACAGAAGATTTCTATTCTGAGAGTTAATTGCTTCTCTCCTTTATGGTGGA

TTCTATTGGGAAGCTTGCATGCCTGCAGGTCGACTCTAGANGATCCCCGGGTACCGAGCTCGAATTCACT

GGCCGTCGTTTTACAACGTCGTGACTGGGAAAACCTGGGCGTTACCCAACTTAATCGCCTTGCAGCACAT

CCCCTTTCGCCAGCTGGGGTTANTANCGAAAAGGCCGCACCGATCGCCTTCCAACANTTGCGCANCTGAA

TGGCGAATGGCGCCTGATGCGGTATTTTCTCTTACCTCTGTGCGGTATTTCCNCCGCNTATGGTGCCTCT

CANTACAATCTGCCTGATGNCGCNTANTTAACCANCCCGAAANCCGCCANNNCCGCTGAANCCCCTGAAG

GGGNTGTTCGGCNCCGGNATCCGCTTTAAAAAAANCTGTTAACGTCTCCGGAACCGCTTTTTTCAAGGTT

TTCCCGTCTCNCNAAN

PE0017 (SEQ ID NO: 101)
CGCCNNGCTTCCTTTAAGAGTTAATTTCATACAAATAAGCCCACTAAACAGCGTTGTTTAAACTTTAAAC

CCTGTCTTCTTACCAAAGCTCCTCTTCTTACATAGTAGCTCTGCTAAACCTTCGCCGCAATAAACCCAAA

GTCGTAAGAAACCGTCGCCATGCCTGCTCTTACGCGTAACAAGCAGAAGGGAGCTAAGTCGCAGACTCCT

CCACTGATTAAGCGGACTAAATCGAATCCCACGCCTCCACCGAAGAAGGCGATGAAGTCCCGTAAGCCTC

CGTTGAAGAAACAGAGGAAAGGTGTTTCGGATGAGAAGCCTGAAGTTTCTAATGATGAGGAGGAAGAGGA

AGAAGAAGAAGAAGAAGTGAGTGAAGAGTCTGATGACGGGAGATGAATTGGGTTCTGACCTTTTCTC

AGATGGTGACG[AAGAAGAAGAAGAAGAAGAAGAAG]ATGATATAGAGCCTTCGGATGACGACTTTC

TTGGTGGTAGCGATGAGGAAAAGGGAACTTTGGGTTCTGATTCTGACTCTGATGAGTCAGATAAGCTTGC

ATGCCTGCAGGTCGACTCTAGANGATCCCCGGGTACCGAGCTCGAATTCCTGGNCGTCGTTTTACNACGTC

GTGACTGGGAAAACCTGGCGTTACCACTTAATCGCCTTGCAGCACATCCCCTTTCGCCNGCTGGCGTTNT

ACCNAAAAGGCCGCNCCGATCGCCTTCCACAGTTGCGCNCCTGAATGGCGAATGGGGCCTGGATGCGGTT

TTTTCCCCTTCCCCTCTGTTGCGGTTTTCCNCCGCCTNTGGTGCCTCTCNTTCATCTGCNCTGATGCCCC

TTNTTTANCCNNCCCGAACCCGCCANNCCCGTGAACCC

PE0063 (SEQ ID NO: 102)
ATCTCTATCGCTATACTTGTCACTTTGTTCACTTTCTCAGCAGTTCCTTCCACATGGTGATGCAACCATC

TCGCCATTACACTCAGCAAGCCTCCCTTAGCCTTCTTGCATCGTTCTGACCTGTCGTTATATCCATAATT

CTTTGCAATTTTTGTCATTCT[CTTCTTCTTCTTCTTCTTCCTCTTCCTCTTCCTCTTCCTCTT

CTTCTT]TATGAACATGAGCAGCCATTTCCTGTCAACTCTTTGACGGATGTGCACCAATTGACAAGAGCT

-continued

TACTCTGTTACACCACTCCAACAAACTCTTCCTTCGTCTCTTAGATATTTTCTCCATTTGTATTCCCAGT

GTCTCAAAGTTATCATTATCCTTTTCGCTCAAAGTATCATCCAAATGCTTTTCAATATCTAGAAAAGTTT

TTTTCCATCTCTTTCTCTTCCTTGTTACTCTTACACCTCCCTCAACCATTTGATCGAACACATGGTGGGC

ATACTTCTCCTTCTTGGTCTCAAGCAACTCCTCTCTTGCATCNTTACCCCTCTCAAAGT

PE0091
(SEQ ID NO: 103)
<u>CGGCAATAATGGACCACTGG</u>TTTGGTTGAACCACTAAAAAGAGTGC[GTGTGTGTGTGTGTGTGTGTGTG

TGT]GAGGGACTCTATTTAAAAGCACTGCTTAACTCAATAATTATTCCATCGCTCCAAAATAAAANAGAA

TAGCTAAAAGATGGCTCT<u>CGAAGTCTGCGTGAAAGCCG</u>CCGTTGGTGCCCCTGATGCTCTCGGCGACTGT

AACTTCCCTTCTCTCTCTCTAGCTCTTTTTTTTTATATCAGATTATGATCTCTGATGATCTTCAAATGTA

AAATTTATAATACATGATTTGTCTGTCGTTTCAGG

PE0131
(SEQ ID NO: 104)
CCGATAAGAGCCATCATCTCGAGGAGGGGTATTAAGGGATATGTATCCCACATTGGAAAATCAATGGGAC

ATTAAGTAATATATAAAGGGTTAGGGCCAATCCACTAATAGCCAATTGGTTTTGAGTTGGAAGCCCATAA

TAAACCCGAATCTAACAAGATTTTAGATTGATTAAGGAAATTAATATATTATATGCAATATTTCATGGTT

AACGTCAAAATAAGTCCAATTTATAAACAAGCGGATAAACATTTCCCTATATA<u>TATGGGAAGGTTTGTGG

TTGC</u>CAAACTCAAAGCACATTGGGTCTTATCTCTCTCTAA[CACACACACACACACACACA]AACTCACG

TATATATTTAGAGCTA[GAGAGAGAGA]TGGGTGAAGAGATGAAAGA<u>AGTGAGAGTAATCGAGGAGTGGT

CTCCGGTTATAGTAATGGTGAT</u>

PE0133
(SEQ ID NO: 105)
CC<u>TCCTGTGCCAAGTTTTACAAGG</u>CACCCAACCTGTGAACCTAAATTGCTTTGAAAGAGAAGTTTCTCTA

TCTATAT[CACACACACACACACACACACACA]AATCTAATCTTTCTCTTTCAACCGTAAATTTTGCTCACC

ACCAAGGCAAGTTTCCTTCTTTTGCTCCCCTAGCAATATTAATTGCTACTAA<u>AATATCTTGCTAAGGGTA

ACC</u>AAATCTTGCTTCATTCCTCTGTAATATCACAGAAAGAAACTAAAATTTAGGGTTTTTTTTGGGTTC

TTTCCATGTGATGTGAGCATTTTTGGGTGAGAAAGATGAAGACTATAATTAAGTTAGGGATTGGGTTGAG

TTTGGTGTTTGGGTTTCTTCTCTTAGCACTTATTGCAGAAGTCTATTACCTTCTGAGATGGAAGAAGCAC

AAGAAGAGAGTCATAAGCCAAGAGAGTGAGGAAGAGAAAGAAGAAGAGCAACAACAACAAACTGGGT

PE0177
(SEQ ID NO: 106)
TACCCAAGCTTCCACGATCGGAGGGATCTATCGGGACTTCTCGGAGATTTGTTTCACGGTGATG<u>TCTATT

GATCTTTGGCTCTC</u>TGTTTCGATTGTTGTTGTC[TTCTTCTTCTTCTTTTTCTTCTTCTTC]TCGAGAGG

TTGCGGGGTTTTGAAATCGTCTCCTTCGTCCATGTAGTCGTTTTGGTGTTTGTCCGCCAT[GAGAGAGAG

AGAGAGAGAGAGAGAGAGAGAGAGAGA<u>GAGA</u>]<u>GCGAAGACGTTACG</u>AAAAACTTCGATAGAGAGTATA

AGAGAGAGATGCTGAAACTGCTTAAACCCTAATTTTGATCGAGTGTGTTTTGGGAAATTTGCAGAGTAAG

TCCTTATATTTGAGCCGAATTAATTAAAGTAAGCTTGCATGCCTGCAGGTCGACTCTAGAGGATCCCCGG

GTACCGAGCTCGAATTCACTGGCCGTCGTTTTACAACGTCGTGACTGGGAAAACCCTGGCGTTACCCAAC

TTAATCGCCTTGCAGCACATCCCCCTTTCGCCAGCTGGCGTTATAGCGAANAGGCCCGCACCGATCGCCC

TTCCCAACAGTTGCGCNCCTGAATGGCGAATGGCCCTGATGCNGTATTTCTCCTTACNCNTCTGTGCGGT

ATTCCCNCCGCATATGGTGCCTCTCNTTACATCTGCTCTGAAGCCGCNTNTTTANCCAGCCCGACACCCG

CCAACACCCGCTGACCCCCTGAAGGGCTTGTCTGCCCCCGGGNTCCCTTNCAAACAACTGTTNACCGNC

CCCGGGAACCGCNTNTTTCAAANGTTTCCCCCGCCTCCCCGAAACCCCCAAAAAAAGGGGCNCTNANACC

CCNNTTTTNNGGGTTANGTCNGAAAANAANGGTTCCTAAANTTCGGGGGGCCTTN

-continued

PE0187

(SEQ ID NO: 107)

ATCTAGGACCCCATGATCCGAATAAGGATAATAAAAAAATGGATCTGCCGAATAAGTATCTGGATAACTT

AAAATTCCCTAGATACCCCCCCCCCGC[CACACACACACACACACACACACA]TCAATTTTCCTTGTAAT

TTTTCTCTTGTTCTCTATTTTTCTAAACTCCAATAAAGCAAGTCTTTAACATATACTCCACCTTTATTTG

AGTAAATAATCATGGATTTAATCTCTAAAGTGAAGGACACTTTGTTTATGTTTTCTGTTTTTCTAAATTG

TAAAATCTATTTTCTACCTTTTTAATGTGCTAATTTTAGGAAAAATTATATCAATATTTTGTGTCGTAAT

TAAATCTGTCAACATGAAGTAAATCTGTGTCAAAAAGAAAAAAAAATCTATAGAAACATAATTAAAGTAA

ATGTATGAACATATAAAATAAATCTATGAATGATGTATAAATCTATCAAAATTAAATAAATATGTGG

PE0203

(SEQ ID NO: 108)

CTTTAATGCTTAAAGCTCGTTCCAGCTCAGGGGTTGGGAGTTTAAGCCTAAAACTCGAGATCTGCTCATC

CGCAGTTGCTGATTTGGCAGCTTATTCACCTTCGCATACCTACAAATCAACGAATACAACGCAAACGTTC

CTCCTG[CACACACACACACACACACACACA]TATACTTAGAACCACATAACACCACTTTTTACAAAAAAA

ACAAGGATTAGGGATGTAATATTATTACCTTCGCCATTGTCGTTGGCTTTAAGGACAACAAAGACATACT

TTGCTAAAGGAATGACAGCAATGGTGTAGATAACGAGAGACAAGGCACCAAGAACATCAACTTCTGATCT

GATAGGAACTTTACTGAAGACATCACTAAACATACAAAGGGCTTGTTCCCATGTCTCCATACACAACA

CCTAACGTCTGAAACGCTATCCCAATCGT

PE0250

(SEQ ID NO: 109)

ACTCAATAACATCAGGCTTTTCTGGATGCAATCTTGCATTGGTTTGGTCCAGTTTGCATCGGGACAAATA

TTGTTGCTGGTGTATATGGGATCGGAATCTTTGCTCCGACATTCTCTTCGGTGTCTT[CATCATCATCAT

CATCATCATCATCATCATCATCAT]CAGTATCAGTATCATCTCTTATTCCAAACTTCTTATATTGTA

GATGTTCTTGACCGGAGTGGCAAATGAAGACATCTCATATATGGCATTGCTTTTAGGGTTTTTAAGAAGA

TGTGGTGTTGCTATGTTGGTCTTTGATGCAACCACGGTGGTCGGAATGGGCGAGAATGGTCTGCAAACTA

ATGGAGATTGTAGGTGTTCACATGGGTTCATCGACTATTACTTTGGGAGAAGTCCAACAACATCAAGCCC

TCTTCTTCCTGCAGGAAAATAAAATATTTCGTTCATCAATTAAAGTAAGAGAATTAACTCATCACTATGG

TGATATGTTAGTTTCTGTTTATTGTAAGACTTAAAATTACCAG

PE0281

(SEQ ID NO: 110)

ACAAAACCGCTTCCACCTGCGTTTCGTCGCAGNCAAGCATTTGCGTTTCATTGGGTTTTCTCGGTGAACC

AAGCTCGCGTTAGTATCCAAACATGTTTTCACAGAATCTCGTAGTAACGACATTTCTTGTTGAAGTTGTT

GGATCTGTGTTCTCATTTCGCTTATCAGCTCCATTTCCTGAAACGTTTTTAATTAAGCGGTTCAATGATT

CTCTTCTATGGGATAACAATAAAATCTAAAAACCTTACAGGTGACGGAGGGTTGTGAACAGACAAGACA

GGAGTTGAAGTTACTTCAGTGTCTTGACAACTCCATGATCCTGCAGGAGACGATGCAAAGATCGGCGAAG

AAGACGAGTCATCTCCATCGTCTTGCTCTTCACCTTCTTCAGTAAATGGCT[CTTCTTCTTCTTCTTCTT

CTTCTTCTTCTTCTTCTTCTT]CAGTTCCTCCACATTTTCATTCTATGGTCTTCCTCTTCTTCTTCA

TGTTGCAATTCCCATTTTTCAGAATGTTTGTTCGAATGTGTCTGCACACGAGACATCATGAGCCTATCGA

TCTGATCTCTTAAACCGGTCTGGGAGAANGTCTGTGACCGGTCCTCTGTAATATCCAAAACCACACATT

TTTCTTAGTNAATGGGTACCCAATTAGGAAAATGGGATTTAAAAGATTGGATCAG

PE0283

(SEQ ID NO: 111)

AATGAACGAGACAGGAGGTGCCACCCTATTGTCTTTGATGGACCAGAGTCTAGCTATCCGGTAAACAGTA

TTTTATAACAAAGACATGATCATGAAATGATTTTTTTCTTCTGAAGTTTAACTGATGACTCATATATCTA

TATCTGACTAGTTCATCGTGGACATGGAGCATTCACAGGACCAGAGCACACATCGAAGCTGACATACAAA

TGAATCTCTTATTGCCTCTAGTTTCACACGTAAATATTCAGTTTCTAG[GATGATGATGATGAATTGATG

```
ATGATGATGACGATGATGAT]CAGTCAAAAGTACTGTAAATTGATGGTTATGGTTGTCTTGGCTTTGCTT

AATCATGT

PE0286
                                                                (SEQ ID NO: 112)
ACAAGTTACCATTTGAGGATATATCAGAGAAGAAGGAGTTGCTTGAAGATGACGAGAAAACCAAAAGAA

GATGAGTTCTAATGGTCGTTGGTACGAGGAGCTTGATGTCTTCATAGAGAAACCTGAAACTGGTGTTCTT

ACTGGTGATGGTGCTGTGGTGGACGCATGACTGGGAACGAACCTGTTGATGGTGACGAGTTGGATGTTGA

GCAACAAGATGATAATTCTGATGGTGATCATGGTGATCATGAAGCAG[GAGAGAGTGAAGA]TGAGTATC

AAGCGAGTGATGAATCTGATAAAGAAGAGGATATTGACAGAATTTTGAAGAGGATGTTGAGATGTTCCA

GGGATGAGAACTACGATGGAGGAGATTCCAGACGAGGAGGAGGTATATTCTGACACGGAGGAGTCATCTG

ATGATGAAGAGGAACAAGCTGAGAAGGATGCTAATAGGGGTGAATTAGATGGCATTTTTAAGTCTTAGGC

AGGAANTTGCAATGCCTGCAAGTCGACCTCTAGAGGATNCCCGGGTACCGAGCTCGAATTTCCACTGGGC

CGTCCGTTTTACAACGTCCGNGACTGGGAAAAACCCTGGGGTTAACCCAACTTAATCGCCTTTCAGCACA

TNCCCCNTTCGCCANGNTNGGGGTAATAGCCNANAAGGCCCGCAACCGATNGGNCCTTTCCCAANAGTNG

CCGCACCTNAAATGGNGNATTGGCGCCTTANGNGGGAANTTTNNCCTTANGNATT

PE0324
                                                                (SEQ ID NO: 113)
ACATAAGCCCTTTTTATTATCTCTGCATATCATTACATTCATTTTATGTCACATATGTTTATTGCTCTTC

TCTTCAGATTACTATTACATCGCAAGTAAAACAAAAGAGTTAGAAAATAAAGTAAACACTCCATACATAG

TCAAAGTATCTCCATTACTCCTCTTCTTCGTGTTAACAAGTCTTTAGGCGTTTCTAAACCGCAGAAACCA

TCATAGCCGGTGATGCACCAACCATCAAGT[CTTCTTCTTCTTCATCATCATCATCATCATCAT]CCTCT

GCTTCCCACATGAAATGAGCGTATGATCCCAAAACCATACTACAAAAGTCACAAACCTTTAACATTCTGA

AAAAAAAACTCATCAAAGAATCCAAACTCTACATATAACATAACATACCAATCATCAGGAGAAGCGTTAA

CAGCTTGATCAAAGTAACACTGAGCTCTCTTCTCATCTCTCTTCGTCTCCCAAATCAGCTTCCCATACAT

CGACAACGCTTCACCATCACCTGGATCCGCAAGTATAGCTCTCCCGTAATACTCCTCCG

PE0340
                                                                (SEQ ID NO: 114)
CTTAGTGACCCAAAAGCCATTGGTGTATGATAGAAAAGTTAGTTAAATACCGTTACTCGCAAGGAAGACC

ACACATTTTTTAATTCTATCTCACTTAGTCAGACCAGCTCGGATCCTTCTCTAGAAC[CACACACACACA

CACACA]CTCAGAGTGAGAGATTCATCAATGGCGGTTTCTTGCAGCCACTCATCGATTCTCTTGCCCCCA

ACCACCTCCTCCGTTGGCTTCAACCGCTTCCCTTGTCTCCAAACGCTGCGTTTCAAATCCAGAAACGTTT

ATCAGAAAGCGAGGATCTCTACAGTGTCGGCGTCATCTTCACGGTCTCTCGAAGCTCTGATCTTCGACTG

CNACGGTGTGATACTCGAATCGGAGAATCTACACCGTC

PE0355
                                                                (SEQ ID NO: 115)
TCAAAGAGCACTTACAAGGATCCAGACGATGGAAGGCAACGATTCTTACTCGAACTTGAGTTCATTCAGT

GTCTCGCGAATCCTACTTACATACACTGTAAGCTCTTATGATTCCTTATCACATAGTATCTACTTATAGC

ATTTAGGAAGTGATAAGAGATCTT[GTGTGTGTGTGTGTGTGTGT]TTTATGCTCTATGATGAACTTA

CCACTTAGCTTTTNGATTCTGTTTTGGCAGACCTAGCACAGAATCGTTATTTTGAAGATGAAGCATTTAT

TGAATACTTGAAGTATCTTCAGTATTGGCAGCGACCAGAGT

UB0015
                                                                (SEQ ID NO: 116)
ACTTTAGTGGTCGAAAATCAAAATATTCTTCCATCATTTTAGTTTTTTTTTTTCTCTATGTTCGCATCAA

GAAAACGAAATGAAAGGGATTATAAAAGGAAGAAGAACTTGTGAATCACGGTAAGTTTCGGGGTTTGTTG

TGAGGAGATTTCGAGAGAATCAAGAATAAAATTATATCACGAGATTTTTTGTTTGAAGTGAGAAAGAAA
```

```
TCAAAGATTTTATTTTTTCTCTTTTGGTGAGTGATA[GAGAGAGAGAGAGAGAGAGAGAGAGAGAGAGAG

AGAGAGAGAGAGAGAGAGAGAGAGAGAGAGAGAGAGAGAGAGAGAGA]CGTGTTTTGGAACTACGG

TGATTTTTACTATTTTGATGATGTTTTCAACTTTGAAGAAGACCTTCTCTCATGCTCACTCTTAGCATCC

TCCTCATTTATAGGATTAGATGGGAGAGAGAGAGCGTTTTAGCCATTAATACTTTAATAACAAAATGAAA

AATCTGATATTAACATTTCTTTTTTCACTTCTCCATCAGTGGCATTTTCGATATTTT

UB0126
                                                              (SEQ ID NO: 117)
ACCTCCTGATGACTGCTTAAACAGCGCCTGCGAAGATCTGGATTCTGTAGTTAACCAGGCTAGGGAGTTC

TTAGAGGACTGGTCCCCAAAGTTGAGCAAGCTCTTTGGTGTAAGTTGATGAACAAGCTCTCATTTTCAGT

TTTCTTT[CTCTCTCTCTCTCTCTCTCTCTCTCTCTCTCTCTCTCTCTCTCTCTCTCTCTCTCTCTCTCT

CTCTCT]TTGCATCATTCATTGAGTTGTGTGTGTGCAGGTGTTTCACTCCGAGCTTTTGTTGGAGAAGGT

CCAGACTTGTTCACTGGAGATTAATCGCATACTTCTTCAGTTATCACAGTCAAGTCCTGTAACTTCAAGT

GT

UB0163
                                                              (SEQ ID NO: 118)
ACAGAAACAGTAACATCAACACACACAACAAACAGCTCGCGAAATGAATTACAGATTCCTCTCCGAAATC

AAAACAGGAAACGGACACA[GAGAGAGAGAGAGAGAGAGAGAGAGAGAGAGAGAGAGAGATGAGA]AGGTGA

TACCGTCGAGAGGTTTGATGTTGCCGTCGCGGCGATCGACGGAGAAGCCTTCATGAGGCGAATCGACGGG

TTTGACGACGT

UB0181
                                                              (SEQ ID NO: 119)
ACAGACGCGATGATGACACTTCTGGTCCTAAGCGTTGTGTTACGTTTGATACTCCTGCGCTTGTTTACTT

GGAGTATTCTGATGTGGTTGCTGATAAGTATGAGAATCTGAGTTTGGACAGCTTGGTTGAAGTTAGGCTT

GATCTTCAGTTGACTGCAGATCAAATCATGCGCAAGAATGCTACAGACAGTGTTGGTTTTGTTCCCGGTG

ATGTTTCAACTTTGTTCATGGGGGTCAAGAACGTCAAGATCCTCTGCTTATCTCCTGATTCTTTAGATGT

GAGTCCAGTCCTTTTTAAGTTAGCTTCATCACTGTGTAGCATTTGTTTTTTTTTTAAATTTGATTGGTTA

GTGATGATACAAAATATTTGATTCTG[GTGTGTGTGTGTGTGT]TTGTGAAAGTTCAGTCCCTTTAACTT

AGCTTCATGAGTGTGTAGCCTTTGTTTTTTAATTGGTTACTGATGATATGGTGTGTGTGTGTGTGTGT

GTTTCAGACGCTCTACTACCGTGGTGGTGACATGCCGGTGTTCAACAATCTGATTT

UB0196
                                                              (SEQ ID NO: 120)
ACATGAGAACAAGATGGGTTCGAATTACCTCTAGCCTAGATCTGGATCTGGAAACAAGAGACAAGGGAGA

GACGAGATCTTGTCACCACCACCAATCGGCTGCCACCACCACCACCACAACACGGCGCCAGCGAAAGGGA

GATA[GAGAGAGAGAGAGAGAGAGAGAGAGAGAGAGAGAGAGAGAGAGAGAGAGAGAGAGAGAGAGAGAG

AGAGAGA]AGAAGAAGAAGAGAGAAAAGGAAAAGAGAAGCTTGATGGCTAGGGTTTCTTAGTCTCTCTAA

ATCTCTGCAGGGCTTTGCTCAAGTTTCAGAATGAGAGAAAAAAGAGAGGAGGCAACTTTATTTATAGGAA

ATGGAGGGAACCCTAGGTCATTTACCTTAATGGGCTGCAGTCCTAACGAGCTCTCGTTAAAAAAATTTGG

GCCGGGTATCGGGATGTTACACTAACGGTGTGTGGCGATGAAGGCTCTTCGACTCTCAAAATTAATGATG

TCCATAACTAAATAAAAACTACTCGACTTTATTAAGATATAGCTTCAATGATTTAAAATTAAATATAGAA

CTCT

UB0307
                                                              (SEQ ID NO: 121)
ACCTNTGGGTAAGTAACTGTGGTGGC[CTCTCTCTCTCTCTCTCTCTCTCTCTCTCTCT]CAATACAC

TCTTCACTTAATAAATGTGAANACGTTAACTNGTTTCTTTTNTCACTTCTCAGTTATGTAGCTCCAGAGT

ATGCGAACTCTGATCTTCTGAATGAGAAAAGTGATGTCTATAGCTTTGGTGTTGT
```

-continued

UB0315

(SEQ ID NO:122)
CACGAAAGCAGGCCCCACCCAATAAGCGATGAGCTGTATATTTATTTTGTCTTGTTTTCACAAAAAATAA

CCCTTCATGTTTACAGTTAATTACACAACAGCCCCTTTCTTTCCTCCATGACCAACGACAAGGTCGAATT

T[CTCTCTCTCTCTCTCTCTCTCTCTCTCTCTCTCT]CCGTCGTCTTCATTCAATCTATCTCAG

TGATTTACTCGCAATAGAAGTCGCCTCTTAATCTCTCGAGAGAGAAGCTCAAGT

UB0331

(SEQ ID NO: 123)
CGTGGACTAACGCTCGTGTGCAGGAAACGATGTTCGTGAAAAGGTATCCGATCAGAGGAGCCTCCGCCGG

TAAAAACCCTTCG[CCGCCGCCGCCTCCG]TTGAATGGTAATAACTCTTGTTCTCGCTTTCTCTTCAAAC

TCCCTTTTTTTTCTCTGATTATTTTTGTTGGTTA

KK66

(SEQ ID NO: 124)
GAATGGGAAGCATCACAATGATAATGCTAATGGCGGTTTTGGTCTGGTCCATTACTCTAGAGACCTGCAT

TGCTAGAAGAGGAAGACATTGGAGACATAACCACCGAAGCTCCTC[A/T]GACTTGTCTGATTCCTTGTC

AAGCAAGAAACCAAAAAGCCACAGTCACCACCACAGCTCTCA[C/T]AACAACAACCATAATCATCACCA

CAAGTCTAAACCTAAACCAAA[A/G]CCAAAGCTGAAAACGCCGCCAAAAAGTGACCACA[A/C]TAAAT

CTCCGGTGGTTTCACCGCCACCAAAAGTCCAACCACCGTCTCTTCCGCCGCCAAAGGGATCCAAAGTTTT

CAATGTGATGGATTTTGGCGCAAAGGGTGATGGCAAATGTGATGACACTAAGTCGTTTGAAGCGGCTTGG

GCAGCAGCTTGCAAAGTGGAGGCATCCATGATGATCATACCGCCTGAATACACTTTCCTTGTGGGTCCAA

TCTCATTCTCTGGTCCTTATTGTCAAGCTAACATTGTGTTTCAGCTTGATGGTACTATTATAGCTCCAAC

GGATTCAAAATCATGGGGAAAAGGGTTAATGTGGTGGCTTGAATTCACAAAGCTGAAAGGAATTAAAGTA

CAAGGTAAAGGTGTGATTGATGGAAGAGGCTCTGGT

KK98G (SEQ ID NO: 125)
GACAGAGATAGCCCTAACTTAGTCACTCTCTCTCACACACACTCCAGTTCAAAGTTCAAA[A/C]AATGG

CTCCTCCACAGAAGCTCTTTCTCGCCGCCATTGTCGCTGCCGTCATTGTAGCCGCCACCACCGGATATGC

ACCTAATAGTGCTGCGGAAGATATTGTGCATTCCTCATGCGTGCACGCGAGCTATCCATCGCTATGCGTC

CGTACACTCTCTACCTACTC[C/T]GGTCCAACCATCACAAACCGTCGCGAGCTAGCTCAAGCCGCCGTC

AAGATAAGCCTCTCCCACGCTCGAGCAGC[C/T]GCTAAGAAACTCGCGGCTGTGAGAGAAACCGTGGG

[A/G]AAGAAACGGGTGAAAGCGGCGGTTGTGGACTGCGTGGAGATGATTGGAGACTCGGTGGACGAGCTG

[A/C]GCCGCACGCTAGGCGTTTTAAAGCATCT[A/C]CACGTTTCGGGCGTTTCGGCGAACGAGTTCA

[A/G]GTGGCAGATGAGCAACGCGCAGACGTGGGCTAGTGCGGCGTTGACGGATGACGACACGTGTCTCG

ATGGGTTTAAAGGGGTCGAGGGTAAGGTTAAAACGGAGGTGAAGCA[G/T]TGGATGACGAAAGTGGCGA

GGGTTAC[A/G]AGCAACGCGCTTTACATGATCAACCAGCTAGATGAATCACGTGGCTAGCCCCACGTAG

TACGTTCTTGATGTTATGATGTGCTTGTCCTAATGGACAGTTATGATTTGGTGTTAGTTTTTTTCGTGTT

TGCTTAATTGCGAGTTATCTACTATTTAAAAATGAGAGGCATTGTCCTTTTAAGTAGTTCTGATAATGGT

ATACTAAATAAATGGTTTATCTCTTTTTTCGGACGGTATGTCATTGTATCGTATTGTGTTGTTCCCTTCG

GATTCGATAGCATGTGATTTTGTCTTGACGTGTAGTAGCGCCTTGGCTGAGCTAATGCTCTAAATAAAAG

TTTTAAGTGGC

Table 14 below sets forth additional information about the markers of QTLs associated with whole field plant resistance to *Sclerotinia*, as well as exemplary sets of forward and reverse primer sequences for each polymorphic region.

TABLE 14

List of SSR and SNP markers and primer sequences used for amplification of loci associated with *Sclerotinia* whole plant field resistance

| Marker

TABLE 14-continued

List of SSR and SNP markers and primer sequences used for amplification of loci associated with *Sclerotinia* whole plant field resistance

| Marker | Repeat | Forward Primer Sequence | Seq ID NO | Reverse Primer Sequence | Seq ID NO |
|---|---|---|---|---|---|
| BG0295 | (AGGG)-(TCC) | CACATCTCTCCGATTTCATCGC | 198 | AAGAGGATTTTGTCGGTGGGTG | 199 |
| BG0452 | (TGG)-(GAT) | TCCCTTTGGTGATGTTGGACTG | 200 | CACATAATCTGCATTGTCGTCTTCG | 201 |
| BG0516 | (GAT)-(TAA)-(TTGGT) | TGGTCAACAGAAAATGGCCTGA | 202 | TGGCATGTCCTTTCATGCTCTC | 203 |
| BG0647 | (CTT) | ATGCAAAGATGGGCGAAGAAGA | 204 | CGAGAGCGGGTTACGAGATCAG | 205 |
| BG0651 | (CTT) | TGCATAACAAAAGATTTGAACCCG | 206 | GGAGCAAAAGAGCGGAACAGAA | 207 |
| BG0713 | (CT) | ACCGCCAAAGAAGACGAAAATG | 208 | CTCGGCGGACAGATACACTCAG | 209 |
| BG0864 | (GA) | GAAGCTAAATGCGTTGCGTTGC | 210 | TTTGGCTGTAAAATGAAGTGAGCA | 211 |
| BG0869 | (CT)-(CT) | GAGTCGGCCACAAATCAAGGAA | 212 | TCGGAGGAGGAGGAGATTGAGA | 213 |
| BG0988 | (CT) | CCCAAGACTCCAACCGGAAAAT | 214 | TCGCATTAAACGAGGACGTGAG | 215 |
| BG1062 | (CT) | CCAACTCGTTCCATCCCAGTCT | 216 | CGGTGGCTCGTACTGCTTCTCT | 217 |
| BG1090 | (GTA)-(GA) | CCGTTGAGGTAGGTTTCTGCCTT | 218 | TTGCCTCGCTCACATCTTTTTG | 219 |
| BG1101 | (CAT) | ACATGCTTGTGGATAAATCATCAT | 220 | GAAAATGAGAAAACCCAAACTAAA | 221 |
| BG1123 | (GA) | AGGCCACCTTTTGTCACCAGTC | 222 | GGGGGGTTAATTTGTCCCATTT | 223 |
| BG1127 | (GA) | CCGCCATAACAAAAATCTTCCC | 224 | TGTTTCCTACAAAGGTATAACCGGC | 225 |
| BG1149 | (GAT) | TTGCTACACTTCCCTGTGGGTG | 226 | CCTCTCTCACTGAGTGCATTTC | 227 |
| BG1182 | (AG) | CGGCGCACTGATGATGTTTCTA | 228 | GGGAGAGAGTTTGTTCGGTGCT | 229 |
| BG1197 | (CATTT) | TTGTGAGCGCCAAGATAAGGCT | 230 | AAACCCTATCCCGCGAACAACT | 231 |
| BG1230 | (GA/TGG) | GGCCTCTTGTGTTTCCTCCAAC | 232 | CACCACTACCGCCATCTCTCCT | 233 |
| BG1241 | (CAG/AAC/CAG) | TTAACAAACCGAATCCGCAAGC | 234 | GATTGTTGTTGCTGCTGCTGCT | 235 |
| BG1244 | (CTT)-(CTT)-(CTT)-(AGT) | CAACGAACTCTTCTTCTCTGCTTTACA | 236 | TCACGACAAATGGTCAAATTCTCA | 237 |
| BG1286 | (AGC) | GTCCGAGACAGAGTATGCTAAGC | 238 | TCATTGGTGGATCACTTCAAATA | 239 |
| BG1288 | (AGC) | GATTCTATCAGCCACGGAACGC | 240 | CACCTATTTACCCCACGAGGCA | 241 |
| BG1321 | (AAG) | TGCATAGACTCGAACCAAACCG | 242 | TCTGATACGCCAAGCTCTGCTG | 243 |
| BG1368 | (CGT) | CGACGGTTTCACGGCACT | 244 | TCATCCTCCGACGACGAC | 245 |
| BG1392 | (GA) | GCTCGGCTTCCAAGGGTAAGAT | 246 | GATGTACTGCTTAGCTGCCGCC | 247 |
| BG1442 | (GA) | CGAGGAGGAAGAAGATGACCGA | 248 | ACGAGCAGGCGGTGAAAATAAA | 249 |
| BG1449 | (GA) | AGTTGTGGTGAACAGGCTGCAT | 250 | CCAACTCGTTCCATCCCAGTCT | 251 |
| BG1453 | (GA)-(GA)-(GA) | TCACCTTCCTTCCTTCAATGGC | 252 | TGACCCACCTCCTCTGCTTTTC | 253 |
| BG1513 | (GA) | TGAAGGTTGCGATAGCGAAGAG | 254 | TTGGGGTCGGAACTGAAACATT | 255 |
| CA0105 | (GAA) | TGTTTCCTTCACCATGATCGGA | 256 | CACACCCTACCTCTCTTGTGTCCC | 257 |
| CA0120 | (CCA)-(TCA) | GACTAAACCAGACCAAGAGAAAAGTCG | 258 | TGTTGAACCGGATAGGCAAGGT | 259 |
| CA0163 | (CAT)-(CAT) | CCATCATCACCACCACCATCAT | 260 | CTTGCTGGAGAAGGTCGGATGT | 261 |
| CA0221 | (CTT) | GGAGAAGGGTCGTCGTCAAGAA | 262 | TCGAACACACAAACGATGCTCA | 263 |
| CA0226 | (GA)-(ACC) | CATGGATCACCTGCACCCTTAG | 264 | GCGACTCCGGTGAAGACGTATC | 265 |
| CA0233 | (GAA)-(CAC) | GGCAAGCATGGTCTCGTCAGAT | 266 | AAAAAAAGATTCCAGCCGCCTC | 267 |
| CA0328 | (CGT)-(CAT)-(CCA) | ACTTTGGAGCATCCTTCCTTGG | 268 | GATGTTGGACTGCGCTCTGGTA | 269 |

TABLE 14-continued

List of SSR and SNP markers and primer sequences used for amplification of loci associated with *Sclerotinia* whole plant field resistance

| Marker | Repeat | Forward Primer Sequence | Seq ID NO | Reverse Primer Sequence | Seq ID NO |
|---|---|---|---|---|---|
| CA0410 | (CAG) | CTGTTGAGCCATCGAGATCAGC | 270 | CCAGAAAGTGATGGTGTGCATAA | 271 |
| CA0423 | (AGC) | AATCAGTCCGATCACTCCCTGC | 272 | GGAAGTTACCTCGTCGTCGGAA | 273 |
| CA0456 | (TTG)-(TCAA)-(CCA)-(CTC) | TTCTGTTAGAATTCTACCGTTGTTG | 274 | AGCTTTGTGAGGAGAGTGTGGT | 275 |
| CA0488 | (CTT)-(CTT)-(CAA)-(CAA) | CAGCAATGTCGTCGTTCAATCC | 276 | CTGTAACTCGCCGGAGCTTGAT | 277 |
| CA0546 | (GAA) | CCCCTTCCTTATCCACACACACA | 278 | TGGGTTCGTGAAGGTGAAGGTT | 279 |
| CA0552 | (CTT)-(CTT) | CGCTAGGGGGTGAACCAAGAAT | 280 | GCGTCGATCCTCCTCTCCAATA | 281 |
| CA0603 | (CTT) | CCTCCCAAAGTCGTCTCTTCCA | 282 | GTAGACAGGGGACGAAACTCGG | 283 |
| CA0624 | (TA) | TTCCAAGTGGTTCTGCAATGTG | 284 | TCAGCTATCCCAATAAAGGGCAA | 285 |
| CA0636 | (CCT)-(CCA) | CCAGGTCCTTGCGTTGAATCAT | 286 | ACCACACTGCATATCCCTGCAA | 287 |
| CA0682 | (AAGG) | CCTCTTCAACCCCACACTGGAT | 288 | TTGCGAATGTATCAGCCGTCTC | 289 |
| CA0729 | (GGTT) | CCGAACCGGAATCATACAGCTC | 290 | TGCGTTTGAACCAGTCAGATCC | 291 |
| CA0736 | (ATAG) | CCGGGCTTAGACAAACTTTATGAG | 292 | ATTGATCGCACAAACGCCTGTA | 293 |
| CA0739 | (AT)-(GTAT) | AAAAACTGATAAGATTATTGTTGGTAAC | 294 | CCAAAAATAAAAGTTAAACTTGCATA | 295 |
| CA0753 | (TAA)-(ATAC)-(TC)-(CGG) | CAGGCAGCTAAGGAATCTGGAAA | 296 | TAAAAGAGGCGTCCCGATGAGA | 297 |
| CA0834 | (AAT)-(AAT) | AAAATGCAACCATGCAATACGTG | 298 | GTTTGTAGTATTTGTTGTCACTGCTGC | 299 |
| CA0837 | (ATT) | TGCGAAAGCCATGAACCTTTCT | 300 | TGTTCTTCACAAAAAAAATCAGCAA | 301 |
| CA0896 | (AAT) -(AAT) | CTCATGGGAGGTTCGCTTGATA | 302 | GCAACTGCAAGATCAAATGGTCA | 303 |
| CA0991 | (AAT) | CACATTGGTTTACAGAGTCTACATGA | 304 | ACAAATACATGTGAAAGTTGAAAACA | 305 |
| CA1027 | (ATT) | TCAGTCTAGGCGTTTACCAATACCA | 306 | CTTAGGCGGTGCTTTGGCTCTA | 307 |
| CA1032 | (AAT)-(AAT) | TTGAACTTGACGACGACATCCC | 308 | GATTGCATGATTTAGCTGCTGGA | 309 |
| CA1034 | (AAT)-(AAT) | AAAATGCAACCATGCAATACGTG | 310 | TTTGTAGTATTTGTTTGTCACTGCTGC | 311 |
| CA1035 | (ATT) | CTCCCAGGTGAGACCGACAATC | 312 | CGTAGCGCGGAAAAGGAATCTA | 313 |
| CA1066 | (ATT) | CTCTTGCCTTCATCGGCGTACT | 314 | ATCCAGGGCTCAAAAACAGCCT | 315 |
| CA1080 | (ATT) | TGACAAAATCCACATCTCTAATGGTG | 316 | AGGCTACATCGGTTTTGGGCTT | 317 |
| CA1090 | (TAA) | CCATGCAGCTTTTTGTTACGACA | 318 | GGCCAACAATGCAAATACACGA | 319 |
| CA1097 | (ATT) | AAAGTGGTGGAGCTTTTTCCAGTT | 320 | GCCAAGACCAGTGGGATGTGTT | 321 |
| CA1107 | (AAT) | TAGTGTCAAAAAACATTTGTCTTTCA | 322 | TTGTCATTTTTTTGTCATCATATTTT | 323 |
| PE0012 | (CTT) | CACCGTCGGAGTCTGAAT | 324 | GAGCCGTTAAACCNTAGTGTG | 325 |
| PE0017 | (AAG) | ATTGGGTTCTGACCTTTTCTC | 326 | CTTTTCCTCATCGCTACCAC | 327 |
| PE0063 | (CTT) | TCGTTCTGACCTGTCGTTAT | 328 | GGAAATGGCTGCTCATGTT | 329 |
| PE0091 | (GT) | CGGCAATAATGGACCACTGG | 330 | CGGCTTTCACGCAGACTTCG | 331 |
| PE0131 | (CA)-(GA) | TATGGGAAGGTTTGTGGTTGC | 332 | CACTCCTCGATTACTCTCACT | 333 |
| PE0133 | (CA) | TCCTGTGCCAAGTTTTACAAG | 334 | GGTTACCCTTAGCAAGATATT | 335 |
| PE0177 | (TTC)-(GA) | TCTATTGATCTTTGGCTCTCT | 336 | CGTAACGTCTTCGCTCTC | 337 |
| PE0187 | (CA) | GACCCCATGATCCGAATA | 338 | AAGACTTGCTTTATTGGAGTT | 339 |
| PE0203 | (CA) | TACAACGCAAACGTTCCT | 340 | TTGATGTTCTTGGTGCCT | 341 |

TABLE 14-continued

List of SSR and SNP markers and primer sequences
used for amplification of loci associated with
*Sclerotinia* whole plant field resistance

| Marker | Repeat | For

<400> SEQUENCE: 1

```
cgaattcgcc cttctcttgc ttagatctgg actaactact tcnnaaagaa aacattnnnt      60
taatgtttat gtcgaatgtc atttatgctg aacaaaataa ccttgaaaat atgttctgta     120
ggctaaagtt gggagagaga aggaggttga agagattttg tcaagattgc gaggagaaaa     180
ttctgatgta tcagatgagg caggagagat attagtaagc atatatatgc atgaataatc     240
atatgatcaa tgtatatatt ttttacttca caatattttg atgatcatca ggcatataca     300
gaacatgtta acaacaagg agatgatcgc ggtttcctca agttgtttca gcgaaaatac      360
gcgttctcac ttactgtaat tcttcttctt cttcttcttc ttcttttttct tcttcttctt    420 cttctttaat aacccgtttg gtttacacag attggagttg ttcttatagc tttgcctcaa     480
cttggaggtc ttagtggtta ttcttttttac actgagtcca ttttcatatc tacaggtann    540
ntaactctta cttcttcaac aaaatcttga tttttatata tttatttacc gtaacgataa     600
ttgttgataa ttacgnnnat caggtgtatc gagtgatgtt ggattcatat cgacatctat    660
agttc                                                                665
```

<210> SEQ ID NO 2
<211> LENGTH: 726
<212> TYPE: DNA
<213> ORGANISM: Brassica napus
<220> FEATURE:
<221> NAME/KEY: misc_feature
<222> LOCATION: (36)..(40)
<223> OTHER INFORMATION: n is a, g, c, or t
<220> FEATURE:
<221> NAME/KEY: misc_feature
<222> LOCATION: (194)..(196)
<223> OTHER INFORMATION: n is a, g, c, or t
<220> FEATURE:
<221> NAME/KEY: misc_feature
<222> LOCATION: (203)..(207)
<223> OTHER INFORMATION: n is a, g, c, or t
<220> FEATURE:
<221> NAME/KEY: misc_feature
<222> LOCATION: (248)..(250)
<223> OTHER INFORMATION: n is a, g, c, or t
<220> FEATURE:
<221> NAME/KEY: misc_feature
<222> LOCATION: (309)..(312)
<223> OTHER INFORMATION: n is a, g, c, or t
<220> FEATURE:
<221> NAME/KEY: misc_feature
<222> LOCATION: (336)..(336)
<223> OTHER INFORMATION: n is a, g, c, or t
<220> FEATURE:
<221> NAME/KEY: misc_feature
<222> LOCATION: (704)..(706)
<223> OTHER INFORMATION: n is a, g, c, or t

<400> SEQUENCE: 2

```
acgaattcgc ccttctcttg cttagatctg gactannnnn tgatttgccc gctatgttcg      60
acgggtggag attttagttt tacttcctcg atctgattgt atgggttggg agtagggtct     120
aatatatcaa ctgcgagtgt atgttcgttt cctcctcagt ttcgaagttg ggttcttatg     180
tgtttagcct aagnnnctgt gannngntag tttttttta atcagttcca acaggattca      240
tttcaggnnn ttggaacttg tgtatatgtg ttagcctgag atctctgtag tgtccggaaa     300 tgatattnn nnattatcat taatttagtt cgaagnatga agctcagtgt tgttggactt     360
gtgtatatgg agctcgaaga gtgaagctca gtgcgttttc atctgaggat gatgatgatg     420
gagctaatgt gctgagcaat gagaactcga gatgataagg cttgagggac atgccagtga     480
```

```
gtgaagaaac cgtcgggcta tagcttagtg aagaagaaga agaagagctc gtggagtgat    540
caaatttgca ggtatgccca aacttgccaa tcccacattg tggagaatgg ctgcattttt    600
accacaaagc tgtttctgtg gagccaaaaa tgaatggagg atagtaaaac agaacgtcat    660
aatcaaatca agaaatttta actttttttg tcagcacaaa tttnnncttt atctttaatt    720
atttac                                                                726

<210> SEQ ID NO 3
<211> LENGTH: 782
<212> TYPE: DNA
<213> ORGANISM: Brassica napus
<220> FEATURE:
<221> NAME/KEY: misc_feature
<222> LOCATION: (24)..(27)
<223> OTHER INFORMATION: n is a, g, c, or t
<220> FEATURE:
<221> NAME/KEY: misc_feature
<222> LOCATION: (694)..(697)
<223> OTHER INFORMATION: n is a, g, c, or t
<220> FEATURE:
<221> NAME/KEY: misc_feature
<222> LOCATION: (748)..(749)
<223> OTHER INFORMATION: n is a, g, c, or t
<220> FEATURE:
<221> NAME/KEY: misc_feature
<222> LOCATION: (752)..(752)
<223> OTHER INFORMATION: n is a, g, c, or t
<220> FEATURE:
<221> NAME/KEY: misc_feature
<222> LOCATION: (772)..(774)
<223> OTHER INFORMATION: n is a, g, c, or t

<400> SEQUENCE: 3
cgaattcgcc cttctcttgc ttannnnctg gactaacaac aattccaaaa tactaattca     60
caaactttgt ttacaatcca agaaaatcc gctcttttga agcgcggatc aagatctagt    120
gttataatat atctagaaca tgggagtttg gtccaatgaa ctactgtata gttctatcga    180 aattttgag tgataagatt gaagctccag cactcactta tctatttgag aagcaaataa    240
tagaaaaaga agtagatttg aggaagagat gatggagttg aacaaggagc tttaagattt    300
gagttctgac agtgtagaag ctgcaatact gaggcaccaa ggaagaaatc atcatcatca    360
tcatcatcat catcatcaag aattagtttc agttcatatc cacaaccatt ttttctttca    420
aagaaatttg ctggtagtaa ttttgaagtt gtaaattttta cattttcagt gtttcatttt    480
tctcacgttt tcttaataat tgtttacttg ccaaatgatt ccatcacttg gaaactcact    540
attgtttgac attttggtgt gcttaagtga ctcttttcga gtattcatac attatagaaa    600
ttgtttggga caacaggtaa gaattgcttg gcacaagtaa tggcatccct ccctgcaaat    660
atatataaat attacagttg tcctggaact tttnnnntct atcctctgct gacaggatga    720
gatatatgca tatagaatat taacttcnnt cngcccgtat gttcatggat gnnnagctcc    780
at                                                                   782

<210> SEQ ID NO 4
<211> LENGTH: 657
<212> TYPE: DNA
<213> ORGANISM: Brassica napus
<220> FEATURE:
<221> NAME/KEY: misc_feature
<222> LOCATION: (289)..(289)
<223> OTHER INFORMATION: n is a, g, c, or t
<220> FEATURE:
<221> NAME/KEY: misc_feature
<222> LOCATION: (632)..(632)
<223> OTHER INFORMATION: n is a, g, c, or t
```

<400> SEQUENCE: 4

```
cgaggagttg aatgaccctg actgtacttt ggcctcgaga cagtcccatc aagaataatt        60
tactgggtcg attttttattt ttaattctgg tcgagccaac tccgaactgg tcgagcggga      120
tttttttaatt ctggtcgacc aaaatcatat ccgctcgtga gggtctttac aaccaccatc     180
accacactcg gacgatcacc ccaccaccac ttggacgacc accaccacca ccaccggcgg      240
ctcggctagc tctcggggg ctcgcggcga ggagagagga agatatccna cggaaagaga        300
aaagagaggg agagagagag agaggcgtga gagaagaaga gagaaaagga aaagagaagc      360
ttgacggcta gggtttccta gtctctataa attcctgcag agcttcactc aagtttcaga      420
atgagagaag agtaagagga ggcagcttca tttatagaaa caggaggaaa ccctaggtca      480
tttaccctaa tgggctgcag tcttaatggg ctctccttaa gaaaattttg ggctaggaac      540
cgggacgtta caataatgct tcttatgaat atgtctgagt agttctttg ttagatttag       600
ggttcttcaa ggggtgaatt atggtttgct anatttatat tgttgtttgt gtgattt          657
```

<210> SEQ ID NO 5
<211> LENGTH: 649
<212> TYPE: DNA
<213> ORGANISM: Brassica napus
<220> FEATURE:
<221> NAME/KEY: misc_feature
<222> LOCATION: (626)..(627)
<223> OTHER INFORMATION: n is a, g, c, or t

<400> SEQUENCE: 5

```
gctcgccgac ttcggagtcg cctcgccgct cgatatccct ttcagcctcg cctccatctc        60
ttttccccaa actctaggct gttgctgttg cgtcgccgcc gccgccgccg tggctgttat      120
cgagctattt gatctaccgt acagcatttt aaaccgttga tcagattcgg gatcagactt      180
tgtcgtcacc ggagggctct tgatcggcgg ttgcacttcc ccctccgtac acggcgtaca      240
atgtcggtaa gcaccggaag cttttcagagc catatctttg agctgagaat gaatttacga     300
aaatacccctt gatcagtata gagaatgaca agaggtggag gatgagcaaa gagagagaga     360
gagagagaga agtctacctg agatgttaga gatttggctt gcttggaatc cggatcgtcg      420
ggttgacccg aggtttcatc gccggctcgc ttcgaacgag ctatacaagt cagcatttc       480
cggcagctgc tgtttcttgg taatgtgatt ttgtttcttc tcttttttgga tacggagaga     540
cagtagatgc tgtcagtttc taactttggt ttgtgttgtg tgtttggtca tggtgctctt      600
tttatgtttt atactcactt taccanngaa aacggttcca tttttttaa                   649
```

<210> SEQ ID NO 6
<211> LENGTH: 687
<212> TYPE: DNA
<213> ORGANISM: Brassica napus
<220> FEATURE:
<221> NAME/KEY: misc_feature
<222> LOCATION: (541)..(541)
<223> OTHER INFORMATION: n is a, g, c, or t
<220> FEATURE:
<221> NAME/KEY: misc_feature
<222> LOCATION: (564)..(564)
<223> OTHER INFORMATION: n is a, g, c, or t
<220> FEATURE:
<221> NAME/KEY: misc_feature
<222> LOCATION: (594)..(594)
<223> OTHER INFORMATION: n is a, g, c, or t
<220> FEATURE:
<221> NAME/KEY: misc_feature
<222> LOCATION: (617)..(617)

```
<223> OTHER INFORMATION: n is a, g, c, or t
<220> FEATURE:
<221> NAME/KEY: misc_feature
<222> LOCATION: (640)..(640)
<223> OTHER INFORMATION: n is a, g, c, or t
<220> FEATURE:
<221> NAME/KEY: misc_feature
<222> LOCATION: (662)..(662)
<223> OTHER INFORMATION: n is a, g, c, or t

<400> SEQUENCE: 6
taggagatga gatgtactgt tgcttagggc tcttatttct cttgaaacta gaataagctg      60
ccatcgggtc ggtgtaataa tcaaaccttg gcttatcata cgattcctgc tgatgtatgg    120
atgcttcagc caagggattt gagaggtgac ttgtgttcat agaggttcca agctctgtag    180
aaccatcatt ctctgcagca gcagcagcag cagcttccat ccgcattgct tttagcattt    240
cttttctttt ctctgaatct tccattactg ctcagcttca aagctaatca actacaaaaa    300
tataaacttt ttttcgaaat tatcaatcga atcgcaccaa aagagctaag atctccacgc    360
gagaacaatc taactaaccc taaaccccca aattatccca aactctgtac ggatactcaa    420
attggaaaag cgaaattgag aggatgctaa ccttggttta ctcaacttct tcacttcctg    480
gtcgccagag gtagaggatg aatgacaagt gaaaacccag aacacgatga tgacgacaac    540
naagcctcca caaataaata taanacccgg ttcgtgttcg accgtgtttt tccnattaaa    600
accggtttac ggcgatnaga atcataaacc aaatacgatn atcacgaagg gtgacgatta    660
anacgagact tcccaaaacc ggttcgt                                        687

<210> SEQ ID NO 7
<211> LENGTH: 659
<212> TYPE: DNA
<213> ORGANISM: Brassica napus
<220> FEATURE:
<221> NAME/KEY: misc_feature
<222> LOCATION: (476)..(476)
<223> OTHER INFORMATION: n is a, g, c, or t
<220> FEATURE:
<221> NAME/KEY: misc_feature
<222> LOCATION: (501)..(501)
<223> OTHER INFORMATION: n is a, g, c, or t
<220> FEATURE:
<221> NAME/KEY: misc_feature
<222> LOCATION: (523)..(523)
<223> OTHER INFORMATION: n is a, g, c, or t
<220> FEATURE:
<221> NAME/KEY: misc_feature
<222> LOCATION: (541)..(541)
<223> OTHER INFORMATION: n is a, g, c, or t
<220> FEATURE:
<221> NAME/KEY: misc_feature
<222> LOCATION: (564)..(564)
<223> OTHER INFORMATION: n is a, g, c, or t
<220> FEATURE:
<221> NAME/KEY: misc_feature
<222> LOCATION: (586)..(586)
<223> OTHER INFORMATION: n is a, g, c, or t

<400> SEQUENCE: 7
ctgttgaggg gaggaaacaa gagcctggga ggagaactcc ttgctgggga agacgagatc      60
attctcctca gaggcaatgg attcacctaa gaccacagcg tttaactgag agatcttgcc    120
ggcacctgag ggtagcagag acatggactc cacatgcctt aggtgattgg atgacattgt    180
cttacaccgg agaagtttgt ccaacggaga tgatctgcca caccttaca agtcagatgt     240 catttgaata aaatttaaaa caaaaccaca atgtcttttt tgacttattt atcaaaactg    300
cctaaacccc aaacccaatc atcatcatca tcatcatcat aaccatattc atcaatcatt    360
```

```
ctatcattat tgtcatcatt ggatcagatt attcattcac ctttgagaag ccggaagaat    420
ccgagatcca agtgatccgc ttgttttcag atcctgaaga aacaaaaaca gatcanaggc    480
gaatattctt ttttgattac natcagatca taagaagaag aanagattga aactttcgta    540
nacccaaaac atatcattat gacnaaagat cacatcttta actccnatga tccctaagat    600
tcgacttaca ggtcgagaac gaagagagga aattttttga aaaattgtaa gaagggcg     659
```

<210> SEQ ID NO 8
<211> LENGTH: 687
<212> TYPE: DNA
<213> ORGANISM: Brassica napus

<400> SEQUENCE: 8

```
cttgagagag agattgaaag tgagctgcgc caagaaccaa aacggacata tcacaaggct     60
tactttagca acacgcatcc ttgtccaacg tcccttctca tctaaacctt tagcacaaat    120
ctcaccacta acatcaagct ctacactttc cacaccagat tcaatcccac taccatctcc    180
ctcctcttct ctaacaacaa ccctgatcc ttcagacaca tctgacacca ccaccacacc    240
acctcctcct agcaaaacat ccttctgtga ctcagccgac tcctgcaaat gagacctttt    300
gcttctccga aacagtatac tcccatacgc atctgctaaa taccgaccga tctcgaagag    360
aggaaggtta gtccagatct aagcaagaga agggcgaatt cgcggccgct aaattcaatt    420
cgccctatag tgagtcgtat tacaattcac tggaccgtcg ttttacaacg acatgactgg    480
gaaaaccctg gcgttaccca acttaatcgc cttgcagcac atccccctt cgccatctgg    540 cgtaatagct aacaggcccg gaccgatcgc ccttcccaac agttgcgcag cctatacgta    600
cggcggatta aggtttacac ctatcagaga gagagccgtt atcgtctgtt tgtggatgta    660
cagagtgata ttattgacac gccgggg                                        687
```

<210> SEQ ID NO 9
<211> LENGTH: 693
<212> TYPE: DNA
<213> ORGANISM: Brassica napus
<220> FEATURE:
<221> NAME/KEY: misc_feature
<222> LOCATION: (630)..(632)
<223> OTHER INFORMATION: n is a, g, c, or t
<220> FEATURE:
<221> NAME/KEY: misc_feature
<222> LOCATION: (656)..(658)
<223> OTHER INFORMATION: n is a, g, c, or t

<400> SEQUENCE: 9

```
cactttgcat aaatactttt acgagcaatt ttaaaaaaaa attctaaaaa tgtctattat     60
ttgtggactt ggaatagccg tttatctgct ttgattttgt cgtttcttaa atcaaagtcc    120
taatcagggt cccttatataa gatcagtcct ctagaatctg aatagctttt taagacaaaa    180
aaaaaacaaa acagattaga gtccgaatcg gactcgaaca tctccaattt aacttctatc    240
tttttttttt ctaaaataaa atgtaaaata aaatatttt aattgtatga aaaattgcat    300
tcaatagcta aaaaaaaata aaaattcaat acataactaa aatcccactt tctctcctct    360
tttctcttcc tatctctctc ttctctctct ctaaaaatct aattttcttt ttttttctg    420 gttattccct aaataagccc taattgtatt ctattttcac tctaaaaaat agcttgattt    480
tataaataga ataattcatt tgttttttta aaaataaatt atcattagaa tataatttaa    540
ctttattata aaattattct cttttagagc aaaaaaataa aataaaccat tagaaattgt    600
```

```
tttagagaaa tcatcagtca aaatctcacn nnttccacta tttagtttca tctctnnngc      660
aatcagacgt aagaacacaa aaacatatgt tat                                  693

<210> SEQ ID NO 10
<211> LENGTH: 660
<212> TYPE: DNA
<213> ORGANISM: Brassica napus
<220> FEATURE:
<221> NAME/KEY: misc_feature
<222> LOCATION: (541)..(549)
<223> OTHER INFORMATION: n is a, g, c, or t
<220> FEATURE:
<221> NAME/KEY: misc_feature
<222> LOCATION: (602)..(602)
<223> OTHER INFORMATION: n is a, g, c, or t
<220> FEATURE:
<221> NAME/KEY: misc_feature
<222> LOCATION: (645)..(647)
<223> OTHER INFORMATION: n is a, g, c, or t
<220> FEATURE:
<221> NAME/KEY: misc_feature
<222> LOCATION: (660)..(660)
<223> OTHER INFORMATION: n is a, g, c, or t

<400> SEQUENCE: 10
cagccattct ctatggcctt ggtgaccatg gagatcaagt gccttaacag caaccggttg       60
ggcttctaaa cccggtttaa ccttgtcatc aatgaaccct ttgtaaactg gcccaaaccc      120
tccttctccc agcatgttac ttcttgagaa attatgcgta ataactctca gctcagacaa      180
ggtgaacata cgaagctttt gagatgtgga ggagtttgag aggtcatcca tgaccgacat      240
gggcgagctt ggatcactta tgtccgataa cgacagcctc ttgatcaccg gacaagttct      300
tattttcatt gcgttgcccc tctcctctac ttcgtatcta ctcgcgttct ttgtcctgta      360
acatcctaaa aacagagatg tcaatgatgt cttcttgttc ttggttactg ccattttctt      420
cttcttcttc ttcttcttct tcttcttctt cttcttcttc ttcttcttct tcaactttt       480 ggagaaaatg gaagatagat agtgttttac tcttttgat gtatcttttg tagattgcgt      540
nnnnntnnna attaagggtg ttttagttaa cctacttgtc ttcaaagtcc tgtatttata     600
gnggttgttg tgtcttattc gtagtgacta ccttggaact ttctnnngac atatactgtn    660

<210> SEQ ID NO 11
<211> LENGTH: 631
<212> TYPE: DNA
<213> ORGANISM: Brassica napus
<220> FEATURE:
<221> NAME/KEY: misc_feature
<222> LOCATION: (486)..(486)
<223> OTHER INFORMATION: n is a, g, c, or t
<220> FEATURE:
<221> NAME/KEY: misc_feature
<222> LOCATION: (530)..(533)
<223> OTHER INFORMATION: n is a, g, c, or t
<220> FEATURE:
<221> NAME/KEY: misc_feature
<222> LOCATION: (597)..(598)
<223> OTHER INFORMATION: n is a, g, c, or t
<220> FEATURE:
<221> NAME/KEY: misc_feature
<222> LOCATION: (618)..(620)
<223> OTHER INFORMATION: n is a, g, c, or t
<220> FEATURE:
<221> NAME/KEY: misc_feature
<222> LOCATION: (629)..(631)
<223> OTHER INFORMATION: n is a, g, c, or t

<400> SEQUENCE: 11
aagcaaccta cggtgttctc ttattaccga gtgctattag gcttgtctta atgtcctaaa      60
```

```
caattacgtt tttactttga atgtgaacct gctcttgaac gaaatatctt catgacttca    120
tatcatttgt ttaattctac tactgtctgg ttaaaaatgg ttgtatgttg catatattgc    180
tattttaacc acatgtaaga aaagagaaac gatcccacgt ttatactcaa attcaagaat    240
ccaacacaaa tcctctcaca attctattag attggaagaa agaaactcat aaaataatta    300
taaataacaa aaggacaagt aaatagagtc tatctggaac ataaaaacac taacgggtct    360
tgtggggttt acagattttc ttctttctct tcttgacaga tttgggtgtc ttgttcttcc    420
tagcctctct cttctcttct tttactttct tcttgagctc tttccttgct gctttcttgt    480
cttcangacc caactcctct tcactctcac ttccactttc ctcttcttcn nnntcacttt    540
cttcttctcc ttctccttttt tcttcctctt tccctcttc aacatcaacc tttactnnct    600
gctcatctac tttaggannn catccttann n                                   631
```

```
<210> SEQ ID NO 12
<211> LENGTH: 613
<212> TYPE: DNA
<213> ORGANISM: Brassica napus
<220> FEATURE:
<221> NAME/KEY: misc_feature
<222> LOCATION: (24)..(24)
<223> OTHER INFORMATION: n is a, g, c, or t
<220> FEATURE:
<221> NAME/KEY: misc_feature
<222> LOCATION: (28)..(28)
<223> OTHER INFORMATION: n is a, g, c, or t
<220> FEATURE:
<221> NAME/KEY: misc_feature
<222> LOCATION: (152)..(154)
<223> OTHER INFORMATION: n is a, g, c, or t
<220> FEATURE:
<221> NAME/KEY: misc_feature
<222> LOCATION: (162)..(164)
<223> OTHER INFORMATION: n is a, g, c, or t
<220> FEATURE:
<221> NAME/KEY: misc_feature
<222> LOCATION: (420)..(420)
<223> OTHER INFORMATION: n is a, g, c, or t
<220> FEATURE:
<221> NAME/KEY: misc_feature
<222> LOCATION: (467)..(468)
<223> OTHER INFORMATION: n is a, g, c, or t
<220> FEATURE:
<221> NAME/KEY: misc_feature
<222> LOCATION: (536)..(537)
<223> OTHER INFORMATION: n is a, g, c, or t
<220> FEATURE:
<221> NAME/KEY: misc_feature
<222> LOCATION: (544)..(545)
<223> OTHER INFORMATION: n is a, g, c, or t
<220> FEATURE:
<221> NAME/KEY: misc_feature
<222> LOCATION: (600)..(601)
<223> OTHER INFORMATION: n is a, g, c, or t

<400> SEQUENCE: 12
tttagaatca acacaagaca tagncaantt gattttggct actgggtatt aataatcccc    60
aaaatcacat ccttcaaacc gaacgaacaa tcaacaagaa aataagagct acgattcaga   120
aaaagcctat gatcaaaacg cctaaaataa cnnnaaaaaa annnggagca attttaaaca   180
aatggaattg aatagtatga gatgagatga gaaacaaaag agaaagcagt gtgcatagat   240
catcagggaa gctaacctga aatgatttgt tgattggggg atgagattgt tggaagggga   300
cagagagaag aagaaggttt gcttgaagac tcgaaaatta agcttgttaa aggaagaaga   360
agaggaagaa gaagaggata taaattgaca tggacctatt aaatgcccat tttgttctgn   420
```

```
ttatttactt aagattgcca ctatgacctt tgacttttgg acggcgnntg tagctaagct    480
actgtttctt cattaatcac gcttgccatg attagttttt tttttcctcc tatagnnttc    540
atanntagcc cgaaattact gacttttatg agataaagat cgtattttt tatttcttan    600 ngtttaatac cct                                                       613

<210> SEQ ID NO 13
<211> LENGTH: 669
<212> TYPE: DNA
<213> ORGANISM: Brassica napus
<220> FEATURE:
<221> NAME/KEY: misc_feature
<222> LOCATION: (404)..(406)
<223> OTHER INFORMATION: n is a, g, c, or t
<220> FEATURE:
<221> NAME/KEY: misc_feature
<222> LOCATION: (465)..(465)
<223> OTHER INFORMATION: n is a, g, c, or t
<220> FEATURE:
<221> NAME/KEY: misc_feature
<222> LOCATION: (524)..(526)
<223> OTHER INFORMATION: n is a, g, c, or t
<220> FEATURE:
<221> NAME/KEY: misc_feature
<222> LOCATION: (582)..(585)
<223> OTHER INFORMATION: n is a, g, c, or t
<220> FEATURE:
<221> NAME/KEY: misc_feature
<222> LOCATION: (633)..(637)
<223> OTHER INFORMATION: n is a, g, c, or t

<400> SEQUENCE: 13
ctacttccaa aagaaaacat taaattaatg tttatgtcga atgtcattta tactgaacaa     60
aataaccttg aaaatatgtt ctgtacgcta aagttgggag agagaaggag gttgaagaga    120
ttttgtcaag attgcgagga gaaaattctg atgtatcaga tgaagcagga gagatattag    180
taagcatata tatgcatgaa taatcatatg atcaatgtat atatttttta cttcataata    240
ttttgatgat catcacgcat atacagaaca tgttaaacaa caacgagatg atcgcggttt    300
cctcaagttg tttcagcgaa aatacacgtt ctcacttact gtaattcttc ttcttcttct    360 tcttttttctt cttcttcttc ttcttcttct tctttaataa cccnnntggt ttacacagat    420
tggagttgtt cttatagctt tgcctcaact tggaggtctt agtgngtatt ctttttacac    480
tgagtccatt tcatatcta caggtaaaat aattcttctt cttnnncaaa atattgattt    540
ttatatattt atttaccta acgataattg ttgataatta cnnnnatcac gtgtatcgag    600
tgatgttgga ttcatatcga catctatagt tcnnnnntta ccgatttcga gtgaccttgt    660
ttagagttc                                                            669

<210> SEQ ID NO 14
<211> LENGTH: 592
<212> TYPE: DNA
<213> ORGANISM: Brassica napus
<220> FEATURE:
<221> NAME/KEY: misc_feature
<222> LOCATION: (508)..(510)
<223> OTHER INFORMATION: n is a, g, c, or t
<220> FEATURE:
<221> NAME/KEY: misc_feature
<222> LOCATION: (537)..(539)
<223> OTHER INFORMATION: n is a, g, c, or t
<220> FEATURE:
<221> NAME/KEY: misc_feature
<222> LOCATION: (545)..(545)
<223> OTHER INFORMATION: n is a, g, c, or t
<220> FEATURE:
<221> NAME/KEY: misc_feature
```

```
<222> LOCATION: (547)..(547)
<223> OTHER INFORMATION: n is a, g, c, or t
<220> FEATURE:
<221> NAME/KEY: misc_feature
<222> LOCATION: (555)..(557)
<223> OTHER INFORMATION: n is a, g, c, or t

<400> SEQUENCE: 14
acaaacataa ttgcaattaa acggatagta agggtcacag atcacacaat actgcatcga      60
agttttgtca tcaacacaag tgcgcatcgt ttcattcttt tctttcttcc ggcttacctg     120
agcccggccg tggcacaatc ttcttcaaca gacagcgttt aaataaaact taacttggta     180
gggctgagga ttcaagaatc atttcttgta attcactggc acatcgtcgt catcttcttc     240
aagatcacta aacgttacat cttcatcctc atccacaaca tgtttggttg ctacggtgga     300
gctaacagtt cctgcattat cttcatcctt caaccaatca tcaacatcat catcatcatc     360
atcatcgact tgaacgtcaa taactctagg tgaagatcca gtgactggct tgtcatgggg     420
cgctggtgct ggttttcctt caatcacagg cttgtcaaca acttgtatct ccttgctctc     480
gattgggtgc ttctccgtct caacctcnnn tgtatcactc aaatgtattg tttccannna     540
gatgnanttg actgnnnctg gtgaagacac agtaagtggt tcctcattgg ca             592

<210> SEQ ID NO 15
<211> LENGTH: 639
<212> TYPE: DNA
<213> ORGANISM: Brassica napus
<220> FEATURE:
<221> NAME/KEY: misc_feature
<222> LOCATION: (580)..(580)
<223> OTHER INFORMATION: n is a, g, c, or t
<220> FEATURE:
<221> NAME/KEY: misc_feature
<222> LOCATION: (624)..(626)
<223> OTHER INFORMATION: n is a, g, c, or t

<400> SEQUENCE: 15
aatcatccta aatttaccta acccatggat tcaaaaggta actaactact cgctaataga      60
catgataaac ccaaaaccaa tagtgattga aggttaatca tgattagtga tcaagataat     120
ccaataaaca caagacaaag atgaaaagag ctaaagatt gaatctttca ccaaaatatg     180
ttcatgtcta gagaaaacaa gatagatcct aagaatctaa caatactaaa agcatgatag     240
taagccctct aagcgtgtcc acgtaagtta atatattcag ctaatcagag attactagct     300
atttgccat gtcataacaa ttttaagtcg accaatacaa aaaccgggca aggcgtctgg     360
gccattagta atatccagtg gccaatacga aacccatctc attaatatca aatctccaat     420
gaaagccatt atcgtggcga ctcttctttt tcatcatcat catcatcctc atcatcatca     480
tcatcatcat catcgcttgg gatcacaaca atttcctgtt agcacaaccc actctccatc     540
aatcaatcag ggtctttact actcttttca tgctttcgtn tcaactccct tgtttatcc     600
tcctatataa atcattgaat atcnnnattt tgatccaag                             639

<210> SEQ ID NO 16
<211> LENGTH: 656
<212> TYPE: DNA
<213> ORGANISM: Brassica napus
<220> FEATURE:
<221> NAME/KEY: misc_feature
<222> LOCATION: (369)..(370)
<223> OTHER INFORMATION: n is a, g, c, or t
<220> FEATURE:
<221> NAME/KEY: misc_feature
<222> LOCATION: (578)..(578)
```

```
<223> OTHER INFORMATION: n is a, g, c, or t
<220> FEATURE:
<221> NAME/KEY: misc_feature
<222> LOCATION: (589)..(591)
<223> OTHER INFORMATION: n is a, g, c, or t
<220> FEATURE:
<221> NAME/KEY: misc_feature
<222> LOCATION: (612)..(613)
<223> OTHER INFORMATION: n is a, g, c, or t
<220> FEATURE:
<221> NAME/KEY: misc_feature
<222> LOCATION: (630)..(632)
<223> OTHER INFORMATION: n is a, g, c, or t
<220> FEATURE:
<221> NAME/KEY: misc_feature
<222> LOCATION: (652)..(652)
<223> OTHER INFORMATION: n is a, g, c, or t

<400> SEQUENCE: 16
tagtctcacc aactccaaac ttgttaacat ctgaaggagt ctgaatattc tcctcctcat    60
catcatcatc atcatcatca tcatcatcat cacaatcaac aacttcaacc ttcttcttat   120
tgttatcatc atcctttact aatttctcct catcacaatc aataacttca atgactgaat   180
cttgagaaac tgcttcttct tcttcttcct ccaaatcgat aaactcttta tctttggtaa   240
ggaacctgaa ggcattcaaa gccgatctct tggcgttatc atactcgcga gtgaaaagct   300
cccccttctc gcagcaatcg ttaggcttag ccgtgggtga tcctccgtat ataaggttcg   360
ctctgctann agcgtggatt gctcgtctaa gtggagtttt ggcgtcggga tacctcgaaa   420
tcctcgaaga tggcttgttg ggatcctgag acatggttcc gaaggagaat ctgcgtttct   480
tcggagcttg gaagtagggc gaatgtcagc ggaattgggc ggtggaaggg tggttggagt   540
ataaggaatc ttcgctgcgc ttgcgattga tggcgacngc gctcatttnn ngagtcgatc   600
actgaacccc anngattggg agatcgacgn nnggagagga accataagag tngaga        656

<210> SEQ ID NO 17
<211> LENGTH: 711
<212> TYPE: DNA
<213> ORGANISM: Brassica napus
<220> FEATURE:
<221> NAME/KEY: misc_feature
<222> LOCATION: (641)..(643)
<223> OTHER INFORMATION: n is a, g, c, or t
<220> FEATURE:
<221> NAME/KEY: misc_feature
<222> LOCATION: (698)..(700)
<223> OTHER INFORMATION: n is a, g, c, or t

<400> SEQUENCE: 17
ttgccaaaac atttaaccag gtgagcactt aaactcttgt ctggcccaaa aaaaaaagag    60
tgagactgta tagaggatca agccaacagt agatgaggaa gaggaaggcc atgtaatctc   120
taatccacaa cgatcttgat tacccatata ggtccattga ctttgaatct taatttcaga   180
acatcaacaa atcttcatct ttactaaaat tacaaaaaat cttttaactt tttaattttt   240
gaaaaaaata catatacaca catacagcta gtctcttacg aaacactaca caactagata   300
actccaaaca tttacaactg aaagtttatc agcttggaaa atcatcactc agatttcttg   360
tggaacttca cggagtctat caagtgtatt aacaatctca ctcagacaag cgatgagctc   420
gtctccttgc tgtctcacaa actttaactt gtcctcaatg ccaacatcat cctctgtttc   480
acttccattt gctagatttc tcccgactat tgcatgtatc atgtcagctt tctcacctag   540 cttttgcttcc aacgctttaa cctcttcttc tatgctcatc gtttcttcct cttcttcttc   600
ttcttcttct tcttcttctt cttcttcttc ttctacatca nnngaaattt ctaccaccgg   660
```

```
cttcttcttc acttccatgg ttttattctt ctgatggnnn gcttttgcac g          711
```

```
<210> SEQ ID NO 18
<211> LENGTH: 692
<212> TYPE: DNA
<213> ORGANISM: Brassica napus
<220> FEATURE:
<221> NAME/KEY: misc_feature
<222> LOCATION: (12)..(12)
<223> OTHER INFORMATION: n is a, g, c, or t
<220> FEATURE:
<221> NAME/KEY: misc_feature
<222> LOCATION: (38)..(38)
<223> OTHER INFORMATION: n is a, g, c, or t
<220> FEATURE:
<221> NAME/KEY: misc_feature
<222> LOCATION: (476)..(478)
<223> OTHER INFORMATION: n is a, g, c, or t
<220> FEATURE:
<221> NAME/KEY: misc_feature
<222> LOCATION: (691)..(692)
<223> OTHER INFORMATION: n is a, g, c, or t

<400> SEQUENCE: 18
ctcttgctta gntctggact aacccatatc cgaaaagntt cgaggaccga ctcgaaaacc    60
caacccgaag atctgcacgc ctaggcctag tttacaagca agcctaccaa aatatgtcaa   120
ctcgttaaaa gccttttaac ctgtctggtt cggtgcacgg ttcaattccc ggtttagttg   180
taaccggttt gtgattgctc aaaaccctag tcgtcaccct tttttatcat tattgtgaac   240
aagtagtcac ctctacaagt aaaaccttaa accctattga gcgagtagca gagcgcagca   300
agaagaaaca aaaccaaaat atgagaccac cacgtggcgg cggaagcttc agaggaagag   360
gaggaagaga tggcagcgga cgcggaggtg gcggacgttt taatcgtgga ggtggccgct   420
ttggtggtgg tggtggtggt ggctggcgtg acgaaggacc tcccgaccaa gtcgtnnntt   480
cgttttctct cctctcttgg ttttcgctct cactttacag ctcaagcaga agtctttatt   540
aacaaaagtt gtcacctttg acaaattagt cttatccctt tgttagagtc atctttaagt   600
taaaggtata aactttgtga agttattcgt tatgacaaag tttctttctt tcgttgggtt   660
ataacagaag ttgcaacgtt tgttcatgct nn                                 692
```

```
<210> SEQ ID NO 19
<211> LENGTH: 439
<212> TYPE: DNA
<213> ORGANISM: Brassica napus

<400> SEQUENCE: 19
ttttgaagga ggttgcttgg gtgattttttg atgagattca ttacatgaag gatagggaga   60
gaggggttgt ttgggaggag agtattattt tcttgccgcc tgctattaag atggttttttc  120 tttcggccac gatgtctaat gctactgagt ttgcggagtg gatttgctat ctgcataagc  180
agccgtgtca cgtggtgtat acggacttta ggcccacgcc tctgcagcat tatgcttttc  240
ctatgggtgg gagtgggctg taccttgtag ttgatgagaa tgagcagttt agagaggcta  300
atttcattaa gatgcatgat actttcccaa aaccaaaatc tgagggaaa aagagtgcaa   360 atggcaaatc aggtggtagg ggcggcgcta aaggtggtgg cggcggcggt ggtgattctg  420
atgtttacaa aattgtaaa                                                439
```

```
<210> SEQ ID NO 20
<211> LENGTH: 703
<212> TYPE: DNA
```

```
<213> ORGANISM: Brassica napus
<220> FEATURE:
<221> NAME/KEY: misc_feature
<222> LOCATION: (673)..(675)
<223> OTHER INFORMATION: n is a, g, c, or t
<220> FEATURE:
<221> NAME/KEY: misc_feature
<222> LOCATION: (703)..(703)
<223> OTHER INFORMATION: n is a, g, c, or t

<400> SEQUENCE: 20
taaaaaatac cttaaatata taaaaaatct atctttgtcg aacaagtaaa aaatttaaaa    60
catcttactt ttggaaacga gggaatatga tattttggaa tgaatcaaaa ttgacaatca   120
ccttgtatag aacccatagg ttcgtggatt cgcggtcctc accactaata ggttggacct   180
ggttaagaat ccttgcacac agaaataaac ttaaccattg ccgccttaca ttgtattcca   240
aatttgttaa ttaccggcca acaacacaat tatgttatct ccattattac aaccacccgc   300
cgcaataatt atctcaatca gttttgtttt gttttattt atattcaaac ggaatatcgt   360
tatttaatta ttagagcttt aaataatcta tataaagtcc atacaatttt tgtttatgga   420
aatagacact acaaacgcgt attttcagtt ttttttcat atggagagaa ctaccaatca   480
gttgaaagaa aaaagagaac taccaatcta ccatataata taaaaacaat aatagtatta   540
aaaaaaggag agggcaacgg aacgggacgg aagagaatgg aaatggttac gtttataata   600
gcaatgatct gttgaacagc ttatgacacc tcactctgcg cttgcttcca ttcctcatct   660
ctctctctct ctnnnaactc tctacgaaac cctaccttct tcn                    703

<210> SEQ ID NO 21
<211> LENGTH: 617
<212> TYPE: DNA
<213> ORGANISM: Brassica napus

<400> SEQUENCE: 21
tacaagacag acggacataa taagaagaaa tgcaaataga caagtcctga gagagagtat    60
ccaaaataga gattttaaaa tctgtcacta acttttaggc atagcttgtt tagttcgctt   120
agtccctcct ttcttcacaa aaccaaaacc aaaaaaaaaa agatgagaga gagcagtttg   180
ttgataaaga agcaaatgaa atgtaactta cttttctacc ggcggtggtg gttgctggtg   240
gagttgctgc tgcaattgag taacgtcaca acaaaaagga agatggaaat gaaaaaaagg   300
aggattcaat ggatatcaac aaaaacgtgt tagaaagact caccactctg ttgagcttca   360
ccaccttggc tgcctcctct tctcgtcggg gtctacacat ttcaatagat tcgtcaacaa   420
cagtaacgag attgcgtcga aacctaactc agaaaaaaaa agagatgacg taccgcactc   480
ggacctgccg ccgccgccgc cgaagatgaa gcagtcgcat ctacaaattt cagatgccaa   540
attagggttt aacctagaaa ataaaaatat caataaggca aagagagaga gagagagtac   600
tagttggatt gcgatct                                                  617

<210> SEQ ID NO 22
<211> LENGTH: 619
<212> TYPE: DNA
<213> ORGANISM: Brassica napus

<400> SEQUENCE: 22
gtcttctcac ggccgtacgg ataacgccgt gaaaaaccac tggaactcga cgctcaagag    60
gaaatgctta ggcggcggtg gagatggtaa tctcattgtg atgaggacgg aggaggagga   120
ggatcaggat cggcggaaga agaggagatc ggtgagctct gagtctgcta ctccggtgga   180
```

```
cactgggttg tacatgagcc cggagagtcc caccggaatc ccatctccgc cgtctccggt    240
tgatgctcag cttttaaaac caatggcgat gccgtcaccg gtggaaatgt cttcggtgga    300
ggaggatccg acagcgtcat tgagcctgtc actgtcactt cctggtcctg atgtcagaca    360
ggagttgaag aacgcgggtt cgaaacacaa ctcgttgctg tttccccggt ttgggagtca    420
aatgaaaatt aatgttgagg agagaggaga agcacgtgtt ggacataaag ctgagttttt    480
gacggtggtg caagagatga ttaaggtgga agtgaggagt tatatggcgg agatgcaaaa    540
aaatagcggt ggtggcggtg gtgaattcat cgtcagtggt ttttatgatg ccggcaacgg    600
cggtttcagg gatagtggg                                                619

<210> SEQ ID NO 23
<211> LENGTH: 430
<212> TYPE: DNA
<213> ORGANISM: Brassica napus

<400> SEQUENCE: 23
aaaaggaaag tttaagactt taagctttac ctgatgatcc atatcgggga aaatcgcggc     60
gaggtgatcg aggagaagcg aggaggaggc aggaggagga ggagggggaa aacgcggcgg    120
agaagaggat gagaagtaac ggagtttctt ggagacggga ggggaagaag cggcggacaa    180
atcctcgaac agagatctct tgctaccgca acaatcgca gacatgttat ctgcttccac     240 cttcttttc ttcttctttc ttccttcctt cagatctcaa cctttccttt tgtttggtt     300 ttttttttc ctttttcctc taatccatct ctgatctgtt tctgtcggaa accaagcaaa    360
aaaaagtcaa aacacatcgg atcttcttcc gcatctaaat agatccaaca acccggactc    420
ggattcaaat                                                          430

<210> SEQ ID NO 24
<211> LENGTH: 592
<212> TYPE: DNA
<213> ORGANISM: Brassica napus

<400> SEQUENCE: 24
aaaagacgtt gacttgattt gatatgccat agagctaaac cctaattgaa tttcaatcaa     60
ttaggggtaa agatctctca atctacgaac aaaagatcta atatttacag tcaaaatcta    120
cggaaaacac aaagaaaagg cttacggcga ctgggctgcg aggagcgcga ttctgattac    180
ggatcggcat cttccgattc tggatccgag ctaggcgata cgaaagatga tttcttccgg    240
aaacctccga ttgagtaaca agaatctcga cagaagttgt ttcttctcag ttagagagaa    300
gagattaggc ttcggcccctt tttgtgattt tgagaaggat gagagagaga gagagtggag    360
gaggaaggag gaggaggagg aggaggagcc tttgttattt tgaaagtttg aaaatagatc    420
ttgagaataa ttgtaacgtt actcttggtc ctctatatgc ttatttattt attccactaa    480
tactttataa ggtatatggg ctttatatgg actataatct cggcccatct atgttaaact    540
aatccgtaat tttcttggtt tttttaaaac ttgcgcgctc cttaatttga at            592

<210> SEQ ID NO 25
<211> LENGTH: 669
<212> TYPE: DNA
<213> ORGANISM: Brassica napus

<400> SEQUENCE: 25 acttttata accgacactt aaatcaaaac ttgaaaaata gcatcaatta gatttgtaac     60
```

| | | |
|---|---|---|
| ggagtatcat caatcatcaa gaaacaacaa tcttgtaggt gagtaaataa aagataccgt | 120 | |
| gaataatgtc aacaatcgta atctcatacc actaatacgt aattaaagaa ataatcata | 180 | |
| taattaggga gataatgttg ggaatcttaa tcgtataatc agaagcgtat tcatttcatt | 240 | |
| acaaattgat tctcttgtca tttgttatat aataataata aaaaaaacgt taaatcaatt | 300 | |
| caaactaaac cttctctctc tctctctctc tttctatttc gctcatcatc attttatctg | 360 | |
| atgaatacgc ccaattgaaa tcctttcctt atcaactcaa attgagtttt caaaattatt | 420 | |
| caattttcgg atctccgtag atttgctcgg cggaggagga ggaaggatgg ctcagttggc | 480 | |
| ggcggcggcg ggaggagaa taggggatta cgcggtggga agacaaatcg ggtcgggttc | 540 | |
| gttttcggtg gtgtgggaag ggaggcatct gggagatgga aacgtggttg taatcaagga | 600 | |
| gatagccatg gcgaggctta gtaagaagtt gcaagatagt ctcatgtccg agattatcat | 660 | |
| cttgaggaa | 669 | |

<210> SEQ ID NO 26
<211> LENGTH: 695
<212> TYPE: DNA
<213> ORGANISM: Brassica napus
<220> FEATURE:
<221> NAME/KEY: misc_feature
<222> LOCATION: (629)..(629)
<223> OTHER INFORMATION: n is a, g, c, or t
<220> FEATURE:
<221> NAME/KEY: misc_feature
<222> LOCATION: (631)..(633)
<223> OTHER INFORMATION: n is a, g, c, or t

<400> SEQUENCE: 26

| | | |
|---|---|---|
| acccaaacga attgctctgt ccgtagaaag aacaggctcg ggagctgagt ggtggtggtg | 60 | |
| gtggtggaga agcgacggtg gaccatccgg gaacgagtgc agcgagagac ggagatcttg | 120 | |
| actcggagga gcttccgtcg aggagccaac caccgggaaa aacgactccg aatccatcga | 180 | |
| cggcggaaga aaactcggaa gctccgccac tccgtcgaat ccaccggacc gtgcaccacc | 240 | |
| gaactgaagc tgttcccgct gcggcggcgg cggcgacgga gatattttag ttttggcggc | 300 | |
| ggttcttctc ggtttagcgt ttgcggcggc gttgcgaaca cgtcggcgg gactccacgg | 360 | |
| aggaagctga gcgagctcgt cgatggaagt ctgagccttt ctgatcagcc agtcaacggc | 420 | |
| tttgctcggt cggtcgaagc caaggcggtc ttgaacgtcg tagaactgaa tcgccgtgtg | 480 | |
| agccgatagc ctcacgcgcc ggtcacgtgg ccctttggcc gtgcagactt tgctgtgccg | 540 | |
| gtcttttctc cccgtcgacc gcacaatgtg acctccttgc acctccacta tctcgtctga | 600 | |
| cgcagcgcgg tgcctcattg aagaaggcng nnngggttga ggggtggagg aagtggtgag | 660 | |
| cttcgtcgtg gtcgtctgcc attggttgag catac | 695 | |

<210> SEQ ID NO 27
<211> LENGTH: 708
<212> TYPE: DNA
<213> ORGANISM: Brassica napus
<220> FEATURE:
<221> NAME/KEY: misc_feature
<222> LOCATION: (696)..(698)
<223> OTHER INFORMATION: n is a, g, c, or t

<400> SEQUENCE: 27

| | | |
|---|---|---|
| acaactttga agtgtgaata gagtaaaaga ttcaatcttt catatcaaaa gactaaccta | 60 | |
| gactcgaact cacggatctc agcaagttct ttccccatca aatccaccca ctgcaccttc | 120 | |
| ttcttcttct cccttctctc accatcctct gaatctaaag tttcctttt tagactactc | 180 | |

```
ttcaggatct ctccattact ttgaccttcc tctaaggcac aatcttcttc ctttccctct    240
tcttctgttc cctcattcac caaactatca acgtgatcaa caacttcctc tacttgtgca    300
tcaacatact gatcatcatc atcaccgtca tcaacaaccg aagagacttg aggaggagga    360
ggaggaggag gaggaggagt gtcctccaat ttcagagaac cagatgcgta gatgtgagga    420
gaaggcttac agaagcagat gaaagaaggg cactggatct tacaaagcaa aaccctcatc    480
aaaacatatg ttccaatcat caaccaattc aacaagatct cttttgtctt tggcaaagtt    540
agaaactttg tgtgcccatt gatatgccca gattgagaaa aggaaacact tttgatttct    600
gaataaaaag tagaaacaga gcagcaaaga agttagtata tatctctcgt cttggataga    660
atccaaagac cataaataac gagttgatca gatgannnag cagacaaa             708

<210> SEQ ID NO 28
<211> LENGTH: 453
<212> TYPE: DNA
<213> ORGANISM: Brassica napus

<400> SEQUENCE: 28
actggtctca atggaggtgg tggaggagga ggaggaagaa tacgactgga atctctttta     60
gaccttgtag agagttaaaa gatagtttta agaaacaaat gtcaatctct caaaatagga    120
atactatact ctttacctgt gagatagctg agcaaaatca tcatctgatt catcgtcatc    180
atcatgattg atgctgacaa gttgagctgg aggaggagga ggaggaggag ctgttgcacc    240
gcctccattt gaaggaacag aggcgatatc gtcatgacgc tgaagaacac gctgcaagtt    300
atcgttcaat gctaatccct ggcacagaag ctcctcgtct ctgaagaaaa gaaacatcat    360
caaaagggga tgaaacatca ggtgatgaag caagaagaag aagaaaactc acgtggtggt    420
gttgacaaga gtcatcacac gtttctgata ggt                                453

<210> SEQ ID NO 29
<211> LENGTH: 705
<212> TYPE: DNA
<213> ORGANISM: Brassica napus

<400> SEQUENCE: 29
cgaggaagca taggaggagg aggaggaagc agtttgagtg tttggaggag atgcctgagg     60
agagagagga agggagggag tcggacgaag gcgtgtgttt ttgcacgtgc agcggaggag    120
aatccggatc cgaagacgga gagggagagt gggagtcggt ggaatggacg gctgagatgg    180
aggcggaggc tgagggaatg ggatgggccg ttgatttggg gatttggatt atgtgtttag    240
gtgtgggcta cttggtgtcc aaagcctcaa ctaaaacctt gagaggtgga ggaaggagaa    300
gaagatcaaa aagtttcttt tagagttctc tgtaatcagt cagtctagtt gttcaataac    360
gttctaatgt aatagtacag atcaataaac cataaatgta aaacaatcca tgattttgaa    420
taccaagagt cgcacgagtt ccattttatt tgagagcata gaacaataaa ctttctcctc    480
tgacctgatg aactaaggca agttcatgca agaatctaat gaatgcaagc aatcaagtac    540
gtcaaatcat attgcattta caaattatac aaatacacaa aggatccaaa aagtgccttc    600 tccctttct tactaacaat aataataatg cagcaaaaag aataaaagt ttatcaaaaa     660 cgtgtgatga taattcaatg taaataagca aatatgtgga gagct                   705

<210> SEQ ID NO 30
<211> LENGTH: 502
<212> TYPE: DNA
```

<213> ORGANISM: Brassica napus

<400> SEQUENCE: 30

| | | | | | |
|---|---|---|---|---|---|
| gtagccttgt | gtgagttgga | accagacttt | cctgtttccc | tgccttgtct | caaggttatg | 60 |
| catttagaga | gagttatagc | taaccttgag | aggcttataa | ctagctgccc | tgttcttgaa | 120 |
| aagttaacca | taatcaggga | ttcttttgaa | gttctcgaaa | ttatgtgtgt | gcgctccaag | 180 |
| tctttaaaaa | gtttggctct | actgattgaa | gcttctgata | ctgatctctt | agaagatcac | 240 |
| gatttggaga | tcgatgcccc | aaagcttgag | cgtatgagtc | tctgtgatca | cttatccaga | 300 |
| agcatcgtta | tacacagtat | tgctccctct | gcagtggtac | agatcgatgt | taactttaat | 360 |
| agggagggtg | gtgatacatt | attggaccaa | gatgatgatg | atgatgatga | tgatgattcc | 420 |
| aagagaacta | tgatccgtaa | tttcctaacc | gggatatcca | cagtcagcct | catgaagatc | 480 |
| tcctctgata | ctctacaggt | ac | | | | 502 |

<210> SEQ ID NO 31
<211> LENGTH: 468
<212> TYPE: DNA
<213> ORGANISM: Brassica napus

<400> SEQUENCE: 31

| | | | | | |
|---|---|---|---|---|---|
| gtaatcattt | ctttgttatc | tctctttcca | tgatcgtccg | tccaagagat | atgtaattgg | 60 |
| cgttgtttga | ttctgcaatc | cgtacaatcc | atttctagct | gttaatctga | atatagccat | 120 |
| cttattagac | tgaaatctaa | gcgcctggat | ggggtggttt | tatttcatt | ttgacttttg | 180 |
| gcgtttggtt | ttcagatctt | taagatatga | tgatgatgat | gatgatgatg | atgaaaatga | 240 |
| tgagatttag | attttactga | ccacccttt | ttttttttg | tctttacgtt | tctttcagct | 300 |
| caattcagag | aagagcccctt | ttcaacgtac | ttatgcagct | caggtaaatt | tcatgtttat | 360 |
| ctgacacttg | tctagtaatg | tgtgatacaa | tctaagaatg | taaatcttac | aattgtgata | 420 |
| aaaatattct | ctctcgtgtt | tagataaaaa | gatgtggaga | gatggcac | | 468 |

<210> SEQ ID NO 32
<211> LENGTH: 738
<212> TYPE: DNA
<213> ORGANISM: Brassica napus

<400> SEQUENCE: 32

| | | | | | |
|---|---|---|---|---|---|
| gtgcgggttc | gagcagctct | cagcgctcgc | ggagggaggc | atgaacgtgg | ccaggctcaa | 60 |
| catgtgccac | ggcactcgcg | actggcaccg | tgacgtcatc | cgcagcgtca | ggaggctcaa | 120 |
| tgaggagaaa | ggattcgcgg | tcgcgatcat | gatggatacc | gaaggtagcg | agattcacat | 180 |
| gggagatctc | ggcggcgagg | cctcggctaa | agcagaggtt | ccttcctctt | cttgaaatct | 240 |
| tgatgatgat | gatgatgatg | atgatgcatg | ttgttaatca | gattattgga | tataatccgg | 300 |
| tttagttaga | gaccggttta | gttagattaa | ttatggttaa | gttctttttt | gcttaatcat | 360 |
| gtatataaag | aaatgttaac | acagatgagg | tttttgtagg | atggtgaggt | ttggacgttt | 420 |
| accgttagag | cttttgattc | gtctcgtcct | caacgtacca | ttagtgtgag | ttatgatggt | 480 |
| ttcgctgaag | gtaatgtgtc | tttttttttt | gtgttatgaa | agcatcaagt | ggatgtgagt | 540 |
| atgagatggg | gatcgatttt | tttttttttt | ttgtgatttc | agatgtaaga | gttggtgatg | 600 |
| agcttcttgt | tgatggtgga | atggttagat | ttgatgtgat | tgagaagatt | ggttccgatg | 660 |
| tgaagtgtct | gtgtactgac | cctgggctgt | tgcttcctcg | agctaacttg | actttctgga | 720 |
| gagatgggag | tcttgtac | | | | | 738 |

<210> SEQ ID NO 33
<211> LENGTH: 636
<212> TYPE: DNA
<213> ORGANISM: Brassica napus

<400> SEQUENCE: 33

| | |
|---|---|
| gtaacatata caaatacttc taggaatcaa tcgaaatata tatttcatat cgcaatttca | 60 |
| caatactgtt gaacttacaa acgtgtataa ttacaccatt ttttacaca aaatctttaa | 120 |
| catgtcgatt tcttatacca tttgtaatta actcaacata tttttttaac taaatcagcc | 180 |
| tcgccaattt gtgttggttt acggaaccgg tacaaatatt gttggcctgg ccgttattaa | 240 |
| tttcaaatga ttgattcata ggtaacatga aagtttgga gagcttacta acgaaagcag | 300 |
| gagcggagac attgccattg gcagagcaac aagtacgcc ttgaatattg atgagaccta | 360 |
| aaatgcctcc aaggacacca ccaccaccaa gaatcccacc aaggccacca ttaccaagaa | 420 |
| gccccctac taggccacca ttaccaagaa ggccacctag gccaccacca ccaagaaggc | 480 |
| cacctaggcc accaccacca ccaccaccac caccaccacc aagaaggcca cctagacccc | 540 |
| caagctgagc cttaaccatt ggagacacca tcacgagaca cacgaagatc agtgagaagg | 600 |
| ttatgcgttt gttctcaagc attgtcatgt tcttgg | 636 |

<210> SEQ ID NO 34
<211> LENGTH: 1174
<212> TYPE: DNA
<213> ORGANISM: Brassica napus

<400> SEQUENCE: 34

| | |
|---|---|
| gtatctatct cctcttgcct aaatcacacc atgactgact ttcccaaaat aacctagaga | 60 |
| tccagaaaga acggaggaaa gaaagaaaaa atggaggaga cgaagccatt ggtagggaac | 120 |
| catccccagc aacagcagca gcaacaacaa caacaacaac agcagctcct gtatcaacac | 180 |
| caattacaac agagacagca acagatgctt ctattacagc agttgcagaa acagcaacaa | 240 |
| caacaagccg ccatgtctag gttcccctcc aacatcgacg ttcatctccg acctccaggg | 300 |
| tcaatccaga cccgaccaat tgttcccct cagcagcaga ccctaatcc caaccctagc | 360 |
| ttgggacagc ctacaccgaa tcttcagcag cagcagcagc agcagcaaca gcaggttgta | 420 |
| gcgagtcagc agatgctgca gcagcagcaa caacagcagc agcagaagtt gatgcgtcct | 480 |
| ttgaatcaca tcgagcttca attcgcttat caggacgctt ggcgtgtctg ccaccctgat | 540 |
| ttcaagcgac ctttctcttc tctcgaagac gcttgcgaaa ggttcagttc taattttat | 600 |
| ctaattacat ttgtcttttt gagatatttc cttaaataaa atcggttata gacaatctca | 660 |
| tccgttcaat cttatttcag gctatcgtgt gatatatgca tacgggtctt gtgatctttg | 720 |
| aaatgaaaca ttgatctgtt aatgacttac ttactggtca tatctgcaac ttgtatgttc | 780 |
| ttctttagtt cgtgtttggt attatggtga tgatatctgt tagccttttc gttaatttct | 840 |
| atacttcttt tcattgatat tgtttgtgtt agatccaata gatcctgctt cttttggtgt | 900 |
| tcgtgcgaaa cttaaatctc tttctgagtt tagtgtggtt gatttatat tatttttgtc | 960 |
| atctaatgtg gttgatttag aattacaaaa ctttgtgatt gtttcctatt ttagtataac | 1020 |
| cacctgattc actgatactg ataattattc cctgactttt atatttatgc taaaagttta | 1080 |
| caactttaca ttagcatatt attggtttta ttagatacat tgttgccctt gattgaacat | 1140 |
| ttctgtatat tgtttgttt atcttacctc atac | 1174 |

<210> SEQ ID NO 35
<211> LENGTH: 951
<212> TYPE: DNA
<213> ORGANISM: Brassica napus

<400> SEQUENCE: 35

| | | | | | |
|---|---|---|---|---|---|
| ctagtggcta | caaatccaac | tgtcggttct | cacttgggag | acccaggttt | ggatctatca | 60 |
| agtttaaaaa | tccaaactca | gcacagcctt | tcatttctga | acaagaaaa | gagatggaag | 120 |
| aagaagatca | agaagccaaa | agcatcggtt | tcagggagga | agaagaagaa | gaagaagatt | 180 |
| atgatgatgg | agctaagggt | attgatctag | aaggagaaga | gaagaagcat | atatgctgtg | 240 |
| aatgtggcaa | acgtttcaag | tcaggcaagg | cgttaggtgg | ccataaaagg | atccatgtgc | 300 |
| tcgaaactcg | caaattctca | atggtgagac | cgaagatggt | ggtgacgtct | ggtgcggttg | 360 |
| cggttgcggt | tggtagatct | gatgagcaga | gagatgattt | cgaagttgat | tgctgtgttt | 420 |
| gtcataagaa | gtttacatcg | atgaaggctt | tgtctggaca | catgaggttt | catccagaca | 480 |
| gaggatggaa | aggtgttttg | cctcctcatc | atccacttga | tgatcatcat | ggtggggagt | 540 |
| ttataagctc | cgattacgat | gatgatgctg | attatgatta | tcatgaggat | gatgattatg | 600 |
| agaactcgga | gttatgggat | attaatcgtt | gggaattgga | caacgtggtt | gaccttaagg | 660 |
| actcgatcaa | agaaggatgg | acggtgacag | gaaagagagg | aaggagaagt | gctttgaaga | 720 |
| ttgatgaacc | tgatgatatt | gatgctaagg | atctattgtt | cttagctact | acagcagaat | 780 |
| ctgtcgatgc | tgcagagact | tgttgtgatt | cgcttttggg | ggaagagatg | atgatgaaga | 840 |
| agaggaaaaa | gaagaagaaa | agattgtctg | agatggagaa | agagtcatca | tctagtcatg | 900 |
| gtcatcatca | gcttgaggtt | ggtgatgctg | ctgagggagg | tggcggtgca | c | 951 |

<210> SEQ ID NO 36
<211> LENGTH: 1009
<212> TYPE: DNA
<213> ORGANISM: Brassica napus

<400> SEQUENCE: 36

| | | | | | |
|---|---|---|---|---|---|
| gtatatgtct | ttggttattt | tttttggtat | ccaaataacc | gtaaataaaa | attaaaaatg | 60 |
| gcccgttttc | cctcggataa | aaaaattgta | gagtttaaat | catgtctttt | aaaaccatgg | 120 |
| gagcaaaatc | aaaggaagag | agaagataaa | ttaaatggtg | gctgttcagt | tgtttagctg | 180 |
| gaagacattg | attcttctac | cttcacaagc | ttcaagacat | aagggtttca | cttcttttaa | 240 |
| caggttttta | atctgtcttc | ttcttcttct | tcttcttctt | cttcttcttc | ttcttcttct | 300 |
| tcttcttctt | cttcttcttc | ttcttcttct | tattattatt | attattataa | tagtttcaag | 360 |
| tttctgaaaa | acaattgatt | ccatggtggt | gcatgtgttt | tacaagatat | ctcactgaaa | 420 |
| attaactttg | ttgcagaaca | ttgagtttgc | actctctgcc | ttcaaatggg | attgattctt | 480 |
| ttagatcccg | aggtgaggag | gctctgaaac | acattccacg | tcttaatgtc | cttcctctca | 540 |
| acaaagactc | atactttcat | actatcatat | tttcataatt | tcattattac | aggaaccttc | 600 |
| agagtcaaat | ctcaaaagac | aggagacaca | gagtcatcta | cttccaactt | gaatcaacct | 660 |
| aatgatttaa | aatccaaatt | ccataaggtg | cgtgtgtgtc | atgcatgtct | ttactttttt | 720 |
| tatctaatga | tttacttaat | gctttatgtt | ataatctttc | ttaatataca | tatctgcaga | 780 |
| gtctccaata | taaacttgta | ctaggatgca | tcccactgta | tgcggtatcg | agaattgtac | 840 |
| aaaagatcat | tcatgggctt | ccactccaca | ttcagaactc | agtaggggct | ggcttgcctt | 900 |
| ttgcttgtgc | atcagactct | ctgaataaac | catctttaag | tggtatcaaa | tggagtcttg | 960 |

```
caaggttctt tttcctgttc aatattcggc tcgagaagaa cgttgctac       1009
```

<210> SEQ ID NO 37
<211> LENGTH: 1124
<212> TYPE: DNA
<213> ORGANISM: Brassica napus

<400> SEQUENCE: 37

```
ctgttccgtt taactatgct cgcacctcca ttatctctcc tctttcataa ctctctctcc     60
tccttctttc ttctccacat ctctccgatt tcatcgctag aattctccac cgattcttaa    120
ggtatgtttt atcttcactt caactcttgt cggaattcac tctccttgcc tgtctgaaac    180
tttccatttg cagatctgta aaactttcta tttgtgtttc ctcctttccg tagatcgaga    240
agaaacgatg acttcaacgg agggagggat acgatccctc ttgtctctcc tcctcctcct    300
cctccttctc ttatccataa ccactctaat ctcagccgct gactacacac ccaccgacaa    360
aatcctctta aactgcggcg gctcctccga cctaaccgac acagataaca gaacatggat    420
ccccgatgtc aaatccaagt tcctgtcttc ctccggagac tccaaaacat cccccgccgc    480
aacacaagac ccctccgtcc ccaccgtccc ttacatgtcc gccagaatct tcagatctcc    540
cttcacttac tccttcccgg tcgcctcagg tattggttca atcctggttt agtaattgta    600
ctttggttta ctcatttccg gtttactaaa cacttttccc tatcacaggt cgcaagttcg    660
tgcgtctcta cttctacccc aactcctacg acagcctcaa cgcaaccaac tccctcttct    720
ccctctcctc aggaccctac actcttctca aaaacttcag cgccgctcaa acctcccagg    780
cgttgaacta cgctcacatc atcaaagagt tcgtagtcaa cgtcgaaggt gggaccttaa    840
acataacctt cacaccagag tcaacgcctt ctaacgccta cgccttcgtc aacggtatcg    900
aagtaacttc gatgcctgat atctacagta gcgccgacgg gacgttgacc gttgtaggga    960
cttctagtgg cgtcacgatc gataacacca ccgctctcga gaatgtctac aggctcaacg   1020
tcggcgggaa cgacatctct ccttctgctg acaccggttt gtttaggtct tggtacgatg   1080
atcaggatta catcttcgcc gcgagtctcg gtatccccga gaca                    1124
```

<210> SEQ ID NO 38
<211> LENGTH: 1268
<212> TYPE: DNA
<213> ORGANISM: Brassica napus

<400> SEQUENCE: 38

```
ggtctgagat atatcctcga gggttgtcct aaactagaga agcttggat caggggacagt     60
cccctttggtg atgttggact gcgctctggg atgcataggt ataacgacat gaggtttgtt   120
tggatgtcgt catgtcggtt atcccgggga gcctgcaggg acattgctca tactctgcct   180
agtgtggtgg tggaggcgtt tgggtcagat gatgatgatg atgatgatga cgaagacgac   240
aatgcagatt atgtggagac gttgtacatg tatcggtccc ttgatggccc aaggaaggat   300
gctccaaagt ttgtaacaat tttatgaaga caagcttaga gaaagcagga gctgaagtag   360
aagagaatgt gtgtttgtat gattgtttgt accatttgat ttgattggct ccctctgtt    420
tttggatttg tcttgtacca agaaagagtg aagagtcagt gaagaaagag gttgtttgtg   480
gaagtcaaag aatgaaactt ttattatttg tgtgtaatca agaatatgat tttacagcca   540
tttcacgatt atttttgtct acaagaagta ttggttatac attacattat aagatcttca   600
ccaatcttga cttcgtcctc catcagcaga tgctctaagg tgtcgatgaa agcagtaact   660
```

| | |
|---|---|
| ttctccaagc tcttctcatc aagccttggg accgtgtggc ccttgggatg atggaccacc | 720 |
| accggattct tgaaggaatc tatcagctca gttccgtaag gtttcaaaaa atcagtctct | 780 |
| cctgcaaaga aaaaactcat ttttcacatt gaaatttgca aaccagatat acaatttagt | 840 |
| aggtcatcaa attacctaga aagtggaggg agggaatgtc catggtagac gaatacgcat | 900 |
| ccttcgccac cttggtggat ttgaacatag ctcctccaat aattatgata aacttgatct | 960 |
| ttggtacttt ctggagtgca attccctgca atataaaata taattctaag ataatgtaat | 1020 |
| gcgatttccc aacgcaaaag caacactact gacgtacctt agcttgcagt cctggtaatc | 1080 |
| ctccagacaa tattgcaccc tgcaaaatta acatagagat atattattag atcttatata | 1140 |
| agaaactgtt aaatgagaaa tgaagcaatt ttgtaattag agtacctgag aaaagccaat | 1200 |
| gagaccatca aagggaccaa gctcgatcat acgatcctct aaatactcca aacatttctc | 1260 |
| gaaattcg | 1268 |

<210> SEQ ID NO 39
<211> LENGTH: 478
<212> TYPE: DNA
<213> ORGANISM: Brassica napus

<400> SEQUENCE: 39

| | |
|---|---|
| gatgtgttct tcattgtatc tagcagaagc ttggtcaaca gaaatggcc tgaaacatga | 60 |
| tgatgatgat gatgatgatg atgatgtga gactataaaa cttaggacaa ggtataata | 120 |
| atcttggttt ggtttctctt agctcaccta gatggttagt tgcgaattgc agctcaatat | 180 |
| tgtccttaga gagcatgaaa ggacatgcca ttaccccagc gttgttgcta acaagatttg | 240 |
| agagattaca aaacattaaa accgtcacaa aacactagac atgaactact gtgtttcgag | 300 |
| agcttacatc aagatgttta gtggaagacc agtagatttg tagtcagatg caaatctcct | 360 |
| gacagattca attgagctga gatctaactc catgacgtcg agtttagcac cagggacttg | 420 |
| attgaggata tcttgcttaa ctttagcacc ggagacagtg ttcctcaccg ccataacc | 478 |

<210> SEQ ID NO 40
<211> LENGTH: 737
<212> TYPE: DNA
<213> ORGANISM: Brassica napus

<400> SEQUENCE: 40

| | |
|---|---|
| gcacatatgt ccgcacctgt acaaaaccgc ctcgacctgc gtttcgtcgc agacgcagca | 60 |
| tttgcgtttc attgggtttt ctctgtaaac cgattgttgc aagctcgcgt tagcatccaa | 120 |
| acacgttttg acagaatctc gtagtaagga catttcttgt tgaagctgtt ggatctgtgt | 180 |
| tctcatatcg gttatcagct ccatttcctg aaaacgtttt aaagcggttc aaagatttta | 240 |
| ctattctact agttgggggtt tgcgagtttt ctatgcaata acaagaaatc gaaaattact | 300 |
| tacatgtgaa ggaggattgt gaacagacaa gacaggagtg gaagttactt cggtgtcttg | 360 |
| acaactccat gatcctgcag gagacgatgc aaagatgggc gaagaagacg atctgcttga | 420 |
| gtcatctcta tcgttttgtt cttcaccttc cgttgatggc tcttcttcag tttcctccgc | 480 |
| agtgtcatct ctatgttctt cctcttcttc ttcttcttct tcttcttgtt gcaattccca | 540 |
| tgattcagaa tgctttttcg aatgtgtctg cagacgagac atcatgagcc tatcgatctg | 600 |
| atctcgtaac ccgctctcga gaaagtctgt cactgttctt ctgtaatagc aagaaaatat | 660 |
| ttatcttctt agttaatggt ttaacaaata agaaaaggga tttgttgaat cgatgttgcg | 720 |
| taccgctcaa ggagtct | 737 |

<210> SEQ ID NO 41
<211> LENGTH: 427
<212> TYPE: DNA
<213> ORGANISM: Brassica napus

<400> SEQUENCE: 41

| aatgcataac aaaagatttg aacccgggtc tttggtcaaa caataatcat cctaaattta | 60 |
| tgctaatagt gattcttttg ttagccactg aacacaaact ctcttcttct tcttcttctt | 120 |
| cttcttcttc ttcttcctct ttcctctgca ctctctccga cacaagacgg cggtcaacgg | 180 |
| agtccttgtc ggtcaaatga tccctaagga cgaaggagga gttgtggaga tttccgattc | 240 |
| tgttccgctc ttttgctcca acctcgctct ccttcctcct ctctagatct cgctcatcat | 300 |
| ggtcgctctc actacataag tttttgaaat tgaatattga aaaacttagg atctgagtgc | 360 |
| actgttgcga attctcaata ttgttgttct gtagctgtgt ttgggagaga ggcagtgtct | 420 |
| gtaatac | 427 |

<210> SEQ ID NO 42
<211> LENGTH: 820
<212> TYPE: DNA
<213> ORGANISM: Brassica napus

<400> SEQUENCE: 42

| acggttcagc acagtaaaaa aaaagttttt ttgactttt tttctttgac cgccaaagaa | 60 |
| gacgaaaatg agtctttgag aaaatcacaa aaagaagaa gagaaaaat gaatcctttt | 120 |
| tgtttcttct gcacagaatc ttcttctctc tctctctctc tctctctctc tctctctctc | 180 |
| tctctctctc tctctctctc tctctctctc tctctctctc tctctctttc ttgaggtttc | 240 |
| ttttcctcca cgattcctcg tccctcttgc ttctgtgtga tcgattttgg tgaaattgag | 300 |
| ctgagtgtat ctgtccgccg aggccttttg ttcactgttc aattcaacat cagatcaatt | 360 |
| ttaggggctt tcagtcaaag atcgctgctt tggtgtaagt ttgaatttgg gtaactgaat | 420 |
| gaatgtgatc tttggttcca gttcatgtaa ttatgtttga ttgactggga agtatcatc | 480 |
| ctttattacg gattgtaaac atttaaggtt gaatcttaac attagcacca tttggattcg | 540 |
| aatttgtttg gtgggtttgg ctttagatcc ataagcaagc ttatgagctc ttaaagttat | 600 |
| gttgtttttt tttgcttaag ccattcaaac tgatgagata tactctcttt gtcttgcttc | 660 |
| ctaggtttgt gattttagta tagaatcctg ttatcatgga tgaacacaat aggaatccat | 720 |
| ttgcaagtgc aagcggaaga gcaagtggaa gtacaagtgt gagttccaac tccagtttta | 780 |
| gtagcagcgt ggcggataca gaggatgatc aaaccattgc | 820 |

<210> SEQ ID NO 43
<211> LENGTH: 701
<212> TYPE: DNA
<213> ORGANISM: Brassica napus

<400> SEQUENCE: 43

| tgcaaaggaa gcaggtgtag cagctcaagc ttatgaagct ctaaagacac tgagagaaaa | 60 |
| aaaaacatct gcaaagtggt aaacaaactc ttcttatttc acacaacaca tggtaaagaa | 120 |
| aatactttt catggagaat aagaagaaga agaagctaaa tgcgttgcgt tgcaggtgga | 180 |
| gagagagaga gagagagaga gagagagaga gagagagaga gagagagaga gagagagaga | 240 |
| gagagagaga gagagagaga gagagagaga gagagagaga gagagagaga gagaagcgca taagtagtgt | 300 |

```
ttgtgtgttg gtgattttct atttggaaac tcttttgtaa gcaataatct cagatgctaa    360
agccattgta tttattgctc acttcatttt acagccaaac taagttttaa aaactgaaaa    420
tataaaacgc taaaattttc tttggttgac atcagcataa tataaattta gcttactccc    480
tcgattcaac aatacaaaaa aaacgacata agtttgagtt tacatgcttt caaccaataa    540
aatggaactc tttatcataa aataacagtc aacgtattat taagtccaaa ccaccacaaa    600
ccaatatttg cacaaataaa agtttccaac cttagctgcc actataaagt tataaaccac    660
catccaaagt ccattatttt aagatagatt tcgtacggta c                        701

<210> SEQ ID NO 44
<211> LENGTH: 725
<212> TYPE: DNA
<213> ORGANISM: Brassica napus

<400> SEQUENCE: 44
tcgtataaaa taaaattctg aacaaaaata attatataat ttcaaattgc ggctcaaaat     60
ctattatttt taaaaactca acaaaattgt atatgggccg atgaagccca agtattttaa    120
ttaccgtaaa ggagggtttg agtcggccac aaatcaagga attatttcct ctctctctct    180
ctcctgtgac gagttgctct ctctctctct ctctcgtctc gtccgcgctc cgaagaaatt    240
tcacagattc ctgtcatgtc ttccggcgga aactctaccc tctccaacgt cgaaaagatg    300
ttcttctgtt accagtgcaa tcgcacagtc accatctcaa tctcctcctc ctccgacgat    360
cctttctgcc ctcgctgctc cggtgggttt ctagaagaat cgacgagcc aaaccctaat    420 ccgcccccaa atctcaaccc tcgggttc ctccccatgg ccgatccttt ctccaccctg    480
ctcccgctcc tattcggctc ctcctcctct cctccttcct ccacgaacca gagcttcttc    540
ggccagaatc agcaccctcc tcgcggcgga gctttcgatc cggtgtcgtt ctcccagaac    600
catctccagc acctgcaatc cagcggcact cacgtccagt tcgtggtgga ggatcatccc    660
tcggatccgt ttggccggat gccgggaac atggggact acttcttcgg ccctggcctc    720
gagca                                                                725

<210> SEQ ID NO 45
<211> LENGTH: 757
<212> TYPE: DNA
<213> ORGANISM: Brassica napus

<400> SEQUENCE: 45
aacggttttg tataaatagt atattctata tatgtatgca tataatcttt tttcgtaact     60
taaaaggatt aaaccggatt tattaaagac acaaatctaa cttccagatg agaggtgcaa    120
tacacatatg gattattttc cagatattta aatggaccat aaatatagac ccataaccgc    180
gtggccacat atggaactaa tgatttcgca ctagaaggga atcgattcct gacctgaacc    240
aacaggacaa ttcctcctct agcggaaacc attaagccac acaacatgg ttttaaacaa    300 aaaattgtac gcatctgcgt ggcttactat taaaacatct ctatctctct cttaaaatac    360
atcaagagta taatgagaga tatctcagtt tcatgtagta agacaaaacc caagactcca    420
accggaaaat tccaacccta agaggcaaac taaatttcat tgtacaataa aataattaat    480
gctattcagt tttctaaaag cagatttaag tctctaactc caattttcca tctctctctc    540
tctctctctc tctctctctc tctctctctc tctctctctc tctctctctc tctctctctc    600
tctctctctc tctctctctc tctctctctc taaatcccca ctaggattat gggaactcac    660
gtcctcgttt aatgcgattc atgactcctc aaagcccagc attcccactc tgcaaattac    720
```

```
tagtacctct tagtcttaat taccatttga ccaatct                              757
```

<210> SEQ ID NO 46
<211> LENGTH: 394
<212> TYPE: DNA
<213> ORGANISM: Brassica napus

<400> SEQUENCE: 46

```
gtaatgcggc aggacagccc tcctcggagt ccacttcatg gaggagcata ctattcatcc    60
agtgatgatg ataaccactc cacctacctc ttcccagaaa ttggcacccc aactcgttcc   120
atcccagtct ccgccaacac cactgtatga atctctctct ctctctctct atctctcttt   180
caccattgtt tttatgatct tatggacctt aataaataaa catatgcagc ctgttcacca   240
caactaccaa atcattgcgg tggaaaccta cgagcaagag aagcagtacg agccaccgga   300
gctagcggac gagtcacaga gcttctcgat ccaggagatc gccaaaatgc gaggactcaa   360
ggaagagagc caatcgatga tctccgagtc ctac                               394
```

<210> SEQ ID NO 47
<211> LENGTH: 749
<212> TYPE: DNA
<213> ORGANISM: Brassica napus

<400> SEQUENCE: 47

```
gtgaaaccgg ttctggagaa ctctaaggtt gttttgaaag atcgcaaaag agagtggaag    60
cggaattagg gttctggtta tggcaaggag atgaaccgga aggaggtacg aatcctttgg   120
gaagcataac agaaaacgta tccggtcgga ccggtcggtt aaaaccgtta ctgttttctt   180
tggtcatcat cttgaagtag ttggcacggt gacgaagacc acggcgacga atgctatggc   240
ggtagtagta gtagtgatgg ttgtaacgaa gacgacggtc ctgatcacgt tgccgcgggt   300
tcaagataaa cggcgtcatt ttcttgatgt agacgagttg gtgcggtgat tcgtcgccgt   360
tgaggtaggt ttctgccttt tgtgtagata ctcttgtttc ttgattcgat aatgatgagg   420
atgatgatga tggcgatgat ggtaatgatg atgatgatgg tgagataggg aagacgagaa   480
tgagaatgag agagatgatg aagcatttga caaggttgtg tttcatcaaa acatccattg   540
cgattgagag agagagggag taggactttt ggtttaatag agagagggag agtaaagatg   600
aaacaaaaag atgtgagcga ggcaactata acaaatcttg gtatggcgtc taaataattc   660
gtttagttat tcgaatttta attaatttta gtatgatttt tgattgcgta taatttggaa   720
attagttggg cttttgttg gtctgaggc                                      749
```

<210> SEQ ID NO 48
<211> LENGTH: 709
<212> TYPE: DNA
<213> ORGANISM: Brassica napus

<400> SEQUENCE: 48

```
cacatgcttg tggataaatc atcatcatca tcatcatcat caacatcatc atcatcatca    60
tcatcaatat caaatatatg gtaagtccat tttcatttag ctttcagtaa aactgttaat   120
ctatgcattc gataattaag agaatcaaac gaattgtgtt tgcaacatta taattaatgg   180
ttgaaattca ttaagaatat ttagtttggg ttttctcatt ttcatacaaa cattatccat   240
gcatacggtt ggtcattagg ttttgaaaat atatgaaatc agaaacattt taatttttt    300
taatgtaatt tgaaagcata caagttatgt atattaactt tgtgtaattt gaaagcatac   360
```

| | | |
|---|---|---|
| aacttatgta tattaacttt tcaaaatttg gactataaat aaatatttct ttgatctgcc | 420 | |
| caaaatcaca aaagattctt ttacaagata aactgtatct tttactctct tttttgtcaa | 480 | |
| tactgtatgt ttcacttgtc acgaatttgc attcaaataa ctatgtagca gcacattatg | 540 | |
| ataaagttgg aagtgtatga ataaattgat aatgtagatt gtagggtgag aagttaaaaa | 600 | |
| aaatgagtaa ttttaggggg ccaaatgtat tttcgtataa attaagggtg gaaacatgaa | 660 | |
| aattagattt tttatgtccg aactacccac tgacttgtcc gaagtccgt | 709 | |

<210> SEQ ID NO 49
<211> LENGTH: 537
<212> TYPE: DNA
<213> ORGANISM: Brassica napus

<400> SEQUENCE: 49

| | | |
|---|---|---|
| gttcaaaggc atatttatat tatatttaaa ttgggaccaa gatttgcttt gggacaagct | 60 | |
| gtgccccacg actttctcgc tagtgctctc tggtcgcttc tccttctaga gaccaaccat | 120 | |
| ttccaccaac tccgttttca gttcacacca tgcccaccac tgcatcagtt agttgatatg | 180 | |
| agcccaactt ctttcttcac tgtttaacaa aatggactgg tcaacacagt ctctgtcaca | 240 | |
| cccgagaatt ctaatgtggt ggacacaatc ttcactaggc accttttgt caccagtctc | 300 | |
| tctctctctt ttcctgtttt gatccttcca taagattaaa cctttatggt tactaccata | 360 | |
| ttataacgat ctcggtggtg gtagcgtagc ccaaagatga tgatccgaaa ctgaatgtaa | 420 | |
| actatgtacc aaagagagag agagagagag agagagagag agagagggag agagagagag | 480 | |
| agagagagag agagagagag agtaataatt aaaacaaatg ggacaaatta accccccc | 537 | |

<210> SEQ ID NO 50
<211> LENGTH: 625
<212> TYPE: DNA
<213> ORGANISM: Brassica napus

<400> SEQUENCE: 50

| | | |
|---|---|---|
| ccgccataac aaaaatcttc ccacaagcgt gtagagatct ggagagagag agagagagag | 60 | |
| agagagcttt caagtgatta aatccaaaag taataaagag aagacggaga aactaaagtg | 120 | |
| acgcgccccc ttcctaacgg attatattta ttttattctt atatatttat gggcttattg | 180 | |
| cagcaatagc catatttgaa atgaaaatta agagagtagc catgatgttg acataatgta | 240 | |
| ctcactgtct ttttacaatt ttactagccg gttataccstt tgtaggaaac aggttcccag | 300 | |
| ttcctttaac taaagtaaac gatgtggtga tttactgacc catagtaaca atgagagtat | 360 | |
| tttagcaacg cctaaaatta aaatgaaagg aaggaaaaca ttctatagag atgaaaatat | 420 | |
| aaaaaaaaca gaagtgtaaa agaaagaacg ttacaaacgg agaatgcatg gatcgtaatg | 480 | |
| ctgatgccaa aatatggaaa tagttccact tcaaatagaa tacacatagt ataacaatag | 540 | |
| tttaaagttt gtcaccgcta tgtcatatga gaatattttc cattctatcg gatatagatc | 600 | |
| agtttatatt tactaatata atcac | 625 | |

<210> SEQ ID NO 51
<211> LENGTH: 674
<212> TYPE: DNA
<213> ORGANISM: Brassica napus

<400> SEQUENCE: 51

| | | |
|---|---|---|
| gtagagtgat aagagaacat cttgtctgac tcatgcttct tttctgctat gttaggctat | 60 | |
| tgctcttaat gatctgcctt ccactaacgt atcgagactg gggcttgctc ttaacttatc | 120 | |

```
tctttttctac tatgagactc tcatatcaac taaagctgcg cgtaagatcg caaaggcggt      180
atgttgttgc tttctctcat ttagtatttt ggtttatgtt atgcgattat catctattct      240
cccagatgct ctgtttgata aacttaatg  cttttctttc ttttttttg  ttctgacaat      300 cgttactgtt caattgtatt catattgtgg cataaatatg tatatgttgc tacacttccc      360
tgtgggtgtg caatcttcat atgatatagt aatggtttgc agattgctta tcatttggaa      420
gatagatatt gtaattgatt atgatgatga tgtgcataat ttggaaagta gagcctatcg      480 ttattcccctt acactaatgg aattatatat tgatgatgtt ccaattttt  taaatatgat      540 gaattgatga tgatgatgat gatgatggta ggctttcgaa gcgtcaataa cagaaatgca      600
cgcagtgaga gaggaatcat acgagcaaac tgcattgatc acgaatctta tccttgaccg      660 tatcaccccct ctgg                                                       674

<210> SEQ ID NO 52
<211> LENGTH: 519
<212> TYPE: DNA
<213> ORGANISM: Brassica napus

<400> SEQUENCE: 52
gtgtttctaa gcactttttt tttataatca aatcacatac agcaaacata aacatgagtc       60
tcagcttcaa gagccaatga aattagcttc ctttataata ttcaagaact aaccagtttc      120
acttctacta atcctcggcg cactgatgat gtttctaact aaattggata ctaaagaacg      180
tagcttttca cctcgaatca aacaacttga aaccaaaac  aatctaaacg aaatttcata      240
acctaaggag gatcggaaac taaaatttct acatcggaat cgaatcgacg cgaagtgaaa      300
cgaagatcga tagagagaga gagagagaga ggactcactc gccaggagaa gacatgttcg      360
tcgatttcga agatccgatt gattcagaag cggagaacaa tccaagtttt ttattgagag      420
agcaccgaac aaactctctc cctagaacgt tccttcccag cttctctaca aatcacttgt      480
tccgcgactg cgtatcttat ccaatcatgt cttgccacg                            519

<210> SEQ ID NO 53
<211> LENGTH: 664
<212> TYPE: DNA
<213> ORGANISM: Brassica napus

<400> SEQUENCE: 53
gaacatcctg ctgtttcagt tctatttttc ttgtgtagtc aaaagacat  tattccccca       60 ttggaaatta caacaacaca ttagttgtga gcgccaagat aaggctaaag acgtaaaaac      120
gctctgagta ttcattcttt caggtcaggt tcagaaacta gtttcgtttc atttcatttc      180
atttcatttc atttcatcca cctcctcttc acttgagaag ttctgtcttt tgcgatcctt      240 gtcattttg  taaaggtgag tcgatctata tatggtcact agtattctgg aaatgatgct      300
attttaatac tcagttcgaa cattctgtta tcaaatccgg ttctagttag ttgttcgcgg      360
gatagggttt gcttgagatc atttcgcttc ttttattttt ttaatgtcac tgatggatct      420
ggtaatcttc cttatcgaat taggaaaatg aatctgtatt aagtggacta atctcaaatc      480
taggtaaaaa aatgggagg  aggaggagga ggagaaggag ttgcgatttt cagagccaaa      540
gtatggagca tgtctggtgg gccttactgt aggcccaagc actggcgtcg caacaccgcc      600
tttgcaatgc tcggcgtttt ccttgtctgc atcccattg  ccatgaagtc tgccgagctc      660
gagg                                                                  664
```

<210> SEQ ID NO 54
<211> LENGTH: 517
<212> TYPE: DNA
<213> ORGANISM: Brassica napus

<400> SEQUENCE: 54

```
agagagacct ccagtcacct cgtctcttca ggcctcttgt gtttcctcca acttcctttta      60
ccaaaaaaaa acaaatcaaa atcagattca aggagagaa agagagaggg agagagcact      120
acaagagtgg aaaagaagag aatcaggtcg tggagagaga gagagagatg gcggatggtg      180
gtggtgatga atctgagatg cgatggtggt cgtgatgaat ctgagatgcg atggtggtgg      240
tgaggaatga tggcggatgg gaaagatggc gatggtggtg gtggtgacga gtgaatgagc      300
ggtggtggtg gtgacgagtg ggaggagaga tggcggtagt ggtggtggtg gtgatgagga      360
ggtcaaacct gatggattgg aggagaaaag gaggcgtcac aaagagagag agagagattt      420
gtgtgttagg ttaaagattg cacattcaga aatgtgctta acaatgatc tgaagtggtc      480
ttggtcgagg tagtccgtac atgtccgtac acagtgc                               517
```

<210> SEQ ID NO 55
<211> LENGTH: 785
<212> TYPE: DNA
<213> ORGANISM: Brassica napus

<400> SEQUENCE: 55

```
ggatgggatg agtcagctgc tggtgatagg cccagtcgag tttcagtttg ggacattgaa      60
ccagttttaa ctccttttcta catatgtcct cctccatttt ttcgacctcg gtttgctgga    120
caaccaggaa tgccaggtaa agtctttgta cagtttcatt ttgcacatca tctttgaatc    180
tccttagaga tggcaattct ggtggtcttg cagatgatgg gactgacatg gagtctgcgt    240
tgaagagagc aatgccgtgg cttgacaatg gcctagagat gaaggaccct tccagtacga    300
tatttcctgg tctgagttta gttcagtgga tgagtatgca acagcagaac ggccaggtcc    360
cttctgccgc tgcacagcct ggtttcttcc cgtcaatgct ccctccaacc gcggctctgc    420
acaacaatct tggcggggct gatgattcct caaagttact gagcttcag cgcgcctccag    480
ggggggtttc ctcatcaaac ctccaattta acaaaccgaa tccgcaagcg gcaatgtccc    540
agttacctca gccaccaact acgttgtccc aacaacagca gctgcagcag ttgttgcact    600
cctcttgaa ccatcagcag cagcagcaat cacagcctca gcaaccacag tcgttgcagc    660
aacaacaaca accgcaatcc ctgcaacaac aacaatcact gcagcagcaa caacaatcac    720
tactgcagca gcagcagcaa caacaatctc tgcagcagca gcagcaacaa caatctctgc    780
agcaa                                                                  785
```

<210> SEQ ID NO 56
<211> LENGTH: 927
<212> TYPE: DNA
<213> ORGANISM: Brassica napus

<400> SEQUENCE: 56

```
atgatgatga aatagctctg aagaagaagt taattaagga attgttgctg tctaattagg      60
tgttcttgtt gtttggttaa ttatgtttgg ttctcggatt tgaaagctct gttaaagagc    120
ttcagttttta actttaatta tcggatttga aagctctgtg aagagcttta ttttcactt    180
tatctgtaat tgttctcctg ttcttgatga tataaaatat ttaagttgtt cttgtgttgt    240
tcagttatat ttacagttgt tgtttatgat atatcatgtt tctttgtctt gtagagaagt    300
```

```
cacggagtcc acagagatgc ttggactgaa gggagtcacg gagtccacag agagatgtca    360
tgtaccatgt cttgtagtgt gcagggtctg taacgagtca cggaccatgt gtttgtatgt    420
gtcagtatgt gtttgtacgt gtcttgtatg tgtcacagag tccatgtttt tgtttgtgtc    480
tgtatgtgtt tgtatgtgtc gatgtcttgt agtcacggac agtattttg tagtcacgga     540 cttttaccaa actcatcttc tatttataac atcaatctca tcttctattt atatcaacct    600
tctctctcga acatataca acgaactctt cttctctgct ttacaacaac aaactcttct     660
tctcttctta acaacaacaa actcttctta ccatatttat attttttccc cttattataa    720
acaccaaaac catctttata aaactttat atggcttctt cttctcatga tgatgatgcg     780
tttgatgatg catttgatga tgttttgat gatgtctatg atcaatattt tgatcaagca     840
tttgagaatt tgaccatttg tcgtgatcaa gaagaacgaa gaaagaaaag aaaaaaacga    900
gcgtatatcg aaagacatcg tgaggaa                                        927

<210> SEQ ID NO 57
<211> LENGTH: 610
<212> TYPE: DNA
<213> ORGANISM: Brassica napus

<400> SEQUENCE: 57
agtccgagac agagtatgct aagcagcagc agcagcagca gctgaatact gcatatgatg     60
cgtcacagac aaatgctcag aatcagatgc agaatcttgc ttctttatca aatgtgatgg    120
taagctacat gtgcattatt catatttgaa gtgatccacc aatgacattc tccaatggca    180
ttgctaacat tggtactttg tttgtgtgtt tttgactcag cagggatatc cacactcaga    240
tcccaacagt ttattggcac aaaacgctag ggagcttgag ttccagtatt ccaatttgc     300 acagtctatg cagtcaagaa atagcaataa tgcttcttca cttggtggtc aaagcatttc    360
catgccagag gtaaataacc actttgtct tctttttttt taagaaacac aagatgtctt     420
gttaattagg ttttgctcga ctatggagtg atctatatgt atccaaatct atacaacaag    480
aggaatttat atgattttga ttatatattt tcttacattg taggcgcccc gaggcagtgg    540
aatccaagcg acgcagcaaa acttacaagg tgctaatatc gccactggac cagcacttcc    600
tcaacagctt                                                           610

<210> SEQ ID NO 58
<211> LENGTH: 557
<212> TYPE: DNA
<213> ORGANISM: Brassica napus

<400> SEQUENCE: 58
ataagcatac caatgaagat atcaaagaat gcaatatgta tgttttgtgt tgtgaaagct     60
aaaggattct acttatttg tgttgagtga tggttcttta gtttggtgtt aatgtcttgt     120
gaattgtgtt tggcaggtac aagctaggtt tttgtcccaa cggtcctgat tgtcggtaca    180
ggcacgcgaa gctgcctgga ccgccgcctc cagttgagga agttcttcag aagatacagc    240
agctgacttc gtataattac gggcctaata gattctatca gccacggaac gctgctccgc    300
agttgggaga tagtaataag cctcaggtgc aagttcagac gcaagaggcg ggtaacttgc    360
agcagcagca gcagcagcag cagcaacaac ctcagcagtc acaacatcag gtcagccaga    420
ctcagacaca aaacactgct gaccaaacgt ctcatccttt gcctcgtggg gtaaataggt    480
gtgttcagag tttctaaagt ttttaattgg gttgtgtaaa ctatgcttct gtatatctgt    540
```
caagacattg tttattg 557

<210> SEQ ID NO 59
<211> LENGTH: 562
<212> TYPE: DNA
<213> ORGANISM: Brassica napus

<400> SEQUENCE: 59

| | | |
|---|---|---|
| atgaagattg atgtatattc gaatttataa agtctacgtt tagtaaaggt atacaaatca | 60 |
| gaggtctgaa tttgttcaac ttcctcctca ttcccccatc cccaaaagaa tccgagtttt | 120 |
| tttggatcaa gcctatatag atccaaaaac caacataatg gcccattaaa gatgcataga | 180 |
| ctcgaaccaa accggattaa tacactgcgg gtgaaaccgg tttgggaatt ttcacaattg | 240 |
| actgaagaat cagggtttaa ggagaagtca cagacccagg aagaagaaga agaagaagaa | 300 |
| gaagaagaag aagaagaagc agaagaatgg agtcagagca ccaaacgatg gaacagttcc | 360 |
| tacgatgggc agcagagctt ggcgtatcag attccatcga tccttctcga tctcaagatt | 420 |
| catgtctcgg ccattccctt tccgtcgccg acttccctct cgccggcggg tgcgtagaaa | 480 |
| caaaaatcac atcttttat cattcaaatt cctaaacttt ttcgaccatt gatgggaaac | 540 |
| taggagaggg ttgggggctg tt | 562 |

<210> SEQ ID NO 60
<211> LENGTH: 593
<212> TYPE: DNA
<213> ORGANISM: Brassica napus

<400> SEQUENCE: 60

| | | |
|---|---|---|
| cttcaagttt ctattattat cagttcagga agtgacactc actagaccaa cagaagaaga | 60 |
| aaaaaatcaa catacagaaa acagataagc actgctcata ttaatcatga atcgttcaac | 120 |
| aaatttgatc cgaacattac agaaactata cgtgtttgat ccaacaacga aggagcaca | 180 |
| aacaaaatga gatcaatacg atcgttcttc attgtcgttc tattacaaaa ctgtgcttgc | 240 |
| tttgttggtt cgaactcgaa catacaacaa catagatagt tatgtcggga tatacttatt | 300 |
| tatatttaga tttaattatg gataacgacg gcgagagatt ctcggcgacg gaatatcaac | 360 |
| tgtttcgcga tgaatgcttc gatcgttttc tgaaactctt cgtttgtcag attatcctcc | 420 |
| ggaaacggca cttcttcgca cgacgcgacg gtttcacggc acttctccgt ctccgatcgc | 480 |
| cggagcgtag gtttcgtcac cgtctccgga ctctgtttcg cagagatttc cgttttgctt | 540 |
| cttttataga ccttcgtcgt cgtcgtcgtc ggaggatgat cattcgtcga ttc | 593 |

<210> SEQ ID NO 61
<211> LENGTH: 970
<212> TYPE: DNA
<213> ORGANISM: Brassica napus

<400> SEQUENCE: 61

| | | |
|---|---|---|
| ctcaatctt gtgtgggtgg agcaatacat aaattttgtg tggttggaag gttatgaaat | 60 |
| gaaacttta gtggaaacgt gaatagatca tccaacttat tttgtgtgtt ttaagaaaga | 120 |
| ttagatgaat ttgactcagc tcattggaga gagagagaga gagagagaga gaggcttcac | 180 |
| agagcccatc gaatcctatg cgcgtgtgaa aagcacgatc caatcacgaa gctaaaatct | 240 |
| tcagcttcgt tgtataaaaa aaacttattg aaacaaacct caattccaa ttacacccctt | 300 |
| gacagcgata cacactctct ctctctccaa ctaaaacata tctggaaatt ataaataaaa | 360 |
| tttatacttt atctggtaac ccatcaaata aagctattag tcacataata gatgacaaaa | 420 |

| | |
|---|---|
| aaaaaacaaa taaagaaaat ttaggaaaca aatctactga gattaggctg taaatcatac | 480 |
| gtatatcttt cccgtataca gagtgccgtt ttaagtataa tgtcgacacg tgtcggtcag | 540 |
| aggctcggct tccaagggta agattgtaaa atcacgatcg tcatctctct ttaagaattt | 600 |
| ccagagtgct gagagagaga gagagagaga gagagagaga ggtgctttcc catagccatt | 660 |
| cacgtcgaga gagagagaga gagaggaagg agatggagga tatacaggag gaagagaacg | 720 |
| gtacggacga ggaggtgctg ggatcgagct tgaccatgga gaaagtggcg gcagctaagc | 780 |
| agtacatcga gaatcactac aaagctcaga ataagaacat tcaggagagg aaagagaggt | 840 |
| attataaatc gtctctttcg ttgagtgaga gatttgagat ttggaatatc gttttttttt | 900 |
| agagactagt tagggcgaaa ttagttgcgt gagctttgat tagtctctcg tatttgatga | 960 |
| taatcatggt | 970 |

<210> SEQ ID NO 62
<211> LENGTH: 683
<212> TYPE: DNA
<213> ORGANISM: Brassica napus

<400> SEQUENCE: 62

| | |
|---|---|
| gaacaataac ctgatcaagg ctctgctcag ctgctttacg ctcgtcggga ttgggactgc | 60 |
| aagcagccgc agcgatgatt actgccaggt tagacagatc catcgggaaa attcagcaac | 120 |
| agattctccg aggaatagtc ggcgtgtcaa gaattttccg gtgaatcgaa gaggcgagga | 180 |
| ggaagaagat gaccgacgaa gacgaggacg aggagagaga gagagagaga gagagagaga | 240 |
| gagagaggta agaaggaa ggtctaagct agggttttaa tgtatggttc gttggtctgt | 300 |
| tatggtaagt ctatcgcacg cacgcgcgtg gtaaaaaagt gaaaaaaaag aaaaatcgac | 360 |
| gtgagacacg atacacaacc cagacttgcc tggacctcta gtcacctatt tattttcacc | 420 |
| gcctgctcgt ttagttagtt acggtcaatc gattgacttt tggttatttt ctatgtgttt | 480 |
| tcaatataat caaattcaaa tgattttta atcaaatcaa atgtaaataa taaataataa | 540 |
| aaatccaaat ggaattaatt agtttaaact tattaaacta ttttgtcatc tttttagtta | 600 |
| tttaagaatt atattaaaac ttgtaaaatt ctagttacaa atataattta atgcataaat | 660 |
| ctaatgaatt tgggagaaaa tag | 683 |

<210> SEQ ID NO 63
<211> LENGTH: 766
<212> TYPE: DNA
<213> ORGANISM: Brassica napus

<400> SEQUENCE: 63

| | |
|---|---|
| ggtttccgcc gcaatgattt ggtagttgtg gtgaacaggc tgcatatgtt tatttattaa | 60 |
| ggtccataag atcatagaaa caatggtgaa agagagagag agagagagag agagagagag | 120 |
| agagagagag attcatacag tggtgttggc ggagactggg atggaacgag ttggggtgcc | 180 |
| aatttctggg aagaggtagg tggagtggtt atcatcatca ctggatgagt agtatgctcc | 240 |
| tccatgaagt ggactccgag gagggctgtc ctgccgcata acgtagccat ctggctcata | 300 |
| cattgcttcc atttgctcat cattatgatt gttgctgcga cggtcaggct gcgatttgtt | 360 |
| taggagagct gattatttat tgtcaagaat atgttttatc actagagaga agctcaggct | 420 |
| tgagaatgtt gtttgagtac cgttctgtat tgttgtggtg gtggcgaacg ggtcgcagct | 480 |
| ggatgaaatg ggcttggtgg agagctgttt cgtggtgtta cttcgccgtc tcgctcatac | 540 |

```
acttcctcgg attgctgatt atcagggtgg tttctacgac gatcaggctg ttagaattag      600
aataacgaac tttattgtca ggttaagtga atcactttat ctgtttctgg aaaataaggc      660
tgagttttat ggtaccgttc tgtatggttg tggtggtggt ggcgaacgtc ttgcggctgg      720
atgaaagggg ctcggtggag agctggttcg tggtgttacc tcgccg                     766

<210> SEQ ID NO 64
<211> LENGTH: 483
<212> TYPE: DNA
<213> ORGANISM: Brassica napus

<400> SEQUENCE: 64
agtgctttag gagaggagga tcttgataca aaattgttct caagaattga gaagaggaag       60
aagaaaaaag ggtattaaaa ggaagaagag gagggcttta ttaatcatgt attgctaaag      120
aggaagatga ggaactcatc accttccttc cttcaatggc aatgaaatga aagagagag      180 atatgaatga gagagtgagt gaaaagagag agagagagag agagagagag agagagagag      240
gagagagaga gagagagaga gttgggtcta ccatgaaaag cagaggaggt gggtcaaagc      300
aaaagttttc gactcttttt ttagggcttt tcaatttcct ttttttcttt actttccatg      360
tttgtatatt tcccaaaact cgaattcata cacaagtatc tcgggaaaac ggcttattca      420
tgcccgaact aggggttgct gagagaatac atacctcaac ttttactgca agtcgaaaca      480
tac                                                                    483

<210> SEQ ID NO 65
<211> LENGTH: 623
<212> TYPE: DNA
<213> ORGANISM: Brassica napus

<400> SEQUENCE: 65
ataggttctg tgtcgtaacc attagagtct aaaaccgtc aatttcgatt ctcacatcca        60
aaaggtttta acatttatat atatagtaag atgggtaaag tttgtaaccg ctcgtgtata      120
aaaatcaggt ttacgaaaat cgcattactt ttgattttct gatcgaaaca gagcttcgaa      180
aaggaactac tacgcagtaa ataaacttac ttgaagaaac gaaacttact tcgaaagga      240 attactttct gaaggttgcg atagcgaaga gaaacttgag agagagagag agagagcgag      300
cgagagagat atgagagtga taccgcggcg gaaatgaaga aaaaaaaaaa aggtttaggg      360
tttaacgacg actgttgcaa gttgtaacct ttgacttgtt ttttttttaat aaatctttt      420 ttctttaaat taaagaata aactctagag tggaaacccc ctgataagta ataatgtttc       480
agttccgacc ccaaagtaaa gtttcaaata atttaaccca actttattgt aaataaaaaa       540
aatatttcga tgaaacgaat atgtgcaaaa tttcatatat ccataattca ttacgatgtg      600
ttttatcaaa aaaaaaatct ttt                                              623

<210> SEQ ID NO 66
<211> LENGTH: 704
<212> TYPE: DNA
<213> ORGANISM: Brassica napus

<400> SEQUENCE: 66
ggttagtcat ccaagaacag aaaaatctct aagaaaaca acaaaccctt gatgtaataa        60
gccttgcgaa tctcttcctc agaagcggag ggagtgacac caagaacatc ataatatact      120
gtttccttca ccatgatcgg atcaaagcaa gagatgtaac ttttttgtgt agataagaaa      180
ataaaggttg gttttgtgga ttgtgtgtga agcttttagg agatatgggg aagaagaaga      240
```

```
agaagaagaa gaagaagaag aagaagttgg gacacaagag aggtagggtg tgtgatctgc    300
ttgaagaagc aaataaagag atgtctttac agttatgcac ttttgattta ataaataaaa    360
aactttatag cggggaggct acactacact ttcaccatct ctttttaact gtccactcaa    420
ttgctttatt gatctcatgc ctcctttttt attattccat tgcttttctg tattgttgaa    480
catactgaag aaaaagaaga tgatgatttt tgcaatacga ttgtgatctg gtgtatctta    540
tcatttagcc aaatggatat taagttggaa aaaaattcaa aaatataggt cctaccggga    600
gtcgaaccca ggtcgctgga ttcaaagtcc agagtgctaa ccactacacc atagaacctt    660
gttgtcttaa ctttacttta tttatttata atgaaacatt atat                    704

<210> SEQ ID NO 67
<211> LENGTH: 815
<212> TYPE: DNA
<213> ORGANISM: Brassica napus

<400> SEQUENCE: 67
tttaagccaa aatgtcataa cacaacaaaa tgagacaata ataacattac tgtaacaaat     60
acatagtttc taattagaac aaagactaaa ccagaccaag agaaaagtcg acaacaactt    120
ttaactctgt ccttccacca tcatcatcat catcatcatc atcatcatca tcatcatcat    180
cctcataact tattgttgta ccagaacaca ccttttcttct caccttgcct atccggttca    240
acatagatac actccttcgc ctccctccac atcgccttaa ccaccggcgt tccatcaaac    300
tggtaatact ctccaagtat cggctttatc gccttggtcg cttccatcgc gttataatgc    360
ggcatcgtcg agaacagatg atgcgccacg tgcgtgtccg tgatgttatg aaacaccttg    420
ttcaagattc catagtctct atccacagta gccaaagctc ctctcaacca atcccactcc    480
gaagaatata gtgaggcagc aagggtgcg tgtgctgcaa gtaagtgatc aagacgagga    540
aacagttgac aatcataagc ggaactccgt agacacagac catcgaggcc actcctcgcg    600
aaccagcgta gcggtagaga ccgtaacata cggagaggac gccagcgtca gagatgtata    660
tctggagacg ctcgcggtcg ttgtagatgg gagcgttcgg gtggaaatgg caagcgaaac    720
cgtcgctgta aggtcttcca gagacgttga aggctaagta caacggccag ccgagcgtga    780
actggacggt tagcatcacc gtgcgtccta gcggg                              815

<210> SEQ ID NO 68
<211> LENGTH: 784
<212> TYPE: DNA
<213> ORGANISM: Brassica napus

<400> SEQUENCE: 68
tgagctatta aaactacatt atcttaacgt catatcaatt tgacatttgc ttaatattca     60
ttttcttaga accgcttgtc aaaagctttc ccagttttcc attaactaaa gaatgctatc    120
aggagaagtt tctgaaatta gatcatcatc atcatcattt cttagcaact tttctgagat    180
tgagatcata tattatcatc accatcatca ccaccaccat catcataatc atatttgctt    240 agcaaaatttt tctaagaatc gtatattata accacaaaat ctatatttac taacttacaa    300
gatagatccc ataaatttat aacattctgc gattactcat tccctatata ataacgttc    360 catctattat atcctacatt atcatcatca tcatcatcac catcacaatc atcatcatca    420
ccatcacaat catcaccatc acagtcatca tttttttcata gcaaacttac aattcgaaga    480
aacgagcgcc aaaacatccg accttctcca gcaagactga atccaaaaat ccgaaatcga    540
```

```
caacatctcc agctcatcac gaaccctagg cagccacacc cgcacgaatt cgacatcggt    600
aaggtacaat tcgtcggaat cgtcttcgac caagtcgtcg aacgacatcc cgctgagcgc    660
cttatcaacc ccaaccgata tgaccctaac gttgcgagaa tcttcgatca gattcctgaa    720
gaccgtcttg aacggcgtga cggaggtcga gcgcgatttg gagtaccgtg acaacgtgca    780
tagg                                                                784
```

<210> SEQ ID NO 69
<211> LENGTH: 554
<212> TYPE: DNA
<213> ORGANISM: Brassica napus

<400> SEQUENCE: 69

```
tgttcctctg tttcttcaac ctcaaaagct cttt ccacag aacagtgcag ttcggtggac    60
gaggagaagg gtcgtcgtca agaaaccagc ttcctctgtt attattctcc tgctccttgg   120
tgctgttgtg aacagtctcc tctttcttaa ctctacgatc ttcttcttct tcttcttctt   180
cttctactac ttctacttcg tctacgtcga cgacttttgt tttcaaggta acgttttgaa   240
gcttctccga gtgtttggct tgccagaaag gaagcagctt ccttcggag aacagctcgt    300 ctgcggcggt gagcatcgtt tgtgtgttcg acagaaactc aaagtctcca gctttcactt   360
gttcttcttt tccccttagg agattctcag ggttgatgca gatgtagtct ccctcgctgt   420
ctgatgatga cagatcggcg gagaaggaaa tgcgaggtcc ttccgtcgtg aaaaccatcg   480
tagcctccgc cgtttccgct actaccatga tcgtacaaat gtgtagttat gaagtgaaag   540
acaaatcaag tgga                                                     554
```

<210> SEQ ID NO 70
<211> LENGTH: 858
<212> TYPE: DNA
<213> ORGANISM: Brassica napus

<400> SEQUENCE: 70

```
tcttaaattt aaattctatt cctcaaacac taaatcttaa atctacactc tatatctaat    60
actctatacc acaaatttaa actctatata caaaatcata aactcaatct ttacaaactt   120
ataatagaaa ctttaaattt aaacctaagt atattataaa actcaaatta tatacttaat   180
cctaaatctt aaccctaact cataaaccac atatttcata aaatattaaa tcttaatttt   240
taaataaatt atagttccat aaataaatta aaatttcaaa taaaaaattt agattttaaa   300
tttgaaatta tgatatcaaa gtatttaaaa cttaaataat ttttataata gctataaata   360
aataagaaga taatttgtat tgttttttta taccattgat tgatttgaat caaagactca   420
agatagctct tgtatctatt ttcgccttttt ttcttatcg gtagttgttg tttatggcat    480
ggatcacctg caccc ttaga taatattgaa ccagagatta attgttcttt tattcttttt    540
tttttaattt acttttctca gatctacgaa agagagagag agaagagatg gagttcaagg    600
tagagaagga gaacgcgacg gctgttcgtc accaccacca ccaccaccac caccaccatc    660
gttcgtcact accaccttcg cttctcagat acgtcttcac cggagtcgcc agaaccaccg    720
tcacgctcgt cataaccaac atcgctcgtt cccacaacca ccgccatctc tcccatcagc    780
catcgctcgt caccaccaca tcacttctca gatccgtctt caccggagtc gccaccacaa   840
ccgtcacgct cctcataa                                                  858
```

<210> SEQ ID NO 71
<211> LENGTH: 591

```
<212> TYPE: DNA
<213> ORGANISM: Brassica napus

<400> SEQUENCE: 71 ttttttttggt tcttttaact tttaataatt aattcaataa tctgtaacct ctctatgtat    60
ctcttcctca ttgtatctga ttgagtttga atcagttttt gagcaggacg tggtgatgcc   120
agaagatcta gcgaatgtcc ttaggacagc gaaagagatt gtcgttgcca cagtccttcc   180
cgtcacactt tgcttttttgt acatctctat gccttgacgc cgcctagga acacgctatc    240
aaagcttgcg gggttggagg gagctcgacg acggaggagg caagcatggt ctcgtcagat   300
acaacagagt cagcattatc tcaacattcc ggtcatgtaa gcggtgtagt cgtttataca   360
aatttgattt tcagatctga gattcgcttt ttgactttac agttttttgtg tatattttttg   420
taggatagga tgaaggggaa gaagaagaag gaggagacga agacgagagg ctgtgtggtt    480
ggcgtcagtt atatcaccac caccaccacc accaccacta ccgtcacgct tgtcaccacc   540
atgctccttt ccattcgagg cggctggaat cttttttttt ctaggtttag a            591

<210> SEQ ID NO 72
<211> LENGTH: 815
<212> TYPE: DNA
<213> ORGANISM: Brassica napus

<400> SEQUENCE: 72
atggtacaaa caatcataca gacacgcatt ctcttctagt tcagctgctg ctttctctaa    60
gcttgtcttc ataaaattgt tacaaacttt ggagcatcct tccttgggcc atcaagggac   120
cgatacatgt acaacgtctc cacataatct gcattgtcgt cttcgtcgtc gtcgtcgtct   180
tcgtcgtcgt cgtcatcatc atctgaccca acacctcca ccaccacact aggcagagta   240
tgagcaacat ccctgcaggc tccccgggac aacctacatg acgacatcca acaaacctc    300
atctcgttat acctatgcat accagagcgc agtccaacat caccaaaggg actgtccctg   360
atctcaagct tctctagttt aggacacccc tcgaggatat atctcagacc catgtcactg   420
tccccctgcaa aagctacaga tagagtacgt atcagtttcc catactctcc tataaggcta   480
aaggcttggt ccgttagtaa tccagatact gcaagcctgg ttagcttctt gcagttttta   540
acaatggcgc caaatccatc gtccattggc ttccttgtca cgtggtcagg cctatggcga   600
cccattatgc aaagctaaa cacggtaagc tggggacagt tctcagacat ggctgtcaca   660
gctacatttg tcatccgctg gcagaagtag agaatagact caagtttctt acaacctttc    720
tgaaattgct tggaggccta atcccgagac aggaccttca ctgtcttcac taggatccaa    780
agggaaaatc cctagctcac ggagctcctt gcatg                                815

<210> SEQ ID NO 73
<211> LENGTH: 640
<212> TYPE: DNA
<213> ORGANISM: Brassica napus

<400> SEQUENCE: 73
cgccgcgtct cctcactctc cggattactc tccgtctgaa tcctctcctt ctcgctcgcg    60
atctccctct cctccttccc gcgacgctcc ctaccgtctc cgatcgaaag ccgccgccgc   120
ctccgcgaat caaggagctg gtggtaatcc atcgggaagc cgtactacta ggagccgtca   180
acaagctggg aacatccgta cgttcgccga tctgaaccgt tccccgctg acggcgcgga    240
tagtgattcc gacgaaggcc aagagtacta tactggtgga cagaggaggt aaaattgtgt   300
```

```
ttatattgaa tgatcataaa ctgagtaatg tggaatcatg gagaattgtg ctattgattg      360
tttgtgttgg cttctcttta gctaatggat tgggccttgt gtgtttagtg ggatgatggt      420
tcaagatcct actaagaaag caaaagatgt tgatgcactc tttgagcaag ctaggctttc      480
agctgtggac aggcctgttg agccatcgag atcagcttct acaagcttca ctggagcttc      540
taagatgtta tctggtgagc ctgttccctc tgctactcct cagcagcagc agcagcagca      600
agaccagcct cagttggtta tgcacaccat cactttctgg                           640

<210> SEQ ID NO 74
<211> LENGTH: 731
<212> TYPE: DNA
<213> ORGANISM: Brassica napus

<400> SEQUENCE: 74
ccctatttcg ctgaatctgc tttctaaccc taattttctc gattttcctg ctcaagcgtg       60
ttggcaatgt cggaggacat ggtgatgcat ttctcctcca attcctccaa tcagtccgat      120
cactccctgc cgacaaaat cgcgaagctc gaggctcgct tgaccggcaa aaccgcctcc       180
tccgccaagc cgcagcctca gcagcagcag cagctctccg tctggtcatc tgcttccgcc      240
cctgccaaag tcgcggcggg ttcgtcggat gtctctatca gtgattccga cgacgaggta      300
acttccgatg attttttttt attattttt tttttaagat tgatgtctca atagtattct       360
cgttgttact actgtctcag aacacaggag atttcctgat ccgagcaaat accaagaagc      420
gccagaaagt tcaagacttt aacaacaaca actccactct tgttgatcat gctgaggtag      480
tgaattttca gtttaaatat cgatcttttc gtcccttgcc tggttcgtag ttatattgat      540
atggtaacta aggttgtgcg atactgaaac aatctgatat gatgcaagtt ttgtattccc      600
ttttgatgaa ttattataat gtcgaaattg aagccgcaag aggcagcata tgatggaagg      660
aaaaacgacg ctgagaacca gacaggcgtc gatgtgagta agaagaagca aggtcgaggt      720
cgaggttcat c                                                          731

<210> SEQ ID NO 75
<211> LENGTH: 690
<212> TYPE: DNA
<213> ORGANISM: Brassica napus

<400> SEQUENCE: 75
cttctgttag aattctaccg ttgttgttgt tgttgttgtt gtcttggttg tcttagaagc       60
tcaatcaacg cctccgcctt tagcttagct cgactcttac tactctgcga caaagccacc      120
acaggagcaa tcgcaccttc tcgcgccacc atggttcgat acaccacact ctcctcacaa      180
agctgcagca atatcgacac gcccatctcc ttctgcctct gcgttcccac ctccactatc      240
tccacaagca ccggaactcc tccttcctcc accaccgccg gcttcgactc cggcgccgac      300
atcagcagat tcatcacgta cgccgattta tccaccatgt tcgaatcgaa atccgccatc      360
agctccacga gcggcttcat aactcccgat tccacggccc tggtcttgtt ctccttggcc      420
gagcagagcg agtaaagagc cgtcgccgcg tccttcttcc ccctgaaccc gccggtttcc      480
agaaggttca ccaagtgagg aatcgctccg gatctcccga tcgcgatctt gttgtcttcg      540
atctgcgata ggcggaggag agcgcaggcg gcgttctctt tcgccgtcgg cgttcccgat      600
ttcaaaaccc taacgagcgg tttaatcgcg ccggaggaag cgatcagctc cttggtctcg      660
tcgcagaggg agaggttcag cacagcggtg                                      690
```

<210> SEQ ID NO 76
<211> LENGTH: 607
<212> TYPE: DNA
<213> ORGANISM: Brassica napus

<400> SEQUENCE: 76

| | | | | | | |
|---|---|---|---|---|---|---|
| gccaagctct | ccgacttgtc | accggtgcca | agaagcagcc | actgagaaaa | taaaactcat | 60 |
| tcaagattca | aaatccttgt | gtgcttcttc | aatgccattt | tagtttgact | tcttcatttg | 120 |
| ctacagttca | ttagttattt | ccttatttgc | aaaagagccc | tcgagtttgt | tagaaacgtg | 180 |
| aaataaagcc | attaaatacc | aattccctcc | actttgaagg | ggttttgaat | atctttccct | 240 |
| cgactccaaa | atcctcgccg | gcgataagca | aaccctagat | tcgattcgcc | gtctgttcat | 300 |
| ccagcaatgt | cgtcgttcaa | tccattctct | accccacagc | gacatcagca | gacgcctcag | 360 |
| ccgcagagca | tctccttctt | ctcgccaccg | cagagcactc | ccttcttctc | tcaactgcaa | 420 |
| caacagcaaa | cgccgtcgtt | tcagccgcac | cagttccagc | agcaacaaca | acaacaacaa | 480 |
| caaagtcagc | agcagctgta | tttgttcacg | aacgatcaag | ctccggcgag | ttacagcacc | 540 |
| gaatgggagt | gatctttcat | ccgattctca | gaaacttctc | cttgagattg | agtattgctc | 600 |
| ttcttc | | | | | | 607 |

<210> SEQ ID NO 77
<211> LENGTH: 880
<212> TYPE: DNA
<213> ORGANISM: Brassica napus

<400> SEQUENCE: 77

| | | | | | | |
|---|---|---|---|---|---|---|
| atcaaaccat | agaaatacat | gacttactac | attcactcat | ctgtgttgga | aaacttttca | 60 |
| aatttattat | atcttaattt | atattattta | caaatgttta | taattgcatg | atttcaatta | 120 |
| tcccccatca | caacatattt | taaaaaattt | aaaaattatt | tttaagatat | acaatatgag | 180 |
| aagattttca | gaaggcttct | atgagtatgt | tcttaaaaat | acattctatt | ttttttttt | 240 |
| ggtctaatgg | actatttata | atttcagtag | cattttagat | taattttgca | tttgatccat | 300 |
| gaggtatatc | tttgtgttta | aaccaagtt | ttaggttata | tttggaaatt | tcctcttgat | 360 |
| agtttgaagg | tttgaagttt | tgatgcggat | agcaatggat | aataaaacgg | attttggatc | 420 |
| taggacaata | attcgtccat | ctcctacgtg | gggtctttag | tgataatgaa | aaaactcttc | 480 |
| tggtaaaaac | aaaatgtttt | aataaatatg | gggctcatcc | ataagtgaaa | aatacctctc | 540 |
| ttcttcactg | caaatgaatt | ataaaccct | tccttatcca | cacacacaca | gacttgttcg | 600 |
| ctctcttaaa | ccctgaaga | ggaagaagaa | gaagaagaag | aagaagaaga | agaagaagaa | 660 |
| gaaggcgaat | catgcagatt | tgccaagcag | cggtaacctt | caccttcacg | aacccaacaa | 720 |
| accctaattt | ctgcaaaccc | aaacctctct | tcccaagctt | ccaaccccct | cgccgcgtcg | 780 |
| ccttgccgcc | atgccgtggc | ttcagctccg | acgagttccc | cgtcgacgaa | accttcctcg | 840 |
| agaaattcgg | accccaggac | aaagacacag | aggacgaagc | | | 880 |

<210> SEQ ID NO 78
<211> LENGTH: 676
<212> TYPE: DNA
<213> ORGANISM: Brassica napus

<400> SEQUENCE: 78

| | | | | | | |
|---|---|---|---|---|---|---|
| gatttaaaat | gacaatttt | tattggttgg | ttccgctagg | gggtgaacca | agaataactc | 60 |
| ttcttttatt | tctacgttct | cattctttct | tcttcttctt | cttcttcttc | ttcttcttct | 120 |

```
tctacgattt ttaatttcat tcaatgaaac aacaaagtag atctgatttt tatttgagtt    180
tgggtccaag aagtgaagaa aaatattgga gaggaggatc gacgcctctg ttcaatagcc    240
atggaaactc tgtacgcttc ctctcaagct ccgtggagaa gaataccagg aagacggcga    300
gcaagctccg tggagaagaa gaccacgaag acggcgagcg actatgaagg tggctggatg    360
caacgacaag tacgcctcat ctctgaagct tgactctcaa atcccacagc gaagaagaag    420
aatcaaggcg gatgtgaaga gcatagaaga gacaacgacg aaggtggtgg tggggctggt    480
gaggactgga agatgaagaa gaccacgtag gtggtgccat ggtggtgtgc ggcggcgtac    540
aagatgaaga agacgacata tggtagttaa ttagaaatta ggtttaagct tggtttaggg    600
ttttggttta tttggtttgg ttttagtact ttttatcta attagatttt ttttaatatt    660
tttgtaaaac aattaa                                                   676

<210> SEQ ID NO 79
<211> LENGTH: 556
<212> TYPE: DNA
<213> ORGANISM: Brassica napus

<400> SEQUENCE: 79
catcatcatc cattcatcat catcatcatc atcatcatca tcatcagcca cctttctact     60
ttgtctgttt cacaactgcc caatctacct cccaaagtcg tctcttccat gtgatacact    120
tcgcttggct tcttctgcct ttagctgttc ccgtctcaac gttcgtacgt aaaggtaaa    180
gtcttcttct tcttcttctt cttcccttac gtattttcgt tttccatcta aagattcatt    240
ctctcctccg agtttcgtcc cctgtctact ctgtttctgt gatgttgacc tctctcttaa    300
gctgatctga tatgtgttct tcttcctctt tgatgcttct gtctctgtaa ttctttgact    360
actttagata ttttatctta tgggtttcat taaactcgca caaagctcgt gactttgagt    420
tatataacca gttcagctct attaaagttt tcttgtagac caaacactca tgagttacag    480
tgtcttgttc ttaatcttcc ttttgactat tttatgaaaa gttcttgatc ttcgttactt    540
ttcaatagtc tgattc                                                   556

<210> SEQ ID NO 80
<211> LENGTH: 791
<212> TYPE: DNA
<213> ORGANISM: Brassica napus

<400> SEQUENCE: 80
cgagggacac gaggatagga cctgggatgc cttgagtgca ggctgtgcag caccataggc     60
gggcaccttt ttaatattgt atgttgtaat atttcatcta aaattataag ataatagggt    120
atacataact tatttgcgtg taaatagatc tcatttctac atttgagaat catgaaaaat    180
atatatgttc caagtggttc tgcaatgtgt taaatatata tatatatata tatatatata    240
gatattattt tcaattaata tactcacaaa gttggttatg acttatagta caaaacaaaa    300
tgtggagttc attaactaca cgaaacccat ttgtccacaa tattgaagta gtcttttgtg    360
atgattgaca taaattctca ttttaattgc cctttattgg gatagctgac aacaacaaaa    420
taagtaattc ttttcagatt tgagaaaatt tcaactacat atgtaaacaa ttcaaagaac    480
ataaatataa taagaaatgt gcacaaaaaa aaatatagag atatataaga aataggtaaa    540
tgaggccaaa gattgttgtt atatagaaag caagtcactg catcataata tcatgtggtg    600
gttcaacttt atgacgatag tgaataggtc ctctcttacg ccttgagatt ttgtttccgt    660
tgaagctgca gataacacac ctacacctat atcttggatg atagtgatga tgataattat    720
```

```
gatgatgagg atgatgacgc aagtgatgat ggttttcct aagagcgcaa caaaccgagc    780
tgtctgatac c                                                        791

<210> SEQ ID NO 81
<211> LENGTH: 708
<212> TYPE: DNA
<213> ORGANISM: Brassica napus

<400> SEQUENCE: 81
ctcggaagaa cgaatcgggt cagctcaatg ctccatcggg tcaaccttat ctctactcgg     60
atctctctct cgggtcgaac ttacttgcg cgacgcgaag ctcgaacagc tctgtgactt    120
gctggggagg aggagcggag aggttcaaca atgtaaccga aaagatctca ttcgagtcag    180
ttacatccgg gtcgggtcta atctgcgggt tgatatccgg taacctctcg gtcatgtgtt    240
ggagccctaa taacttctca agaatcttcc ttcctttccc agatatctta ccaggtcctt    300
gcgttgaatc atctatttgc aaatgtggtg tgtatccacg atctgatcag ctatgctccg    360
gctcgggttc gatctgcagc aaatgcaaaa tctcacctcc tccacaacca ccatcaccac    420
caccaccacc accgtcagat tcatctccat ctccatctcc gccgccgtcg aaggcgttaa    480
cgagaggatt actagcgttt gcgatcgttg gatcagtagg agcgtttgca gggatatgca    540
gtgtggtgta ctgtttgtgg accggagctt tcttggggaa agagaaagtt cataactcgg    600
ttcaaccgac gataacccgc ggcggttcga gtacccggtc aagcagctcg ccgccttctc    660
ggtccttgac gaatagacgt cagggatcga gaatattttc gatgagaa               708

<210> SEQ ID NO 82
<211> LENGTH: 829
<212> TYPE: DNA
<213> ORGANISM: Brassica napus

<400> SEQUENCE: 82
tatactgcta actatttaca tgtaaaatct ctgtcaatta tcttttccta ttctatacaa     60
ttttccacag ttatttttgt agttctgttg ctgaacttga agctgagttt gtggtgaaga    120
aacaataaca ccaaacacag catatcacct ccttccttct tctaatgcat ctcttctcct    180
cttcaacccc acactggatg cgaacctgtt gttcttgctt caatcgtttg agcttggatt    240
ttttcaatct ccatctcccc tcctcttcca ccaacattac tctcttcatc cccatccaat    300
accaacttct caaacctaca ctgttttgtt gcaaaacaca cagtctcagc cacatcatta    360
aaaaaaagga gaggaagga aggaaggaag gaaagtttta cattttcaca ttcccataag    420
ggtaggtgag acggctgata cattcgcaac tctgtttgag acacgtacag ctgatggttg    480
ttatccacca cacgaggggc ctttcctttc ttagttgctt tccacggctc ctcagcactc    540
tgctttataa caacctccgg aaacacgtta cttccagaac ccgaagttga tccacctcct    600
ccatatacgt cactctgctg atcttgcatc tctcttctag atcggttctg gaccatgtac    660
caccttcgta tcctcacaac cggtccttca gtctctgcac cagactcgga atcaatcccc    720
gtcatcacaa agcctcacca ccatccccag ccttcaacgc gtactgtgtc atacatccag    780
aaggagcaaa aacagtagat tcctcgttac gctattatca gaagcagta              829

<210> SEQ ID NO 83
<211> LENGTH: 634
<212> TYPE: DNA
<213> ORGANISM: Brassica napus
```

<400> SEQUENCE: 83

```
gctacatatg tccctaaaga gtgaaactaa agcgaattgc gaggattatt gaacaagttt    60
ccttccaact ttctaacgaa tcagccatca tagtagctcg caatcaacat ttagtttctg   120
ggaagatgaa caaacacaaa ttacccaaga acacgagaca cccagaacat aaacaaaatc   180
aaatacatca tgaatccgat taaaaagaac gaagatggag caaagtacct tttctcgatt   240
cgacttggag agaaactcga acgaaaggga ataaaacccg aggagtgact taattgggtc   300
acataatttt gttaaccgga aagttaccga accggaatca tacagctcgt tgtgtagtgg   360
ttggttggtt ggttttacaa cttccacaga ctaaaaatga catgaaaaat taatcaatta   420
tttacctgaa atgtacgatt agccaacaat tagttctgtt attcataaca aagaaaaca    480
ttttaattac agaggtgaac gtatcctaaa gagaaatctt tttttcaaa acaattaaac    540
ttccattcat taacattaac catcgcaaat acaaatcaag gtccaatcac acatatacga   600
ctcagactca ggatctgact ggttcaaacg cagc                               634
```

<210> SEQ ID NO 84
<211> LENGTH: 849
<212> TYPE: DNA
<213> ORGANISM: Brassica napus

<400> SEQUENCE: 84

```
gcttttatcc cggtttaata actttgaaat tcaatccatc gacgtggtcg gttcatggtc    60
gaaccaatta ctggacccaa cccgactata caaccggttc atggtcgaac ccggtccaac   120
catcgggtcg gtccggtttt aaaaacactg ctctaaatgg aaaatatag tccttttaa    180
ctattgttta attcaaaatc tgttgactat agtgatggat aatacaattt atatgggatt   240
tgaatttatg tattagatgt aaaaattgaa aagaaaaca tattatatac gctctacgag   300
cttttttaaat agatttattg gacctaagta tttcataagt tttgaaaaca tgggcttaca   360
aaacctttt aacgatgttc aacccgggct tagacaaact ttatgagatc acggctaggc   420
ctttgagtgc tattatttta ttttatttat ttcttgaatt ttagggatta ataaatgtga   480
gaaggagtag atagtacata attagagatt gatggaacaa attgcaataa tttaaaagta   540
aaaggatta aaatgcaaaa aaaaatatga ggacacatgt caacaaaccc tccttctata   600
tgtcataaga agggaaaaaa tcaactttat atatatagat agatagatag atatgtataa   660
tttgggataa aagtcggtat agccgtacag gcgtttgtgc gatcaatcgg tcatcaacta   720
aacaaaattt taaatgatt ttttaaacaa aaaaaatat tatttaatat ttattaaata    780
atttgcaatt tttaataaaa aatagttttc atatgggata aaatttatca atctcatcta   840
ctatataaa                                                          849
```

<210> SEQ ID NO 85
<211> LENGTH: 679
<212> TYPE: DNA
<213> ORGANISM: Brassica napus

<400> SEQUENCE: 85

```
gatcttatca ccaaatttta tattgtcacg tttaagtata tctttcgtag aaacatattt    60
tcctcgaaat gaaactatat gatataatat tttttttgtc taaacatttt tatactaaaa   120
actgataaga ttattgttgg taactacaat tatatttacc ttgataaata tataagata    180
tatatatata tatatatata tatgtatgta tgtatgtatg tatgtatata tatcatcttt   240
tattgaattt ggataatagc agattaatta atattttta gataatgata atatataatt    300
```

```
aaatttttgat ttactcaatt attatttatg caagtttaac ttttatttt gggtgattta    360
ttattgtata tgaatatata aatatattat gaataaaat aattatctaa ttattaagca     420
ttataaatat aattattcat taaatgtaaa atgactctaa ttactctagt ttttaatgcg    480
atagttcaga tcaaaaatat caatcagaaa ctaataatat cacaatttta tattagagta   540
tatttgttta attaactaac taatacaatc tgtgaatttg tatcattacc agaaacaacc   600
aattgagcaa gtcggttaaa aagttcatgc catgttttaa tttttgagct catacatttt   660
tcatttactc aggattcac                                                679
```

<210> SEQ ID NO 86
<211> LENGTH: 734
<212> TYPE: DNA
<213> ORGANISM: Brassica napus

<400> SEQUENCE: 86

```
gagtatcagc tctacaacat cgtccggaag caattgcaac tcttcgcgat gccttttcag    60
tgttcttgtt ttgaacggaa acatccttct cgtcctcgtc gtctctaaat tttattgaat   120
ttgatcaaca gatctgatat atatatatag atacaggcag ctaaggaatc tggaaacaca   180
aaaaaaaaaa aaagagaaaa tttcctctcc gtttaagtaa gatttccttt tttgaattta   240
aacagaatcg aaacatcaaa tctaataata ataataatac aaatatacat acatacatac   300
atattacctc agactcaggc aatgaacaag ccttttctaa tcctcaggaa tcatccatct   360
ctctctctct ctctctcgtt ttgttgtga gcatcgatgc ggcggcggcg cttagacaaa    420
gacatctcat cgggacgcct cttttacaac tcctcctcct gtcttctttt gggctttctg   480
taaggcccga cccggtttcc cttaacgccg gtacgtcctt agttcgctta cctcgaccaa   540
actgcccta tccgaattta ttctcttaac ttaggattat tatgcaattt tcctctaaga    600
ggttcagttc agtacacaag gttcgctaag tctaatccag caacttagca gtctactagt   660
aatcgcagca taatgaacat gtacctactg cctctgtact ttggtatctg ataatccatc   720
catacactcc ttca                                                    734
```

<210> SEQ ID NO 87
<211> LENGTH: 681
<212> TYPE: DNA
<213> ORGANISM: Brassica napus

<400> SEQUENCE: 87

```
gccattttcc tgattcgaat ccagatactg cataataaat ttgagaataa taatcacttt    60
ttattcactg cgacattgta agagtgactg ttattcataa ggctgttact gttagggtcg   120
aaggcaacta ttattctttt ttttgttaaa gcctttattc tttcttttc ttttgaatc     180
tttagttcgt aaatattctc tttcatattc ataaaaaata cacaacacaa catatgtatt   240
actattagag gcataaccat taacattgga tttattgagg ttagtaatta ttatggttgt   300
ttgacaacaa aaaaaaagt aatttttttt tgagcaaaca aaagtaatt atctgacaat     360
agtagaaact aaaaaatgca accatgcaat acgtggtttt ataatcattc tattgttaaa   420
tatgatgata ataataataa tgataataat aataataata ataataataa taataataat   480
aataatatta cagaatgttg atgtaataaa caaaaatagt ttgttagcta acgcctcaga   540
tcgatcaatg agtaattcat tcagttacca cataaagaaa caaataaaaa ctatgataaa   600
aaagttttga catcattttt tattgacatg tcaatatgtg ataatacact ctctgcagca   660
```

```
gtgacaacaa atactacaaa c                                              681
```

<210> SEQ ID NO 88
<211> LENGTH: 655
<212> TYPE: DNA
<213> ORGANISM: Brassica napus

<400> SEQUENCE: 88

```
ttggagtcct ccgacttggt cttgatacaa gattgtgagg aaatcactgt ccgtgtgtgg     60
catcaaacca tacacctccg atggtttcgg acatggtgga taacggttca tccttagata   120
acatgtgttt cgcacacagg ttttttttgaa gaaacttgat ttccgtcctg atttctctgc   180
aaggacctct gccaatgaat atgccagagc ctcggattct gaagcaaaat tttccattgt   240
tgagctgcga tataaaatgt acatattata actaaggtta atttattata gagacaaata   300
aatcatgtta aataaattag gtgaaataat tgcgaaagcc atgaaccttt cttgttcctt   360
ttgtttaatc caagccatga attgttcatt tgttttaacg tagaattgct aagattttttt   420
tttttgtaaa ccatgaattg aagttatgat aagaaaagaa atgaaaata ttattattat   480
tattattatt attatttaat ggtagaatga tatagtataa ataattattt cacggtaatt   540
atttgatttg gtagaaaatt gcggaaatta tttgatttgc tgattttttt tgtgaagaac   600
aaaattcacc taacaaaaga aacacgtaag attatttgtt atttgtggta catat         655
```

<210> SEQ ID NO 89
<211> LENGTH: 797
<212> TYPE: DNA
<213> ORGANISM: Brassica napus

<400> SEQUENCE: 89

```
taaatttaca tgtaaattac cacgaaacat tttctttgta acttttactac gaccttacta     60
cgaaattcag ttttgtcgta aaatcgtagt aattttctcg taaatttacg aggaatatat   120
ttcctcgtaa ttttttccttg ttataggcat gttttcttgt agtgtttatg ttgccgttgt   180
tctgaccacg atagttatga tacctttgtg attttctggt cacatattca cttaattatt   240
ttgtatgctg acatacctca tgggaggttc gcttgatata aatcatcact tacaaacaaa   300
aaatattcat aaaaaaaaat attcacacgt ttacaaaatc aaaaagagtt atatataaat   360
agctataata ataataatga tactaatatt aataacagta ataataataa tgtttagaaa   420
gctaaacaac aaggattaga acatgtatttt ttacaattgc aaaaacaaca acaaagtcgt   480
agcttaggac atttaaaaca agatgaccat ttgatcttgc agttgcagct gcaacatgag   540
ctcttcttat taagacatga tggtcgactg caactgcgga aacatgtggg tatgcaacaa   600
cataagtccg gacaagaaca acagcaacct aggaagcatg aacagctcgg gcagctcagg   660
catttggggc agctcggttt cgggcaacaa cagctgtttg agcagcagga cccgttgcag   720
catttggaac aacgcagcta caacatgtgg aagtgcagca ttttggcttc ctcagatggc   780
acgaacactc gggtcgg                                                   797
```

<210> SEQ ID NO 90
<211> LENGTH: 705
<212> TYPE: DNA
<213> ORGANISM: Brassica napus
<220> FEATURE:
<221> NAME/KEY: misc_feature
<222> LOCATION: (645)..(645)
<223> OTHER INFORMATION: n is a, g, c, or t

<400> SEQUENCE: 90

```
ggccgacggc gatctgtatc atcgccctgt ggtggaattc ctcctccgag ggtatagaag    60
gaagctaact tggtctgctt gtgaagctaa aatgaaaggc tcgaatttgt tgtaccttcg   120
tccaccgttg acatcaataa caccgaattt cttagaccga acacctctgt tgacgacggg   180
gcaatggaat gtatgaaaaa cttaaggcag tttcaggtta cgtttgcaat ggattattct   240
caattggtga agatggtttt ctgaaccaga tgaatgacca gcatttgaaa gctacctgga   300
agatattaag cttttgcgac gaagtttcgt caactcagat attattcatg ttcatagggc   360
ggagaacata agggcggata gcttggcaca cgtagtactc agaaacaacc gtctttcgtc   420
gtgcatatgg acgcagagtt gccacattgg tttacagagt ctacatgagt ctgtaaatat   480
ttgctgttaa aataataata ataataataa tatatatctg tctatcaatt tttaaaacac   540
aataagttta cggtatattt ttcattgaat agattgtttt caactttcac atgtatttgt   600
atcttcttct atatatatat tttcagatta ttatttcatt attanaatcg taacaatatg   660
tataaaaatt agtaaaatat tgttttgttg tcatattcaa agata              705

<210> SEQ ID NO 91
<211> LENGTH: 693
<212> TYPE: DNA
<213> ORGANISM: Brassica napus

<400> SEQUENCE: 91
agcggcgatc tgattctcgc cctgtggtgg attcttcttt ctttagtctt tccattattc    60
tatgacggtg taattcccta tatataaaag gctccttata tttatgaata atatagaaac   120
atagatttca ttacgactat attattagta tatcagtcta ggcgtttacc aataccaata   180
tacttaatat atttagtata atatcttatg atttacaatt attttcatat gattttgtac   240
tataatatgt caattattat aatttataaa aaacttattc attatttatt attattatta   300
ttataaacct acaacctttc aacttaatta gaattcacaa cctttagaat taattgagat   360
tcttattatt aatagatatt ataatctttt aaatggtata aagataatc accacggtac    420 tagaaagcct agagccaaag caccgcctaa gccgccgcct agaacaatta cctaatttaa   480
agaaaaacta atacttatat ttgattttga aatttttatta aactttgcaa aaaaagaaga   540
agatggaaac atgttagaaa catatatcca aatataaaaa tataagaata atttttataaa  600 aattaatgat taaaaacata tgcaagattt cgtatgaaaa aactattctg cacaaaaata   660
atttataata ttagtttaat atttacatat ttc                                693

<210> SEQ ID NO 92
<211> LENGTH: 729
<212> TYPE: DNA
<213> ORGANISM: Brassica napus
<220> FEATURE:
<221> NAME/KEY: misc_feature
<222> LOCATION: (1)..(1)
<223> OTHER INFORMATION: n is a, g, c, or t
<220> FEATURE:
<221> NAME/KEY: misc_feature
<222> LOCATION: (667)..(667)
<223> OTHER INFORMATION: n is a, g, c, or t

<400> SEQUENCE: 92
nggcgacggc gattgattct cgccctgtgg tggaattcca gtttgaccag gactgtcgta    60
agcttagttt aatttcacca gcagacaccg actcaatagc ccctggaaa aaacacactc    120 aaaccagaag caaatgaact ataatagtcc aagtagaaga aacacaatca atcatccaag   180
```

```
aaaagatact actacatcac caacaatact gctagataat gtaaaaaatg gacagaagaa    240
ataaaactac actggtcttc caccgaaaga gtccaaatag aaacacaagg aataaagcaa    300
aagaaaacta aaattaccat agcactagca agataatgta aaaacctaca ttgatcttct    360
acagaagcag tttgttttat tttttctccg tttagagaat tttggggtgc ttctcacctt    420
attgaacttg acgacgacat ccctgaggca tttccaaccg ccaaaacgga acacaacaga    480
tgctcccagc actcggctaa gaatccatgc aaagaatctt gaacgagtc tggagagtca     540 aaatgaaata ataaataaa tataataata ataataataa taagaccact atagcagcat     600
agtccagcag ctaaatcatg caatctcagc tactgaagga aattagagaa tgtgcaaacc    660
gaactanaat catcactaga actaactcac acgaagatca tccacaagac catggaaaga    720
atcaggaac                                                            729

<210> SEQ ID NO 93
<211> LENGTH: 717
<212> TYPE: DNA
<213> ORGANISM: Brassica napus

<400> SEQUENCE: 93 aacgagagact gatatctcgc cctgtggtgg aattctctga caatagtaga aactaaaaaa     60
tgcaaccatg caatacgtgg ttttataatc attctattgt aaatatgat gataataata    120 ataatgataa taataataat aataataata ataataataa taataataat attacagaat    180
gttgatgtaa taaacaaaaa tagtttgtta gctaacgcct cagatcgatc aatgagtaat    240
tcattcagtt acaacataaa gaaacaaata aaaactatga taaaaaaagt tttgacatca    300
ttttttattg acatgtcaat atgtgataat acactctctg cagcagtgac aaacaaatac    360
tacaaactct tattttttaat cgttcaaaga taagagtcta tactagtaga ctagaaagtg    420 ggggaaaca ataaattta ggaggattca ttgacaattt aagaagacat ttttgatacg      480
cctcgtctta ttagaattgg gaatggccta tggagaggat atgaatgtga tgggcatagt    540
gataaggtag aggagataat gcagaaaagc gagaagaaga atcttaaact atcatttatg    600
aattatgagt taacctcaga aagccagttt acaaaaaaaa aaaattatga tatctccact    660
cgtttctatt aacttattcc tccatgattg gtcgtttttg taaacttctg atgattc       717

<210> SEQ ID NO 94
<211> LENGTH: 702
<212> TYPE: DNA
<213> ORGANISM: Brassica napus

<400> SEQUENCE: 94
agcggagatt gattctcgcc actgtggtgg aattcagtag ctatgtgcta ttagtgcatt      60
gattgttctt ttgtgtggtg taatagacac ctgtttgttc catgctagag ctaggcctaa    120 attttttgtag tgctattaac taagtcagtg gtttgtggtt tagcatccca tacctcactg    180
agtgactccc ttattgctca cccctccttc gttctcccag gtgagaccga caatcatgag    240 tgatttatc ggattggtac ttttgagctt ttatcgttac tgagcttttta gacctttgga    300 cttttatctt ttatgctatt tcatatttca gactttcggt tttatattgc tatctatatt    360
tcagatgtta tcggaccttc tgatattgac ttttgtatta tgaagtggag attattatta    420
ttattattat tattattatt attattacta gattcctttt ccgcgctacg cgcggatagt    480
atcttataaa ttttaaattt attttaaaa aaaaaaatat ttaagttta atttacatta      540 ttttataccaa aaaatcacaa atatggctaa gaattggttg attttatttg tgatttttg    600
```

-continued

| | | |
|---|---|---|
| acaatattaa attgatttat ttattgctca tagttaacag atttgtttga ttggttttca | | 660 |
| gttcatagta atgtatagta ttatatttgg tgagtgtata ta | | 702 |

<210> SEQ ID NO 95
<211> LENGTH: 725
<212> TYPE: DNA
<213> ORGANISM: Brassica napus

<400> SEQUENCE: 95

| | | |
|---|---|---|
| tctcagcgct gagctccatg tggtggaatt catcctaaat ctctttgatg cgattgatct | | 60 |
| cttttataac tcattttgac tcttttggaa ttggaagaga tggactggac ggctattgca | | 120 |
| aagcctttgg aagagatgca aaggagctgg ctattgcaat cttctacgct caagaataag | | 180 |
| aagacatatg tcaagaagaa gaagatatat gcctggactc ttgccttcat cggcgtactt | | 240 |
| gtggttattg catttagttt gaacataaag ctcttagggg ctcatgcata acgctttctt | | 300 |
| aattagctct gttttttcca actgatgttt actctttctg atattattat tattattatt | | 360 |
| attaattgtt agttgctgtt gaccggttga ggctgttttt gagccctgga tatctttctg | | 420 |
| agttgagaaa aatttcataa ccaaatcgag attgttatgt gctctttctt gcctcctttc | | 480 |
| aacaagttta atagaaccaa aggcaaatag tttgtcttta ttctatacta ggattgcgaa | | 540 |
| tccccgcggt ccgcgggggaa aaaagatgt tttaccgcaa aaaaatgat gttaaaactt | | 600 |
| aaatgtaata gtaaaatttt agtttgtaac aatcaaccgg ttgaatggtt aataatcaaa | | 660 |
| tattgcaatg ttaactatta aaattacag tggaacattt aaaagttgtg aatatttata | | 720 |
| taaaa | | 725 |

<210> SEQ ID NO 96
<211> LENGTH: 686
<212> TYPE: DNA
<213> ORGANISM: Brassica napus

<400> SEQUENCE: 96

| | | |
|---|---|---|
| agcggcaatt gtatctcgcc ctgtggtgga attctgtgat gatcaaaaac aagtttcaat | | 60 |
| ccaaatatcc tgattttgca aattatttga caaaatccac atctctaatg gtgttagaac | | 120 |
| actaataaga ttattattat tattattatt attattatta ttattattat tattaacagt | | 180 |
| ctttccaaaa taaatgattg ataaaatatt gaaaagaag gcaaagaaga ggttgagaaa | | 240 |
| caattcttat ttcaaaattt tacaaaaata caaattgttc gcgtaacatt ttcattttct | | 300 |
| atttagttta attttgtca tttaaaatta tcttgttggt gttgttggcg taagcccaaa | | 360 |
| accgatgtag cctacactgg gccaatctcc tgcgcaagcc caagacataa agcattaggg | | 420 |
| ttttgttgct agctcatatg taaacaaaac ttaagctatc ttgttgccta aggttttaag | | 480 |
| ttttctaaga tacaaagctt gtacatacac aagctagatc atagttgtga tcacctctgt | | 540 |
| actctcttat tcatagtgaa gtttgggagg acagtctccc acgagacgta ccggttagag | | 600 |
| gccgggaact cgttaaattg tgtgtgttct tattgcttta gtttaatctc ttcttaaaca | | 660 |
| accataagca tgataagaac tagtta | | 686 |

<210> SEQ ID NO 97
<211> LENGTH: 776
<212> TYPE: DNA
<213> ORGANISM: Brassica napus
<220> FEATURE:
<221> NAME/KEY: misc_feature
<222> LOCATION: (753)..(753)

<223> OTHER INFORMATION: n is a, g, c, or t

<400> SEQUENCE: 97

```
ggaaacggca gtctgatatc atcgccactg tggtggaatt ctaacataac atatgattga      60
tagtacattg tatattctaa ttcaaattaa aaaatataaa tatacaaata taaatcacca     120
atatagtatt tttacatatt aattttataa tgctttattc taatattttc ttatacctac     180
ttattaattt ttaacttatt aattctaatc aatggtctat tctgtattta ttctcataaa     240
gagaaaataa agatctacca gaaattgata tttatgtaca ttcattacat gtacagtaat     300
aagacccaca taatcatttt gttttagcta tggctcgtgt taggaaaaat ctataagatg     360
tatctaatag tgtgttgcaa tactagacta ccagttgatc cagttgtttc aaataattag     420
ttatgtttcg gaactttgt agattggctt attttccatg cagcttttg ttacgacaga      480
acaaattacg cataaacctt taggctgagc aaagttgatg actttaacca agattgagtc    540
ttgaatatgt gtcattacat cgaaatatcg aatgttaaaa atataataat aataataata    600
ataataataa taacaataac gggttcatat atcattacaa ttataacgta atagctgaaa    660
attcaaaatt gactaaaata atattatgac ccgtcccttt ttatggttcc cccgttcgtg    720
tatttgcatt gttggccgtt ggtgatccca tgncgcactt accctccaag tcttca        776
```

<210> SEQ ID NO 98
<211> LENGTH: 760
<212> TYPE: DNA
<213> ORGANISM: Brassica napus

<400> SEQUENCE: 98

```
tctggagctg aagtccatgt ggtggaattc tgatttttga aaaaattaag cgttattttt     60
gtgattttg actttgagtg ctaatttgga acaaaaact tgatttagag atattttgt       120
cttttttct tctccaagcg tgtatcttta tttttatttt ttataattaa acaggcggct     180
ttttatccta attcaattca ggtggggttt tgttcttttta cacatgtcaa ttttgttctt    240
ttaatggtaa aaatttaaga taaattataa actgaaccgg aatcgcaatt ggtaataaac    300
tgaacaaaat tcctaataag atatattcct gaaaaaatcc ccggaagatt ttgatacgta    360
ttaaaatcat attaagtttg aaatatcaag ttttatataa taagatatac attatatgca    420
acatctttga ataactctca acctttggt catatcacaa taaagtggtg gagctttttc     480
cagttactga tgaatgagtt aaaaagtact taagttgcaa taatctattc atattccatg    540
atcaaaagct cttacaagaa acaaaagatt acatgaaaat gtccaaaagg gtactttatt    600
attattatta ttattattat tattatcagg attgagaccc acgtatacgt aataagaaaa    660
tatataacta atagcgaatg ctaccttatg tcatatacac gtaaacacat cccactggtc    720
ttggcaacac aaggtgtcat ccttctctta aacattcaac                          760
```

<210> SEQ ID NO 99
<211> LENGTH: 757
<212> TYPE: DNA
<213> ORGANISM: Brassica napus

<400> SEQUENCE: 99

```
agacggaaat ctgatatcat cgccactgtg gtggaatact aaacaaggca tatagcataa      60
tattatttca tgatataaaa gcaaaaaaaa aatagaataa ttaaatatac aataaaaaaa     120
ataaacaata actaaatata caatagcaaa aatgaaaaaa actaaatgaa acatctatct    180
gaaaaatgta taataaataa ataataagta aatatataat atgagaaata aaaatattac    240
```

-continued

```
actaaatatc tatcgtaata ttaaaataaa aatggaggtg gaggcgttaa tatgggcaat    300
ggagtgtatg aggaatttgc gtcagtttca tgtcacgttt gcaacagatt ttcctcaatt    360
ggtgaagatg gtttgagaac cagaaaaatg accagcattt gaaagttatc tagaagacat    420
caagattttg aaagaaagtt tcatcaactc agagatcatt catgtacctc ggacggagaa    480
tttaagagcg gagagtctag cacgtagtgt caaaaaacat ttgtctttca tcgttcacat    540
ggatttagag ttaccagtta ggtttacaaa gtcggtatga gtctgtaaaa gtcgattaca    600
aaataataat aataataata ataataataa taataagtaa atatatgata caaaaaatag    660
aaaaactaca ttgaaaatgt gtagtaaaat aaataataaa taaatataaa atatgatgac    720
aaaaaaatga caaaaaagta aatataaaat ataacat                             757
```

```
<210> SEQ ID NO 100
<211> LENGTH: 854
<212> TYPE: DNA
<213> ORGANISM: Brassica napus
<220> FEATURE:
<221> NAME/KEY: misc_feature
<222> LOCATION: (340)..(340)
<223> OTHER INFORMATION: n is a, g, c, or t
<220> FEATURE:
<221> NAME/KEY: misc_feature
<222> LOCATION: (459)..(459)
<223> OTHER INFORMATION: n is a, g, c, or t
<220> FEATURE:
<221> NAME/KEY: misc_feature
<222> LOCATION: (581)..(581)
<223> OTHER INFORMATION: n is a, g, c, or t
<220> FEATURE:
<221> NAME/KEY: misc_feature
<222> LOCATION: (584)..(584)
<223> OTHER INFORMATION: n is a, g, c, or t
<220> FEATURE:
<221> NAME/KEY: misc_feature
<222> LOCATION: (615)..(615)
<223> OTHER INFORMATION: n is a, g, c, or t
<220> FEATURE:
<221> NAME/KEY: misc_feature
<222> LOCATION: (623)..(623)
<223> OTHER INFORMATION: n is a, g, c, or t
<220> FEATURE:
<221> NAME/KEY: misc_feature
<222> LOCATION: (681)..(681)
<223> OTHER INFORMATION: n is a, g, c, or t
<220> FEATURE:
<221> NAME/KEY: misc_feature
<222> LOCATION: (686)..(686)
<223> OTHER INFORMATION: n is a, g, c, or t
<220> FEATURE:
<221> NAME/KEY: misc_feature
<222> LOCATION: (701)..(701)
<223> OTHER INFORMATION: n is a, g, c, or t
<220> FEATURE:
<221> NAME/KEY: misc_feature
<222> LOCATION: (718)..(718)
<223> OTHER INFORMATION: n is a, g, c, or t
<220> FEATURE:
<221> NAME/KEY: misc_feature
<222> LOCATION: (722)..(722)
<223> OTHER INFORMATION: n is a, g, c, or t
<220> FEATURE:
<221> NAME/KEY: misc_feature
<222> LOCATION: (725)..(725)
<223> OTHER INFORMATION: n is a, g, c, or t
<220> FEATURE:
<221> NAME/KEY: misc_feature
<222> LOCATION: (733)..(733)
<223> OTHER INFORMATION: n is a, g, c, or t
<220> FEATURE:
<221> NAME/KEY: misc_feature
<222> LOCATION: (741)..(741)
```

<223> OTHER INFORMATION: n is a, g, c, or t
<220> FEATURE:
<221> NAME/KEY: misc_feature
<222> LOCATION: (748)..(750)
<223> OTHER INFORMATION: n is a, g, c, or t
<220> FEATURE:
<221> NAME/KEY: misc_feature
<222> LOCATION: (759)..(759)
<223> OTHER INFORMATION: n is a, g, c, or t
<220> FEATURE:
<221> NAME/KEY: misc_feature
<222> LOCATION: (772)..(772)
<223> OTHER INFORMATION: n is a, g, c, or t
<220> FEATURE:
<221> NAME/KEY: misc_feature
<222> LOCATION: (781)..(781)
<223> OTHER INFORMATION: n is a, g, c, or t
<220> FEATURE:
<221> NAME/KEY: misc_feature
<222> LOCATION: (786)..(786)
<223> OTHER INFORMATION: n is a, g, c, or t
<220> FEATURE:
<221> NAME/KEY: misc_feature
<222> LOCATION: (803)..(803)
<223> OTHER INFORMATION: n is a, g, c, or t
<220> FEATURE:
<221> NAME/KEY: misc_feature
<222> LOCATION: (849)..(849)
<223> OTHER INFORMATION: n is a, g, c, or t
<220> FEATURE:
<221> NAME/KEY: misc_feature
<222> LOCATION: (851)..(851)
<223> OTHER INFORMATION: n is a, g, c, or t
<220> FEATURE:
<221> NAME/KEY: misc_feature
<222> LOCATION: (854)..(854)
<223> OTHER INFORMATION: n is a, g, c, or t

<400> SEQUENCE: 100

```
atacgccaag cttcaatcaa aggagggaag tggtgagaat acaaacctag ccttattctc        60
tctatgtatc ttcctcaact ctgcatcttc caactgtgcc tgaaaaaaga aaagcaaaac       120
ccattagacg ctaagctaat gcaatttcga gtttaatgtt tcagcttaat ccacataaag       180
acggaaacat acctgctcct gggtgaattc ctccggtgca ccgtcggagt ctgaatcgga       240
gttgtgatct ttgttatccg acatctgatt attatcttct tcttcttctt cttcttcttc       300
ttcttcgttg ctttcttctc cctcagacga cacacactan ggtttaacgg ctcttcagtt       360
tctcaaaaac agaagatttc tattctgaga gttaattgct tctctccttt atggtggatt       420
ctattgggaa gcttgcatgc ctgcaggtcg actctagang atccccgggt accgagctcg       480
aattcactgg ccgtcgtttt acaacgtcgt gactgggaaa acctggcgt tacccaactt        540
aatcgccttg cagcacatcc cctttcgcca gctggggtta ntancgaaaa ggccgcaccg       600
atcgccttcc aacanttgcg canctgaatg gcgaatggcg cctgatgcgg tattttctct       660
tacctctgtg cggtatttcc nccgcntatg gtgcctctca ntacaatctg cctgatgncg       720
cntanttaac cancccgaaa nccgccannn ccgctgaanc ccctgaaggg gntgttcggc       780
nccggnatcc gctttaaaaa aanctgttaa cgtctccgga accgcttttt tcaaggtttt       840
cccgtctcnc naan                                                          854
```

<210> SEQ ID NO 101
<211> LENGTH: 876
<212> TYPE: DNA
<213> ORGANISM: Brassica napus
<220> FEATURE:
<221> NAME/KEY: misc_feature
<222> LOCATION: (5)..(6)
<223> OTHER INFORMATION: n is a, g, c, or t

```
<220> FEATURE:
<221> NAME/KEY: misc_feature
<222> LOCATION: (581)..(581)
<223> OTHER INFORMATION: n is a, g, c, or t
<220> FEATURE:
<221> NAME/KEY: misc_feature
<222> LOCATION: (611)..(611)
<223> OTHER INFORMATION: n is a, g, c, or t
<220> FEATURE:
<221> NAME/KEY: misc_feature
<222> LOCATION: (623)..(623)
<223> OTHER INFORMATION: n is a, g, c, or t
<220> FEATURE:
<221> NAME/KEY: misc_feature
<222> LOCATION: (687)..(687)
<223> OTHER INFORMATION: n is a, g, c, or t
<220> FEATURE:
<221> NAME/KEY: misc_feature
<222> LOCATION: (697)..(697)
<223> OTHER INFORMATION: n is a, g, c, or t
<220> FEATURE:
<221> NAME/KEY: misc_feature
<222> LOCATION: (702)..(702)
<223> OTHER INFORMATION: n is a, g, c, or t
<220> FEATURE:
<221> NAME/KEY: misc_feature
<222> LOCATION: (713)..(713)
<223> OTHER INFORMATION: n is a, g, c, or t
<220> FEATURE:
<221> NAME/KEY: misc_feature
<222> LOCATION: (737)..(737)
<223> OTHER INFORMATION: n is a, g, c, or t
<220> FEATURE:
<221> NAME/KEY: misc_feature
<222> LOCATION: (799)..(799)
<223> OTHER INFORMATION: n is a, g, c, or t
<220> FEATURE:
<221> NAME/KEY: misc_feature
<222> LOCATION: (806)..(806)
<223> OTHER INFORMATION: n is a, g, c, or t
<220> FEATURE:
<221> NAME/KEY: misc_feature
<222> LOCATION: (818)..(818)
<223> OTHER INFORMATION: n is a, g, c, or t
<220> FEATURE:
<221> NAME/KEY: misc_feature
<222> LOCATION: (828)..(828)
<223> OTHER INFORMATION: n is a, g, c, or t
<220> FEATURE:
<221> NAME/KEY: misc_feature
<222> LOCATION: (841)..(841)
<223> OTHER INFORMATION: n is a, g, c, or t
<220> FEATURE:
<221> NAME/KEY: misc_feature
<222> LOCATION: (846)..(846)
<223> OTHER INFORMATION: n is a, g, c, or t
<220> FEATURE:
<221> NAME/KEY: misc_feature
<222> LOCATION: (849)..(850)
<223> OTHER INFORMATION: n is a, g, c, or t
<220> FEATURE:
<221> NAME/KEY: misc_feature
<222> LOCATION: (864)..(865)
<223> OTHER INFORMATION: n is a, g, c, or t

<400> SEQUENCE: 101
cgccnngctt cctttaagag ttaatttcat acaaataagc ccactaaaca gcgttgttta      60
aactttaaac cctgtcttct taccaaagct cctcttctta catagtagct ctgctaaacc    120
ttcgccgcaa taaacccaaa gtcgtaagaa accgtcgcca tgcctgctct tacgcgtaac    180
aagcagaagg gagctaagtc gcagactcct ccactgatta agcggactaa atcgaatccc    240
acgcctccac cgaagaaggc gatgaagtcc cgtaagcctc cgttgaagaa acagaggaaa    300
ggtgtttcgg atgagaagcc tgaagtttct aatgatgagg aggaagagga agaagaagaa    360
```

```
gaagaagaag tgagtgaaga gtctgatgac gggagatgaa ttgggttctg acctttctc     420 agatggtgac gaagaagaag aagaagaaga agaagaagat gatatagagc cttcggatga     480
cgactttctt ggtggtagcg atgaggaaaa gggaactttg ggttctgatt ctgactctga     540
tgagtcagat aagcttgcat gcctgcaggt cgactctaga ngatcccggg taccgagctc     600
gaattcctgg ncgtcgtttt acnacgtcgt gactgggaaa acctggcgtt accacttaat     660
cgccttgcag cacatcccct ttcgccngct ggcgttntac cnaaaaggcc gcnccgatcg     720
ccttccacag ttgcgcncct gaatggcgaa tggggcctgg atgcggtttt ttcccttcc     780 cctctgttgc ggttttccnc cgcctntggt gcctctcntt catctgcnct gatgccctt     840 ntttanccnn cccgaacccg ccannccgt gaaccc                                876
```

<210> SEQ ID NO 102
<211> LENGTH: 547
<212> TYPE: DNA
<213> ORGANISM: Brassica napus
<220> FEATURE:
<221> NAME/KEY: misc_feature
<222> LOCATION: (531)..(531)
<223> OTHER INFORMATION: n is a, g, c, or t

<400> SEQUENCE: 102

```
atctctatcg ctatacttgt cactttgttc actttctcag cagttccttc cacatggtga     60
tgcaaccatc tcgccattac actcagcaag cctcccttag ccttcttgca tcgttctgac     120
ctgtcgttat atccataatt ctttgcaatt tttgtcattc tcttcttctt cttcttcttc     180
ctcttcctct tcctcttcct cttcctcttc ttctttatga acatgagcag ccatttcctg     240
tcaactcttt gacggatgtg caccaattga caagagctta ctctgttaca ccactccaac     300
aaactcttcc ttcgtctctt agatattttc tccatttgta ttcccagtgt ctcaaagtta     360
tcattatcct tttcgctcaa agtatcatcc aaatgctttt caatatctag aaaagttttt     420
ttccatctct ttctcttcct tgttactctt acacctccct caaccatttg atcgaacaca     480
tggtgggcat acttctcctt cttggtctca agcaactcct ctcttgcatc nttaccctc    540 tcaaagt                                                              547
```

<210> SEQ ID NO 103
<211> LENGTH: 313
<212> TYPE: DNA
<213> ORGANISM: Brassica napus
<220> FEATURE:
<221> NAME/KEY: misc_feature
<222> LOCATION: (134)..(134)
<223> OTHER INFORMATION: n is a, g, c, or t

<400> SEQUENCE: 103

```
cggcaataat ggaccactgg tttggttgaa ccactaaaaa gagtgcgtgt gtgtgtgtgt     60
gtgtgtgtgt gtgagggact ctatttaaaa gcactgctta actcaataat tattccatcg    120
ctccaaaata aanagaata gctaaaagat ggctctcgaa gtctgcgtga aagccgccgt    180
tggtgcccct gatgctctcg gcgactgtaa cttcccttct ctctctctag ctctttttt    240 ttatatcaga ttatgatctc tgatgatctt caaatgtaaa atttataata catgatttgt    300
ctgtcgtttc agg                                                       313
```

<210> SEQ ID NO 104
<211> LENGTH: 438
<212> TYPE: DNA
<213> ORGANISM: Brassica napus

<400> SEQUENCE: 104

```
ccgataagag ccatcatctc gaggaggggt attaagggat atgtatccca cattggaaaa      60
tcaatgggac attaagtaat atataaaggg ttagggccaa tccactaata gccaattggt     120
tttgagttgg aagcccataa taaacccgaa tctaacaaga ttttagattg attaaggaaa     180
ttaatatatt atatgcaata tttcatggtt aacgtcaaaa taagtccaat ttataaacaa     240
gcggataaac atttccctat atatgggaa aggtttgtgg ttgccaaact caaagcacat      300
tgggtcttat ctctctctaa cacacacaca cacacacaca aactcacgta tatatttaga     360
gctagagaga gagatgggtg aagagatgaa agaagtgaga gtaatcgagg agtggtctcc     420
ggttatagta atggtgat                                                    438
```

<210> SEQ ID NO 105
<211> LENGTH: 485
<212> TYPE: DNA
<213> ORGANISM: Brassica napus

<400> SEQUENCE: 105

```
cctcctgtgc caagttttac aaggcaccca acctgtgaac ctaaattgct ttgaaagaga      60
agtttctcta tctatatcac acacacacac acacacacaa atctaatctt tctctttcaa     120
ccgtaaattt tgctcaccac caaggcaagt ttccttcttt tgctccccta gcaatattaa     180
ttgctactaa aatatcttgc taagggtaac caaatcttgc ttcattcctc tgtaatatca     240
cagaaagaaa ctaaaattta gggttttttt tgggttcctt tccatgtgat gtgagcattt     300
ttgggtgaga aagatgaaga ctataattaa gttagggatt gggttgagtt tggtgtttgg     360
gtttcttctc ttagcactta ttgcagaagt ctattacctt ctgagatgga agaagcacaa     420
gaagagagtc ataagccaag agagtgagga agagaaagaa gaagagcaac aacaacaaac     480
tgggt                                                                  485
```

<210> SEQ ID NO 106
<211> LENGTH: 891
<212> TYPE: DNA
<213> ORGANISM: Brassica napus
<220> FEATURE:
<221> NAME/KEY: misc_feature
<222> LOCATION: (537)..(537)
<223> OTHER INFORMATION: n is a, g, c, or t
<220> FEATURE:
<221> NAME/KEY: misc_feature
<222> LOCATION: (573)..(573)
<223> OTHER INFORMATION: n is a, g, c, or t
<220> FEATURE:
<221> NAME/KEY: misc_feature
<222> LOCATION: (599)..(599)
<223> OTHER INFORMATION: n is a, g, c, or t
<220> FEATURE:
<221> NAME/KEY: misc_feature
<222> LOCATION: (614)..(614)
<223> OTHER INFORMATION: n is a, g, c, or t
<220> FEATURE:
<221> NAME/KEY: misc_feature
<222> LOCATION: (616)..(616)
<223> OTHER INFORMATION: n is a, g, c, or t
<220> FEATURE:
<221> NAME/KEY: misc_feature
<222> LOCATION: (633)..(633)
<223> OTHER INFORMATION: n is a, g, c, or t
<220> FEATURE:
<221> NAME/KEY: misc_feature
<222> LOCATION: (652)..(652)
<223> OTHER INFORMATION: n is a, g, c, or t
<220> FEATURE:

```
<221> NAME/KEY: misc_feature
<222> LOCATION: (674)..(674)
<223> OTHER INFORMATION: n is a, g, c, or t
<220> FEATURE:
<221> NAME/KEY: misc_feature
<222> LOCATION: (676)..(676)
<223> OTHER INFORMATION: n is a, g, c, or t
<220> FEATURE:
<221> NAME/KEY: misc_feature
<222> LOCATION: (681)..(681)
<223> OTHER INFORMATION: n is a, g, c, or t
<220> FEATURE:
<221> NAME/KEY: misc_feature
<222> LOCATION: (740)..(740)
<223> OTHER INFORMATION: n is a, g, c, or t
<220> FEATURE:
<221> NAME/KEY: misc_feature
<222> LOCATION: (747)..(747)
<223> OTHER INFORMATION: n is a, g, c, or t
<220> FEATURE:
<221> NAME/KEY: misc_feature
<222> LOCATION: (760)..(760)
<223> OTHER INFORMATION: n is a, g, c, or t
<220> FEATURE:
<221> NAME/KEY: misc_feature
<222> LOCATION: (765)..(765)
<223> OTHER INFORMATION: n is a, g, c, or t
<220> FEATURE:
<221> NAME/KEY: misc_feature
<222> LOCATION: (779)..(779)
<223> OTHER INFORMATION: n is a, g, c, or t
<220> FEATURE:
<221> NAME/KEY: misc_feature
<222> LOCATION: (781)..(781)
<223> OTHER INFORMATION: n is a, g, c, or t
<220> FEATURE:
<221> NAME/KEY: misc_feature
<222> LOCATION: (789)..(789)
<223> OTHER INFORMATION: n is a, g, c, or t
<220> FEATURE:
<221> NAME/KEY: misc_feature
<222> LOCATION: (828)..(828)
<223> OTHER INFORMATION: n is a, g, c, or t
<220> FEATURE:
<221> NAME/KEY: misc_feature
<222> LOCATION: (831)..(831)
<223> OTHER INFORMATION: n is a, g, c, or t
<220> FEATURE:
<221> NAME/KEY: misc_feature
<222> LOCATION: (833)..(833)
<223> OTHER INFORMATION: n is a, g, c, or t
<220> FEATURE:
<221> NAME/KEY: misc_feature
<222> LOCATION: (839)..(840)
<223> OTHER INFORMATION: n is a, g, c, or t
<220> FEATURE:
<221> NAME/KEY: misc_feature
<222> LOCATION: (845)..(846)
<223> OTHER INFORMATION: n is a, g, c, or t
<220> FEATURE:
<221> NAME/KEY: misc_feature
<222> LOCATION: (853)..(853)
<223> OTHER INFORMATION: n is a, g, c, or t
<220> FEATURE:
<221> NAME/KEY: misc_feature
<222> LOCATION: (857)..(857)
<223> OTHER INFORMATION: n is a, g, c, or t
<220> FEATURE:
<221> NAME/KEY: misc_feature
<222> LOCATION: (863)..(863)
<223> OTHER INFORMATION: n is a, g, c, or t
<220> FEATURE:
<221> NAME/KEY: misc_feature
<222> LOCATION: (866)..(866)
<223> OTHER INFORMATION: n is a, g, c, or t
<220> FEATURE:
<221> NAME/KEY: misc_feature
<222> LOCATION: (877)..(877)
<223> OTHER INFORMATION: n is a, g, c, or t
```

```
<220> FEATURE:
<221> NAME/KEY: misc_feature
<222> LOCATION: (891)..(891)
<223> OTHER INFORMATION: n is a, g, c, or t

<400> SEQUENCE: 106
tacccaagct tccacgatcg gagggatcta tcgggacttc tcggagattt gtttcacggt      60
gatgtctatt gatctttggc tctctgtttc gattgttgtt gtcttcttct tcttctttt     120 cttcttcttc tcgagaggtt gcggggtttt gaaatcgtct ccttcgtcca tgtagtcgtt    180
ttggtgtttg tccgccatga gagagagaga gagagagaga gagagagaga gagagagaga    240
gcgaagacgt tacgaaaaac ttcgatagag agtataagag agagatgctg aaactgctta    300
aaccctaatt ttgatcgagt gtgttttggg aaatttgcag agtaagtcct tatatttgag    360
ccgaattaat taaagtaagc ttgcatgcct gcaggtcgac tctagaggat ccccgggtac    420
cgagctcgaa ttcactggcc gtcgttttac aacgtcgtga ctgggaaaac cctggcgtta    480
cccaacttaa tcgccttgca gcacatcccc ctttcgccag ctggcgttat agcgaaagg     540 cccgcaccga tcgcccttcc caacagttgc gcnccctgaat ggcgaatggc cctgatgcng   600
tatttctcct tacncntctg tgcggtattc ccnccgcata tggtgcctct cnttacatct    660
gctctgaagc cgcntnttta nccagcccga cacccgccaa cacccgctga cccccctgaa    720
gggcttgtct gccccccgggn tcccttncaa acaactgttn accgnccccg ggaaccgcnt   780
ntttcaaang tttcccccgc ctccccgaaa ccccccaaaaa aagggggcnct nanaccccnn  840 ttttnngggt tangtcngaa aanaanggtt cctaaanttc gggggggcctt n            891

<210> SEQ ID NO 107
<211> LENGTH: 485
<212> TYPE: DNA
<213> ORGANISM: Brassica napus

<400> SEQUENCE: 107
atctaggacc ccatgatccg aataaggata ataaaaaaat ggatctgccg aataagtatc      60
tggataactt aaaattccct agataccccc ccccgccac acacacacac acacacacac     120 atcaatttc cttgtaattt ttctcttgtt ctctattttt ctaaactcca ataaagcaag     180
tctttaacat atactccacc tttatttgag taaataatca tggatttaat ctctaaagtg    240
aaggacactt tgtttatgtt ttctgttttt ctaaattgta aaatctatt tctacctttt     300 taatgtgcta atttaggaa aaattatatc aatattttgt gtcgtaatta aatctgtcaa     360
catgaagtaa atctgtgtca aaagaaaaa aaatctata gaaacataat taagtaaat      420 gtatgaacat ataaaataaa tctatgaatg atgtataaat ctatcaaaat taaataaata   480
tgtgg                                                                485

<210> SEQ ID NO 108
<211> LENGTH: 447
<212> TYPE: DNA
<213> ORGANISM: Brassica napus

<400> SEQUENCE: 108
ctttaatgct taagctcgt tccagctcag gggttgggag tttaagccta aaactcgaga      60
tctgctcatc cgcagttgct gatttggcag cttattcacc ttcgcatacc tacaaatcaa    120
cgaatacaac gcaaacgttc ctcctgcaca cacacacaca cacacacata tacttagaac    180
cacataacac cactttttac aaaaaaaaac aaggattagg gatgtaatat tattaccttc    240
```

```
gccattgtcg ttggctttaa ggacaacaaa gacatacttt gctaaaggaa tgacagcaat      300
ggtgtagata acgagagaca aggcaccaag aacatcaact tctgatctga taggaacttt      360
actgaagaca tcactaaaca catacaaagg gcttgttccc atgtctccat acacaacacc      420
taacgtctga aacgctatcc caatcgt                                          447

<210> SEQ ID NO 109
<211> LENGTH: 531
<212> TYPE: DNA
<213> ORGANISM: Brassica napus

<400> SEQUENCE: 109
actcaataac atcaggcttt tctggatgca atcttgcatt ggtttggtcc agtttgcatc       60
gggacaaata ttgttgctgg tgtatatggg atcggaatct ttgctccgac attctcttcg     120
gtgtcttcat catcatcatc atcatcatca tcatcatcat catcatcagt atcagtatca     180
tctcttattc caaacttctt atattgtaga tgttcttgac cggagtggca aatgaagaca     240
tctcatatat ggcattgctt ttagggtttt taagaagatg tggtgttgct atgttggtct     300
ttgatgcaac cacggtggtc ggaatgggcg agaatggtct gcaaactaat ggagattgta     360
ggtgttcaca tgggttcatc gactattact ttgggagaag tccaacaaca tcaagccctc     420
ttcttcctgc aggaaaataa aatatttcgt tcatcaatta agtaagaga attaactcat      480 cactatggtg atatgttagt ttctgtttat tgtaagactt aaaattacca g              531

<210> SEQ ID NO 110
<211> LENGTH: 683
<212> TYPE: DNA
<213> ORGANISM: Brassica napus
<220> FEATURE:
<221> NAME/KEY: misc_feature
<222> LOCATION: (33)..(33)
<223> OTHER INFORMATION: n is a, g, c, or t
<220> FEATURE:
<221> NAME/KEY: misc_feature
<222> LOCATION: (587)..(587)
<223> OTHER INFORMATION: n is a, g, c, or t
<220> FEATURE:
<221> NAME/KEY: misc_feature
<222> LOCATION: (638)..(638)
<223> OTHER INFORMATION: n is a, g, c, or t

<400> SEQUENCE: 110
acaaaaccgc ttccacctgc gtttcgtcgc agncaagcat ttgcgtttca ttgggttttc       60
tcggtgaacc aagctcgcgt tagtatccaa acatgttttc acagaatctc gtagtaacga     120
catttcttgt tgaagttgtt ggatctgtgt tctcatttcg cttatcagct ccatttcctg     180
aaacgttttt aattaagcgg ttcaatgatt ctcttctatg gggataacaa taaaatctaa     240
aaaccttaca ggtgacggag ggttgtgaac agacaagaca ggagttgaag ttacttcagt     300
gtcttgacaa ctccatgatc ctgcaggaga cgatgcaaag atcggcgaag aagacgagtc     360
atctccatcg tcttgctctt caccttcttc agtaaatggc tcttcttctt cttcttcttc     420
ttcttcttct tcttcttctt cttcagttcc tccacatttt cattctatgg tcttcctctt     480
cttcttcatg ttgcaattcc catttttcag aatgtttgtt cgaatgtgtc tgcacacgag     540
acatcatgag cctatcgatc tgatctctta accggtctg ggagaangtc tgtgaccggt      600
cctctgtaat atccaaaaac cacacatttt tcttagtnaa tgggtaccca attaggaaaa     660
tgggatttaa aagattggat cag                                            683
```

-continued

<210> SEQ ID NO 111
<211> LENGTH: 356
<212> TYPE: DNA
<213> ORGANISM: Brassica napus

<400> SEQUENCE: 111

```
aatgaacgag acaggaggtg ccaccctatt gtctttgatg gaccagagtc tagctatccg    60
gtaaacagta ttttataaca aagacatgat catgaaatga ttttttttctt ctgaagttta   120 actgatgact catatatcta tatctgacta gttcatcgtg gacatggagc attcacagga   180
ccagagcaca catcgaagct gacatacaaa tgaatctctt attgcctcta gtttcacacg   240
taaatattca gtttctagga tgatgatgat gaattgatga tgatgatgac gatgatgatc   300
agtcaaaagt actgtaaatt gatggttatg gttgtcttgg ctttgcttaa tcatgt       356
```

<210> SEQ ID NO 112
<211> LENGTH: 753
<212> TYPE: DNA
<213> ORGANISM: Brassica napus
<220> FEATURE:
<221> NAME/KEY: misc_feature
<222> LOCATION: (494)..(494)
<223> OTHER INFORMATION: n is a, g, c, or t
<220> FEATURE:
<221> NAME/KEY: misc_feature
<222> LOCATION: (527)..(527)
<223> OTHER INFORMATION: n is a, g, c, or t
<220> FEATURE:
<221> NAME/KEY: misc_feature
<222> LOCATION: (579)..(579)
<223> OTHER INFORMATION: n is a, g, c, or t
<220> FEATURE:
<221> NAME/KEY: misc_feature
<222> LOCATION: (630)..(630)
<223> OTHER INFORMATION: n is a, g, c, or t
<220> FEATURE:
<221> NAME/KEY: misc_feature
<222> LOCATION: (635)..(635)
<223> OTHER INFORMATION: n is a, g, c, or t
<220> FEATURE:
<221> NAME/KEY: misc_feature
<222> LOCATION: (643)..(643)
<223> OTHER INFORMATION: n is a, g, c, or t
<220> FEATURE:
<221> NAME/KEY: misc_feature
<222> LOCATION: (645)..(645)
<223> OTHER INFORMATION: n is a, g, c, or t
<220> FEATURE:
<221> NAME/KEY: misc_feature
<222> LOCATION: (647)..(647)
<223> OTHER INFORMATION: n is a, g, c, or t
<220> FEATURE:
<221> NAME/KEY: misc_feature
<222> LOCATION: (660)..(660)
<223> OTHER INFORMATION: n is a, g, c, or t
<220> FEATURE:
<221> NAME/KEY: misc_feature
<222> LOCATION: (662)..(662)
<223> OTHER INFORMATION: n is a, g, c, or t
<220> FEATURE:
<221> NAME/KEY: misc_feature
<222> LOCATION: (679)..(679)
<223> OTHER INFORMATION: n is a, g, c, or t
<220> FEATURE:
<221> NAME/KEY: misc_feature
<222> LOCATION: (682)..(682)
<223> OTHER INFORMATION: n is a, g, c, or t
<220> FEATURE:
<221> NAME/KEY: misc_feature
<222> LOCATION: (693)..(693)
<223> OTHER INFORMATION: n is a, g, c, or t
<220> FEATURE:
<221> NAME/KEY: misc_feature
<222> LOCATION: (697)..(697)

```
<223> OTHER INFORMATION: n is a, g, c, or t
<220> FEATURE:
<221> NAME/KEY: misc_feature
<222> LOCATION: (707)..(707)
<223> OTHER INFORMATION: n is a, g, c, or t
<220> FEATURE:
<221> NAME/KEY: misc_feature
<222> LOCATION: (714)..(714)
<223> OTHER INFORMATION: n is a, g, c, or t
<220> FEATURE:
<221> NAME/KEY: misc_feature
<222> LOCATION: (716)..(716)
<223> OTHER INFORMATION: n is a, g, c, or t
<220> FEATURE:
<221> NAME/KEY: misc_feature
<222> LOCATION: (729)..(729)
<223> OTHER INFORMATION: n is a, g, c, or t
<220> FEATURE:
<221> NAME/KEY: misc_feature
<222> LOCATION: (731)..(731)
<223> OTHER INFORMATION: n is a, g, c, or t
<220> FEATURE:
<221> NAME/KEY: misc_feature
<222> LOCATION: (737)..(737)
<223> OTHER INFORMATION: n is a, g, c, or t
<220> FEATURE:
<221> NAME/KEY: misc_feature
<222> LOCATION: (741)..(742)
<223> OTHER INFORMATION: n is a, g, c, or t
<220> FEATURE:
<221> NAME/KEY: misc_feature
<222> LOCATION: (748)..(748)
<223> OTHER INFORMATION: n is a, g, c, or t
<220> FEATURE:
<221> NAME/KEY: misc_feature
<222> LOCATION: (750)..(750)
<223> OTHER INFORMATION: n is a, g, c, or t

<400> SEQUENCE: 112
acaagttacc atttgaggat atatcagaga agaaggagtt gcttgaagat gacgagaaaa      60
ccaaaaagaa gatgagttct aatggtcgtt ggtacgagga gcttgatgtc ttcatagaga     120
aacctgaaac tggtgttctt actggtgatg gtgctgtggt ggacgcatga ctgggaacga     180
acctgttgat ggtgacgagt tggatgttga gcaacaagat gataattctg atggtgatca     240
tggtgatcat gaagcaggag agagtgaaga tgagtatcaa gcgagtgatg aatctgataa     300
agaagaggat attgacagaa attttgaaga ggatgttgag atgttccagg gatgagaact     360
acgatggagg agattccaga cgaggaggag gtatattctg acacggagga gtcatctgat     420
gatgaagagg aacaagctga gaaggatgct aatagggtg aattagatgg cattttttaag    480 tcttaggcag gaanttgcaa tgcctgcaag tcgacctcta gaggatnccc gggtaccgag     540
ctcgaatttc cactgggccg tccgttttac aacgtccgng actgggaaaa accctggggt     600
taacccaact taatcgcctt tcagcacatn ccccnttcgc cangntnggg gtaatagccn     660
anaaggcccg caaccgatng gnccttttcc aanagtngcc gcacctnaaa tggngnattg     720
gcgccttang ngggaanttt nnccttangn att                                  753

<210> SEQ ID NO 113
<211> LENGTH: 547
<212> TYPE: DNA
<213> ORGANISM: Brassica napus

<400> SEQUENCE: 113
acataagccc tttttattat ctctgcatat cattacattc attttatgtc acatatgttt      60
attgctcttc tcttcagatt actattacat cgcaagtaaa acaaaagagt tagaaaataa     120
agtaaacact ccatacatag tcaaagtatc tccattactc ctcttcttcg tgttaacaag     180
```

```
tctttaggcg tttctaaacc gcagaaacca tcatagccgg tgatgcacca accatcaagt      240
cttcttcttc ttcatcatca tcatcatcat catcctctgc ttcccacatg aaatgagcgt      300
atgatcccaa aaccatacta caaaagtcac aaaccttaa cattctgaaa aaaaaactca       360
tcaaagaatc caaactctac atataacata acataccaat catcaggaga agcgttaaca     420
gcttgatcaa agtaacactg agctctcttc tcatctctct tcgtctccca aatcagcttc     480
ccatacatcg acaacgcttc accatcacct ggatccgcaa gtatagctct cccgtaatac     540
tcctccg                                                               547
```

<210> SEQ ID NO 114
<211> LENGTH: 386
<212> TYPE: DNA
<213> ORGANISM: Brassica napus
<220> FEATURE:
<221> NAME/KEY: misc_feature
<222> LOCATION: (350)..(350)
<223> OTHER INFORMATION: n is a, g, c, or t

<400> SEQUENCE: 114

```
cttagtgacc caaaagccat tggtgtatga tagaaaagtt agttaaatac cgttactcgc      60
aaggaagacc acacattttt taattctatc tcacttagtc agaccagctc ggatccttct     120
ctagaaccac acacacacac acacactcag agtgagagat tcatcaatgg cggtttcttg     180
cagccactca tcgattctct tgcccccaac cacctcctcc gttggcttca accgcttccc     240
ttgtctccaa acgctgcgtt tcaaatccag aaacgtttat cagaaagcga ggatctctac     300
agtgtcggcg tcatcttcac ggtctctcga agctctgatc ttcgactgcn acggtgtgat    360
actcgaatcg gagaatctac accgtc                                          386
```

<210> SEQ ID NO 115
<211> LENGTH: 319
<212> TYPE: DNA
<213> ORGANISM: Brassica napus
<220> FEATURE:
<221> NAME/KEY: misc_feature
<222> LOCATION: (222)..(222)
<223> OTHER INFORMATION: n is a, g, c, or t

<400> SEQUENCE: 115

```
tcaaagagca cttacaagga tccagacgat ggaaggcaac gattcttact cgaacttgag      60
ttcattcagt gtctcgcgaa tcctacttac atacactgta agctcttatg attccttatc     120
acatagtatc tacttatagc atttaggaag tgataagaga tcttgtgtgt gtgtgtgtgt     180
gtgtgtttta tgctctatga tgaacttacc acttagcttt tngattctgt tttggcagac     240
ctagcacaga atcgttattt tgaagatgaa gcatttattg aatacttgaa gtatcttcag     300
tattggcagc gaccagagt                                                  319
```

<210> SEQ ID NO 116
<211> LENGTH: 545
<212> TYPE: DNA
<213> ORGANISM: Brassica napus

<400> SEQUENCE: 116

```
acttcagtgg tcgaaaatca aaatattctt ccatcatttt agttttttt tttctctatg       60 ttcgcatcaa gaaacgaaa tgaaagggat tataaaagga agaagaactt gtgaatcacg      120
gtaagtttcg gggtttgttg tgaggagatt tcgagagaat caagaataaa attatatcac     180
```

```
gagattttt  tgtttgaagt  gagaaagaaa  tcaaagattt  tatttttct   cttttggtga   240 gtgatagaga  gagagagaga  gagagagaga  gagagagaga  gagagagaga  gagagagaga   300
gagagagaga  gagagagaga  gagagagaga  cgtgttttgg  aactacggtg  attttactac   360
ttttgatgat  gttttcaact  ttgaagaaga  ccttctctca  tgctcactct  tagcatcctc   420
ctcatttata  ggattagatg  ggagagagag  agcgttttag  ccattaatac  tttaataaca   480
aaatgaaaaa  tctgatatta  acatttcttt  tttcacttct  ccatcagtgg  cattttcgat   540
atttt                                                                   545
```

```
<210> SEQ ID NO 117
<211> LENGTH: 350
<212> TYPE: DNA
<213> ORGANISM: Brassica napus

<400> SEQUENCE: 117
acctcctgat  gactgcttaa  acagcgcctg  cgaagatctg  gattctgtag  ttaaccaggc    60
tagggagttc  ttagaggact  ggtccccaaa  gttgagcaag  ctctttggtg  taagttgatg   120
aacaagctct  cattttcagt  tttctttctc  tctctctctc  tctctctctc  tctctctctc   180
tctctctctc  tctctctctc  tctctctctc  tctctttgca  tcattcattg  agttgtgtgt   240
gtgcaggtgt  ttcactccga  gcttttgttg  gagaaggtcc  agacttgttc  actggagatt   300
aatcgcatac  ttcttcagtt  atcacagtca  agtcctgtaa  cttcaagtgt                350
```

```
<210> SEQ ID NO 118
<211> LENGTH: 219
<212> TYPE: DNA
<213> ORGANISM: Brassica napus

<400> SEQUENCE: 118
acagaaacag  taacatcaac  acacacaaca  aacagctcgc  gaaatgaatt  acagattcct    60
ctccgaaatc  aaaacaggaa  acggacacag  agagagagag  agagagagag  agagagagag   120
agagagatga  gaaggtgata  ccgtcgagag  gtttgatgtt  gccgtcgcgg  cgatcgacgg   180
agaagccttc  atgaggcgaa  tcgacgggtt  tgacgacgt                            219
```

```
<210> SEQ ID NO 119
<211> LENGTH: 544
<212> TYPE: DNA
<213> ORGANISM: Brassica napus

<400> SEQUENCE: 119
acagacgcga  tgatgacact  tctggtccta  agcgttgtgt  tacgtttgat  actcctgcgc    60
ttgtttactt  ggagtattct  gatgtggttg  ctgataagta  tgagaatctg  agtttggaca   120
gcttggttga  agttaggctt  gatcttcagt  tgactgcaga  tcaaatcatg  cgcaagaatg   180
ctacagacag  tgttggtttt  gttcccggtg  atgtttcaac  tttgttcatg  ggggtcaaga   240
acgtcaagat  cctctgctta  tctcctgatt  ctttagatgt  gagtccagtc  cttttttaagt  300 tagcttcatc  actgtgtagc  atttgttttt  tttttaaatt  tgattggtta  gtgatgatac   360
aaaatatttg  attctggtgt  gtgtgtgtgt  gtttgtgaaa  gttcagtccc  tttaacttag   420
cttcatgagt  gtgtagcctt  tgttttttaa  ttggttactg  atgatatggt  gtgtgtgtgt   480
gtgtgtgtgt  ttcagacgct  ctactaccgt  ggtggtgaca  tgccggtgtt  caacaatctg   540
attt                                                                    544
```

<210> SEQ ID NO 120
<211> LENGTH: 562
<212> TYPE: DNA
<213> ORGANISM: Brassica napus

<400> SEQUENCE: 120

| | | | | | |
|---|---|---|---|---|---|
| acatgagaac | aagatgggtt | cgaattacct | ctagcctaga | tctggatctg | gaaacaagag | 60 |
| acaagggaga | gacgagatct | tgtcaccacc | accaatcggc | tgccaccacc | accaccacaa | 120 |
| cacggcgcca | gcgaaaggga | gatagagaga | gagagagaga | gagagagaga | gagagagaga | 180 |
| gagagagaga | gagagagaga | gagagagaga | gagagaagaa | gaagaagaga | gaaaaggaaa | 240 |
| agagaagctt | gatggctagg | gtttcttagt | ctctctaaat | ctctgcaggg | ctttgctcaa | 300 |
| gtttcagaat | gagagaaaaa | agagaggagg | caactttatt | tataggaaat | ggagggaacc | 360 |
| ctaggtcatt | taccttaatg | ggctgcagtc | ctaacgagct | ctcgttaaaa | aaatttgggc | 420 |
| cgggtatcgg | gatgttacac | taacggtgtg | tggcgatgaa | ggctcttcga | ctctcaaaat | 480 |
| taatgatgtc | cataactaaa | taaaaactac | tcgactttat | taagatatag | cttcaatgat | 540 |
| ttaaaattaa | atatagaact | ct | | | | 562 |

<210> SEQ ID NO 121
<211> LENGTH: 193
<212> TYPE: DNA
<213> ORGANISM: Brassica napus
<220> FEATURE:
<221> NAME/KEY: misc_feature
<222> LOCATION: (5)..(5)
<223> OTHER INFORMATION: n is a, g, c, or t
<220> FEATURE:
<221> NAME/KEY: misc_feature
<222> LOCATION: (90)..(90)
<223> OTHER INFORMATION: n is a, g, c, or t
<220> FEATURE:
<221> NAME/KEY: misc_feature
<222> LOCATION: (100)..(100)
<223> OTHER INFORMATION: n is a, g, c, or t
<220> FEATURE:
<221> NAME/KEY: misc_feature
<222> LOCATION: (110)..(110)
<223> OTHER INFORMATION: n is a, g, c, or t

<400> SEQUENCE: 121

| | | | | | |
|---|---|---|---|---|---|
| acctntgggt | aagtaactgt | ggtggcctct | ctctctctct | ctctctctct | ctctctctct | 60 |
| caatacactc | ttcacttaat | aaatgtgaan | acgttaactn | gtttcttttn | tcacttctca | 120 |
| gttatgtagc | tccagagtat | gcgaactctg | atcttctgaa | tgagaaaagt | gatgtctata | 180 |
| gctttggtgt | tgt | | | | | 193 |

<210> SEQ ID NO 122
<211> LENGTH: 262
<212> TYPE: DNA
<213> ORGANISM: Brassica napus

<400> SEQUENCE: 122

| | | | | | |
|---|---|---|---|---|---|
| cacgaaagca | ggcccacccc | aataagcgat | gagctgtata | tttattttgt | cttgttttca | 60 |
| caaaaaataa | cccttcatgt | ttacagttaa | ttacacaaca | gccccttct | ttcctccatg | 120 |
| accaacgaca | aggtcgaatt | tctctctctc | tctctctctc | tctctctctc | tctctctctc | 180 |
| tccgtcgtct | tcattcaatc | tatctcagtg | atttactcgc | aatagaagtc | gcctcttaat | 240 |
| ctctcgagag | agaagctcaa | gt | | | | 262 |

<210> SEQ ID NO 123

<211> LENGTH: 172
<212> TYPE: DNA
<213> ORGANISM: Brassica napus

<400> SEQUENCE: 123

```
cgtggactaa cgctcgtgtg caggaaacga tgttcgtgaa aaggtatccg atcagaggag      60
cctccgccgg taaaaaccct tcgccgccgc cgcctccgtt gaatggtaat aactcttgtt     120
ctcgctttct cttcaaactc ccttttttt ctctgattat ttttgttggt ta             172
```

<210> SEQ ID NO 124
<211> LENGTH: 650
<212> TYPE: DNA
<213> ORGANISM: Brassica napus

<400> SEQUENCE: 124

```
gaatgggaag catcacaatg ataatgctaa tggcggtttt ggtctggtcc attactctag      60
agacctgcat tgctagaaga ggaagacatt ggagacataa ccaccgaagc tcctcwgact     120
tgtctgattc cttgtcaagc aagaaaccaa aaagccacag tcaccaccac agctctcaya    180
acaacaacca taatcatcac cacaagtcta aacctaaacc aaarccaaag ctgaaaacgc    240
cgccaaaaag tgaccacamt aaatctccgg tggtttcacc gccaccaaaa gtccaaccac    300
cgtctcttcc gccgccaaag ggatccaaag ttttcaatgt gatggatttt ggcgcaaagg    360
gtgatggcaa atgtgatgac actaagtcgt ttgaagcggc ttgggcagca gcttgcaaag    420
tggaggcatc catgatgatc ataccgcctg aatacacttt ccttgtgggt ccaatctcat    480
tctctggtcc ttattgtcaa gctaacattg tgtttcagct tgatggtact attatagctc    540
caacggattc aaaatcatgg ggaaaagggt taatgtggtg gcttgaattc acaaagctga    600
aaggaattaa agtacaaggt aaaggtgtga ttgatggaag aggctctggt              650
```

<210> SEQ ID NO 125
<211> LENGTH: 954
<212> TYPE: DNA
<213> ORGANISM: Brassica napus

<400> SEQUENCE: 125

```
gacagagata gccctaactt agtcactctc tctcacacac actccagttc aaagttcaaa      60
maatggctcc tccacagaag ctcttctcg ccgccattgt cgctgccgtc attgtagccg     120
ccaccaccgg atatgcacct aatagtgctg cggaagatat tgtgcattcc tcatgcgtgc    180
acgcgagcta tccatcgcta tgcgtccgta cactctctac ctactcyggt ccaaccatca    240
caaaccgtcg cgagctagct caagccgccg tcaagataag cctctcccac gctcgagcag    300
cygctaagaa actcgcggct gtgagagaaa ccgtggggraa gaaacgggtg aaagcggcgg    360
ttgtggactg cgtggagatg attggagact cggtggacga gctgmccgc acgctaggcg    420 ttttaaagca tctmcacgtt tcgggcgttt cggcgaacga gttcargtgg cagatgagca    480
acgcgcagac gtgggctagt gcggcgttga cggatgacga cacgtgtctc gatgggttta    540
aaggggtcga gggtaaggtt aaaacggagg tgaagcaktg gatgacgaaa gtggcgaggg    600
ttacragcaa cgcgctttac atgatcaacc agctagatga atcacgtggc tagcccacg    660 tagtacgttc ttgatgttat gatgtgcttg tcctaatgga cagttatgat ttggtgttag    720 ttttttttcgt gtttgcttaa ttgcgagtta tctactattt aaaaatgaga ggcattgtcc    780
ttttaagtag ttctgataat ggtatactaa ataaatggtt tatctctttt ttcggacggt    840
atgtcattgt atcgtattgt gttgttccct tcggattcga tagcatgtga ttttgtcttg    900
```

```
acgtgtagta gcgccttggc tgagctaatg ctctaaataa aagttttaag tggc        954
```

<210> SEQ ID NO 126
<211> LENGTH: 22
<212> TYPE: DNA
<213> ORGANISM: Artificial Sequence
<220> FEATURE:
<223> OTHER INFORMATION: Primer

<400> SEQUENCE: 126

```
acaaggagat gatcgcggtt tc                                           22
```

<210> SEQ ID NO 127
<211> LENGTH: 23
<212> TYPE: DNA
<213> ORGANISM: Artificial Sequence
<220> FEATURE:
<223> OTHER INFORMATION: Primer

<400> SEQUENCE: 127

```
ccaatctgtg taaaccaaac ggg                                          23
```

<210> SEQ ID NO 128
<211> LENGTH: 22
<212> TYPE: DNA
<213> ORGANISM: Artificial Sequence
<220> FEATURE:
<223> OTHER INFORMATION: Primer

<400> SEQUENCE: 128

```
ataaggcttg agggacatgc ca                                           22
```

<210> SEQ ID NO 129
<211> LENGTH: 22
<212> TYPE: DNA
<213> ORGANISM: Artificial Sequence
<220> FEATURE:
<223> OTHER INFORMATION: Primer

<400> SEQUENCE: 129

```
tggctccaca gaaacagctt tg                                           22
```

<210> SEQ ID NO 130
<211> LENGTH: 22
<212> TYPE: DNA
<213> ORGANISM: Artificial Sequence
<220> FEATURE:
<223> OTHER INFORMATION: Primer

<400> SEQUENCE: 130

```
gaagctgcaa tactgaggca cc                                           22
```

<210> SEQ ID NO 131
<211> LENGTH: 24
<212> TYPE: DNA
<213> ORGANISM: Artificial Sequence
<220> FEATURE:
<223> OTHER INFORMATION: Primer

<400> SEQUENCE: 131

```
gcaattctta cctgttgtcc caaa                                         24
```

<210> SEQ ID NO 132
<211> LENGTH: 22
<212> TYPE: DNA

<210> SEQ ID NO 132
<211> LENGTH: 22
<212> TYPE: DNA
<213> ORGANISM: Artificial Sequence
<220> FEATURE:
<223> OTHER INFORMATION: Primer

<400> SEQUENCE: 132
aactggtcga gcgggatttt tt                                    22

<210> SEQ ID NO 133
<211> LENGTH: 22
<212> TYPE: DNA
<213> ORGANISM: Artificial Sequence
<220> FEATURE:
<223> OTHER INFORMATION: Primer

<400> SEQUENCE: 133
taggaaaccc tagccgtcaa gc                                    22

<210> SEQ ID NO 134
<211> LENGTH: 22
<212> TYPE: DNA
<213> ORGANISM: Artificial Sequence
<220> FEATURE:
<223> OTHER INFORMATION: Primer

<400> SEQUENCE: 134
caatgtcggt aagcaccgga ag                                    22

<210> SEQ ID NO 135
<211> LENGTH: 22
<212> TYPE: DNA
<213> ORGANISM: Artificial Sequence
<220> FEATURE:
<223> OTHER INFORMATION: Primer

<400> SEQUENCE: 135
tgccggaaaa tgctgacttg ta                                    22

<210> SEQ ID NO 136
<211> LENGTH: 22
<212> TYPE: DNA
<213> ORGANISM: Artificial Sequence
<220> FEATURE:
<223> OTHER INFORMATION: Primer

<400> SEQUENCE: 136
gcttcagcca agggatttga ga                                    22

<210> SEQ ID NO 137
<211> LENGTH: 22
<212> TYPE: DNA
<213> ORGANISM: Artificial Sequence
<220> FEATURE:
<223> OTHER INFORMATION: Primer

<400> SEQUENCE: 137
agctcttttg gtgcgattcg at                                    22

<210> SEQ ID NO 138
<211> LENGTH: 22
<212> TYPE: DNA
<213> ORGANISM: Artificial Sequence
<220> FEATURE:
<223> OTHER INFORMATION: Primer

<400> SEQUENCE: 138
ccacatgcct taggtgattg ga                                    22

<210> SEQ ID NO 139
<211> LENGTH: 22
<212> TYPE: DNA
<213> ORGANISM: Artificial Sequence
<220> FEATURE:
<223> OTHER INFORMATION: Primer

<400> SEQUENCE: 139
ttcttccggc ttctcaaagg tg                                    22

<210> SEQ ID NO 140
<211> LENGTH: 22
<212> TYPE: DNA
<213> ORGANISM: Artificial Sequence
<220> FEATURE:
<223> OTHER INFORMATION: Primer

<400> SEQUENCE: 140
catccttgtc caacgtccct tc                                    22

<210> SEQ ID NO 141
<211> LENGTH: 22
<212> TYPE: DNA
<213> ORGANISM: Artificial Sequence
<220> FEATURE:
<223> OTHER INFORMATION: Primer

<400> SEQUENCE: 141
ttcctctctt cgagatcggt cg                                    22

<210> SEQ ID NO 142
<211> LENGTH: 25
<212> TYPE: DNA
<213> ORGANISM: Artificial Sequence
<220> FEATURE:
<223> OTHER INFORMATION: Primer

<400> SEQUENCE: 142
ggactcgaac atctccaatt taact                                 25

<210> SEQ ID NO 143
<211> LENGTH: 25
<212> TYPE: DNA
<213> ORGANISM: Artificial Sequence
<220> FEATURE:
<223> OTHER INFORMATION: Primer

<400> SEQUENCE: 143
tgaaaataga atacaattag ggctt                                 25

<210> SEQ ID NO 144
<211> LENGTH: 22
<212> TYPE: DNA
<213> ORGANISM: Artificial Sequence
<220> FEATURE:
<223> OTHER INFORMATION: Primer

<400> SEQUENCE: 144
gcgttgcccc tctcctctac tt                                    22

<210> SEQ ID NO 145
<211> LENGTH: 28
<212> TYPE: DNA
<213> ORGANISM: Artificial Sequence
<220> FEATURE:

<223> OTHER INFORMATION: Primer

<400> SEQUENCE: 145
cgcaatctac aaaagataca tcaaaaag          28

<210> SEQ ID NO 146
<211> LENGTH: 23
<212> TYPE: DNA
<213> ORGANISM: Artificial Sequence
<220> FEATURE:
<223> OTHER INFORMATION: Primer

<400> SEQUENCE: 146
aagaaaagag aaacgatccc acg               23

<210> SEQ ID NO 147
<211> LENGTH: 23
<212> TYPE: DNA
<213> ORGANISM: Artificial Sequence
<220> FEATURE:
<223> OTHER INFORMATION: Primer

<400> SEQUENCE: 147
tgagagtgaa gaggagttgg gtc               23

<210> SEQ ID NO 148
<211> LENGTH: 22
<212> TYPE: DNA
<213> ORGANISM: Artificial Sequence
<220> FEATURE:
<223> OTHER INFORMATION: Primer

<400> SEQUENCE: 148
gattggggga tgagattgtt gg                22

<210> SEQ ID NO 149
<211> LENGTH: 22
<212> TYPE: DNA
<213> ORGANISM: Artificial Sequence
<220> FEATURE:
<223> OTHER INFORMATION: Primer

<400> SEQUENCE: 149
gccgtccaaa agtcaaaggt ca                22

<210> SEQ ID NO 150
<211> LENGTH: 22
<212> TYPE: DNA
<213> ORGANISM: Artificial Sequence
<220> FEATURE:
<223> OTHER INFORMATION: Primer

<400> SEQUENCE: 150
agatgatcgc ggtttcctca ag                22

<210> SEQ ID NO 151
<211> LENGTH: 26
<212> TYPE: DNA
<213> ORGANISM: Artificial Sequence
<220> FEATURE:
<223> OTHER INFORMATION: Primer

<400> SEQUENCE: 151
gaggcaaagc tataagaaca actcca            26

```
<210> SEQ ID NO 152
<211> LENGTH: 22
<212> TYPE: DNA
<213> ORGANISM: Artificial Sequence
<220> FEATURE:
<223> OTHER INFORMATION: Primer

<400> SEQUENCE: 152
catgtttggt tgctacggtg ga                                              22

<210> SEQ ID NO 153
<211> LENGTH: 22
<212> TYPE: DNA
<213> ORGANISM: Artificial Sequence
<220> FEATURE:
<223> OTHER INFORMATION: Primer

<400> SEQUENCE: 153
gaggttgaga cggagaagca cc                                              22

<210> SEQ ID NO 154
<211> LENGTH: 22
<212> TYPE: DNA
<213> ORGANISM: Artificial Sequence
<220> FEATURE:
<223> OTHER INFORMATION: Primer

<400> SEQUENCE: 154
gaccaataca aaaccgggc aa                                               22

<210> SEQ ID NO 155
<211> LENGTH: 22
<212> TYPE: DNA
<213> ORGANISM: Artificial Sequence
<220> FEATURE:
<223> OTHER INFORMATION: Primer

<400> SEQUENCE: 155
ttgatggaga gtgggttgtg ct                                              22

<210> SEQ ID NO 156
<211> LENGTH: 25
<212> TYPE: DNA
<213> ORGANISM: Artificial Sequence
<220> FEATURE:
<223> OTHER INFORMATION: Primer

<400> SEQUENCE: 156
gtctcaccaa ctccaaactt gttaa                                           25

<210> SEQ ID NO 157
<211> LENGTH: 25
<212> TYPE: DNA
<213> ORGANISM: Artificial Sequence
<220> FEATURE:
<223> OTHER INFORMATION: Primer

<400> SEQUENCE: 157
caggttcctt accaaagata aagag                                           25

<210> SEQ ID NO 158
<211> LENGTH: 22
<212> TYPE: DNA
<213> ORGANISM: Artificial Sequence
<220> FEATURE:
<223> OTHER INFORMATION: Primer
```

```
<400> SEQUENCE: 158
agctcgtctc cttgctgtct ca                                              22

<210> SEQ ID NO 159
<211> LENGTH: 22
<212> TYPE: DNA
<213> ORGANISM: Artificial Sequence
<220> FEATURE:
<223> OTHER INFORMATION: Primer

<400> SEQUENCE: 159
ggaagtgaag aagaagccgg tg                                              22

<210> SEQ ID NO 160
<211> LENGTH: 23
<212> TYPE: DNA
<213> ORGANISM: Artificial Sequence
<220> FEATURE:
<223> OTHER INFORMATION: Primer

<400> SEQUENCE: 160
tgctcaaaac cctagtcgtc acc                                             23

<210> SEQ ID NO 161
<211> LENGTH: 23
<212> TYPE: DNA
<213> ORGANISM: Artificial Sequence
<220> FEATURE:
<223> OTHER INFORMATION: Primer

<400> SEQUENCE: 161
tgagagcgaa aaccaagaga gga                                             23

<210> SEQ ID NO 162
<211> LENGTH: 24
<212> TYPE: DNA
<213> ORGANISM: Artificial Sequence
<220> FEATURE:
<223> OTHER INFORMATION: Primer

<400> SEQUENCE: 162
gagtgggctg taccttgtag ttga                                            24

<210> SEQ ID NO 163
<211> LENGTH: 24
<212> TYPE: DNA
<213> ORGANISM: Artificial Sequence
<220> FEATURE:
<223> OTHER INFORMATION: Primer

<400> SEQUENCE: 163
tttgtaaaca tcagaatcac cacc                                            24

<210> SEQ ID NO 164
<211> LENGTH: 22
<212> TYPE: DNA
<213> ORGANISM: Artificial Sequence
<220> FEATURE:
<223> OTHER INFORMATION: Primer

<400> SEQUENCE: 164
tccattatta caaccacccg cc                                              22

<210> SEQ ID NO 165
<211> LENGTH: 22
```

```
<212> TYPE: DNA
<213> ORGANISM: Artificial Sequence
<220> FEATURE:
<223> OTHER INFORMATION: Primer

<400> SEQUENCE: 165
gttccgttgc cctctccttt tt                                              22

<210> SEQ ID NO 166
<211> LENGTH: 21
<212> TYPE: DNA
<213> ORGANISM: Artificial Sequence
<220> FEATURE:
<223> OTHER INFORMATION: Primer

<400> SEQUENCE: 166
gttgctggtg gagttgctgc t                                               21

<210> SEQ ID NO 167
<211> LENGTH: 25
<212> TYPE: DNA
<213> ORGANISM: Artificial Sequence
<220> FEATURE:
<223> OTHER INFORMATION: Primer

<400> SEQUENCE: 167
tttgtagatg cgactgcttc atctt                                           25

<210> SEQ ID NO 168
<211> LENGTH: 22
<212> TYPE: DNA
<213> ORGANISM: Artificial Sequence
<220> FEATURE:
<223> OTHER INFORMATION: Primer

<400> SEQUENCE: 168
cgacgctcaa gaggaaatgc tt                                              22

<210> SEQ ID NO 169
<211> LENGTH: 22
<212> TYPE: DNA
<213> ORGANISM: Artificial Sequence
<220> FEATURE:
<223> OTHER INFORMATION: Primer

<400> SEQUENCE: 169
cagtgtccac cggagtagca ga                                              22

<210> SEQ ID NO 170
<211> LENGTH: 22
<212> TYPE: DNA
<213> ORGANISM: Artificial Sequence
<220> FEATURE:
<223> OTHER INFORMATION: Primer

<400> SEQUENCE: 170
tgatccatat cggggaaaat cg                                              22

<210> SEQ ID NO 171
<211> LENGTH: 22
<212> TYPE: DNA
<213> ORGANISM: Artificial Sequence
<220> FEATURE:
<223> OTHER INFORMATION: Primer

<400> SEQUENCE: 171
```
tttttgcttg gtttccgaca ga                                                    22

<210> SEQ ID NO 172
<211> LENGTH: 22
<212> TYPE: DNA
<213> ORGANISM: Artificial Sequence
<220> FEATURE:
<223> OTHER INFORMATION: Primer

<400> SEQUENCE: 172
ccggaaacct ccgattgagt aa                                                    22

<210> SEQ ID NO 173
<211> LENGTH: 25
<212> TYPE: DNA
<213> ORGANISM: Artificial Sequence
<220> FEATURE:
<223> OTHER INFORMATION: Primer

<400> SEQUENCE: 173
ggattagttt aacatagatg ggccg                                                 25

<210> SEQ ID NO 174
<211> LENGTH: 27
<212> TYPE: DNA
<213> ORGANISM: Artificial Sequence
<220> FEATURE:
<223> OTHER INFORMATION: Primer

<400> SEQUENCE: 174
gggagataat gttgggaatc ttaatcg                                               27

<210> SEQ ID NO 175
<211> LENGTH: 22
<212> TYPE: DNA
<213> ORGANISM: Artificial Sequence
<220> FEATURE:
<223> OTHER INFORMATION: Primer

<400> SEQUENCE: 175
actgagccat ccttcctcct cc                                                    22

<210> SEQ ID NO 176
<211> LENGTH: 22
<212> TYPE: DNA
<213> ORGANISM: Artificial Sequence
<220> FEATURE:
<223> OTHER INFORMATION: Primer

<400> SEQUENCE: 176
tccgtagaaa gaacaggctc gg                                                    22

<210> SEQ ID NO 177
<211> LENGTH: 22
<212> TYPE: DNA
<213> ORGANISM: Artificial Sequence
<220> FEATURE:
<223> OTHER INFORMATION: Primer

<400> SEQUENCE: 177
gaaccgccgc caaaactaaa at                                                    22

<210> SEQ ID NO 178
<211> LENGTH: 22
<212> TYPE: DNA
<213> ORGANISM: Artificial Sequence

```
<220> FEATURE:
<223> OTHER INFORMATION: Primer

<400> SEQUENCE: 178
atcaaatcca cccactgcac ct                                              22

<210> SEQ ID NO 179
<211> LENGTH: 22
<212> TYPE: DNA
<213> ORGANISM: Artificial Sequence
<220> FEATURE:
<223> OTHER INFORMATION: Primer

<400> SEQUENCE: 179
gccttctcct cacatctacg ca                                              22

<210> SEQ ID NO 180
<211> LENGTH: 24
<212> TYPE: DNA
<213> ORGANISM: Artificial Sequence
<220> FEATURE:
<223> OTHER INFORMATION: Primer

<400> SEQUENCE: 180
tcatctgatt catcgtcatc atca                                            24

<210> SEQ ID NO 181
<211> LENGTH: 23
<212> TYPE: DNA
<213> ORGANISM: Artificial Sequence
<220> FEATURE:
<223> OTHER INFORMATION: Primer

<400> SEQUENCE: 181
tgactcttgt caacaccacc acg                                             23

<210> SEQ ID NO 182
<211> LENGTH: 21
<212> TYPE: DNA
<213> ORGANISM: Artificial Sequence
<220> FEATURE:
<223> OTHER INFORMATION: Primer

<400> SEQUENCE: 182
gaggaagcat aggaggagga g                                               21

<210> SEQ ID NO 183
<211> LENGTH: 21
<212> TYPE: DNA
<213> ORGANISM: Artificial Sequence
<220> FEATURE:
<223> OTHER INFORMATION: Primer

<400> SEQUENCE: 183
acataaccca aatccccaaa t                                               21

<210> SEQ ID NO 184
<211> LENGTH: 22
<212> TYPE: DNA
<213> ORGANISM: Artificial Sequence
<220> FEATURE:
<223> OTHER INFORMATION: Primer

<400> SEQUENCE: 184
cgaaattatg tgtgtgcgct cc                                              22
```

<210> SEQ ID NO 185
<211> LENGTH: 23
<212> TYPE: DNA
<213> ORGANISM: Artificial Sequence
<220> FEATURE:
<223> OTHER INFORMATION: Primer

<400> SEQUENCE: 185
cccggttagg aaattacgga tca                                              23

<210> SEQ ID NO 186
<211> LENGTH: 23
<212> TYPE: DNA
<213> ORGANISM: Artificial Sequence
<220> FEATURE:
<223> OTHER INFORMATION: Primer

<400> SEQUENCE: 186
tcattttgac ttttggcgtt tgg                                              23

<210> SEQ ID NO 187
<211> LENGTH: 25
<212> TYPE: DNA
<213> ORGANISM: Artificial Sequence
<220> FEATURE:
<223> OTHER INFORMATION: Primer

<400> SEQUENCE: 187
tgcataagta cgttgaaaag ggctc                                            25

<210> SEQ ID NO 188
<211> LENGTH: 22
<212> TYPE: DNA
<213> ORGANISM: Artificial Sequence
<220> FEATURE:
<223> OTHER INFORMATION: Primer

<400> SEQUENCE: 188
atgaggagaa aggattcgcg gt                                               22

<210> SEQ ID NO 189
<211> LENGTH: 22
<212> TYPE: DNA
<213> ORGANISM: Artificial Sequence
<220> FEATURE:
<223> OTHER INFORMATION: Primer

<400> SEQUENCE: 189
cggtaaacgt ccaaacctca cc                                               22

<210> SEQ ID NO 190
<211> LENGTH: 22
<212> TYPE: DNA
<213> ORGANISM: Artificial Sequence
<220> FEATURE:
<223> OTHER INFORMATION: Primer

<400> SEQUENCE: 190
gcagagcaac gaagtacgcc tt                                               22

<210> SEQ ID NO 191
<211> LENGTH: 22
<212> TYPE: DNA
<213> ORGANISM: Artificial Sequence
<220> FEATURE:
<223> OTHER INFORMATION: Primer

```
<400> SEQUENCE: 191
tcgtgatggt gtctccaatg gt                                              22

<210> SEQ ID NO 192
<211> LENGTH: 22
<212> TYPE: DNA
<213> ORGANISM: Artificial Sequence
<220> FEATURE:
<223> OTHER INFORMATION: Primer

<400> SEQUENCE: 192
gagacgaagc cattggtagg ga                                              22

<210> SEQ ID NO 193
<211> LENGTH: 22
<212> TYPE: DNA
<213> ORGANISM: Artificial Sequence
<220> FEATURE:
<223> OTHER INFORMATION: Primer

<400> SEQUENCE: 193
cggcttgttg ttgttgctgt tt                                              22

<210> SEQ ID NO 194
<211> LENGTH: 22
<212> TYPE: DNA
<213> ORGANISM: Artificial Sequence
<220> FEATURE:
<223> OTHER INFORMATION: Primer

<400> SEQUENCE: 194
ccaaactcag cacagccttt ca                                              22

<210> SEQ ID NO 195
<211> LENGTH: 22
<212> TYPE: DNA
<213> ORGANISM: Artificial Sequence
<220> FEATURE:
<223> OTHER INFORMATION: Primer

<400> SEQUENCE: 195
acgtttgcca cattcacagc at                                              22

<210> SEQ ID NO 196
<211> LENGTH: 24
<212> TYPE: DNA
<213> ORGANISM: Artificial Sequence
<220> FEATURE:
<223> OTHER INFORMATION: Primer

<400> SEQUENCE: 196
tggctgttca gttgtttagc tgga                                            24

<210> SEQ ID NO 197
<211> LENGTH: 22
<212> TYPE: DNA
<213> ORGANISM: Artificial Sequence
<220> FEATURE:
<223> OTHER INFORMATION: Primer

<400> SEQUENCE: 197
cccatttgaa ggcagagagt gc                                              22

<210> SEQ ID NO 198
```

```
<211> LENGTH: 22
<212> TYPE: DNA
<213> ORGANISM: Artificial Sequence
<220> FEATURE:
<223> OTHER INFORMATION: Primer

<400> SEQUENCE: 198
cacatctctc cgatttcatc gc                                              22

<210> SEQ ID NO 199
<211> LENGTH: 22
<212> TYPE: DNA
<213> ORGANISM: Artificial Sequence
<220> FEATURE:
<223> OTHER INFORMATION: Primer

<400> SEQUENCE: 199
aagaggattt tgtcggtggg tg                                              22

<210> SEQ ID NO 200
<211> LENGTH: 22
<212> TYPE: DNA
<213> ORGANISM: Artificial Sequence
<220> FEATURE:
<223> OTHER INFORMATION: Primer

<400> SEQUENCE: 200
tccctttggt gatgttggac tg                                              22

<210> SEQ ID NO 201
<211> LENGTH: 25
<212> TYPE: DNA
<213> ORGANISM: Artificial Sequence
<220> FEATURE:
<223> OTHER INFORMATION: Primer

<400> SEQUENCE: 201
cacataatct gcattgtcgt cttcg                                           25

<210> SEQ ID NO 202
<211> LENGTH: 22
<212> TYPE: DNA
<213> ORGANISM: Artificial Sequence
<220> FEATURE:
<223> OTHER INFORMATION: Primer

<400> SEQUENCE: 202
tggtcaacag aaaatggcct ga                                              22

<210> SEQ ID NO 203
<211> LENGTH: 22
<212> TYPE: DNA
<213> ORGANISM: Artificial Sequence
<220> FEATURE:
<223> OTHER INFORMATION: Primer

<400> SEQUENCE: 203
tggcatgtcc tttcatgctc tc                                              22

<210> SEQ ID NO 204
<211> LENGTH: 22
<212> TYPE: DNA
<213> ORGANISM: Artificial Sequence
<220> FEATURE:
<223> OTHER INFORMATION: Primer

<400> SEQUENCE: 204
```

```
atgcaaagat gggcgaagaa ga                                              22

<210> SEQ ID NO 205
<211> LENGTH: 22
<212> TYPE: DNA
<213> ORGANISM: Artificial Sequence
<220> FEATURE:
<223> OTHER INFORMATION: Primer

<400> SEQUENCE: 205
cgagagcggg ttacgagatc ag                                              22

<210> SEQ ID NO 206
<211> LENGTH: 24
<212> TYPE: DNA
<213> ORGANISM: Artificial Sequence
<220> FEATURE:
<223> OTHER INFORMATION: Primer

<400> SEQUENCE: 206
tgcataacaa aagatttgaa cccg                                            24

<210> SEQ ID NO 207
<211> LENGTH: 22
<212> TYPE: DNA
<213> ORGANISM: Artificial Sequence
<220> FEATURE:
<223> OTHER INFORMATION: Primer

<400> SEQUENCE: 207
ggagcaaaag agcggaacag aa                                              22

<210> SEQ ID NO 208
<211> LENGTH: 22
<212> TYPE: DNA
<213> ORGANISM: Artificial Sequence
<220> FEATURE:
<223> OTHER INFORMATION: Primer

<400> SEQUENCE: 208
accgccaaag aagacgaaaa tg                                              22

<210> SEQ ID NO 209
<211> LENGTH: 22
<212> TYPE: DNA
<213> ORGANISM: Artificial Sequence
<220> FEATURE:
<223> OTHER INFORMATION: Primer

<400> SEQUENCE: 209
ctcggcggac agatacactc ag                                              22

<210> SEQ ID NO 210
<211> LENGTH: 22
<212> TYPE: DNA
<213> ORGANISM: Artificial Sequence
<220> FEATURE:
<223> OTHER INFORMATION: Primer

<400> SEQUENCE: 210
gaagctaaat gcgttgcgtt gc                                              22

<210> SEQ ID NO 211
<211> LENGTH: 24
<212> TYPE: DNA
```

```
<213> ORGANISM: Artificial Sequence
<220> FEATURE:
<223> OTHER INFORMATION: Primer

<400> SEQUENCE: 211
tttggctgta aaatgaagtg agca                                              24

<210> SEQ ID NO 212
<211> LENGTH: 22
<212> TYPE: DNA
<213> ORGANISM: Artificial Sequence
<220> FEATURE:
<223> OTHER INFORMATION: Primer

<400> SEQUENCE: 212
gagtcggcca caaatcaagg aa                                                22

<210> SEQ ID NO 213
<211> LENGTH: 22
<212> TYPE: DNA
<213> ORGANISM: Artificial Sequence
<220> FEATURE:
<223> OTHER INFORMATION: Primer

<400> SEQUENCE: 213
tcggaggagg aggagattga ga                                                22

<210> SEQ ID NO 214
<211> LENGTH: 22
<212> TYPE: DNA
<213> ORGANISM: Artificial Sequence
<220> FEATURE:
<223> OTHER INFORMATION: Primer

<400> SEQUENCE: 214
cccaagactc caaccggaaa at                                                22

<210> SEQ ID NO 215
<211> LENGTH: 22
<212> TYPE: DNA
<213> ORGANISM: Artificial Sequence
<220> FEATURE:
<223> OTHER INFORMATION: Primer

<400> SEQUENCE: 215
tcgcattaaa cgaggacgtg ag                                                22

<210> SEQ ID NO 216
<211> LENGTH: 22
<212> TYPE: DNA
<213> ORGANISM: Artificial Sequence
<220> FEATURE:
<223> OTHER INFORMATION: Primer

<400> SEQUENCE: 216
ccaactcgtt ccatcccagt ct                                                22

<210> SEQ ID NO 217
<211> LENGTH: 22
<212> TYPE: DNA
<213> ORGANISM: Artificial Sequence
<220> FEATURE:
<223> OTHER INFORMATION: Primer

<400> SEQUENCE: 217
cggtggctcg tactgcttct ct                                                22
```

```
<210> SEQ ID NO 218
<211> LENGTH: 23
<212> TYPE: DNA
<213> ORGANISM: Artificial Sequence
<220> FEATURE:
<223> OTHER INFORMATION: Primer

<400> SEQUENCE: 218
ccgttgaggt aggtttctgc ctt                                              23

<210> SEQ ID NO 219
<211> LENGTH: 22
<212> TYPE: DNA
<213> ORGANISM: Artificial Sequence
<220> FEATURE:
<223> OTHER INFORMATION: Primer

<400> SEQUENCE: 219
ttgcctcgct cacatctttt tg                                               22

<210> SEQ ID NO 220
<211> LENGTH: 24
<212> TYPE: DNA
<213> ORGANISM: Artificial Sequence
<220> FEATURE:
<223> OTHER INFORMATION: Primer

<400> SEQUENCE: 220
acatgcttgt ggataaatca tcat                                             24

<210> SEQ ID NO 221
<211> LENGTH: 24
<212> TYPE: DNA
<213> ORGANISM: Artificial Sequence
<220> FEATURE:
<223> OTHER INFORMATION: Primer

<400> SEQUENCE: 221
gaaaatgaga aacccaaac taaa                                              24

<210> SEQ ID NO 222
<211> LENGTH: 22
<212> TYPE: DNA
<213> ORGANISM: Artificial Sequence
<220> FEATURE:
<223> OTHER INFORMATION: Primer

<400> SEQUENCE: 222
aggccacctt ttgtcaccag tc                                               22

<210> SEQ ID NO 223
<211> LENGTH: 22
<212> TYPE: DNA
<213> ORGANISM: Artificial Sequence
<220> FEATURE:
<223> OTHER INFORMATION: Primer

<400> SEQUENCE: 223 gggggggttaa tttgtcccat tt                                              22

<210> SEQ ID NO 224
<211> LENGTH: 22
<212> TYPE: DNA
<213> ORGANISM: Artificial Sequence
<220> FEATURE:
```

```
<223> OTHER INFORMATION: Primer

<400> SEQUENCE: 224
ccgccataac aaaaatcttc cc                                          22

<210> SEQ ID NO 225
<211> LENGTH: 25
<212> TYPE: DNA
<213> ORGANISM: Artificial Sequence
<220> FEATURE:
<223> OTHER INFORMATION: Primer

<400> SEQUENCE: 225
tgtttcctac aaaggtataa ccggc                                       25

<210> SEQ ID NO 226
<211> LENGTH: 22
<212> TYPE: DNA
<213> ORGANISM: Artificial Sequence
<220> FEATURE:
<223> OTHER INFORMATION: Primer

<400> SEQUENCE: 226
ttgctacact tccctgtggg tg                                          22

<210> SEQ ID NO 227
<211> LENGTH: 22
<212> TYPE: DNA
<213> ORGANISM: Artificial Sequence
<220> FEATURE:
<223> OTHER INFORMATION: Primer

<400> SEQUENCE: 227
cctctctcac tgcgtgcatt tc                                          22

<210> SEQ ID NO 228
<211> LENGTH: 22
<212> TYPE: DNA
<213> ORGANISM: Artificial Sequence
<220> FEATURE:
<223> OTHER INFORMATION: Primer

<400> SEQUENCE: 228
cggcgcactg atgatgtttc ta                                          22

<210> SEQ ID NO 229
<211> LENGTH: 22
<212> TYPE: DNA
<213> ORGANISM: Artificial Sequence
<220> FEATURE:
<223> OTHER INFORMATION: Primer

<400> SEQUENCE: 229
gggagagagt ttgttcggtg ct                                          22

<210> SEQ ID NO 230
<211> LENGTH: 22
<212> TYPE: DNA
<213> ORGANISM: Artificial Sequence
<220> FEATURE:
<223> OTHER INFORMATION: Primer

<400> SEQUENCE: 230
ttgtgagcgc caagataagg ct                                          22
```

```
<210> SEQ ID NO 231
<211> LENGTH: 22
<212> TYPE: DNA
<213> ORGANISM: Artificial Sequence
<220> FEATURE:
<223> OTHER INFORMATION: Primer

<400> SEQUENCE: 231
aaaccctatc ccgcgaacaa ct                                            22

<210> SEQ ID NO 232
<211> LENGTH: 22
<212> TYPE: DNA
<213> ORGANISM: Artificial Sequence
<220> FEATURE:
<223> OTHER INFORMATION: Primer

<400> SEQUENCE: 232
ggcctcttgt gtttcctcca ac                                            22

<210> SEQ ID NO 233
<211> LENGTH: 22
<212> TYPE: DNA
<213> ORGANISM: Artificial Sequence
<220> FEATURE:
<223> OTHER INFORMATION: Primer

<400> SEQUENCE: 233
caccactacc gccatctctc ct                                            22

<210> SEQ ID NO 234
<211> LENGTH: 22
<212> TYPE: DNA
<213> ORGANISM: Artificial Sequence
<220> FEATURE:
<223> OTHER INFORMATION: Primer

<400> SEQUENCE: 234
ttaacaaacc gaatccgcaa gc                                            22

<210> SEQ ID NO 235
<211> LENGTH: 22
<212> TYPE: DNA
<213> ORGANISM: Artificial Sequence
<220> FEATURE:
<223> OTHER INFORMATION: Primer

<400> SEQUENCE: 235
gattgttgtt gctgctgctg ct                                            22

<210> SEQ ID NO 236
<211> LENGTH: 27
<212> TYPE: DNA
<213> ORGANISM: Artificial Sequence
<220> FEATURE:
<223> OTHER INFORMATION: Primer

<400> SEQUENCE: 236
caacgaactc ttcttctctg ctttaca                                       27

<210> SEQ ID NO 237
<211> LENGTH: 24
<212> TYPE: DNA
<213> ORGANISM: Artificial Sequence
<220> FEATURE:
<223> OTHER INFORMATION: Primer
```

```
<400> SEQUENCE: 237
tcacgacaaa tggtcaaatt ctca                                          24

<210> SEQ ID NO 238
<211> LENGTH: 23
<212> TYPE: DNA
<213> ORGANISM: Artificial Sequence
<220> FEATURE:
<223> OTHER INFORMATION: Primer

<400> SEQUENCE: 238
gtccgagaca gagtatgcta agc                                           23

<210> SEQ ID NO 239
<211> LENGTH: 23
<212> TYPE: DNA
<213> ORGANISM: Artificial Sequence
<220> FEATURE:
<223> OTHER INFORMATION: Primer

<400> SEQUENCE: 239
tcattggtgg atcacttcaa ata                                           23

<210> SEQ ID NO 240
<211> LENGTH: 22
<212> TYPE: DNA
<213> ORGANISM: Artificial Sequence
<220> FEATURE:
<223> OTHER INFORMATION: Primer

<400> SEQUENCE: 240
gattctatca gccacggaac gc                                            22

<210> SEQ ID NO 241
<211> LENGTH: 22
<212> TYPE: DNA
<213> ORGANISM: Artificial Sequence
<220> FEATURE:
<223> OTHER INFORMATION: Primer

<400> SEQUENCE: 241
cacctattta ccccacgagg ca                                            22

<210> SEQ ID NO 242
<211> LENGTH: 22
<212> TYPE: DNA
<213> ORGANISM: Artificial Sequence
<220> FEATURE:
<223> OTHER INFORMATION: Primer

<400> SEQUENCE: 242
tgcatagact cgaaccaaac cg                                            22

<210> SEQ ID NO 243
<211> LENGTH: 22
<212> TYPE: DNA
<213> ORGANISM: Artificial Sequence
<220> FEATURE:
<223> OTHER INFORMATION: Primer

<400> SEQUENCE: 243
tctgatacgc caagctctgc tg                                            22

<210> SEQ ID NO 244
<211> LENGTH: 18
```

```
<212> TYPE: DNA
<213> ORGANISM: Artificial Sequence
<220> FEATURE:
<223> OTHER INFORMATION: Primer

<400> SEQUENCE: 244
cgacggtttc acggcact                                                   18

<210> SEQ ID NO 245
<211> LENGTH: 18
<212> TYPE: DNA
<213> ORGANISM: Artificial Sequence
<220> FEATURE:
<223> OTHER INFORMATION: Primer

<400> SEQUENCE: 245
tcatcctccg acgacgac                                                   18

<210> SEQ ID NO 246
<211> LENGTH: 22
<212> TYPE: DNA
<213> ORGANISM: Artificial Sequence
<220> FEATURE:
<223> OTHER INFORMATION: Primer

<400> SEQUENCE: 246
gctcggcttc caagggtaag at                                              22

<210> SEQ ID NO 247
<211> LENGTH: 22
<212> TYPE: DNA
<213> ORGANISM: Artificial Sequence
<220> FEATURE:
<223> OTHER INFORMATION: Primer

<400> SEQUENCE: 247
gatgtactgc ttagctgccg cc                                              22

<210> SEQ ID NO 248
<211> LENGTH: 22
<212> TYPE: DNA
<213> ORGANISM: Artificial Sequence
<220> FEATURE:
<223> OTHER INFORMATION: Primer

<400> SEQUENCE: 248
cgaggaggaa gaagatgacc ga                                              22

<210> SEQ ID NO 249
<211> LENGTH: 22
<212> TYPE: DNA
<213> ORGANISM: Artificial Sequence
<220> FEATURE:
<223> OTHER INFORMATION: Primer

<400> SEQUENCE: 249
acgagcaggc ggtgaaaata aa                                              22

<210> SEQ ID NO 250
<211> LENGTH: 22
<212> TYPE: DNA
<213> ORGANISM: Artificial Sequence
<220> FEATURE:
<223> OTHER INFORMATION: Primer

<400> SEQUENCE: 250
```
agttgtggtg aacaggctgc at                                          22

<210> SEQ ID NO 251
<211> LENGTH: 22
<212> TYPE: DNA
<213> ORGANISM: Artificial Sequence
<220> FEATURE:
<223> OTHER INFORMATION: Primer

<400> SEQUENCE: 251
ccaactcgtt ccatcccagt ct                                          22

<210> SEQ ID NO 252
<211> LENGTH: 22
<212> TYPE: DNA
<213> ORGANISM: Artificial Sequence
<220> FEATURE:
<223> OTHER INFORMATION: Primer

<400> SEQUENCE: 252
tcaccttcct tccttcaatg gc                                          22

<210> SEQ ID NO 253
<211> LENGTH: 22
<212> TYPE: DNA
<213> ORGANISM: Artificial Sequence
<220> FEATURE:
<223> OTHER INFORMATION: Primer

<400> SEQUENCE: 253
tgacccacct cctctgcttt tc                                          22

<210> SEQ ID NO 254
<211> LENGTH: 22
<212> TYPE: DNA
<213> ORGANISM: Artificial Sequence
<220> FEATURE:
<223> OTHER INFORMATION: Primer

<400> SEQUENCE: 254
tgaaggttgc gatagcgaag ag                                          22

<210> SEQ ID NO 255
<211> LENGTH: 22
<212> TYPE: DNA
<213> ORGANISM: Artificial Sequence
<220> FEATURE:
<223> OTHER INFORMATION: Primer

<400> SEQUENCE: 255
ttggggtcgg aactgaaaca tt                                          22

<210> SEQ ID NO 256
<211> LENGTH: 22
<212> TYPE: DNA
<213> ORGANISM: Artificial Sequence
<220> FEATURE:
<223> OTHER INFORMATION: Primer

<400> SEQUENCE: 256
tgtttccttc accatgatcg ga                                          22

<210> SEQ ID NO 257
<211> LENGTH: 24
<212> TYPE: DNA
<213> ORGANISM: Artificial Sequence

```
<220> FEATURE:
<223> OTHER INFORMATION: Primer

<400> SEQUENCE: 257
cacaccctac ctctcttgtg tccc                                              24

<210> SEQ ID NO 258
<211> LENGTH: 27
<212> TYPE: DNA
<213> ORGANISM: Artificial Sequence
<220> FEATURE:
<223> OTHER INFORMATION: Primer

<400> SEQUENCE: 258
gactaaacca gaccaagaga aaagtcg                                           27

<210> SEQ ID NO 259
<211> LENGTH: 22
<212> TYPE: DNA
<213> ORGANISM: Artificial Sequence
<220> FEATURE:
<223> OTHER INFORMATION: Primer

<400> SEQUENCE: 259
tgttgaaccg gataggcaag gt                                                22

<210> SEQ ID NO 260
<211> LENGTH: 22
<212> TYPE: DNA
<213> ORGANISM: Artificial Sequence
<220> FEATURE:
<223> OTHER INFORMATION: Primer

<400> SEQUENCE: 260
ccatcatcac caccaccatc at                                                22

<210> SEQ ID NO 261
<211> LENGTH: 22
<212> TYPE: DNA
<213> ORGANISM: Artificial Sequence
<220> FEATURE:
<223> OTHER INFORMATION: Primer

<400> SEQUENCE: 261
cttgctggag aaggtcggat gt                                                22

<210> SEQ ID NO 262
<211> LENGTH: 22
<212> TYPE: DNA
<213> ORGANISM: Artificial Sequence
<220> FEATURE:
<223> OTHER INFORMATION: Primer

<400> SEQUENCE: 262
ggagaagggt cgtcgtcaag aa                                                22

<210> SEQ ID NO 263
<211> LENGTH: 22
<212> TYPE: DNA
<213> ORGANISM: Artificial Sequence
<220> FEATURE:
<223> OTHER INFORMATION: Primer

<400> SEQUENCE: 263
tcgaacacac aaacgatgct ca                                                22
```

```
<210> SEQ ID NO 264
<211> LENGTH: 22
<212> TYPE: DNA
<213> ORGANISM: Artificial Sequence
<220> FEATURE:
<223> OTHER INFORMATION: Primer

<400> SEQUENCE: 264
catggatcac ctgcaccctt ag                                              22

<210> SEQ ID NO 265
<211> LENGTH: 22
<212> TYPE: DNA
<213> ORGANISM: Artificial Sequence
<220> FEATURE:
<223> OTHER INFORMATION: Primer

<400> SEQUENCE: 265
gcgactccgg tgaagacgta tc                                              22

<210> SEQ ID NO 266
<211> LENGTH: 22
<212> TYPE: DNA
<213> ORGANISM: Artificial Sequence
<220> FEATURE:
<223> OTHER INFORMATION: Primer

<400> SEQUENCE: 266
ggcaagcatg gtctcgtcag at                                              22

<210> SEQ ID NO 267
<211> LENGTH: 22
<212> TYPE: DNA
<213> ORGANISM: Artificial Sequence
<220> FEATURE:
<223> OTHER INFORMATION: Primer

<400> SEQUENCE: 267
aaaaaaagat tccagccgcc tc                                              22

<210> SEQ ID NO 268
<211> LENGTH: 22
<212> TYPE: DNA
<213> ORGANISM: Artificial Sequence
<220> FEATURE:
<223> OTHER INFORMATION: Primer

<400> SEQUENCE: 268
actttggagc atccttcctt gg                                              22

<210> SEQ ID NO 269
<211> LENGTH: 22
<212> TYPE: DNA
<213> ORGANISM: Artificial Sequence
<220> FEATURE:
<223> OTHER INFORMATION: Primer

<400> SEQUENCE: 269
gatgttggac tgcgctctgg ta                                              22

<210> SEQ ID NO 270
<211> LENGTH: 22
<212> TYPE: DNA
<213> ORGANISM: Artificial Sequence
<220> FEATURE:
<223> OTHER INFORMATION: Primer
```

<400> SEQUENCE: 270
ctgttgagcc atcgagatca gc                                          22

<210> SEQ ID NO 271
<211> LENGTH: 23
<212> TYPE: DNA
<213> ORGANISM: Artificial Sequence
<220> FEATURE:
<223> OTHER INFORMATION: Primer

<400> SEQUENCE: 271
ccagaaagtg atggtgtgca taa                                         23

<210> SEQ ID NO 272
<211> LENGTH: 22
<212> TYPE: DNA
<213> ORGANISM: Artificial Sequence
<220> FEATURE:
<223> OTHER INFORMATION: Primer

<400> SEQUENCE: 272
aatcagtccg atcactccct gc                                          22

<210> SEQ ID NO 273
<211> LENGTH: 22
<212> TYPE: DNA
<213> ORGANISM: Artificial Sequence
<220> FEATURE:
<223> OTHER INFORMATION: Primer

<400> SEQUENCE: 273
ggaagttacc tcgtcgtcgg aa                                          22

<210> SEQ ID NO 274
<211> LENGTH: 25
<212> TYPE: DNA
<213> ORGANISM: Artificial Sequence
<220> FEATURE:
<223> OTHER INFORMATION: Primer

<400> SEQUENCE: 274
ttctgttaga attctaccgt tgttg                                       25

<210> SEQ ID NO 275
<211> LENGTH: 22
<212> TYPE: DNA
<213> ORGANISM: Artificial Sequence
<220> FEATURE:
<223> OTHER INFORMATION: Primer

<400> SEQUENCE: 275
agctttgtga ggagagtgtg gt                                          22

<210> SEQ ID NO 276
<211> LENGTH: 22
<212> TYPE: DNA
<213> ORGANISM: Artificial Sequence
<220> FEATURE:
<223> OTHER INFORMATION: Primer

<400> SEQUENCE: 276
cagcaatgtc gtcgttcaat cc                                          22

<210> SEQ ID NO 277

```
<211> LENGTH: 22
<212> TYPE: DNA
<213> ORGANISM: Artificial Sequence
<220> FEATURE:
<223> OTHER INFORMATION: Primer

<400> SEQUENCE: 277
ctgtaactcg ccggagcttg at                                              22

<210> SEQ ID NO 278
<211> LENGTH: 23
<212> TYPE: DNA
<213> ORGANISM: Artificial Sequence
<220> FEATURE:
<223> OTHER INFORMATION: Primer

<400> SEQUENCE: 278
cccctccctt atccacacac aca                                             23

<210> SEQ ID NO 279
<211> LENGTH: 22
<212> TYPE: DNA
<213> ORGANISM: Artificial Sequence
<220> FEATURE:
<223> OTHER INFORMATION: Primer

<400> SEQUENCE: 279
tgggttcgtg aaggtgaagg tt                                              22

<210> SEQ ID NO 280
<211> LENGTH: 22
<212> TYPE: DNA
<213> ORGANISM: Artificial Sequence
<220> FEATURE:
<223> OTHER INFORMATION: Primer

<400> SEQUENCE: 280
cgctaggggg tgaaccaaga at                                              22

<210> SEQ ID NO 281
<211> LENGTH: 22
<212> TYPE: DNA
<213> ORGANISM: Artificial Sequence
<220> FEATURE:
<223> OTHER INFORMATION: Primer

<400> SEQUENCE: 281
gcgtcgatcc tcctctccaa ta                                              22

<210> SEQ ID NO 282
<211> LENGTH: 22
<212> TYPE: DNA
<213> ORGANISM: Artificial Sequence
<220> FEATURE:
<223> OTHER INFORMATION: Primer

<400> SEQUENCE: 282
cctcccaaag tcgtctcttc ca                                              22

<210> SEQ ID NO 283
<211> LENGTH: 22
<212> TYPE: DNA
<213> ORGANISM: Artificial Sequence
<220> FEATURE:
<223> OTHER INFORMATION: Primer

<400> SEQUENCE: 283
```

```
gtagacagggg gacgaaactc gg                                              22

<210> SEQ ID NO 284
<211> LENGTH: 22
<212> TYPE: DNA
<213> ORGANISM: Artificial Sequence
<220> FEATURE:
<223> OTHER INFORMATION: Primer

<400> SEQUENCE: 284
ttccaagtgg ttctgcaatg tg                                               22

<210> SEQ ID NO 285
<211> LENGTH: 23
<212> TYPE: DNA
<213> ORGANISM: Artificial Sequence
<220> FEATURE:
<223> OTHER INFORMATION: Primer

<400> SEQUENCE: 285
tcagctatcc caataaaggg caa                                              23

<210> SEQ ID NO 286
<211> LENGTH: 22
<212> TYPE: DNA
<213> ORGANISM: Artificial Sequence
<220> FEATURE:
<223> OTHER INFORMATION: Primer

<400> SEQUENCE: 286
ccaggtcctt gcgttgaatc at                                               22

<210> SEQ ID NO 287
<211> LENGTH: 22
<212> TYPE: DNA
<213> ORGANISM: Artificial Sequence
<220> FEATURE:
<223> OTHER INFORMATION: Primer

<400> SEQUENCE: 287
accacactgc atatccctgc aa                                               22

<210> SEQ ID NO 288
<211> LENGTH: 22
<212> TYPE: DNA
<213> ORGANISM: Artificial Sequence
<220> FEATURE:
<223> OTHER INFORMATION: Primer

<400> SEQUENCE: 288
cctcttcaac cccacactgg at                                               22

<210> SEQ ID NO 289
<211> LENGTH: 22
<212> TYPE: DNA
<213> ORGANISM: Artificial Sequence
<220> FEATURE:
<223> OTHER INFORMATION: Primer

<400> SEQUENCE: 289
ttgcgaatgt atcagccgtc tc                                               22

<210> SEQ ID NO 290
<211> LENGTH: 22
<212> TYPE: DNA
```

```
<213> ORGANISM: Artificial Sequence
<220> FEATURE:
<223> OTHER INFORMATION: Primer

<400> SEQUENCE: 290
ccgaaccgga atcatacagc tc                                          22

<210> SEQ ID NO 291
<211> LENGTH: 22
<212> TYPE: DNA
<213> ORGANISM: Artificial Sequence
<220> FEATURE:
<223> OTHER INFORMATION: Primer

<400> SEQUENCE: 291
tgcgtttgaa ccagtcagat cc                                          22

<210> SEQ ID NO 292
<211> LENGTH: 24
<212> TYPE: DNA
<213> ORGANISM: Artificial Sequence
<220> FEATURE:
<223> OTHER INFORMATION: Primer

<400> SEQUENCE: 292
ccgggcttag acaaacttta tgag                                        24

<210> SEQ ID NO 293
<211> LENGTH: 22
<212> TYPE: DNA
<213> ORGANISM: Artificial Sequence
<220> FEATURE:
<223> OTHER INFORMATION: Primer

<400> SEQUENCE: 293
attgatcgca caaacgcctg ta                                          22

<210> SEQ ID NO 294
<211> LENGTH: 28
<212> TYPE: DNA
<213> ORGANISM: Artificial Sequence
<220> FEATURE:
<223> OTHER INFORMATION: Primer

<400> SEQUENCE: 294
aaaaactgat aagattattg ttggtaac                                    28

<210> SEQ ID NO 295
<211> LENGTH: 26
<212> TYPE: DNA
<213> ORGANISM: Artificial Sequence
<220> FEATURE:
<223> OTHER INFORMATION: Primer

<400> SEQUENCE: 295
ccaaaaataa aagttaaact tgcata                                      26

<210> SEQ ID NO 296
<211> LENGTH: 23
<212> TYPE: DNA
<213> ORGANISM: Artificial Sequence
<220> FEATURE:
<223> OTHER INFORMATION: Primer

<400> SEQUENCE: 296
caggcagcta aggaatctgg aaa                                         23
```

```
<210> SEQ ID NO 297
<211> LENGTH: 22
<212> TYPE: DNA
<213> ORGANISM: Artificial Sequence
<220> FEATURE:
<223> OTHER INFORMATION: Primer

<400> SEQUENCE: 297
taaaagaggc gtcccgatga ga                                          22

<210> SEQ ID NO 298
<211> LENGTH: 23
<212> TYPE: DNA
<213> ORGANISM: Artificial Sequence
<220> FEATURE:
<223> OTHER INFORMATION: Primer

<400> SEQUENCE: 298
aaaatgcaac catgcaatac gtg                                         23

<210> SEQ ID NO 299
<211> LENGTH: 27
<212> TYPE: DNA
<213> ORGANISM: Artificial Sequence
<220> FEATURE:
<223> OTHER INFORMATION: Primer

<400> SEQUENCE: 299
gtttgtagta tttgttgtca ctgctgc                                     27

<210> SEQ ID NO 300
<211> LENGTH: 22
<212> TYPE: DNA
<213> ORGANISM: Artificial Sequence
<220> FEATURE:
<223> OTHER INFORMATION: Primer

<400> SEQUENCE: 300
tgcgaaagcc atgaaccttt ct                                          22

<210> SEQ ID NO 301
<211> LENGTH: 25
<212> TYPE: DNA
<213> ORGANISM: Artificial Sequence
<220> FEATURE:
<223> OTHER INFORMATION: Primer

<400> SEQUENCE: 301
tgttcttcac aaaaaaaatc agcaa                                       25

<210> SEQ ID NO 302
<211> LENGTH: 22
<212> TYPE: DNA
<213> ORGANISM: Artificial Sequence
<220> FEATURE:
<223> OTHER INFORMATION: Primer

<400> SEQUENCE: 302
ctcatgggag gttcgcttga ta                                          22

<210> SEQ ID NO 303
<211> LENGTH: 23
<212> TYPE: DNA
<213> ORGANISM: Artificial Sequence
<220> FEATURE:
```

<223> OTHER INFORMATION: Primer

<400> SEQUENCE: 303
gcaactgcaa gatcaaatgg tca					23

<210> SEQ ID NO 304
<211> LENGTH: 26
<212> TYPE: DNA
<213> ORGANISM: Artificial Sequence
<220> FEATURE:
<223> OTHER INFORMATION: Primer

<400> SEQUENCE: 304
cacattggtt tacagagtct acatga					26

<210> SEQ ID NO 305
<211> LENGTH: 26
<212> TYPE: DNA
<213> ORGANISM: Artificial Sequence
<220> FEATURE:
<223> OTHER INFORMATION: Primer

<400> SEQUENCE: 305
acaaatacat gtgaaagttg aaaaca					26

<210> SEQ ID NO 306
<211> LENGTH: 25
<212> TYPE: DNA
<213> ORGANISM: Artificial Sequence
<220> FEATURE:
<223> OTHER INFORMATION: Primer

<400> SEQUENCE: 306
tcagtctagg cgtttaccaa tacca					25

<210> SEQ ID NO 307
<211> LENGTH: 22
<212> TYPE: DNA
<213> ORGANISM: Artificial Sequence
<220> FEATURE:
<223> OTHER INFORMATION: Primer

<400> SEQUENCE: 307
cttaggcggt gctttggctc ta						22

<210> SEQ ID NO 308
<211> LENGTH: 22
<212> TYPE: DNA
<213> ORGANISM: Artificial Sequence
<220> FEATURE:
<223> OTHER INFORMATION: Primer

<400> SEQUENCE: 308
ttgaacttga cgacgacatc cc						22

<210> SEQ ID NO 309
<211> LENGTH: 23
<212> TYPE: DNA
<213> ORGANISM: Artificial Sequence
<220> FEATURE:
<223> OTHER INFORMATION: Primer

<400> SEQUENCE: 309
gattgcatga tttagctgct gga					23

```
<210> SEQ ID NO 310
<211> LENGTH: 23
<212> TYPE: DNA
<213> ORGANISM: Artificial Sequence
<220> FEATURE:
<223> OTHER INFORMATION: Primer

<400> SEQUENCE: 310
aaaatgcaac catgcaatac gtg                                          23

<210> SEQ ID NO 311
<211> LENGTH: 27
<212> TYPE: DNA
<213> ORGANISM: Artificial Sequence
<220> FEATURE:
<223> OTHER INFORMATION: Primer

<400> SEQUENCE: 311
tttgtagtat ttgtttgtca ctgctgc                                      27

<210> SEQ ID NO 312
<211> LENGTH: 22
<212> TYPE: DNA
<213> ORGANISM: Artificial Sequence
<220> FEATURE:
<223> OTHER INFORMATION: Primer

<400> SEQUENCE: 312
ctcccaggtg agaccgacaa tc                                           22

<210> SEQ ID NO 313
<211> LENGTH: 22
<212> TYPE: DNA
<213> ORGANISM: Artificial Sequence
<220> FEATURE:
<223> OTHER INFORMATION: Primer

<400> SEQUENCE: 313
cgtagcgcgg aaaaggaatc ta                                           22

<210> SEQ ID NO 314
<211> LENGTH: 22
<212> TYPE: DNA
<213> ORGANISM: Artificial Sequence
<220> FEATURE:
<223> OTHER INFORMATION: Primer

<400> SEQUENCE: 314
ctcttgcctt catcggcgta ct                                           22

<210> SEQ ID NO 315
<211> LENGTH: 22
<212> TYPE: DNA
<213> ORGANISM: Artificial Sequence
<220> FEATURE:
<223> OTHER INFORMATION: Primer

<400> SEQUENCE: 315
atccagggct caaaaacagc ct                                           22

<210> SEQ ID NO 316
<211> LENGTH: 26
<212> TYPE: DNA
<213> ORGANISM: Artificial Sequence
<220> FEATURE:
<223> OTHER INFORMATION: Primer
```

<400> SEQUENCE: 316
tgacaaaatc cacatctcta atggtg                                  26

<210> SEQ ID NO 317
<211> LENGTH: 22
<212> TYPE: DNA
<213> ORGANISM: Artificial Sequence
<220> FEATURE:
<223> OTHER INFORMATION: Primer

<400> SEQUENCE: 317
aggctacatc ggttttgggc tt                                      22

<210> SEQ ID NO 318
<211> LENGTH: 23
<212> TYPE: DNA
<213> ORGANISM: Artificial Sequence
<220> FEATURE:
<223> OTHER INFORMATION: Primer

<400> SEQUENCE: 318
ccatgcagct ttttgttacg aca                                     23

<210> SEQ ID NO 319
<211> LENGTH: 22
<212> TYPE: DNA
<213> ORGANISM: Artificial Sequence
<220> FEATURE:
<223> OTHER INFORMATION: Primer

<400> SEQUENCE: 319
ggccaacaat gcaaatacac ga                                      22

<210> SEQ ID NO 320
<211> LENGTH: 24
<212> TYPE: DNA
<213> ORGANISM: Artificial Sequence
<220> FEATURE:
<223> OTHER INFORMATION: Primer

<400> SEQUENCE: 320
aaagtggtgg agcttttttcc agtt                                   24

<210> SEQ ID NO 321
<211> LENGTH: 22
<212> TYPE: DNA
<213> ORGANISM: Artificial Sequence
<220> FEATURE:
<223> OTHER INFORMATION: Primer

<400> SEQUENCE: 321
gccaagacca gtgggatgtg tt                                      22

<210> SEQ ID NO 322
<211> LENGTH: 26
<212> TYPE: DNA
<213> ORGANISM: Artificial Sequence
<220> FEATURE:
<223> OTHER INFORMATION: Primer

<400> SEQUENCE: 322
tagtgtcaaa aaacatttgt ctttca                                  26

<210> SEQ ID NO 323
<211> LENGTH: 26

```
<212> TYPE: DNA
<213> ORGANISM: Artificial Sequence
<220> FEATURE:
<223> OTHER INFORMATION: Primer

<400> SEQUENCE: 323
ttgtcatttt tttgtcatca tatttt                                          26

<210> SEQ ID NO 324
<211> LENGTH: 18
<212> TYPE: DNA
<213> ORGANISM: Artificial Sequence
<220> FEATURE:
<223> OTHER INFORMATION: Primer

<400> SEQUENCE: 324
caccgtcgga gtctgaat                                                   18

<210> SEQ ID NO 325
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (14)..(14)
<223> OTHER INFORMATION: n is a, g, c, or t

<400> SEQUENCE: 325
gagccgttaa accntagtgt g                                               21

<210> SEQ ID NO 326
<211> LENGTH: 21
<212> TYPE: DNA
<213> ORGANISM: Artificial Sequence
<220> FEATURE:
<223> OTHER INFORMATION: Primer

<400> SEQUENCE: 326
attgggttct gaccttttct c                                               21

<210> SEQ ID NO 327
<211> LENGTH: 20
<212> TYPE: DNA
<213> ORGANISM: Artificial Sequence
<220> FEATURE:
<223> OTHER INFORMATION: Primer

<400> SEQUENCE: 327
cttttcctca tcgctaccac                                                 20

<210> SEQ ID NO 328
<211> LENGTH: 20
<212> TYPE: DNA
<213> ORGANISM: Artificial Sequence
<220> FEATURE:
<223> OTHER INFORMATION: Primer

<400> SEQUENCE: 328
tcgttctgac ctgtcgttat                                                 20

<210> SEQ ID NO 329
<211> LENGTH: 19
<212> TYPE: DNA
<213> ORGANISM: Artificial Sequence
<220> FEATURE:
```

<223> OTHER INFORMATION: Primer

<400> SEQUENCE: 329
ggaaatggct gctcatgtt                                                      19

<210> SEQ ID NO 330
<211> LENGTH: 20
<212> TYPE: DNA
<213> ORGANISM: Artificial Sequence
<220> FEATURE:
<223> OTHER INFORMATION: Primer

<400> SEQUENCE: 330
cggcaataat ggaccactgg                                                     20

<210> SEQ ID NO 331
<211> LENGTH: 20
<212> TYPE: DNA
<213> ORGANISM: Artificial Sequence
<220> FEATURE:
<223> OTHER INFORMATION: Primer

<400> SEQUENCE: 331
cggctttcac gcagacttcg                                                     20

<210> SEQ ID NO 332
<211> LENGTH: 21
<212> TYPE: DNA
<213> ORGANISM: Artificial Sequence
<220> FEATURE:
<223> OTHER INFORMATION: Primer

<400> SEQUENCE: 332
tatgggaagg tttgtggttg c                                                   21

<210> SEQ ID NO 333
<211> LENGTH: 21
<212> TYPE: DNA
<213> ORGANISM: Artificial Sequence
<220> FEATURE:
<223> OTHER INFORMATION: Primer

<400> SEQUENCE: 333
cactcctcga ttactctcac t                                                   21

<210> SEQ ID NO 334
<211> LENGTH: 21
<212> TYPE: DNA
<213> ORGANISM: Artificial Sequence
<220> FEATURE:
<223> OTHER INFORMATION: Primer

<400> SEQUENCE: 334
tcctgtgcca agttttacaa g                                                   21

<210> SEQ ID NO 335
<211> LENGTH: 21
<212> TYPE: DNA
<213> ORGANISM: Artificial Sequence
<220> FEATURE:
<223> OTHER INFORMATION: Primer

<400> SEQUENCE: 335
ggttaccctt agcaagatat t                                                   21

```
<210> SEQ ID NO 336
<211> LENGTH: 21
<212> TYPE: DNA
<213> ORGANISM: Artificial Sequence
<220> FEATURE:
<223> OTHER INFORMATION: Primer

<400> SEQUENCE: 336
tctattgatc tttggctctc t                                          21

<210> SEQ ID NO 337
<211> LENGTH: 18
<212> TYPE: DNA
<213> ORGANISM: Artificial Sequence
<220> FEATURE:
<223> OTHER INFORMATION: Primer

<400> SEQUENCE: 337
cgtaacgtct tcgctctc                                              18

<210> SEQ ID NO 338
<211> LENGTH: 18
<212> TYPE: DNA
<213> ORGANISM: Artificial Sequence
<220> FEATURE:
<223> OTHER INFORMATION: Primer

<400> SEQUENCE: 338
gaccccatga tccgaata                                              18

<210> SEQ ID NO 339
<211> LENGTH: 21
<212> TYPE: DNA
<213> ORGANISM: Artificial Sequence
<220> FEATURE:
<223> OTHER INFORMATION: Primer

<400> SEQUENCE: 339
aagacttgct ttattggagt t                                          21

<210> SEQ ID NO 340
<211> LENGTH: 18
<212> TYPE: DNA
<213> ORGANISM: Artificial Sequence
<220> FEATURE:
<223> OTHER INFORMATION: Primer

<400> SEQUENCE: 340
tacaacgcaa acgttcct                                              18

<210> SEQ ID NO 341
<211> LENGTH: 18
<212> TYPE: DNA
<213> ORGANISM: Artificial Sequence
<220> FEATURE:
<223> OTHER INFORMATION: Primer

<400> SEQUENCE: 341
ttgatgttct tggtgcct                                              18

<210> SEQ ID NO 342
<211> LENGTH: 18
<212> TYPE: DNA
<213> ORGANISM: Artificial Sequence
<220> FEATURE:
<223> OTHER INFORMATION: Primer
```

-continued

<400> SEQUENCE: 342
tggtgtatat gggatcgg                                                  18

<210> SEQ ID NO 343
<211> LENGTH: 18
<212> TYPE: DNA
<213> ORGANISM: Artificial Sequence
<220> FEATURE:
<223> OTHER INFORMATION: Primer

<400> SEQUENCE: 343
gtttgcagac cattctcg                                                  18

<210> SEQ ID NO 344
<211> LENGTH: 18
<212> TYPE: DNA
<213> ORGANISM: Artificial Sequence
<220> FEATURE:
<223> OTHER INFORMATION: Primer

<400> SEQUENCE: 344
gagacgatgc aaagatcg                                                  18

<210> SEQ ID NO 345
<211> LENGTH: 18
<212> TYPE: DNA
<213> ORGANISM: Artificial Sequence
<220> FEATURE:
<223> OTHER INFORMATION: Primer

<400> SEQUENCE: 345
tgcagacaca ttcgaaca                                                  18

<210> SEQ ID NO 346
<211> LENGTH: 18
<212> TYPE: DNA
<213> ORGANISM: Artificial Sequence
<220> FEATURE:
<223> OTHER INFORMATION: Primer

<400> SEQUENCE: 346
cattcacagg accagagc                                                  18

<210> SEQ ID NO 347
<211> LENGTH: 18
<212> TYPE: DNA
<213> ORGANISM: Artificial Sequence
<220> FEATURE:
<223> OTHER INFORMATION: Primer

<400> SEQUENCE: 347
caaagccaag acaaccat                                                  18

<210> SEQ ID NO 348
<211> LENGTH: 18
<212> TYPE: DNA
<213> ORGANISM: Artificial Sequence
<220> FEATURE:
<223> OTHER INFORMATION: Primer

<400> SEQUENCE: 348
atggtgacga gttggatg                                                  18

<210> SEQ ID NO 349
<211> LENGTH: 18

```
<212> TYPE: DNA
<213> ORGANISM: Artificial Sequence
<220> FEATURE:
<223> OTHER INFORMATION: Primer

<400> SEQUENCE: 349
cctcgtctgg aatctcct                                                 18

<210> SEQ ID NO 350
<211> LENGTH: 18
<212> TYPE: DNA
<213> ORGANISM: Artificial Sequence
<220> FEATURE:
<223> OTHER INFORMATION: Primer

<400> SEQUENCE: 350
cagaaaccat catagccg                                                 18

<210> SEQ ID NO 351
<211> LENGTH: 18
<212> TYPE: DNA
<213> ORGANISM: Artificial Sequence
<220> FEATURE:
<223> OTHER INFORMATION: Primer

<400> SEQUENCE: 351
tgatttggga gacgaaga                                                 18

<210> SEQ ID NO 352
<211> LENGTH: 18
<212> TYPE: DNA
<213> ORGANISM: Artificial Sequence
<220> FEATURE:
<223> OTHER INFORMATION: Primer

<400> SEQUENCE: 352
cgttactcgc aaggaaga                                                 18

<210> SEQ ID NO 353
<211> LENGTH: 18
<212> TYPE: DNA
<213> ORGANISM: Artificial Sequence
<220> FEATURE:
<223> OTHER INFORMATION: Primer

<400> SEQUENCE: 353
ttcgagagac cgtgaaga                                                 18

<210> SEQ ID NO 354
<211> LENGTH: 18
<212> TYPE: DNA
<213> ORGANISM: Artificial Sequence
<220> FEATURE:
<223> OTHER INFORMATION: Primer

<400> SEQUENCE: 354
atggaaggca acgattct                                                 18

<210> SEQ ID NO 355
<211> LENGTH: 18
<212> TYPE: DNA
<213> ORGANISM: Artificial Sequence
<220> FEATURE:
<223> OTHER INFORMATION: Primer

<400> SEQUENCE: 355
```

```
ttctgtgcta ggtctgcc                                                    18
```

```
<210> SEQ ID NO 356
<211> LENGTH: 18
<212> TYPE: DNA
<213> ORGANISM: Artificial Sequence
<220> FEATURE:
<223> OTHER INFORMATION: Primer

<400> SEQUENCE: 356
tcggggtttg ttgtgagg                                                    18
```

```
<210> SEQ ID NO 357
<211> LENGTH: 22
<212> TYPE: DNA
<213> ORGANISM: Artificial Sequence
<220> FEATURE:
<223> OTHER INFORMATION: Primer

<400> SEQUENCE: 357
gaggaggatg ctaagagtga gc                                               22
```

```
<210> SEQ ID NO 358
<211> LENGTH: 20
<212> TYPE: DNA
<213> ORGANISM: Artificial Sequence
<220> FEATURE:
<223> OTHER INFORMATION: Primer

<400> SEQUENCE: 358
atgactgctt aaacagcgcc                                                  20
```

```
<210> SEQ ID NO 359
<211> LENGTH: 20
<212> TYPE: DNA
<213> ORGANISM: Artificial Sequence
<220> FEATURE:
<223> OTHER INFORMATION: Primer

<400> SEQUENCE: 359
cttctccaac aaaagctcgg                                                  20
```

```
<210> SEQ ID NO 360
<211> LENGTH: 20
<212> TYPE: DNA
<213> ORGANISM: Artificial Sequence
<220> FEATURE:
<223> OTHER INFORMATION: Primer

<400> SEQUENCE: 360
acacacaaca aacagctcgc                                                  20
```

```
<210> SEQ ID NO 361
<211> LENGTH: 20
<212> TYPE: DNA
<213> ORGANISM: Artificial Sequence
<220> FEATURE:
<223> OTHER INFORMATION: Primer

<400> SEQUENCE: 361
aacatcaaac ctctcgacgg                                                  20
```

```
<210> SEQ ID NO 362
<211> LENGTH: 21
<212> TYPE: DNA
<213> ORGANISM: Artificial Sequence
```

<220> FEATURE:
<223> OTHER INFORMATION: Primer

<400> SEQUENCE: 362
aagaacgtca agatcctctg c                                              21

<210> SEQ ID NO 363
<211> LENGTH: 20
<212> TYPE: DNA
<213> ORGANISM: Artificial Sequence
<220> FEATURE:
<223> OTHER INFORMATION: Primer

<400> SEQUENCE: 363
accaccacgg tagtagagcg                                                20

<210> SEQ ID NO 364
<211> LENGTH: 21
<212> TYPE: DNA
<213> ORGANISM: Artificial Sequence
<220> FEATURE:
<223> OTHER INFORMATION: Primer

<400> SEQUENCE: 364
catgagaaca agatgggttc g                                              21

<210> SEQ ID NO 365
<211> LENGTH: 20
<212> TYPE: DNA
<213> ORGANISM: Artificial Sequence
<220> FEATURE:
<223> OTHER INFORMATION: Primer

<400> SEQUENCE: 365
ctgaaacttg agcaaagccc                                                20

<210> SEQ ID NO 366
<211> LENGTH: 21
<212> TYPE: DNA
<213> ORGANISM: Artificial Sequence
<220> FEATURE:
<223> OTHER INFORMATION: Primer

<400> SEQUENCE: 366
tgggtaagta actgtggtgg c                                              21

<210> SEQ ID NO 367
<211> LENGTH: 21
<212> TYPE: DNA
<213> ORGANISM: Artificial Sequence
<220> FEATURE:
<223> OTHER INFORMATION: Primer

<400> SEQUENCE: 367
agagttcgca tactctggag c                                              21

<210> SEQ ID NO 368
<211> LENGTH: 21
<212> TYPE: DNA
<213> ORGANISM: Artificial Sequence
<220> FEATURE:
<223> OTHER INFORMATION: Primer

<400> SEQUENCE: 368
tccatgacca acgacaaggt c                                              21

<210> SEQ ID NO 369
<211> LENGTH: 20
<212> TYPE: DNA
<213> ORGANISM: Artificial Sequence
<220> FEATURE:
<223> OTHER INFORMATION: Primer

<400> SEQUENCE: 369
aagaggcgac ttctattgcg                                               20

<210> SEQ ID NO 370
<211> LENGTH: 20
<212> TYPE: DNA
<213> ORGANISM: Artificial Sequence
<220> FEATURE:
<223> OTHER INFORMATION: Primer

<400> SEQUENCE: 370
gtgtgcagga aacgatgttc                                               20

<210> SEQ ID NO 371
<211> LENGTH: 20
<212> TYPE: DNA
<213> ORGANISM: Artificial Sequence
<220> FEATURE:
<223> OTHER INFORMATION: Primer

<400> SEQUENCE: 371
gggagtttga agagaaagcg                                               20

<210> SEQ ID NO 372
<211> LENGTH: 25
<212> TYPE: DNA
<213> ORGANISM: Artificial Sequence
<220> FEATURE:
<223> OTHER INFORMATION: Primer

<400> SEQUENCE: 372
ccacagtcac caccacagct ctcat                                         25

<210> SEQ ID NO 373
<211> LENGTH: 25
<212> TYPE: DNA
<213> ORGANISM: Artificial Sequence
<220> FEATURE:
<223> OTHER INFORMATION: Primer

<400> SEQUENCE: 373
ggcggtgaaa ccaccggaga tttag                                         25

<210> SEQ ID NO 374
<211> LENGTH: 23
<212> TYPE: DNA
<213> ORGANISM: Artificial Sequence
<220> FEATURE:
<223> OTHER INFORMATION: Primer

<400> SEQUENCE: 374
gcctctccca cgctcgagca gcc                                           23

<210> SEQ ID NO 375
<211> LENGTH: 23
<212> TYPE: DNA
<213> ORGANISM: Artificial Sequence
<220> FEATURE:
<223> OTHER INFORMATION: Primer

```
<400> SEQUENCE: 375
ccctcgccac tttcgtcatc caa                                          23
```

What is claimed is:

1. A method of identifying a *Brassica* plant or *Brassica* germplasm that exhibits whole plant field resistance or improved whole plant field resistance to *Sclerotinia*, the method comprising:
   (a) isolating a nucleic acid from a *Brassica* plant or *Brassica* germplasm;
   (b) detecting in the nucleic acid from the plant or germplasm at least one allele of at least one quantitative trait locus (QTL) that is associated with the whole plant field resistance or improved whole plant field resistance to *Sclerotinia*, wherein the QTL is localized to linkage group N18 wherein said linkage group comprises at least one marker that is associated with the whole plant field resistance or improved whole plant field resistance to *Sclerotinia* with a statistical significance of $p \leq 0.01$, wherein the at least one marker comprises BG0278 (SEQ ID NO: 36), CA0636 (SEQ ID NO: 81), UB0315 (SEQ ID NO: 122), or CA0739 (SEQ ID NO: 85), thereby identifying a *Brassica* plant or germplasm that exhibits said resistance to *Sclerotinia*;
   (c) crossing the *Brassica* plant or *Brassica* germplasm of (b) with a second *Brassica* plant or germplasm not having the at least one marker of step (b) in its genome;
   (d) collecting seed from the plant resulting from the cross in step (c); and
   (e) growing a progeny *Brassica* plant or germplasm which exhibits said resistance to *Sclerotinia* from said seed which comprises at least one of said markers in its genome.

2. The method of claim 1, wherein the QTL is localized to a chromosomal interval flanked by and including (i) markers BG0278 and CA0636 or (ii) markers UB0315 and CA0739 on linkage group N18.

3. The method of claim 1, wherein the marker comprises a polymorphism that identifies the at least one allele of the at least one quantitative trait locus (QTL) as being associated with the whole plant field resistance or improved whole plant field resistance to *Sclerotinia*, and the detecting comprises identifying the polymorphism.

4. The method of claim 3, wherein the detecting comprises detecting at least one marker selected from BG0278 (SEQ ID NO: 36); CA0636 (SEQ ID NO: 81); CA0739 (SEQ ID NO: 85); and UB0315 (SEQ ID NO: 122).

5. The method of claim 4, wherein the detecting comprises detecting at least one marker selected from CA0739 (SEQ ID NO: 85) and UB0315 (SEQ ID NO: 122).

6. The method of claim 1, wherein the plant is *Brassica napus*; *Brassica juncea*; *Brassica rapa*; *Brassica oleracea*; or *Brassica carinata*.

* * * * *